US008420052B2

(12) United States Patent  
Kolb et al.

(10) Patent No.: US 8,420,052 B2
(45) Date of Patent: Apr. 16, 2013

(54) IMAGING AGENTS USEFUL FOR IDENTIFYING AD PATHOLOGY

(75) Inventors: Hartmuth C. Kolb, Playa Del Rey, CA (US); Joseph C. Walsh, Pacific Palisades, CA (US); Wei Zhang, Los Angeles, CA (US); Umesh B. Gangadharmath, Los Angeles, CA (US); Dhanalakshmi Kasi, Los Angeles, CA (US); Kai Chen, Rockville, MD (US); Anjana Sinha, San Diego, CA (US); Eric Wang, San Diego, CA (US); Gang Chen, Los Angeles, CA (US); Peter J. H. Scott, Ypsilanti, MI (US); Henry Clifton Padgett, Hermosa Beach, CA (US); Qianwa Liang, Hacienda Heights, CA (US); Zhiyong Gao, Wynnewood, PA (US); Tieming Zhao, Los Angeles, CA (US); Chunfang Xia, Los Angeles, CA (US); Vani P. Mocharla, Los Angeles, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 656 days.

(21) Appl. No.: 12/509,259

(22) Filed: Jul. 24, 2009

(65) Prior Publication Data

US 2010/0098634 A1   Apr. 22, 2010

Related U.S. Application Data

(60) Provisional application No. 61/083,501, filed on Jul. 24, 2008.

(51) Int. Cl.
*A61K 51/00* (2006.01)
*A61M 36/14* (2006.01)

(52) U.S. Cl. ............ 424/1.89; 424/1.11; 424/1.65; 424/1.81; 424/1.85

(58) Field of Classification Search ............... 424/1.11, 424/1.65, 1.81, 1.85, 1.89; 546/1, 249; 548/100, 548/146, 215, 300.1
See application file for complete search history.

(56) References Cited

U.S. PATENT DOCUMENTS

| 5,871,934 | A  | 2/1999 | Lee et al. |
| 2003/0149250 | A1 | 8/2003 | Kung et al. |
| 2006/0110787 | A1 | 5/2006 | Walker |
| 2007/0060618 | A1 | 3/2007 | Cosford et al. |
| 2007/0258887 | A1 | 11/2007 | Tamagnan et al. |

FOREIGN PATENT DOCUMENTS

| EP | 1655287 | 5/2006 |
| EP | 1 815 872 A | 8/2007 |
| EP | 1944281 | 7/2008 |
| EP | 2218464 | 8/2010 |
| JP | 9165378 A | 6/1997 |
| JP | 2001048786 | * 2/2001 |
| JP | 2006100537 | 4/2006 |
| JP | 2007223952 A | 9/2007 |
| WO | WO 94/14477 A | 7/1994 |
| WO | WO 97/14679 A | 4/1997 |
| WO | 02085903 A2 | 10/2002 |
| WO | WO 2004/043496 A | 5/2004 |
| WO | 2004056399 A2 | 7/2004 |
| WO | WO 2007/014467 | 2/2007 |
| WO | WO 2007/057705 A | 5/2007 |
| WO | 2007063946 A1 | 6/2007 |
| WO | WO 2007/094718 A | 8/2007 |
| WO | 2008073350 A2 | 6/2008 |
| WO | WO 2008/083454 A | 7/2008 |
| WO | 2008124812 A1 | 10/2008 |
| WO | WO 2008/131148 A | 10/2008 |
| WO | WO 2008/132454 A | 11/2008 |
| WO | 2009004914 A1 | 1/2009 |
| WO | 2009045535 A2 | 4/2009 |
| WO | 2009055401 | 4/2009 |
| WO | 2010011964 | 1/2010 |
| WO | 2010/073719 | 7/2010 |

OTHER PUBLICATIONS

Qu, et al., Radioiodinated Aza-Diphenylacetylenes As Potential SPECT Imaging Agents for Beta-Amyloid Plaque Detection, Published in Bioorganic & Medicinal Chemistry Letters, vol. 17, No. 13, Jul. 1, 2007 (pp. 3581-3584). Science Direct, Elsevier.
Invitation to Pay Additional Fees in PCT/US2010/028360.
Nordberg, A., "PET imaging of amyloid in Alzheimer's disease", Lancet Neurology, Lancet Publ. Group, London, GB, vol. 3, No. 9, Sep. 1, 2004, pp. 519-527.
Zheng, et al., "Biological Characters of [18F]0-FEt-PIB In a Rat Model of Alzheimer's Disease Using Micro-PET Imaging", Published in Acta Pharmacologica Sinica, vol. 29, No. 5, May 1, 2008 (pp. 548-554).
Wang, et al., "PET Imaging and Optical Imaging With D-Luciferin [<11>C]methyl Ester and D-Luciferin [11C]methyl Ether of Luciferase Gene Expression in Tumor Xenografts of Living Mice", Published in Bioorganic & Medicinal Chemistry Letters, vol. 16, No. 2, Jan. 15, 2006 (pp. 331-337).

(Continued)

*Primary Examiner* — D L Jones
(74) *Attorney, Agent, or Firm* — Joshua Ryan

(57) ABSTRACT

Provided herein are compounds and compositions which comprise the formulae as disclosed herein, wherein the compound is an amyloid binding compound. An amyloid binding compound according to the invention may be administered to a patient in amounts suitable for in vivo imaging of amyloid deposits, and distinguish between neurological tissue with amyloid deposits and normal neurological tissue. Amyloid probes of the invention may be used to detect and quantitate amyloid deposits in diseases including, for example, Down's syndrome, familial Alzheimer's Disease. In another embodiment, the compounds may be used in the treatment or prophylaxis of neurodegenerative disorders. Also provided herein are methods of allowing the compound to distribute into the brain tissue, and imaging the brain tissue, wherein an increase in binding of the compound to the brain tissue compared to a normal control level of binding indicates that the mammal is suffering from or is at risk of developing a neurodegenerative disease.

23 Claims, 23 Drawing Sheets

OTHER PUBLICATIONS

Solbach, et al., "Efficient Radiosynthesis of Carbon-11 Labelled Uncharged Thioflavin T Derivatives Using [11C] methyl Triflate for Beta-Amyloid Imaging in Alzheimer's Disease With PET", Published in Applied Radiation and Isotopes, vol. 62, No. 4, Apr. 1, 2005 (pp. 591-595).

Mathis, et al., "Synthesis and Evaluation of 11C-Labeled 6-Substituted 2-Arylbenzothiazoles As Amyloid Imaging Agents", Published in Journal of Medicinal Chemistry, American Chemical Society, vol. 46, Jun. 19, 2003 (pp. 2740-2754).

Serdons, et al., "Synthesis and Evaluation of 18F-Labeled 2-Phenylbenzothiazoles As Positron Emission Tomography Imaging Agents for Amyloid Plaques in Alzheimer's Disease", Published in Journal of Medicinal Chemistry, American Cancer Society, vol. 52, Feb. 13, 2009 (pp. 1428-1437).

Johnson, et al., "AZD2184: A Radioligand for Sensitive Detection of Beta-Amyloid Deposits", Published in Journal of Neurochemistry, vol. 108, Mar. 1, 2009 (pp. 1177-1186).

Seneca, et al., "Brain and Whole-Body Imaging in Nonhuman Primates With [11C]MeS-IMPY, a Candidate Radioligand for Beta-Amyloid Plaques", Published in Nuclear Medicine and Biology, vol. 34, Aug. 6, 2007 (pp. 681-689).

Vasdev, et al., "Synthesis and Ex Vivo Evaluation of Carbon-11 Labelled N-(4-methoxybenzyl)-N'-(5-nitro-1,3-thiazol-2-yl)urea([11C]AR-A014418): A Radiolabelled Glycogen Synthase Kinase-3beta Specific Inhibitor for PET Studies", Published in Bioorganic & Medicinal Chemistry Letters, vol. 15, No. 23, Dec. 1, 2005 (pp. 5270-5273).

Bergstrom, Mats et al.: "Synthesis of some 11C-labeled MAO—A inhibitors and their in vivo uptake kinetics in rhesus monkey brain", Nuclear Medicine and Biology, 24(5), 381-388 Coden: Nimbieo; ISSN: 0883-2897, 1997.

Sintas, Jose A. et al.: "Iodination, radioiodination and spectroscopic identification of beta.-carboline derivatives", Journal of Labelled Compounds & Radiopharmaceuticals, 42(5), 409-413 Coden: JLCRD4; ISSN: 0362-4803, 1999.

Karimi, Farhad et al.: "Synthesis of 11c-labelled amides by palladium-mediated carboxamination using [11C]carbon monoxide, in situ activated amines and 1,2,2,6,6-pentamethylpiperidine", European Journal of Organic Chemistry, (11), 2132-2137 Coden: Ejocfk; ISSN: 1434-193X, 2003.

Baranowska-Kortylewicz J et al.: "Radioiodination of 7-Methoxy- and 6,7-Dimethoxy-4-Bromomethylcoumarins", Journal of Labelled Compounds and Radiopharmaceuticals, John Wiley, Chichester, DB, vol. 29, No. 12, Jan. 1, 1991, pp. 1301-1307, ISSN: 0362-4803.

Heike Radeke et al.: "Synthesis and biological evaluation of the mitochondrial complex 1 inhibitor 2-[4-(4-fluorobutyl) benzylsulfanyl]-3-meth ylchromene-4-one as a potential cardiac positron emission tomography tracer", J. Med. Chem., vol. 50, 2007, pp. 4304-4315.

Maria Graciela Barolli et al.: "Synthesis of [131I]-iodinated quercetin", J. Label. Compds. Radiopharm., vol. 32, No. 11, 1997, pp. 297-933.

Hollie I. Swanson et al.: "Use of [125I]4'-iodoflavone as a tool to characterize ligand-dependent differences in Ah receptor behavior", J. Biochem. Molecular Toxicology, vol. 16, No. 6, 2002, pp. 298-310.

Takahashi K et al.: "Imaging of aromatase distribution in rat and rhesus monkey brains with [<11>C]vorozole" Nuclear Medicine and Biology, Elsevier, NY, US, vol. 33, No. 5, Jul. 1, 2006, pp. 599-605, XP025103506 ISSN: 0969-8051.

Wenchao Qu et al.: "Quick Assembly of 2,24-diphenyltriazoles as probes targeting beta-amyloid aggregates in alzheimer's disease", J. Med. Chem., vol. 50, 2007, pp. 3380-3387.

Glaser M et al.: "Click Labeling with 2-[18F]Fluoroethylazide for Positron Emission Tomography" Bioconjugate Chemistry, ACS, Washington, DC, US, vol. 18, Apr. 13, 2007, pp. 989-993, ISSN: 1043-1802.

Sirion et al.: "An efficient F-18 labeling method for PET study: Huisgen 1,3-dipolar cycloaddition of bioactive substances and F-18-labeled compounds" Tetrahenron Letters, Elsevier, Amsterdam, vol. 48, No. 23, Jun. 4, 2007, pp. 3953-3957, ISSN: 0040-4039.

Mathias C. J. et al.: "Radiolebeled hypoxic cell sensitizers: Tracers for assessment of ischemia" Life Sciences, Pergamon Press, Oxford, GB, vol. 41, No. 2, Jul. 13, 1987, pp. 199-206, ISSN: 0024-3205.

Jerabek P.A. et al.: "Synthesis and biodistrubtion of <18>F-labeled fluoronitroimidazoles: Potential in vivo markers of hypoxic tissue", Applied Radiation and Isotopes, International Journal of Radiation Applications and Instrumentation, Part A, Pergamon Press, Ltd., GB, vol. 37, No. 7, Jan. 1, 1986, pp. 599-605, ISSN: 0883-2889.

Visser G.W. M. et al.: "The preparation and stability of <211>At-astato-imidazoles" International Journal of Applied Radiation and Isotops, Pergamon Press, New York, NY, US, vol. 31, No. 5, May 1, 1980, pp. 275-278, ISSN: 0020-708X.

Miriko Tanaka et al.: "Radiosynthesis and evaluation of 11C-labeled diaryl-substituted imidazole and indole derivatives for mapping cyclooxygenase-2" Biological & Pharmaceutical Bulletin (of Japan)., vol. 29, No. 10, 2006, pp. 2087-2094, Pharmaceutical Society of Japan, Tokyo.

Gareth Getvoldsen et al.: Microwave-assisted cyclocondensation of 1,2-diaminobenzene with [4-18F] fluorobenzoic acid: microwave synthesis of 2-([4-18F]fluorophenyl) benzimidazole, Journal of Labelled Compounds and Radiopharmaceuticals, research article, J. Label Compd Radiopharm 2004; 47: 139-145.

Piotr Garnuszek et al.: "Synthesis and characterisation of platinum(II) complexes with histamine and iodohistamine", Inorganica Chimica Acta, vol. 338 (2002) 119-126.

Fumihiko Yamamoto et al.: "Synthesis and Evaluation of 4-Bromo-1-(3-[18F]fluoropropyl)-2-nitroimidazole with a Low Entergy LUMO Orbital Designed as Brain Hypoxia-Targeting Imaging Agent", Biol.Pharm. Bull. 25(5) 616-621 (2002), vol. 25, No. 5.

Fumihiko Yamamoto et al.: "Synthesis and Characterization of Lipohilic 1-[18F]Fluoralkyl-2Initroimidazoles for Imaging Hypoxia", Biol. Pharm. Bull. 22(6) 590-597 (1999), vol. 22, No. 6.

Blom, Elisabeth et al.: "Synthesis and in vitro evaluation of 18F-.beta.-carboline alkaloids as PET ligands" Journal of Labelled Compounds and Radiophaarmaceuticlas, 51(6), 277-282 Coden: JLCRD4, May 2008.

Dumont F. et al.: "Synthesis and In Vivo Evaluation of 7-chloro-5-[<123>I]iodo-4-oxo-1,4 dihydroquinoline-2-carboxylic Acid" Applied Radiation and Isotopes, Elsevier, Oxford, GB, vol. 48, No. 9, Sep. 1, 1997, pp. 1173-1177.

Livni E. et al.: "Synthesis and biodistribution of <18>F-labeled Fleroxacin" Nuclear Medicine and Biology, Elsevier, NY, US, vol. 20, No. 1, Jan. 1, 1993, pp. 81-87.

Zijlstra S et al.: "Synthesis and evaluation of fluorine-18 labelled compounds for imaging of bacterial infections with pet" Applied Radiation and Isotopes, Elsevier, Oxford, GB, vol. 64, No. 7, Jul. 1, 2006, pp. 802-807.

Choi, Osaku Wataru et al.: "Preparation of F-18 labeling benzyl N-containing heterocyclyl compounds as PET diagnostic remedies", Chemical Abstracts Service, Columbus, Ohio, US: Database accession No. 127:65770 abstract & JP 09 165378 A, Jun. 24, 1997.

Okamura, et al., "Quinoline and Benzimidazole Derivatives: Candidate Probes for In Vivo Imaging of Tau Pathology in Alzheimer's Disease.", Journal of Neuroscience, Nov. 23, 2005, 25(47):10857-10862.

Aoyama, et al., "Polynnethylated .gamma.-carbolines with potent anti-bovine viral diarrhea virus (BVDV) activity", Heterocycles (2009), 77(2), 779-785.

Sako, et al., "Gamma-carboline derivatives with anti-bovine viral diarrhea virus (BVDV) activity", Bioorg Med Chem Apr. 1, 2008, 16(7), 3780-3790.

Chen, et al., "Microwave-enhanced Fischer reaction: an efficient one-pot synthesis of y-carbolines", Synlett (2008), (1), 77-82.

Engler, et al., "Lewis Acid-Directed Cyclocondensation of Piperidone Enol Ethers with 2-Methoxy-4-(N-phenylsulfonyl)-1,4-benzoquinoneimine: A New Regioselective Synthesis of Oxygenated Carbolines", Journal of Organic Chemistry (2000), 65(8), 2444-2457.

Mehta, et al., "The elimination of an alkoxy group in the photo-Graebe—Ullmann conversion of 1-(2,5-dialkoxyphenyl)

triazolopyridines into carbolines, and the preparation of α-, γ- and δ-carboline quinones", J. Chem. Soc., Perkin Trans. 1, 1993, 1261-1267.

Parrick, et al., "Some carbazole and carboline quinones and an unexpected demethoxylation reaction". Journal of Chemical Research, Synopses (1990), (1), 1.

Molina, et al., "Novel DNA Intercalators Based on the Pyridazino [1',6':1,2]pyrido [4,3-b] indol-5-inium System", J. Org. Chem, 1999, 64, 3907-3915.

Molina, et al., "Synthesis and DNA Binding Properties of y-Carbolinium Derivatives and Benzologues", J. Org. Chem, 1996, 61, 5587-5599.

PCT/US2010/028360 Search Report issued Nov. 22, 2010.

Kruglenko, et al.; "Condensed Imidazo-1,2,4-azines. 31. Synthesis and Chemical Transformations of Substituted 1,2,4-Triazepino[2,3-a]benzimidaloses"; Chemistry of Heterocyclic Compounds, vol. 38, No. 5, 2002—pp. 598-606.

Tseng, et al., "A Simple Regioselective Synthesis of Pyrimido[1,2-a]benzimidazoles"; vol. 24, May 1, 1987; Jun. 1, 1987, pp. 837-843.

Yousefi, et al., "Synthesis and Evaluation of 11C-Labeled Imidazo [2,1-b] benzothiazoles (IBTs) as PET Tracers for Imaging β-Amyloid Plaques in Alzheimer's Disease", J. Med. Chem., Article ASAP, DOI: 10.1021/jm101129a Publication Date (Web): Jan. 28, 2011.

* cited by examiner

AD BRAIN TISSUE STAINING USING $^{18}$F-W372

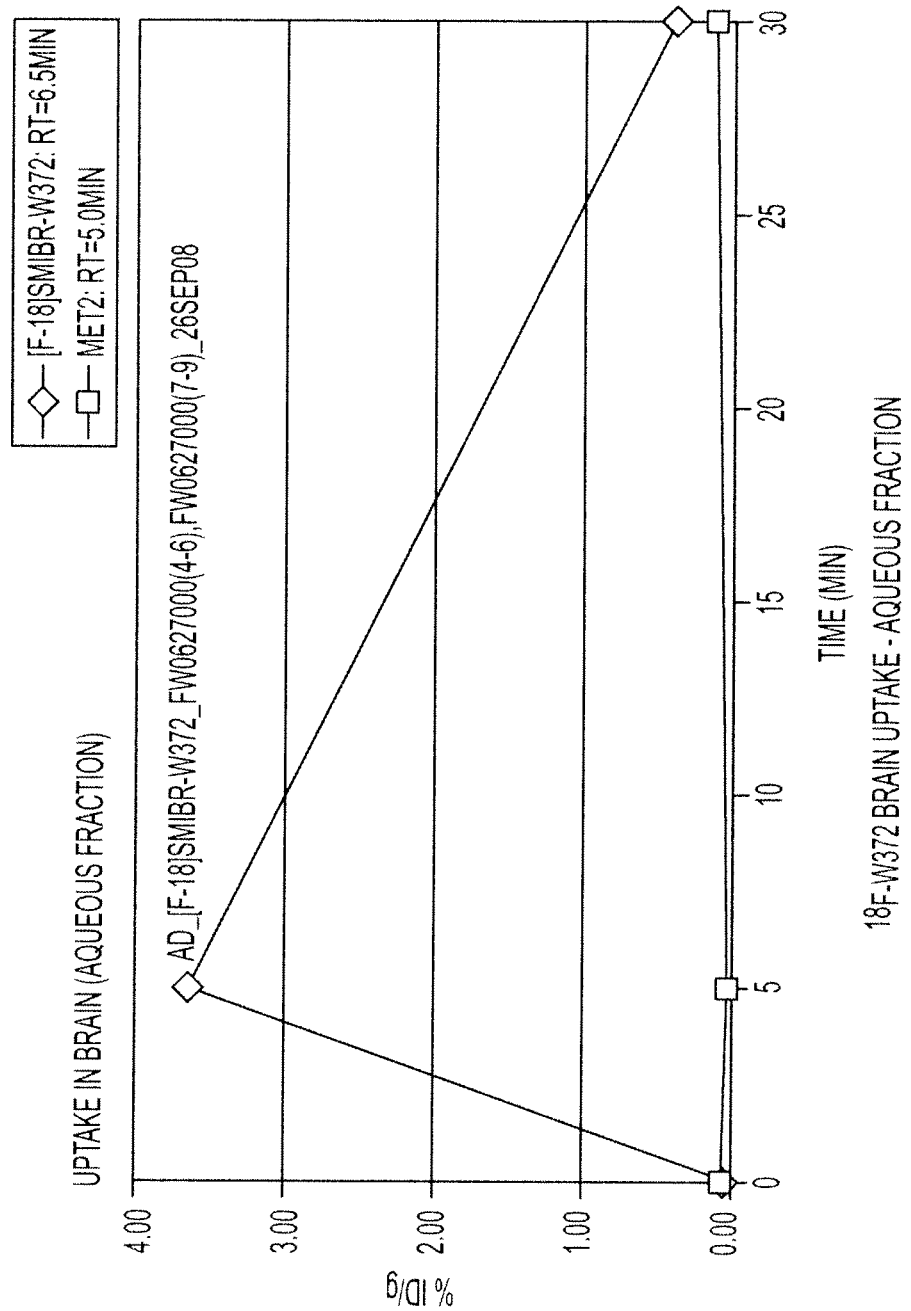

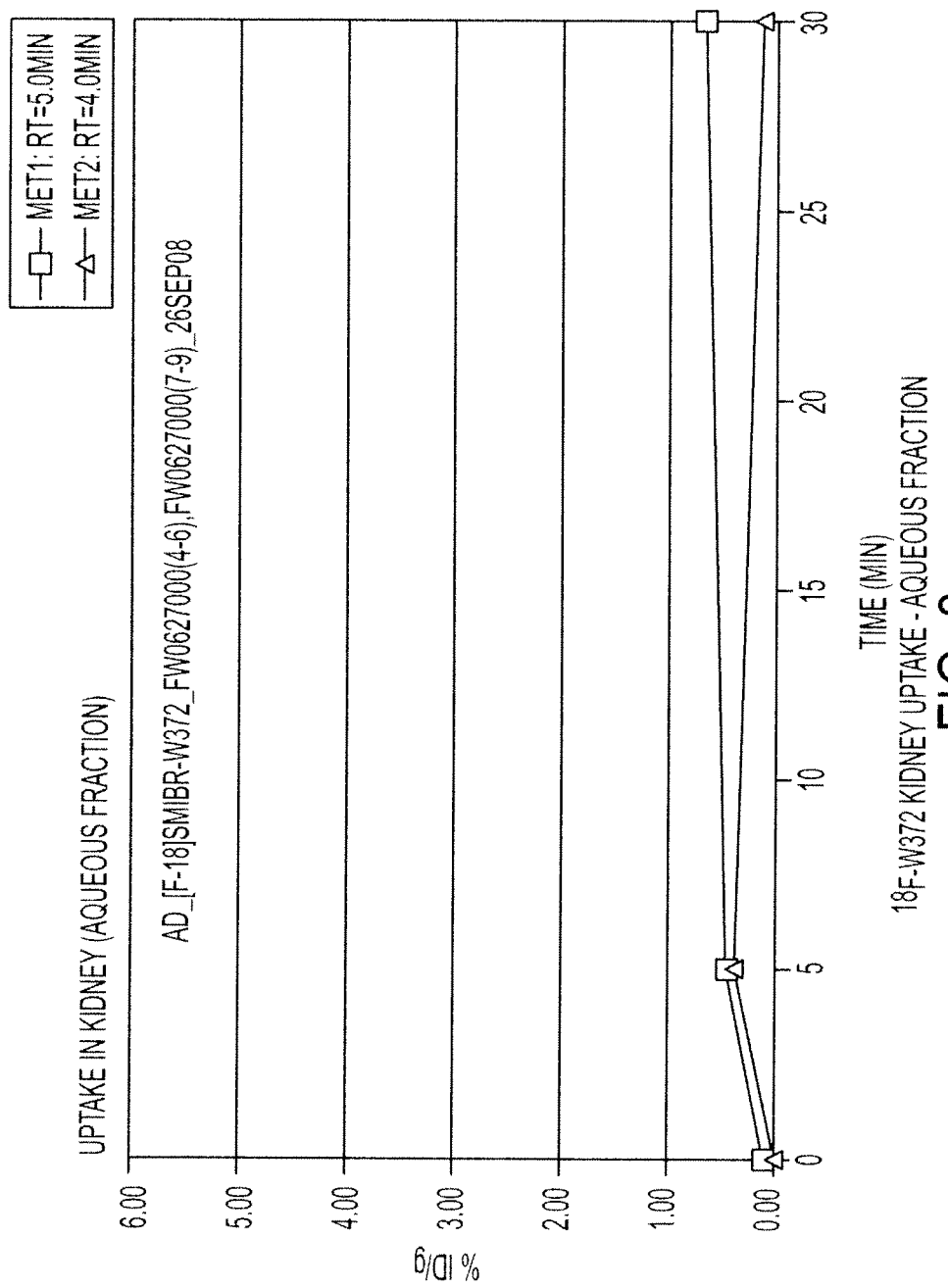

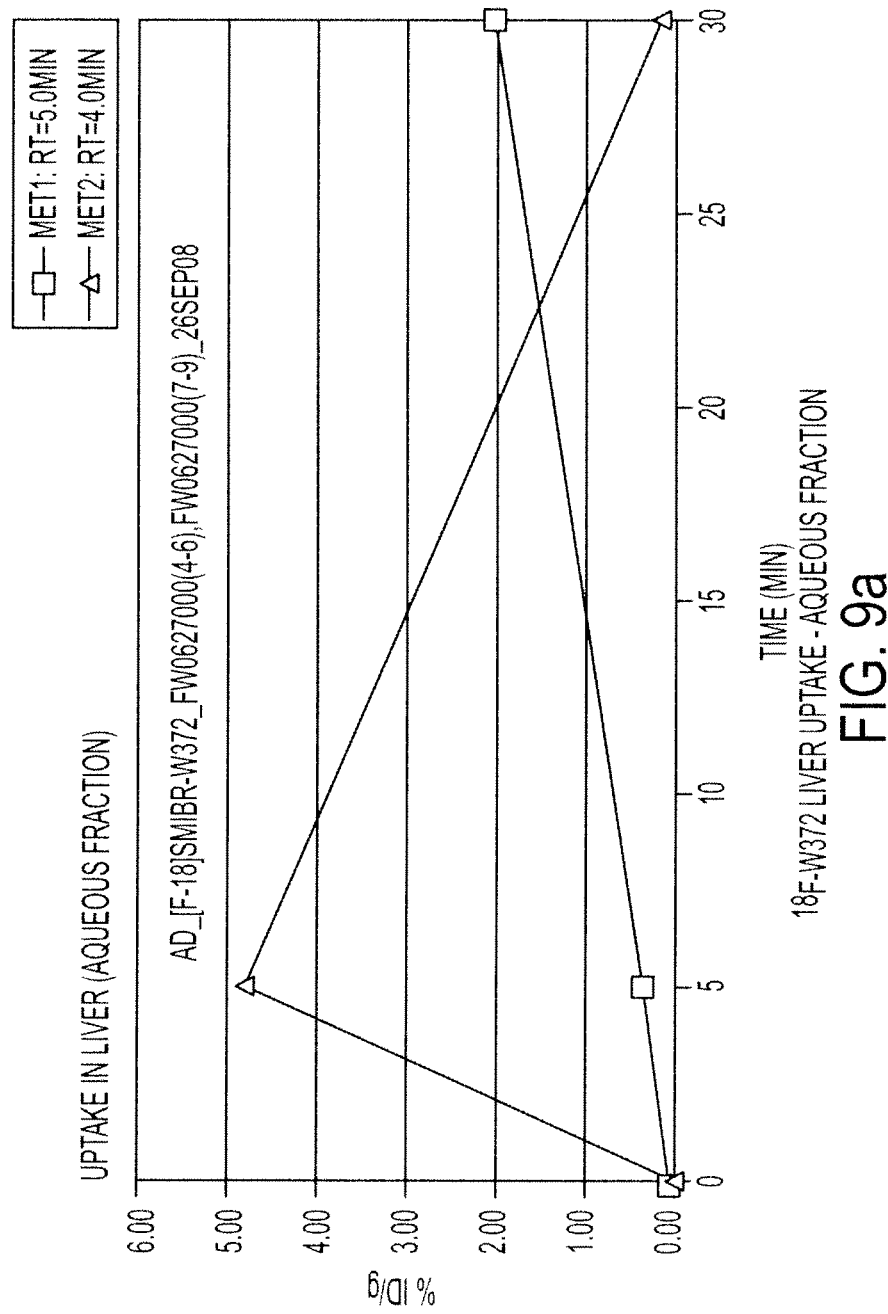

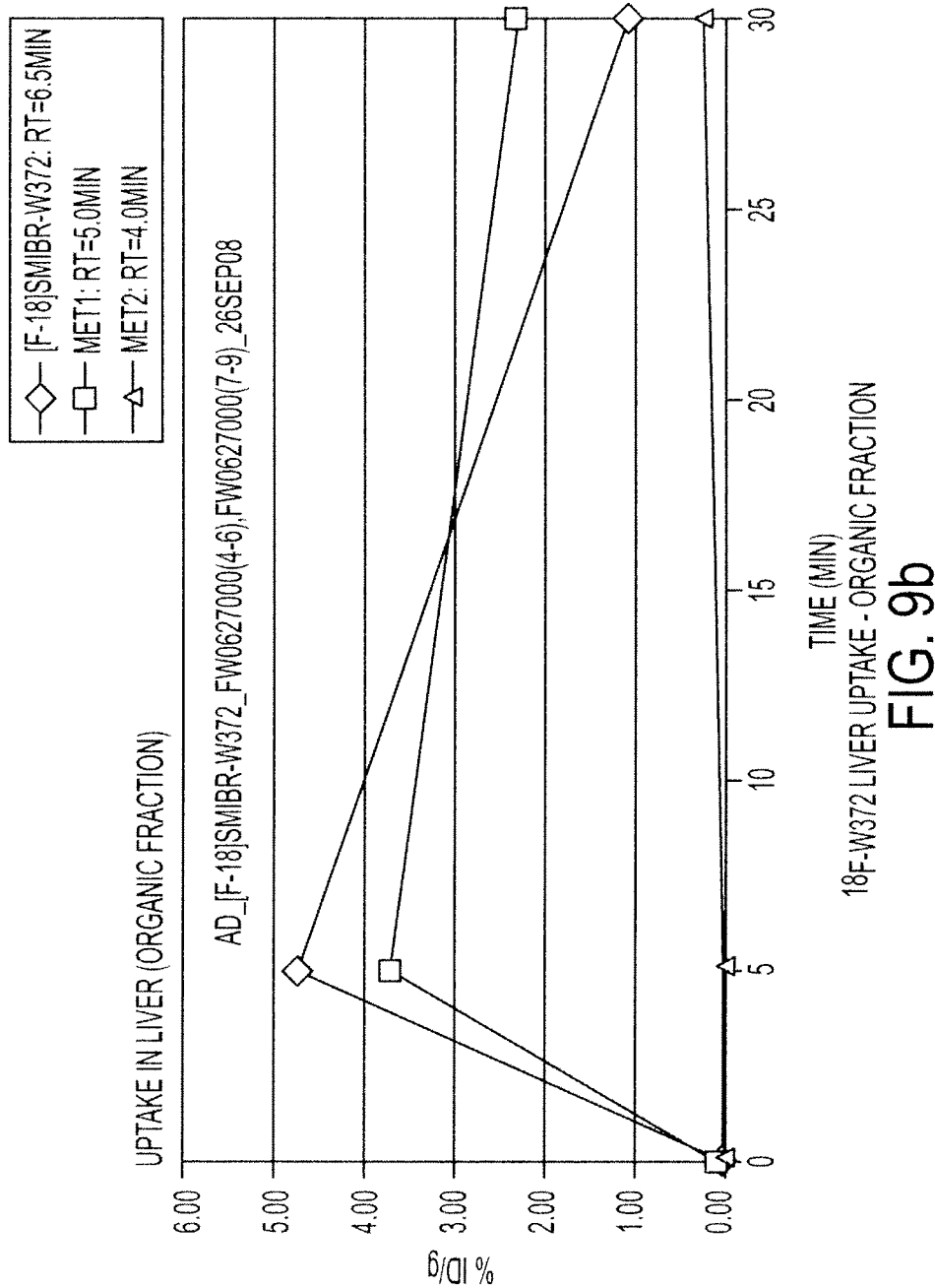

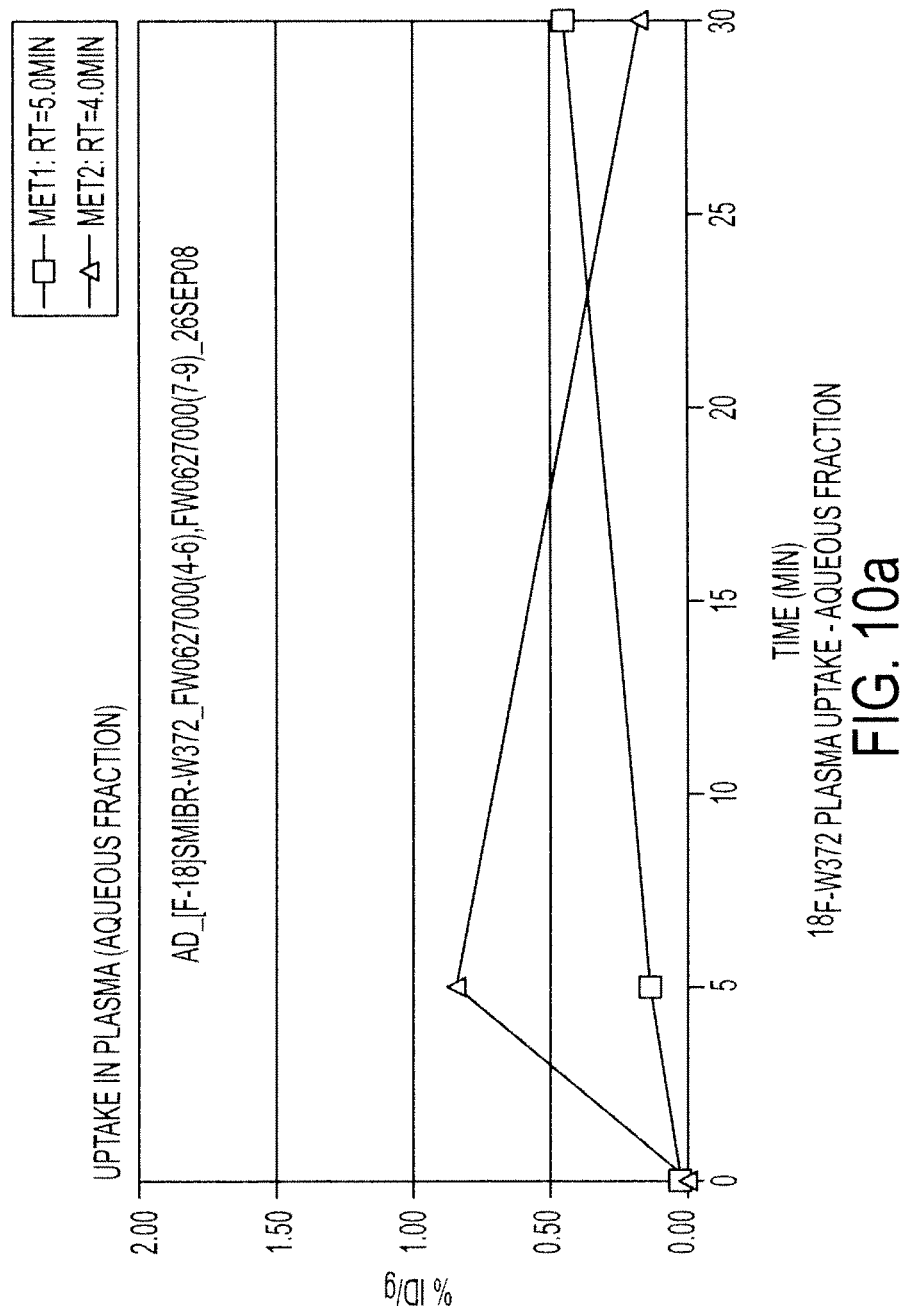

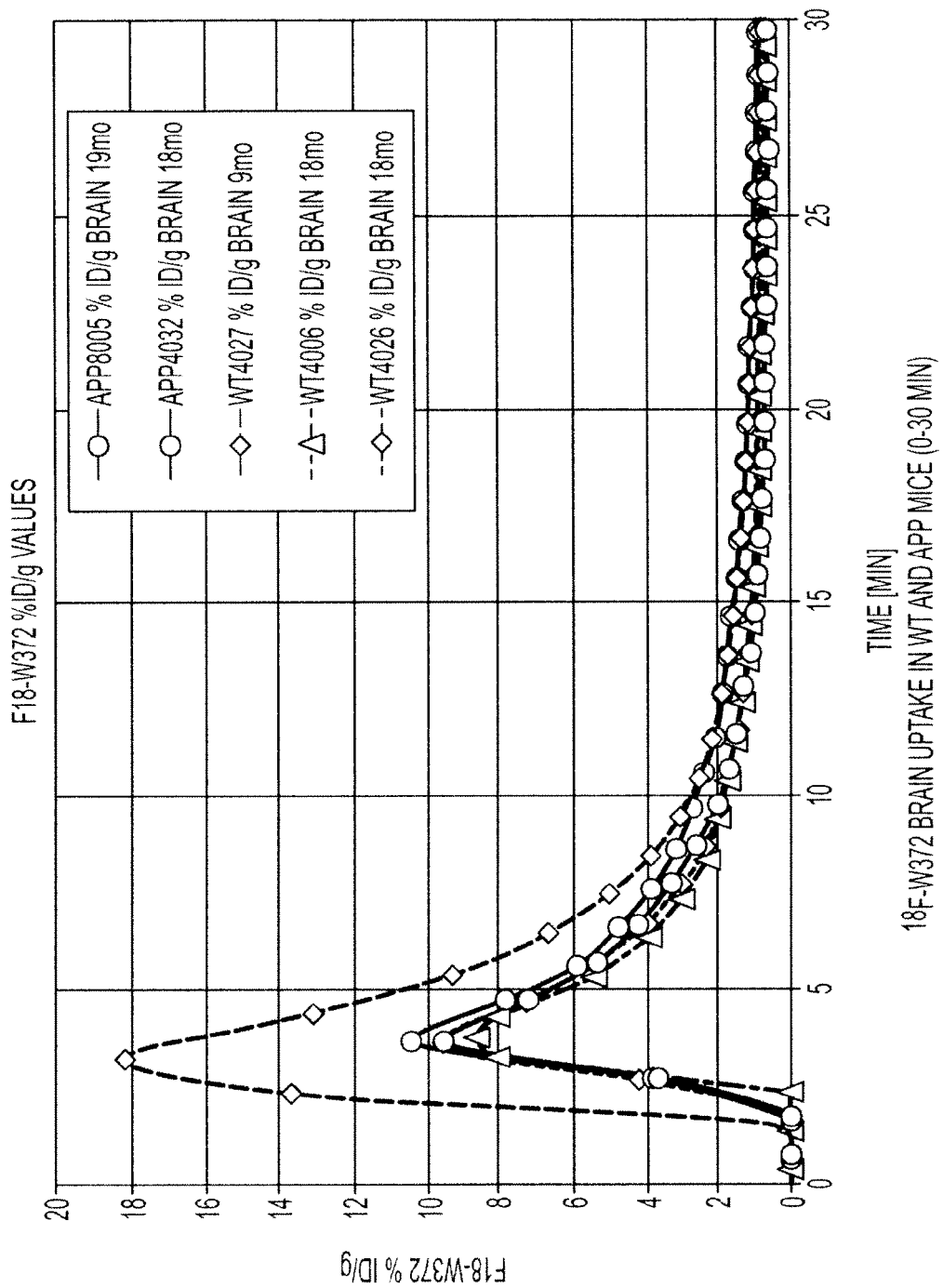

BRAIN MICROPET IMAGING OF $^{18}$F-W372 IN APP MICE

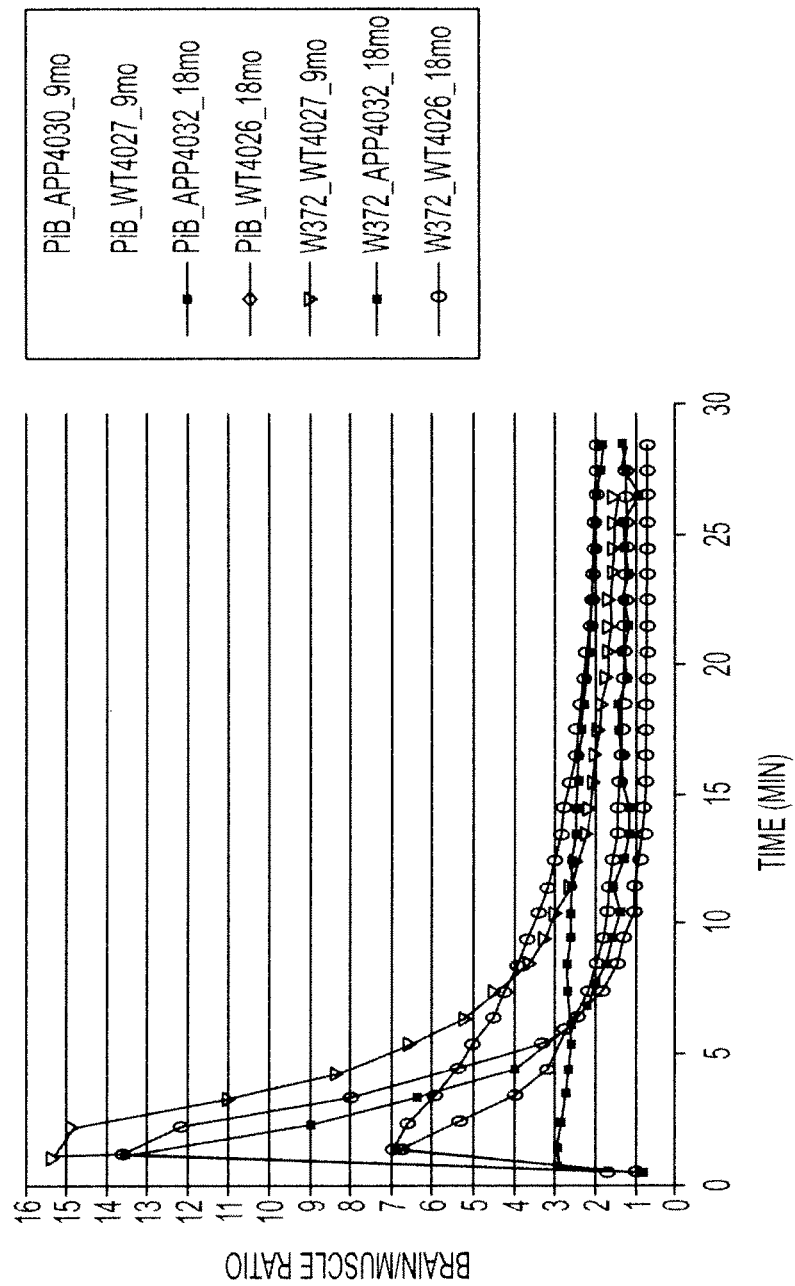

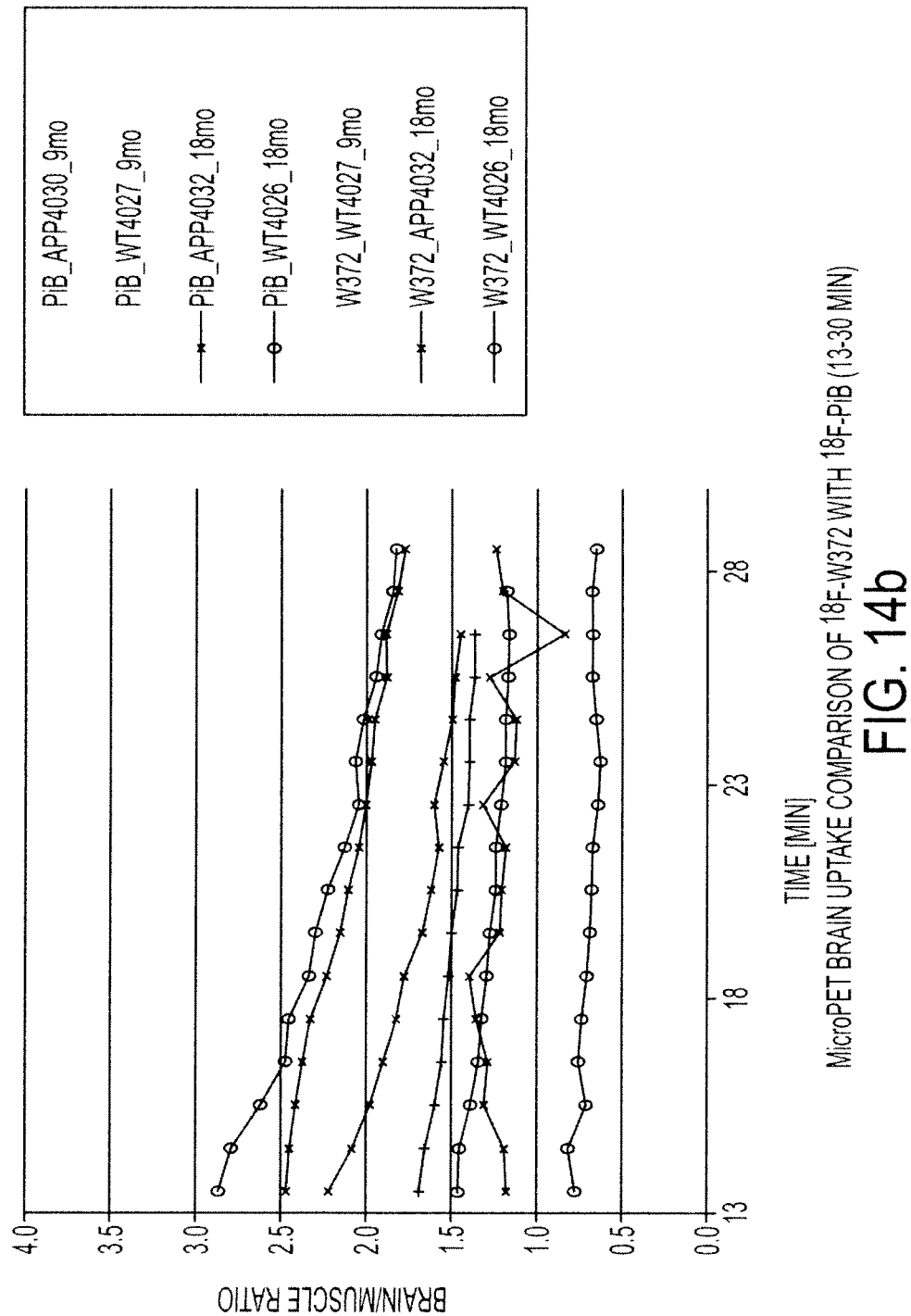

IMAGING AGENTS USEFUL FOR IDENTIFYING AD PATHOLOGY

CLAIM TO PRIORITY

The present application is based on and claims the priority of U.S. provisional application No. 61/083,501, filed Jul. 24, 2008, which is incorporated herein by reference.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

Embodiments of the present invention are directed to amyloid binding compounds, pharmaceutical compositions comprising the amyloid binding compounds, and methods of using the amyloid binding compounds. The present invention also includes embodiments that are further directed to methods of preparing the amyloid binding compounds. Such compounds, as disclosed herein, may be used in imaging studies, such as Positron Emitting Tomography (PET) or Single Photon Emission Computed Tomography (SPECT), to detect and treat neurological disorders.

BACKGROUND OF THE INVENTION

Alzheimer's disease (AD) is the most common form of neurodegeneration and has become a major healthcare issue with the aging population in the United States.

As people advance past the age of 65, the risk for developing Alzheimer's disease increases. As the leading cause of dementia, clinical AD symptomology includes both cognitive impairment and deficits in memory function.

AD patients exhibit heavy senile plaque burden in the cerebral cortex, verified by post mortem histopathological examination. Interestingly, despite the development and presence of senile plaques in elderly persons with normal cognitive function, the severity of neurofibrillary tangles (NFT) and senile plaque deposition purportedly correlates with a loss of cognitive function and neuronal circuitry deterioration. Mature senile plaques consist of intracellular neurofibrillary tangles derived from filaments of hyperphosphorylated tau proteins, and extracellular β-amyloid peptides derived from enzymatic processing of amyloid precursor protein.

Amyloidosis is characterized by the progressive, bulk accumulation of insoluble fibrillary proteins in the patient tissue, leading ultimately to morbidity. Deposition of amyloid occurs via aggregation of the fibrillary proteins, followed by further combination or aggregation thereof. With respect to AD, accumulation of aggregates of amyloid peptides $A\beta_{40}$ and $A\beta_{42}$ are the major peptides found in senile plaque and cerebrovascular deposits in patents (see Xia, et al., *J. Proc. Natl. Acad. Sci. USA,* 97: 9299 (2000) and Hardy, et al, *Science* 2002, 297, 353). Prevention of the deposition of these peptide fragments, which are derived from amyloid precursor proteins, continues to be a primary therapeutic research goal. Due to the central role of γ-secretase in the generation of the Aβ peptides via cleavage of amyloid precursor protein (APP), inhibition of γ-secretase has been identified as an important target in the discovery of novel AD treatments (see, for example, Ziani-Cherif, et al, *Curr. Pharm. Design* 2006, 12, 4313-4335; Evin, et al, *CNS Drugs* 2006, 20, 351-372; and Lahiri, et al., *Drug Dev. Res.* 2002, 56, 267-281).

Diagnosis of AD has been traditionally performed via postmortem tissue studies, brain biopsies or clinical evaluation [see, for example, McKhann, et al., *Neurology,* 34: 939 (1984) and Khachaturian, *Arch. Neurol.,* 42: 1097 (1985)]. AD is clinically characterized by the presence of neurotic plaques (NP), neurofibrillary tangles (NFT) and neuronal loss (see. Mann, *Mech. Aging Dev.* 31: 213 (1985). Neurotic plaques are a ubiquitous aspect of the disease (Mann et al., *J. Neurol. Sci.,* 89: 169), the assessment of which must be performed in postmortem studies.

Unfortunately, at the stage of presentation of symptoms in the clinic, the patients have developed significant amyloid deposition in the neurological tissue. More recently, earlier diagnosis has been the subject of research efforts aimed at immunoassay techniques, genetic testing and radiological imaging technologies.

Discovery of point mutations in amyloid precursor protein (APP) in several rare families with an autosomal dominant form of AD provided evidence that abnormalities in Aβ metabolism are necessary and sufficient for the development of AD (see, for example, Hardy, *Nature Genetics,* 1: 233 (1992); and Hardy, et al., *Science,* 256: 184 (1992). Heterogeneous evidence of AD has also been demonstrated via analysis of a large number of families of AD (see, St. George-Hyslop, et al., *Nature,* 347: 194 (1990). In particular, a gene on chromosome 14 has been identified which may account for up to 70% of early-onset AD, as mutation of which may significantly increase production of the Aβ peptide (Sherrington, et al., *Nature,* 375: 754 (1995)).

Immunoassay methods have been developed for detecting the presence of neurochemical markers in AD patients and to detect an AD related amyloid protein in cerebral spinal fluid, however such methods have not proven reliable in all patients and require invasive procedures such as a spinal tap.

Monoclonal antibodies and radiolabeled peptides have been used as probes for imaging of Aβ, however these macromolecular structures provide inherently poor brain penetration (see, for example, Majocha, et al., *J. Nucl. Med.,* 33: 2184 (1992)). Additionally, the peptide probes may lack specificity for AD as they tend to react with diffuse plaques.

In addition to AD, amyloid deposits have also been associated with other diseases such as, for example, glaucoma, Mediterranean fever, idiopathic myeloma, amyloid polyneuropathy, amyloid cardiomyopathy, systemic senile amyloidosis, hereditary cerebral hemorrhage, Muckle-Wells syndrome, Down's syndrome, Gerstmann-Straussler-Scheinker syndrome, Creutzfeldt-Jacob disease, scrapie, kuru, Islets of Langerhans, isolated atrial amyloid, medullary carcinoma of the thyroid and inclusion body myositis to name a few.

Though treatments exist, efficacy is observed in a palliative sense rather than halting the progression of AD, providing the patient with only a temporarily improved quality of life. It has been reported that delaying AD onset by five years is sufficient to reduce the number of AD cases by half. To this end, there are a number of therapies that delay full onset AD. Typically, clinicians prescribe cholinesterase inhibitors to cognitively impaired patients to help delay AD progression. Rivastigmine, a therapeutic treatment for both AD and Parkinson's disease patients, inhibits both acetylcholinesterase and butyrylcholinesterase, preventing the breakdown of acetyl- and butyrylcholine. Galantamine, a naturally derived acetylcholinesterase inhibitor, increases nicotinic cholinergic receptors' release of acetylcholine into the brain. Finally, the acetylcholinesterase inhibitor Aricept slows progression of AD in patients by inhibiting acetylcholinesterase and thus increasing cortical acetylcholine. In a recent clinical trial, Aricept slowed AD progression in patients, but the therapeutic effects disappeared after 36 months. The effect of treating AD patients with a therapeutic combination of both Aricept and memantine caused an increased cognitive function in those AD patients relative to those treated only with Aricept. Despite the utility of cholinesterase inhibitors, the current array of AD therapeutics merely serves to delay full-onset AD by approximately two to three years, after which they are therapeutically ineffective in inhibiting cognitive decline.

Neurological imaging of AD has seen the emergence of imaging tracers that appear to confirm the presence of AD based on plaque and fibril mediated tracer uptake and, subsequently, are currently undergoing extensive clinical examination. Many of these tracers contain chemotypes that derive from fluorescent dyes or Aβ peptides. For example, increased uptake and binding of the naphthylaniline derivative $^{18}$F-FDDNP in living brains correlates well with the presence of AD when compared to cognitively functional normals of similar age (*High-Yield, Automated Radiosynthesis of* 2-(1-{6-[(2-[$^{18}$*F]Fluoroethyl*)(*methyl*)*amino*]-2-*naphthyl*}*ethylidene*)*malonitrile* ([$^{18}$*F]FDDNP*) *Ready for Animal or Human Administration*, Liu, J., et al., Molecular Imaging and Biology, 2007. 9: p. 6-16). The thioflavin derived AD imaging agent, $^{11}$C-PIB, shows enhanced uptake in frontotemporal and hippocampal brain regions in AD patients compared to healthy age-matched normals.

Several other chemotypes have been identified as plaque imaging agents. These chemotypes are radiolabeled for use as PET or SPECT imaging agents. The scaffolds include compounds derived from benzothiazoles, naphthyl amines, flavones, aurones, isoindoles and styrenes. The chemotypes bind to plaques and fibrils with varying affinities and differing binding sites (see, for example, US 2007/0258887). Disclosed in this application are additional scaffolds that bind to AD plaques and fibrils.

A number of medical diagnostic procedures, including PET and SPECT utilize radiolabeled compounds, are well known in the art. PET and SPECT are very sensitive techniques and require small quantities of radiolabeled compounds, called tracers. The labeled compounds are transported, accumulated and converted in vivo in exactly the same way as the corresponding non-radioactively compound. Tracers, or probes, can be radiolabeled with a radionuclide useful for PET imaging, such as $^{11}$C, $^{13}$N, $^{15}$O, $^{18}$F, $^{64}$Cu and $^{124}$I, or with a radionuclide useful for SPECT imaging, such as $^{99}$Tc, $^{77}$Br, $^{61}$Cu, $^{153}$Gd, $^{123}$I, $^{125}$I, $^{131}$I and $^{32}$P.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

Citation or identification of any document in this application is not an admission that such document is available as prior art to the present invention.

SUMMARY OF THE INVENTION

The present invention relates to compounds and compositions which comprise the formulae as disclosed herein, wherein the compound is an amyloid binding compound. An amyloid binding compound of the invention may be administered to a patient in amounts suitable for in vivo imaging of amyloid deposits, and distinguish between neurological tissue with amyloid deposits and normal neurological tissue. Amyloid probes of the invention may be used to detect and quantitate amyloid deposits in diseases including, for example, Down's syndrome, familial Alzheimer's Disease. In another embodiment, the compounds may be used in the treatment or prophylaxis of neurodegenerative disorders. Also provided herein are methods of allowing the compound to distribute into the brain tissue, and imaging the brain tissue, wherein an increase in binding of the compound to the brain tissue compared to a normal control level of binding indicates that the mammal is suffering from or is at risk of developing a neurodegenerative disease.

The compounds and probes of the invention preferably exhibit low toxicity at dosages effective to treat or image (including diagnostic, detection, quantification and evaluation) amyloid related afflictions.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIGS. 7*a* and 7*b* show the brain uptake of 18F-W372.

FIGS. 8a and 8b show the kidney uptake of 18F-W372.
FIGS. 9a and 9b show the liver uptake of 18F-W372.
FIGS. 10a and 10b show the plasma uptake of 18F-W372.
FIGS. 11a and 11b show the brain uptake of 18F-W372 in WT and APP mice.
FIGS. 14a and 14b compare the micro-PET uptake of 18F-W372 with 18F-PiB in WT and APP mice.

DETAILED DESCRIPTION

Figure 1:
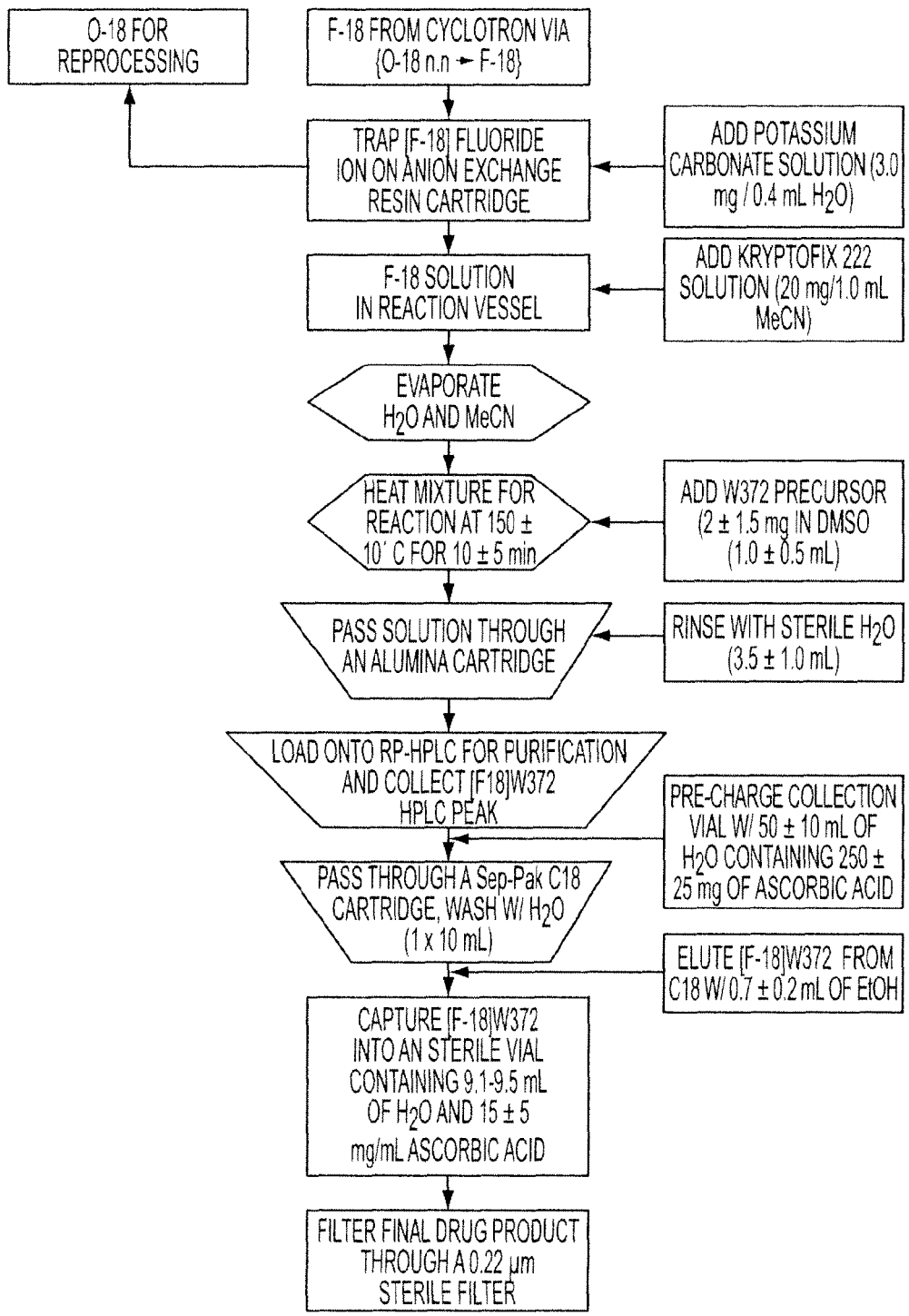
FIG. 1 is an exemplary process flow diagram for the radiolabeling procedure.

The present invention provides for radiolabeled amyloid binding compounds of any of the formula

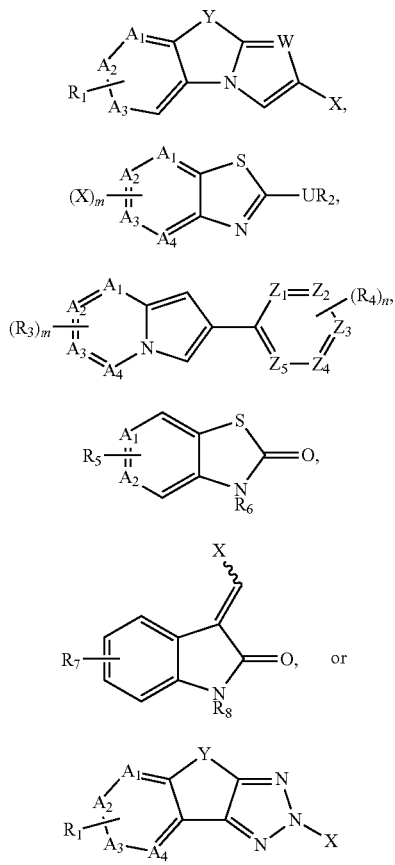

wherein
$A_1$-$A_4$ are independently CH or N, provided that no more than two A groups are simultaneously N;
$R_1$ is H, halogen, alkyl, haloalkyl, alkenyl, haloalkenyl, alkynyl, haloalkynyl, cycloalkyl, OH, $OR_8$, $OR_9$, $R_8$—C(O)—, $R_9$—C(O)—, $R_8$—OC(O), $R_9$—OC(O), $R_8$—N($R_{10}$)C(O), $R_9$—N($R_{10}$)C(O), $R_8$—S(O)$_p$—, $R_9$—S(O)$_p$—;
$R_2$ is H, CN, alkyl, haloalkyl, alkenyl, haloalkenyl, alkynyl, haloalkynyl, cycloalkyl, halocycloalkynyl, alkoxy, haloalkoxy, thioalkyl, halothioalkyl, $NH_2$, $NHR_8$, alkoxyalkyl, haloalkoxyalkyl, cycloalkoxyalkyl, aryl, substituted aryl, heteroaryl, substituted heteroaryl;
$R_3$, $R_4$, $R_5$, $R_6$ and $R_7$ are independently H, halogen, OH, CN, $NO_2$, $R_8$, $R_9$, $CH_2R_9$, $CHCHR_9$, $OR_8$, $OR_9$, $NH_2$, $NHR_8$, $N(R_8)_2$, —C(O)NHR$_8$, —C(O)N($R_8$)$_2$, $R_8$—C(O)—, $R_9$—C(O)—, $R_8$—C(O)O—, $R_9$—C(O)O—, $R_8$—C(O)N—, $R_9$—C(O)N—, $R_8$—OC(O)—, $R_9$—OC(O)—, $R_8$—OC(O)—, $R_9$—OC(O)O—, $R_8$—OC(O)N($R_{10}$)—, $R_9$—OC(O)N($R_{10}$)—, $R_8$—N($R_{10}$)C(O)—, $R_9$—N($R_{10}$)C(O)—, $R_8$—N($R_{10}$)C(O)—, $R_9$—N($R_{10}$)C(O)O—, $R_8$—N($R_{10}$)C(O)N($R_{10}$)—, $R_9$—N($R_{10}$)C(O)N($R_{10}$)—, $R_8$—S(O)$_p$—, $R_9$—S(O)$_p$—, $R_8$—S(O)$_p$N($R_{10}$)—, $R_9$—S(O)$_p$N($R_{10}$)—, $R_8$—N($R_{10}$)S(O)$_p$—, $R_9$—N($R_{10}$)S(O)$_p$—;
$R_8$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, substituted heteroarylalkyl;
$R_9$ is aryl, substituted aryl, heteroaryl, substituted heteroaryl;
$R_{10}$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, arylalkyl, substituted arylalkyl, heteroarylalkyl, substituted heteroarylalkyl;
W=N or CH;
U=Y or a bond;
X=OH, OR$_B$, aryl, substituted aryl, heteroaryl, substituted heteroaryl;
Y=NR$_1$, O, S;
$Z_1$-$Z_5$ are independently CH or N, provided that no more than two Z groups are simultaneously N;
m is 0-4;
n is 0-5; and
p is 0-2;
provided that at least one of X, or $R^1$ to $R^{10}$ comprises a radiolabel, as defined herein;
wherein the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;
or a pharmaceutically acceptable salt thereof.
The present invention also provides for a radiolabeled amyloid binding compound of any of the formula

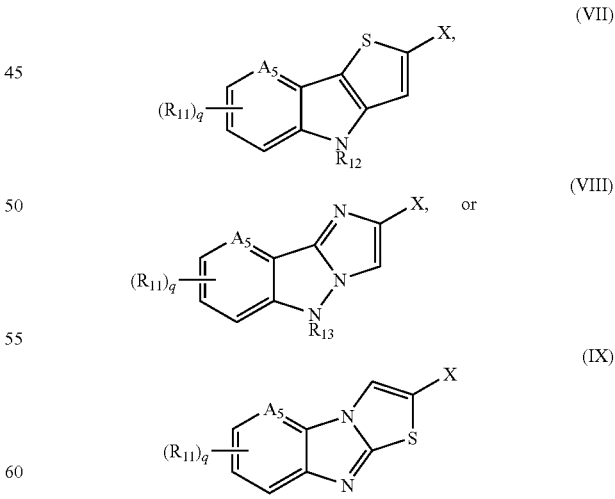

wherein
$A_5$ is CH or N;
$R_{11}$ is $R_{10}$, $R_{10}S$—;
$R_{12}$ and $R_{13}$ are independently H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, arylalkyl, substituted arylalkyl, heteroarylalkyl, substituted heteroarylalkyl;

X=aryl, substituted aryl, heteroaryl, substituted heteroaryl; and q is 1 or 2;

provided that at least one of X, or $R^{11}$ to $R^{13}$ comprises a radiolabel, as defined herein;

wherein the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;

or a pharmaceutically acceptable salt thereof.

The present invention further provides for a radiolabeled amyloid binding compond of any of the formula

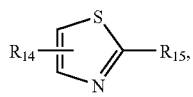
(X)

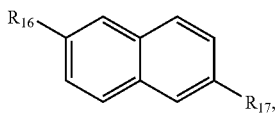
(XI)

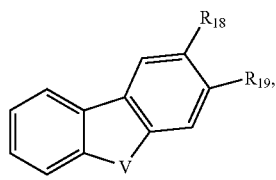
(XII)

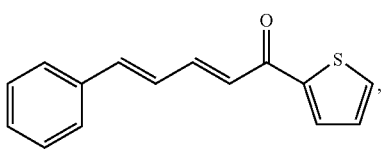
(XIII)

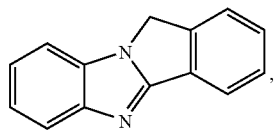
(XIV)

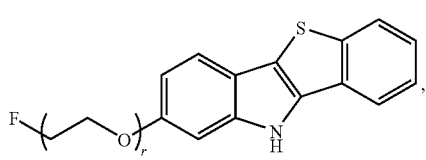
(XV)

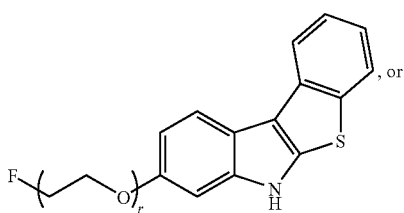
(XVI)

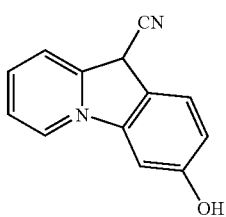
(XVII)

wherein
V is O or S;
$R_{14}$ is aryl, substituted aryl, heteroaryl, substituted heteroaryl, alkenylaryl, alkenyl substituted aryl, alkenylheteroaryl;
$R_{15}$ is $NH_2$, $N(R_{10})_2$, aryl, substituted aryl, heteroaryl, substituted heteroaryl;
$R_{16}$ is heteroaryl or substituted heteroaryl;
$R_{17}$ is $R_{10}O—$ or $R_{10}S—$;
$R_{18}$ is H, $R_{10}O—$ or $R_8$—C(O)N—;
$R_{19}$ is H or $NH_2$; and
r is 1-3;

provided that at least one of X, or $R^{14}$ to $R^{18}$ comprises a radiolabel, as defined herein;

wherein the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;

or a pharmaceutically acceptable salt thereof.

In one embodiment of the compound of formula (I),
$A_1$ and $A_3$ are independently CH or N;
$R_1$ is H, halogen, alkyl, haloalkyl, OH, $OR_8$, $OR_9$;
W=N or CH;
X=aryl, substituted aryl, heteroaryl, substituted heteroaryl; and
Y=N-alkyl, N-haloalkyl, O, S.

In another embodiment of the compound of formula (I), Y is S,
$A_1$ and $A_3$ are independently CH or N;
$R_1$ is halogen, OH, $OR_8$;
W=N or CH; and
X=aryl, substituted aryl, heteroaryl, substituted heteroaryl.

In another embodiment of the compound of formula (I), Y is N-alkyl,
$A_1$-$A_3$ are independently CH;
$R_1$ is H, halogen, alkyl or haloalkyl;
W=N; and
X=aryl, substituted aryl.

In another embodiment of the compound of formula (I), Y is O,
$A_1$ is N or CH;
$A_2$-$A_3$ are independently CH;
$R_1$ is halogen, alkyl, haloalkyl or Oalkyl;
W=N; and
X=substituted aryl or substituted heteroaryl.

In still another embodiment, the invention relates to a radiolabeled amyloid binding compound of the formula (Ia)

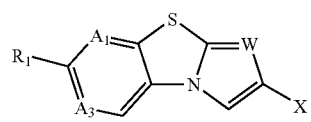
(Ia)

wherein:

$A_1$ and $A_3$ are independently CH or N;

$R_1$ is halogen, $OR_8$, $OR_9$;

$R_8$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, substituted heteroarylalkyl;

$R_9$ is aryl, substituted aryl, heteroaryl, substituted heteroaryl;

W=N or CH; and

X=OH, aryl, substituted aryl, heteroaryl, substituted heteroaryl;

provided that at least one of X and $R_1$ comprises a radiolabel;

wherein the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;

or a pharmaceutically acceptable salt thereof.

In one embodiment of the compound of formula (Ia), $A_1$ is N;

$A_3$ is CH;

$R_1$ is halogen, $OR_8$, $OR_9$;

$R_8$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, substituted heteroarylalkyl;

$R_9$ is aryl, substituted aryl, heteroaryl, substituted heteroaryl;

W=N; and

X=aryl, substituted aryl, heteroaryl, substituted heteroaryl.

In another embodiment of the compound of formula (Ia), $A_1$ is N;

$A_3$ is CH;

$R_1$ is $OR_8$;

$R_8$ is H, alkyl, haloalkyl;

W=N;

X=aryl, substituted aryl, heteroaryl, substituted heteroaryl; and the radionucleide is $^{18}F$.

In a further embodiment of the compound of formula (Ia), $A_1$ is N;

$A_3$ is CH;

$R_1$ is $OR_8$;

$R_8$ is alkyl, haloalkyl;

W=N; and

X is selected from the group consisting of phenyl, 3-F phenyl, 3-hydroxyphenyl, 3-alkoxyphenyl, 3-haloalkoxyphenyl, 4-F phenyl, 4-CN phenyl, 4-alkoxyphenyl, 4-haloalkoxyphenyl, 4-aminophenyl, 4-nitrophenyl, 4-alkylaminophenyl, 4-dialkylaminophenyl, 4-pyrrolidinylphenyl, 3-OH,4-F phenyl, 3,4,5-trifluorophenyl, 2-furyl, 2-thienyl, 2-halo-4-thienyl, 4-haloalkyl-2-furyl, 2-thiazolyl, 2-oxazolyl, 2-pyridyl, 4-halo-2-pyridyl, 5-halo-2-pyridyl, 6-halo-2-pyridyl, 2-halo-5-pyridyl, 3-halo-5-pyridyl, 4-halo-5-pyridyl, 2-dialkylamino-5-pyridyl, pyrazinyl, 2-halo-5-pyrazinyl, pyrimidyl, naphthyl, quinolinyl, benzimidazolyl, N-alkylbenzimidazolyl, thiobenzimidazolyl, 5-benzofuranyl, 5-oxindolyl, 2-(2-pyridyl)-5-thienyl; and the radionucleide is $^{18}F$.

In still another embodiment, the invention relates to a radiolabeled amyloid binding compound of the formula (Ib)

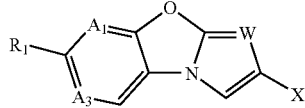

(Ib)

wherein:

$A_1$ and $A_3$ are independently CH or N;

$R_1$ is halogen, $OR_8$, $OR_9$;

$R_8$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, substituted heteroarylalkyl;

$R_9$ is aryl, substituted aryl, heteroaryl, substituted heteroaryl;

W=N or CH; and

X=OH, aryl, substituted aryl, heteroaryl, substituted heteroaryl;

provided that at least one of X and $R_1$ comprises a radiolabel;

wherein the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;

or a pharmaceutically acceptable salt thereof.

In one embodiment of the compound of formula (Ib), $A_1$ is N;

$A_3$ is CH;

$R_1$ is $OR_8$;

$R_8$ is alkyl, haloalkyl;

W=N; and

X is selected from the group consisting of phenyl, 3-F phenyl, 3-hydroxyphenyl, 3-alkoxyphenyl, 3-haloalkoxyphenyl, 4-F phenyl, 4-CN phenyl, 4-alkoxyphenyl, 4-haloalkoxyphenyl, 4-aminophenyl, 4-nitrophenyl, 4-alkylaminophenyl, 4-dialkylaminophenyl, 4-pyrrolidinylphenyl, 3-OH,4-F phenyl, 3,4,5-trifluorophenyl, 2-furyl, 2-thienyl, 2-halo-4-thienyl, 4-haloalkyl-2-furyl, 2-thiazolyl, 2-oxazolyl, 2-pyridyl, 4-halo-2-pyridyl, 5-halo-2-pyridyl, 6-halo-2-pyridyl, 2-halo-5-pyridyl, 3-halo-5-pyridyl, 4-halo-5-pyridyl, 2-dialkylamino-5-pyridyl, pyrazinyl, 2-halo-5-pyrazinyl, pyrimidyl, naphthyl, quinolinyl, benzimidazolyl, N-alkylbenzimidazolyl, thiobenzimidazolyl, 5-benzofuranyl, 5-oxindolyl, 2-(2-pyridyl)-5-thienyl; and the radionucleide is $^{18}F$.

In one embodiment of the compound of formula (II), $A_2$, $A_3$ and $A_4$ are independently CH or N;

$R_2$ is H, CN, alkyl, haloalkyl, alkenyl, haloalkenyl, alkynyl, haloalkynyl, cycloalkyl, halocycloalkynyl, alkoxy, haloalkoxy, thioalkyl, halothioalkyl, $NH_2$, $NHR_8$, alkoxyalkyl, haloalkoxyalkyl, cycloalkoxyalkyl, aryl, substituted aryl, heteroaryl, substituted heteroaryl;

X=OH, aryl, substituted aryl, heteroaryl, substituted heteroaryl; and m=1-3.

In another embodiment of the compound of formula (II), $A_2$, $A_3$ and $A_4$ are independently CH or N;

$R_2$ is H, CN, alkyl, haloalkyl, alkoxy, haloalkoxy, halothioalkyl, $NH_2$, $NHR_3$, aryl, substituted aryl, heteroaryl, substituted heteroaryl;

U is NH, O, S or a bond;

X=OH, aryl, substituted aryl, heteroaryl, substituted heteroaryl; and m=1.

In yet another embodiment, the invention relates to a radio-labeled amyloid binding compound of the formula (IIa)

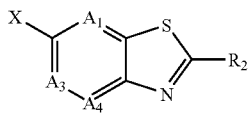

wherein:

$A_1$, $A_3$ and $A_4$ are independently CH or N, provided that no more than two A groups are simultaneously N;

$R_2$ is H, CN, alkyl, haloalkyl, alkoxy, haloalkoxy, $NH_2$, $NHR_8$, alkoxyalkyl, haloalkoxyalkyl, aryl, substituted aryl, heteroaryl, substituted heteroaryl;

$R_8$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, substituted heteroarylalkyl;

X=OH, alkoxy, haloalkoxy, aryl, substituted aryl, heteroaryl, substituted heteroaryl;

provided that at least one of X and $R_1$ comprises a radiolabel; and the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;

or a pharmaceutically acceptable salt thereof.

In one embodiment of the compound of the formula (Ib),
$A_1$, $A_3$ and $A_4$ are CH;
$R_2$ is H, CN, alkyl, haloalkyl, alkoxy, haloalkoxy, NHalkyl, NHhaloalkyl, $N(alkyl)_2$, N(alkyl)(haloalkyl), $N(haloalkyl)_2$, 4-aminomethylphenyl, 2-aminomethylphenyl, 2-aminomethyl-5-pyridyl, 4-(NHalkyl)-3-(halophenyl), 2-amino-5-thiazolyl;
X=OH, alkoxy, haloalkoxy, phenyl, 4-alkylphenyl, 4-F phenyl, 4-CN phenyl, 4-alkoxyphenyl, 4-aminophenyl, 4-alkylaminophenyl, 4-dialkylaminophenyl;
provided that at least one of X and $R_2$ comprises a radiolabel; and
the radiolabel is $^{18}F$;
or a pharmaceutically acceptable salt thereof.

In one embodiment of the compound of formula (III),
$A_1$ and $A_2$ are independently CH or N;
$R_3$ is halogen, OH, $OR_8$, $OR_9$, $—C(O)NHR_8$, $—C(O)N(R_8)_2$;
$R_4$ is halogen, OH, CN, $NO_2$, $NH_2$, $OR_8$, $OR_9$, $NHR_8$, $N(R_8)_2$;
m=0-2; and
n=1-2.

In another embodiment of the compound of formula (III),
$A_1$ and $A_2$ are independently CH or N;
$R_3$ is halogen, OH, Oalkyl, $—C(O)NHR_8$, $—C(O)N(R_8)_2$;
$R_4$ is halogen, OH, CN, $NO_2$, $NH_2$, Oalkyl, Ohaloalkyl;
m=1; and
n=1.

In one embodiment of the compound of formula (IV),
$A_2$ is CH or N; and
$R_5$ and $R_6$ are independently H, halogen, OH, $NO_2$, $R_8$, $R_9$, $CH_2R_9$, $CHCHR_9$, $OR_8$, $OR_9$, $R_8—C(O)—$, $R_9—C(O)—$.

In another embodiment of the compound of formula (IV),
$A_2$ is CH or N;
$R_5$ is H, OH, Oalkyl, Ohaloalkyl, $NO_2$, $—C(O)$alkyl; and
$R_6$ is H, benzyl, aryl, heteroaryl, substituted aryl, $CHCHR_9$.

In one embodiment of the compound of formula (V),
X is H or aryl, wherein the aryl group is optionally substituted with halogen, CN, OH, $OR_8$, $—NHR_8$, or $—N(R_8)_2$;
$R_7$ is H, halogen, CN, $—NO_2$; and
$R_8$ is H, alkyl, haloalkyl.

In another embodiment of the compound of formula (V),
X is H or aryl, wherein the aryl group is optionally substituted with CN, OH, $—NH_2$, $—N(alkyl)_2$, $—N(alkyl)(haloalkyl)$, $—Oalkyl$;
$R_7$ is H, halogen, CN, $—NO_2$; and
$R_8$ is H.

In one embodiment of the compound of formula (VI),
$A_1$ and $A_3$ are independently CH or N;
$R_1$ is H, halogen, alkyl, haloalkyl, OH, $OR_8$, $OR_9$; and
X=aryl, substituted aryl, heteroaryl, substituted heteroaryl.

In another embodiment of the compound of formula (VI),
$A_1$ and $A_3$ are independently CH or N;
$R_1$ is halogen, OH, $OR_8$; and
X=aryl, substituted aryl, heteroaryl, substituted heteroaryl.

In one embodiment of the compound of formula (VII),
$A_5$ is CH or N;
$R_{11}$ is $OR_8$;
$R_{12}$ is H;
X=4-fluorophenyl, 4-cyanophenyl, heteroaryl, substituted heteroaryl; and
q is 1.

In one embodiment of the compound of formula (VIII),
$R_{11}$ is $OR_8$;
$R_{13}$ is H; and
q is 1.

In one embodiment of the compound of formula (IX),
$R_{11}$ is $OR_8$; and
q is 1.

In one embodiment of the compound of formula (X),
$R_{14}$ is aryl, CHCHaryl; and
$R_{15}$ is $NH_2$, $N(R_{10})_2$, aryl, substituted aryl.

In one embodiment of the compound of formula (XI),
$R_{16}$ is heteroaryl; and
$R_{17}$ is $R_{10}O—$.

In one embodiment of the compound of formula (XII):
V is O or S;
$R_{18}$ is H, $R_{10}O—$ or $R_8—C(O)N—$; and
$R_{19}$ is H or $NH_2$.

In one embodiment of the compound of formulas (XV) or (XVI):
r is 1-3.

In one embodiment, the compounds of the invention allow for safe and specific methods of detecting and diagnosing pre-mortem AD via in vivo imaging of amyloid in the brain. The methods delineated herein further provide for imaging of plaques using compounds which traverse the blood-brain barrier and provide low toxicity. The compound probes of the invention may further be suitable for imaging amyloid, tau or synuclein aggregates or similar aggregates.

The inventive compounds may further bind or interact with amyloid precursor protein (APP), other amyloid proteins and protein fragments as well as deposits comprised of APP, other amyloid proteins or protein fragments.

The inventive probes may be further used to detect, diagnose, quantitate or otherwise identify or treat amyloid deposits in diseases such as, by way of non-limiting example, AD, glaucoma, type II diabetes mellitus, Mediterranean fever, idiopathic myeloma, amyloid polyneuropathy, amyloid cardiomyopathy, systemic senile amyloidosis, hereditary cerebral hemorrhage, Muckle-Wells syndrome, Down's syndrome, Gerstmann-Straussler-Scheinker syndrome, Creutzfeldt-Jacob disease, scrapie, kuru, Islets of Langerhans, isolated atrial amyloid, medullary carcinoma of the thyroid and inclusion body myositis.

The inventive probes may also be used in a prophylaxis of diseases characterized by amyloid deposition, which may thereby decrease the predisposition or tendency of the individual to develop disorders related to amyloid deposition. It will be appreciated that treatment may refer to situations wherein the progression of the disease, or amyloid deposition is delayed.

Administration of the compounds of the invention may be performed in conjunction with other probes or therapeutic agents which may further be useful in the identification, prophylaxis or treatment of such amyloid-related diseases.

In one embodiment, the compounds or compositions of the invention may be administered to diagnose, or identify a predisposition to a disease characterized by amyloidosis.

In another embodiment, the compounds or compositions of the invention may be administered in order to treat a disease state characterized by amyloidosis.

The methods of administration may be further combined with other conventional therapeutic agents which may provide synergistic efficacy or other synergistic results. Examples of such agents may include other neurodegenerative therapeutic agents including, but not limited to, those which delay or otherwise disrupt the processing of APP and/or generation of Aβ peptides. Specific examples include, flurbiprofen, beta-secretase inhibitors, gamma-secretase inhibitors, tau inhibitors and gamma secretase modulators. Further examples of therapeutic agents include anti-inflammatory drugs, antibodies and cholesterol-lowering drugs.

For the purposes of this application, unless otherwise stated in the specification, the following terms have the terminology cited below:

(1) Alkyl refers to both straight and branched carbon chains; references to individual alkyl groups are specific for the straight chain (e.g. butyl=n-butyl). In one embodiment of alkyl, the number of carbons atoms is 1-20, in another embodiment of alkyl, the number of carbon atoms is 1-8 carbon atoms and in yet another embodiment of alkyl, the number of carbon atoms is 1-4 carbon atoms. Other ranges of carbon numbers are also contemplated depending on the location of the alkyl moiety on the molecule;

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in another embodiment of alkenyl, the number of carbon atoms is 2-8 and in yet another embodiment of alkenyl, the number of carbon atoms is 2-4. Other ranges of carbon-carbon double bonds and carbon numbers are also contemplated depending on the location of the alkenyl moiety on the molecule;

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in another embodiment of alkynyl, the number of carbon atoms is 2-8 and in yet another embodiment of alkynyl, the number of carbon atoms is 2-4. Other ranges of carbon-carbon double bonds and carbon numbers are also contemplated depending on the location of the alkenyl moiety on the molecule;

(4) Aryl refers to a $C_6$-$C_{10}$ aromatic ring structure. In one embodiment of aryl, the moiety is phenyl, naphthyl, tetrahydronapthyl, phenylcyclopropyl and indanyl; in another embodiment of aryl, the moiety is phenyl. Arylo refers to an aryl substituted at two adjacent sites.

(5) Alkoxy refers to —O-alkyl, wherein alkyl is as defined in (1);

(6) Alkanoyl refers to formyl (—C(═O)H) and —C(═O)-alkyl, wherein alkyl is as defined in (1);

(7) Alkanoyloxy refers to —O—C(═O)-alkyl, wherein alkanoyl is as defined in (6);

(8) Alkanoylamino refers to —NH$_2$—C(═O)-alkyl, wherein alkanoyl is as defined in (6) and the amino (NH$_2$) moiety can be substituted by alkyl as defined in (1);

(9) Aminocarbonyl refers to —NH$_2$—C(═O), wherein the amino (NH$_2$) moiety can be substituted by alkyl as defined in (1);

(10) Alkoxycarbonyl refers to —C(═O)—O-alkyl, wherein alkoxy is as defined in (5);

(11) Alkenoyl refers to —C(═O)-alkenyl, wherein alkenyl is as defined in (2);

(12) Alkynoyl refers to —C(═O)-alkynyl, wherein alkynyl is as defined in (3);

(13) Aroyl refers to —C(═O)-aryl, wherein aryl is as defined above;

(14) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(15) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), trichloromethyl (—CCl$_3$));

(16) Heterocycle, heterocyclic or heterocyclo refer to fully saturated or unsaturated, including aromatic (i.e. "hetaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include, but are not limited to, carbazolyl, benzidolyl, phenanthrolinyl, acridinyl, phenanthridinyl, xanthenyl and the like.

Unless otherwise noted, a compound represented as being substituted by an atom, such as the generic representation by the atom fluorine in fluoroalkyl, F-aryl or F—CH$_2$— for example, is intended to cover both the naturally occurring element $^{19}$F (fluorine-19) as well as the $^{18}$F (fluorine-18) isotope(s) of the element itself. Isotopes may be designated via any notation used in the art such as, by way of non-limiting example, fluorine-18, 18-F, $^{18}$F F-18, etc.

The term "optionally substituted" or "substituted" refers to the specific substituents or groups wherein one to four hydrogen atoms in the group may be replaced by one to four substituents, for example, independently selected from the substituents amino, halo, cyano, nitro, hydroxyl, —SH, —SC$_{1-6}$alkyl, —C(O)NH$_2$, —C(S)NH$_2$, haloC$_{1-6}$alkyl, perhaloC$_{1-6}$alkyl, C$_{1-6}$alkyl, C$_{3-6}$cycloalkyl, C$_{3-12}$cycloalkyl, C$_{6-14}$aryl and heteroaryl, or as specifically disclosed herein. In addition, the substituents may also include alkyl, aryl, alkylene-aryl, hydroxy, alkoxy, aryloxy, perhaloalkoxy, heterocyclyl, azido, amino, guanidino, amidino, halo, alkylthio, oxo, acylalkyl, carboxy esters, carboxyl, carboxamido, acyloxy, aminoalkyl, alkylaminoaryl, alkylaminoalkyl, alkoxyaryl, arylamino, phosphono, sulfonyl, carboxamidoaryl, hydroxyalkyl, haloalkyl, alkoxyalkyl and perhaloalkyl. In addition, the term "optionally substituted" or "substituted" in reference to the variables R$^1$ through R$^{18}$ and X, includes groups substituted by one to four substituents, as identified above, which further comprise a positron or gamma emitter. Such positron emitters include, but are not limited to, $^{11}$C, $^{13}$N, $^{15}$O, $^{18}$F, $^{123}$I, $^{124}$I, $^{125}$I, $^{131}$I and $^{77}$Br.

The term "radiolabeled compound" as used herein refers to compounds having an atom or group that may provide a radiolabel or may be converted to a radiolabel, such as from a non-radioactive atom to a radionuclide that is active, such as for example, $^{11}$C, $^{13}$N, $^{15}$O, $^{18}$F, $^{123}$I, $^{124}$I, $^{125}$I, $^{131}$I and $^{77}$Br. In addition, for the purpose of the present application, such "radiolabeled compound" may also refer to an atom or a group, that comprises a non-active nuclide, such as a halogen, such as $^{19}$F for example, wherein the compound may be used and administered in a therapeutically effective amount.

As used herein, the term "radiolabel," "radioactive isotope" or "radioactive element" refers to isotopes exhibiting radioactive decay (i.e., emitting positrons) and radiolabeling agents comprising a radioactive isotope. Non-limiting examples may include [$^{11}$C]methane, [$^{11}$C]carbon monoxide, [$^{11}$C]carbon dioxide, [$^{11}$C]phosgene, [$^{11}$C]urea, [$^{11}$C]cyanogen bromide, as well as various acid chlorides, carboxylic acids, alcohols, aldehydes and ketones containing carbon-11. Such isotopes or elements are also referred to in the art as radioisotopes or radionuclides. Radioactive isotopes are named herein using various commonly used combinations of the name or symbol of the element and its mass number (e.g., $^{18}$F, F-18, or fluorine-18). Exemplary radioactive isotopes include I-124, F-18 fluoride, C-11, N-13, and O-15, which have half-lives of 4.2 days, 110 minutes, 20 minutes, 10 minutes, and 2 minutes, respectively. The radioactive isotope is preferably dissolved in an organic solvent, such as a polar aprotic solvent. Preferably, the radioactive isotopes used in the present method include F-18, C-11, I-123, I-124, I-127, I-131, Br-76, Cu-64, Tc-99m, Y-90, Ga-67, Cr-51, Ir-192, Mo-99, Sm-153 and Tl-201. Preferably, the radioactive isotope used in the present method is F-18. Other radioactive isotopes that may be employed include: As-72, As-74, Br-75, Co-55, Cu-61, Cu-67, Ga-68, Ge-68, I-125, I-132, In-111, Mn-52, Pb-203 and Ru-97.

Compounds of the formulae (I)-(XII) may have optical centers and therefore may occur in different enantiomeric and diastereomeric configurations. The present invention includes all enantiomers, diastereomers, and other stereoisomers of such compounds of formulae (I)-(XII), as well as racemic compounds and racemic mixtures and other mixtures of stereoisomers thereof.

The compounds of the present application may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Non-limiting examples of such inorganic acids are hydrochloric, hydrobromic, hydroiodic, nitric, carbonic, sulfuric and phosphoric acid. Appropriate organic acids may be selected from aliphatic (or alkyl), cycloalkyl, aromatic, arylalkyl, heterocyclic, carboxylic and sulfonic classes of organic acids, non-limiting examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include, but are not limited to, metallic salts made from aluminum, calcium, lithium, magnesium, potassium, sodium and zinc or organic salts made from amino acids, benzathine, N,NT-dibenzylethylenediamine, chloroprocaine, choline, diethanolamine, diethylamine, diolamine, ethylenediamine, meglumine-(N-methylglucamine), procaine and tromethamine. Ascorbic acid may also be used as an excipient. Hemisalts of acids and bases may also be formed, for example, hemisulphate and hemicalcium salts. Suitable formulations for each of these methods of administration may be found in, for example, Remington: The Science and Practice of Pharmacy, A. Gennaro, ed., 20th edition, Lippincott, Williams & Wilkins, Philadelphia, Pa. and/or Handbook of Pharmaceutical Salts: Properties, Selection, and Use by Stahl and Wermuth (Wiley-VCH, 2002).

Pharmaceutically acceptable salts of compounds of formulae (I)-(XVII) may be prepared by one or more of three methods: (i) by reacting the compound of formulae (I) (XVII) with the desired acid or base; (ii) by removing an acid- or base-labile protecting group from a suitable precursor of the compound of formulae (I)-(XVII); or (iii) by converting one salt of the compound of formulae (I)-(XVII) to another salt by the reaction with an appropriate acid or base or by means of a suitable ion exchange column.

In another embodiment, there is provided a pharmaceutical composition for in vivo imaging of amyloid deposits, comprising (a) a compound of any one of the above, and (b) a pharmaceutically acceptable carrier.

The compounds of the invention, inventive compounds, compositions of the invention and inventive compositions as referred to herein is intended to encompass the compounds of formulae (I) to formulae (XVII), isomers thereof, their pharmaceutically acceptable salts, prodrugs, racemic mixtures, crystalline forms, tautomeric forms and pharmaceutical compositions thereof.

Pharmaceutical compositions of the compounds of the invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Non-limiting examples of suitable diluents are normal isotonic saline solution, 5% dextrose in water or buffered sodium or ammonium acetate solution. Such formulations are especially suitable for parenteral administration but may also be used for oral administration. Excipients, such as, for example, ascorbic acid, polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers may include, but are not limited to, syrup, peanut oil, olive oil, glycerin, saline, alcohols, or water. Solid carriers may include, but are not limited to, starch, lactose, calcium sulfate, dihydrate, terra alba, magnesium stearate or stearic acid, talc, pectin, acacia, agar, or gelatin. The carrier may also include a sustained release material such as glyceryl monostearate or glyceryl distearate, alone or with a wax. The pharmaceutical preparations may be made following the any of the conventional techniques of pharmacy involving, by way of non-limiting example, milling, mixing, granulation, and compressing, when necessary, for tablet forms; or milling, mixing, and filling for hard gelatin capsule forms. When a liquid carrier is used, the preparation may be in the form of a syrup, elixir, emulsion, or an aqueous or non-aqueous suspension. Such a liquid formulation may be administered directly, by way of non-limiting example, orally or subcutaneously, or filled into a soft gelatin capsule. Suitable formulations for each of these methods of administration may be found in, for example, REMINGTON: THE SCIENCE AND PRACTICE OF PHARMACY, A. Gennaro, ed., 20th edition, Lippincott, Williams & Wilkins, Philadelphia, Pa.

The pharmaceutical compositions of the invention may also be in the form of a sterile injectable preparation. Formulations suitable for parenteral administration include, by way of non-limiting example, aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents.

The compounds of the invention may be synthesized and/or radiolabeled using techniques known in the art.

In one embodiment, the compounds of the invention may be radiolabeled.

In another embodiment, the compounds are not comprised of a radioisotope.

In another embodiment, there is provided a method of diagnosing Alzheimer's Disease or a predisposition thereto in a mammal, the method comprising: a) administering to the mammal a diagnostically effective amount of a radiolabeled compound, wherein the compound passes the blood-brain barrier and preferentially binds to a soluble AD oligomers, polymers and fibrils in a brain tissue and wherein the compound is selected from the group consisting of radiolabeled compounds of the invention and their derivatives; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

In another embodiment, there is provided a method of diagnosing Alzheimer's Disease or a predisposition thereto in a mammal, the method comprising: a) administering to the mammal a diagnostically effective amount of a radiolabeled compound or composition of the invention, wherein the compound passes the blood-brain barrier and preferentially binds to a soluble AD oligomers, polymers and fibrils in a brain tissue; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

In one embodiment of the above method, the radiolabeled compound preferentially binds to fibrils.

In another embodiment of the above method, the brain tissue comprises a frontotemporal region or the hippocampal region.

In a yet another embodiment of the above method, the increase in binding is at least 10% greater than said normal control value.

In still another embodiment of each of the above methods, the compound is administered by intravenous injection.

In another embodiment, there is provided a method for detecting Alzheimer's Disease or a predisposition thereto in a living brain of a mammal, the method comprising: a) administering the mammal with a diagnostically effective amount of a radiolabeled compound that passes the blood-brain barrier and preferentially binds to a soluble AD oligomers, polymers and fibrils in the brain, wherein the detectably-labeled compound is a compound of the invention; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

In another embodiment, there is provided a method for detecting Alzheimer's Disease or a predisposition thereto in a living brain of a mammal, the method comprising: a) administering the mammal with a diagnostically effective amount of a radiolabeled compound of the invention, wherein the compound passes the blood-brain barrier and preferentially binds to a soluble AD oligomers, polymers and fibrils in the brain; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

In another embodiment, there is provided a method of diagnosing Alzheimer's Disease or a predisposition thereto in a mammal, the method comprising: a) administering to the mammal a diagnostically effective amount of a radiolabeled compound of the invention, wherein the compound passes the blood-brain barrier and preferentially binds to a soluble or insoluble AD oligomers, polymers, fibrils, hyperphosphorylated tau, neurofibrillary tangles, paired helical filaments and/or neurotoxic soluble oligomers in a brain; and (b) employing a nuclear imaging technique selected from the group consisting of positron emission tomography (PET) and single photon emission computed tomography (SPECT) for monitoring or visualizing a distribution of the radiolabeled compound within the brain or within a portion thereof.

In one embodiment of the above method, the radiolabeled compound or a derivative thereof, is a compound of any one of the above compounds.

In yet another embodiment, there is provided a method for treating a disease or condition, in a mammal in need thereof, selected from the group consisting of anxiety, depression, schizophrenia, Alzheimer's Disease, stress-related disease, panic, a phobia, obsessive compulsive disorder, obesity, post-traumatic stress syndrome, or epilepsy comprising administering to the mammal a therapeutically effective amount of a compound of the invention.

In still a further embodiment, there is a method comprising administering to a subject a quantity of a compound of the invention.

In another embodiment, the compound or composition of the invention binds to the amyloid deposit.

In another embodiment, the subject may be irradiated and imaging data emitted by the compound may be collected, which may further be processed in order to diagnose or study the disease state or lack thereof in the subject.

In one embodiment, the compound is a non-radiolabeled compound of the invention.

In one embodiment, for the methods of detection that accurately detect early onset AD prior to clinical symptomology, the focus may be directed to targeting senile plaque precursors, rather than the plaques and/or fibrils themselves. Accordingly, a potentially more effective strategy for detecting and possibly treating AD, would rely on the detection of biomarkers such as neurotoxic soluble oligomers, which are linked to AD-related synaptic and neuronal damage, rather than the late-stage plaque, and fibril biomarkers associated with fully advanced AD.

Amyloid deposits may also be formed in tissue or organs other than that of the brain such as, by way of non-limiting example, joints, aortic tissue, pituitary tissue, thyroid tissue, cardiac tissue, ocular tissue (lens, cornea, retina, etc.), pancreatic tissue, and mesodermal tissue. Non-limiting examples of detection of amyloid deposits can be found in U.S. Pat. Nos. 6,849,249 and 7,107,092. Agents and compositions of the invention may be used in the study, detection, imaging, prophylaxis or therapeutic treatment of amyloid deposits in any tissue in which such deposits may be formed.

In one embodiment, the compound or composition of the invention is administered to a mammalian subject in an amount or dosage suitable for in vivo imaging or therapeutic use. A unit dosage generally will vary according to the specific patient characteristics such as, but not limited to, age, overall health, weight, sex, and regimen of other medications. The unit dosage will also vary according to the site of administration or target site.

In one embodiment, the compound is administered from about 0.001 to about 100 mg/kg of body weight of the mammal per day.

In another embodiment, the compound is administered from about 0.1 to about 50 mg/kg of body weight of the mammal per day.

Administration may occur via systemic or local methods, and proceed intradermally, intravenously, intraarterially, or intrathecally, for example.

In one embodiment, the compound is administered rectally, topically, orally, sublingually, subcutaneously or parenterally.

The invention will now be further described by way of the following non-limiting examples.

EXAMPLES

Synthesis of UG-4-69

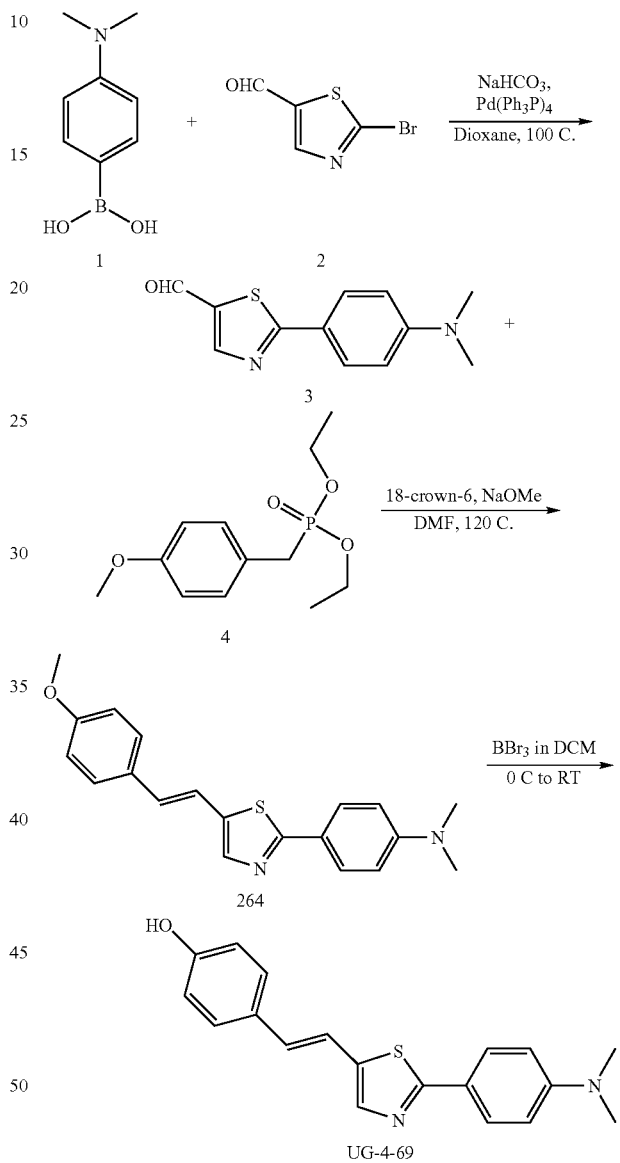

Preparation of 2-(4-(dimethylamino)phenyl)thiazole-5-carbaldehyde (3)

To a 10 mL round bottomed flask equipped with a magnetic stir bar and reflux condenser containing dioxane (3 mL) was placed 1 (0.1 g, 0.61 mmol) and 2 (0.14 g, 0.73 mmol). To this solution sat. NaHCO$_3$ (3 mL) and Pd(Ph$_3$P)$_4$ (0.07 g, 0.06 mmol) were added and the reaction was heated to 100° C. for 4 hrs. The reaction was cooled to RT, filtered through celite, then poured into water (20 mL) and extracted into EtOAc (3×15 mL). The combined organic extracts were washed with water (15 mL), brine (15 mL), dried over MgSO$_4$ and con mixture was cooled to 0° C., BBr$_3$ (0.8 mL of 1M in DCM) was added drop wise and was stirred at RT for 3 hrs. The reaction was neutralized with sat. NaHCO$_3$, extracted into DCM (3×15 mL). The combined organic extracts were washed with water (15 mL), brine (15 mL), dried over MgSO$_4$ and concentrated in vacuo. The residue was purified over silica gel using THF:Hexanes (3:2) as an eluent to afford UG-4-69 (0.01 g, 10%) as a white solid.

LC/MS: Expected for $C_{19}H_{18}N_2OS$: 322.1; found 323.1 (M+H$^+$).

Synthesis of UG-4-73

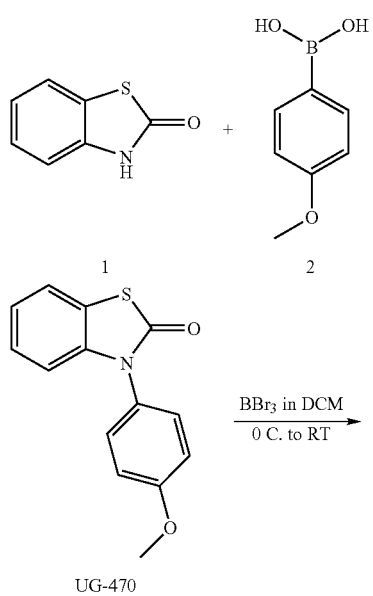

Preparation of 3-(4-methoxyphenyl)benzo[d]thiazol-2(3H)-one (UG-470)

To a 25 mL round bottomed flask equipped with a magnetic stir bar, added sequentially MS (4A$^0$, 0.066 g), 2 (0.2 g, 1.32 mmol), DCM (6.6 mL), TEA (0.2 mL, 1.32 mmol), 1 (0.1 g, 0.66 mmol), Cu(OAc)$_2$ (0.13 g, 0.73 mmol) and TEMPO (0.11 g, 0.73 mmol). The reaction mixture was stirred in air at RT for 12 hrs. The reaction was quenched with 7 N ammonia in MeOH (0.1 mL), added silica and concentrated in vacuo. The residue was purified over silica gel using EtOAc:Hexanes (1:10) as an eluent to afford UG-470 (0.1 g, 59%) as a white solid.

LC/MS: Expected for $C_{14}H_{11}NO_2S$: 257.0; found: 258.0 (M+H$^+$).

Preparation of 3-(4-hydroxyphenyl)benzo[d]thiazol-2(3H)-one (4)

To a 10 mL round bottomed flask equipped with a magnetic stir bar containing DCM (4 mL) was placed UG-470 (0.1 g, 0.39 mmol), the reaction mixture was cooled to 0° C., BBr$_3$ (1.0 mL of 1M in DCM) was added drop wise and was stirred at RT for 3 hrs. The reaction was neutralized with sat. NaHCO$_3$, extracted into DCM (3×15 mL). The combined organic extracts were washed with water (15 mL), brine (15 mL), dried over MgSO$_4$ and concentrated in vacuo. The residue was purified over silica gel using EtOAc:Hexanes (1:4) as an eluent to afford 4 (0.09 g, 95%) as a white solid.

LC/MS: Expected for $C_{13}H_9NO_2S$: 243.0; found 244.0 (M+H$^+$).

Synthesis of UG-4-83

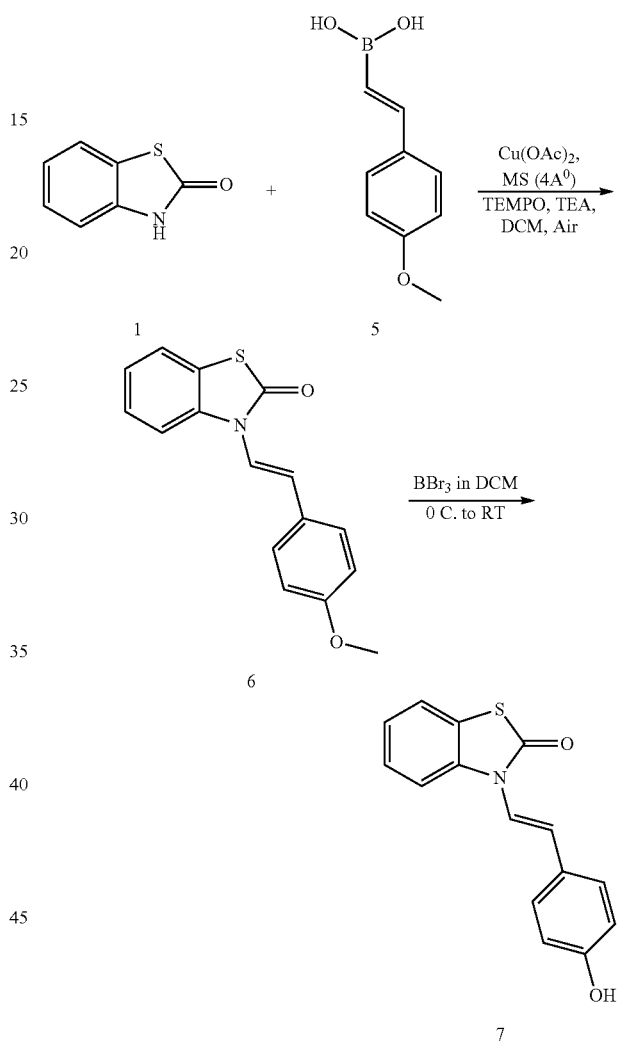

Preparation of (E)-3-(4-methoxystyryl)benzo[d]thiazol-2(3H)-one (6)

To a 25 mL round bottomed flask equipped with a magnetic stir bar, added sequentially MS (4A$^0$, 0.066 g), 5 (0.24 g, 1.32 mmol), DCM (6.6 mL), TEA (0.2 mL, 1.32 mmol), 1 (0.1 g, 0.66 mmol), Cu(OAc)$_2$ (0.13 g, 0.73 mmol) and TEMPO (0.11 g, 0.73 mmol). The reaction mixture was stirred in air at RT for 12 hrs. The reaction was quenched with 7 N ammonia in MeOH (0.1 mL), added silica and concentrated in vacuo. The residue was purified over silica gel using EtOAc:Hexanes (1:10) as an eluent to afford 6 (0.1 g, 53%) as a white solid.

LC/MS: Expected for $C_{16}H_{13}NO_2S$: 283.0; found: 284.0 (M+H$^+$).

Preparation of (E)-3-(4-hydroxystyryl)benzo[d]thiazol-2(3H)-one (7)

To a 10 mL round bottomed flask equipped with a magnetic stir bar containing DCM (4 mL) was placed 6 (0.1 g, 0.39 mmol), the reaction mixture was cooled to 0° C., BBr$_3$ (1.0 mL of 1M in DCM) was added drop wise and was stirred at RT for 3 hrs. The reaction was neutralized with sat. NaHCO$_3$, extracted into DCM (3×15 mL). The combined organic extracts were washed with water (15 mL), brine (15 mL), dried over MgSO$_4$ and concentrated in vacuo. The residue was purified over silica gel using EtOAc:Hexanes (1:4) as an eluent to afford 7 (0.09 g, 95%) as a white solid.

LC/MS: Expected for $C_{15}H_{11}NO_2S$: 269.0; found 269.0 (M+H$^+$).

Synthesis of W136

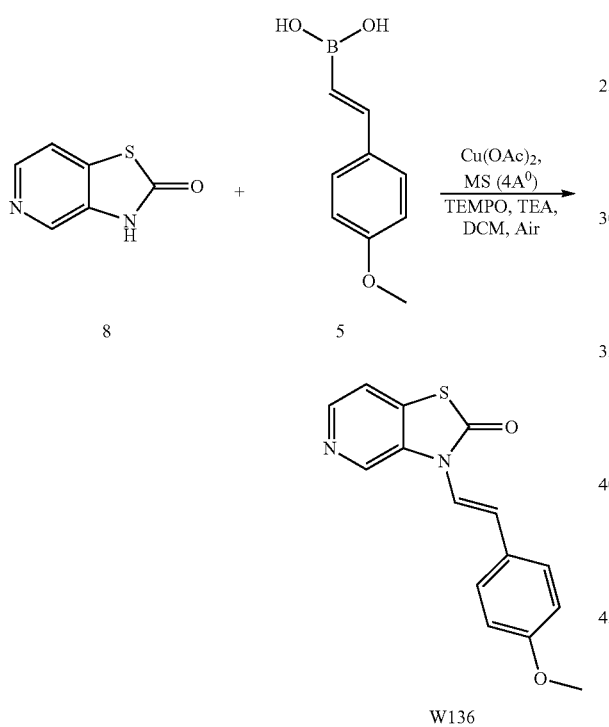

Preparation of (E)-3-(4-methoxystyryl)thiazolo[4,5-c]pyridin-2(3H)-one (W136)

To a 10 mL round bottomed flask equipped with a magnetic stir bar, added sequentially MS (4A°, 0.066 g), 5 (0.14 g, 0.79 mmol), DCM (6.6 mL), TEA (0.2 mL, 1.32 mmol), 8 (0.1 g, 0.66 mmol), Cu(OAc)$_2$ (0.13 g, 0.73 mmol) and TEMPO (0.11 g, 0.73 mmol). The reaction mixture was stirred in air at RT for 12 hrs. The reaction was quenched with 7 N ammonia in MeOH (0.1 mL), added silica and concentrated in vacuo. The residue was purified over silica gel using EtOAc:Hexanes (2:3) as an eluent to afford W136 (0.01 g, 5%) as a white solid.

LC/MS: Expected for $C_{15}H_{12}N_2O_2S$: 284.3; found: 285.3 (M+H$^+$).

Synthesis of W137

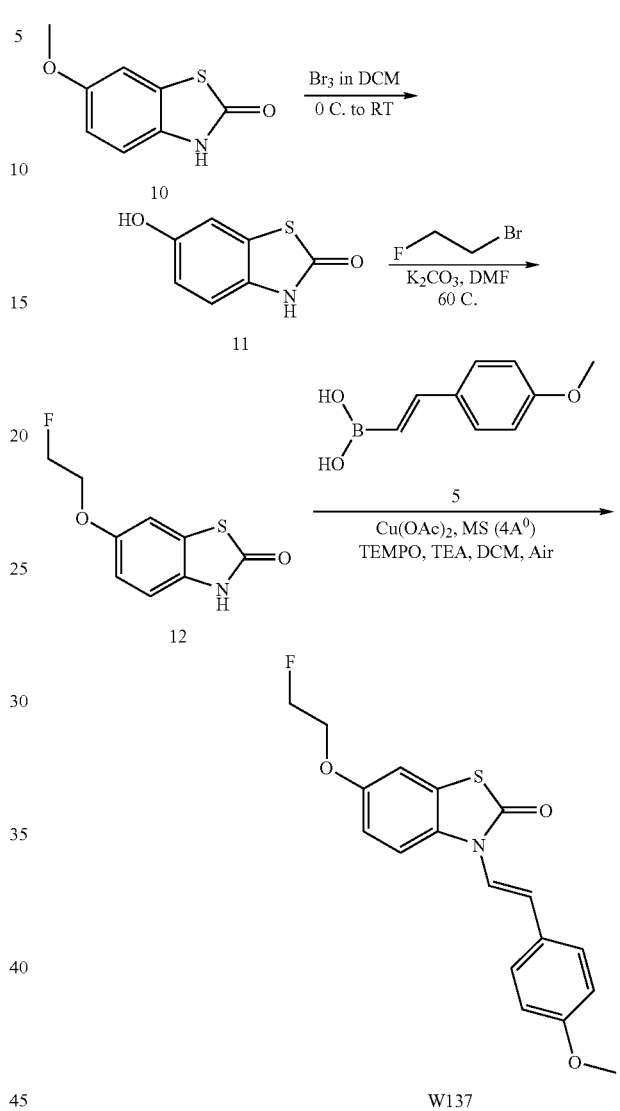

Preparation of 6-hydroxybenzo[d]thiazol-2(3H)-one (11)

To a 50 mL round bottomed flask equipped with a magnetic stir bar containing DCM (14 mL) was placed 10 (0.5 g, 2.76 mmol), the reaction mixture was cooled to 0° C., BBr$_3$ (6.9 mL of 1M in DCM) was added drop wise and was stirred at RT for 3 hrs. The reaction was neutralized with sat. NaHCO$_3$. The solvent evaporated, product dissolved in DMF, filtered through celite and used for the next step.

LC/MS: Expected for $C_7H_5NO_2S$: 167.0; found 168.0 (M+H$^+$).

Preparation of (6-(2-fluoroethoxy)benzo[d]thiazol-2(3H)-one (12)

To the DMF (15 mL) solution from the above step in a 50 mL round bottomed flask equipped with a magnetic stir bar, rubber septum and argon inlet was added K$_2$CO$_3$ (0.46 g, 3.3 mmol) and 1-bromo-2-fluoroethane (0.42 g, 3.3 mmol) were added and the reaction was allowed to stir at 60° C. for 12 hrs. The reaction was then poured into water (50 mL) and extracted into EtOAc (3×20 mL). The combined organic extracts were washed with water (20 mL), brine (20 mL), dried over MgSO$_4$ and concentrated in vacuo. The residue was purified over silica gel using EtOAc:Hexanes (1:3) as an eluent to afford 12 (0.13 g, 22%) as a white solid.

LC/MS: Expected for C$_9$H$_8$FNO$_2$S: 213.0; found: 214.0 (M+H$^+$).

Preparation of (E)-6-(2-fluoroethoxy)-3-(4-methoxystyryl)benzo[d]thiazol-2(3H)-one (W137)

To a 25 mL round bottomed flask equipped with a magnetic stir bar, added sequentially MS (4A$^0$, 0.061 g), 5 (0.162 g, 0.92 mmol), DCM (6.0 mL), TEA (0.2 mL, 1.22 mmol), 9 (0.13 g, 0.61 mmol), Cu(OAc)$_2$ (0.12 g, 0.67 mmol) and TEMPO (0.1 g, 0.67 mmol). The reaction mixture was stirred in air at RT for 12 hrs. The reaction was quenched with 7 N ammonia in MeOH (0.1 mL), added silica and concentrated in vacuo. The residue was purified over silica gel using EtOAc:Hexanes (1:4) as an eluent to afford W137 (0.016 g, 9%) as a white solid.

LC/MS: Expected for C$_{18}$H$_{16}$FNO$_3$S: 345.0; found: 346.0 (M+H$^+$).

Benzothiazolinone Compounds

General Procedure for N-Arylation

To a 50 mL round bottomed flask equipped with a magnetic stir bar containing DCM (100 vol) was placed benzothiazolinone (1 equiv). To this solution was added boronic acid (2 equiv). Cu(OAc)$_2$ (1.1 equiv), TEMPO (1.1 equiv), MS ( ), Et$_3$N (2 equiv) and the reaction was allowed to stir at RT for 24-48 h. After the reaction was complete, DCM was removed in vacuo. The residue was purified over silica gel using Hexanes:EtOAC as the eluent to afford the final compound.

Preparation of 3-(4-(dimethylamino)phenyl)benzo[d]thiazol-2(3H)-one: DHK-4-61

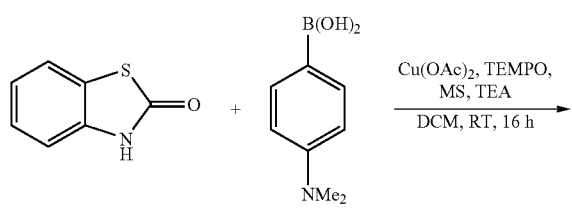

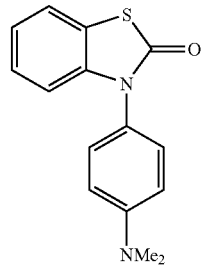

DHK-4-61

General experimental procedure for N-arylation was followed. Reaction was performed on a 0.1 g scale. Product eluted out in 20-30% EtOAc:Hexanes mixture in a gradient elution on a Combiflash purification system. Isolated 0.12 g (67%) of DHK-4-61 as colorless oil. MS: 271.0 (M+H$^+$).

Preparation of 3-(pyridin-2-yl)benzo[d]thiazol-2(3H)-one: DHK-4-62

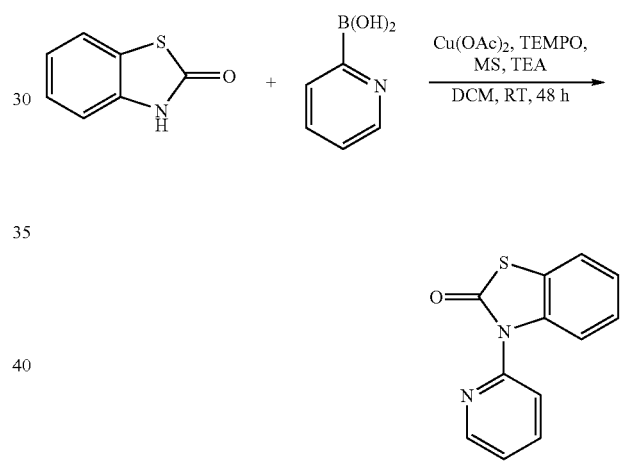

DHK-4-62

General experimental procedure for N-arylation was followed. Reaction was performed on a 0.1 g scale. Product eluted out in 20-30% EtOAc:Hexanes mixture in a gradient elution on a Combiflash purification system. Isolated 0.004 g (3%) of DHK-4-62 as white solid. MS: 229.0 (M+H$^+$)

Synthesis of CB-18 Std

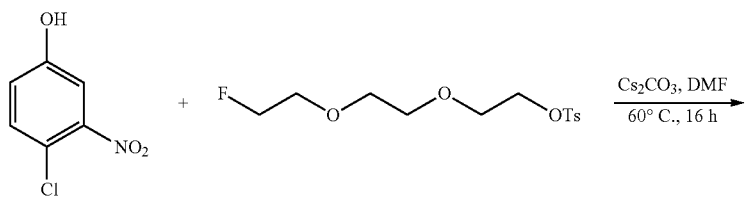

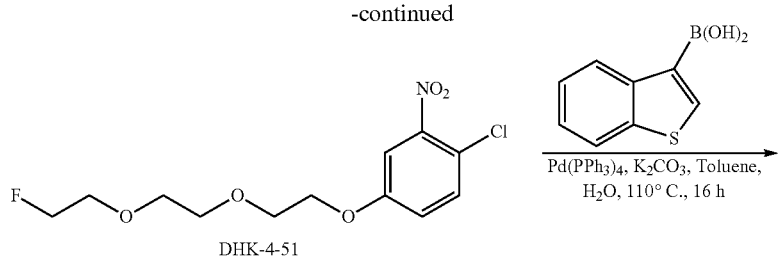

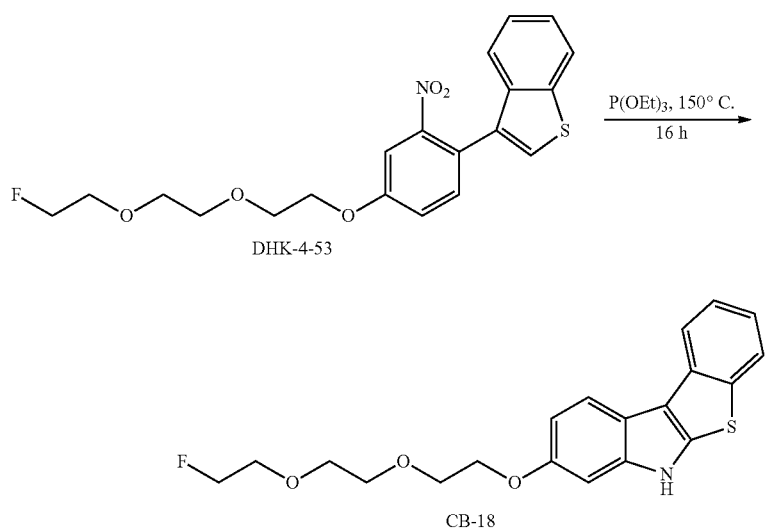

Preparation of 1-chloro-4-(2-(2-(2-fluoroethoxy)ethoxy)ethoxy)-2-nitrobenzene: DHK-4-51

General experimental procedure for phenolic alkylation was followed. Reaction was performed on a 0.25 g scale. Product eluted out in 20-30% EtOAc:Hexanes mixture in a gradient elution on a Combiflash purification system. Isolated 0.44 g (99%) of DHK-4-51 as yellow oil. MS: 308.0 (M+H$^+$).

Preparation of 3-(4-(2-(2-(2-fluoroethoxy)ethoxy)ethoxy)-2-nitrophenyl)benzo[b]thiophene: DHK-4-53

General experimental procedure for Suzuki coupling reaction was followed. Reaction was performed on a 0.10 g scale. Product eluted out in 40-50% EtOAc:Hexanes mixture in a gradient elution on a Combiflash purification system. Isolated 0.08 g (61%) of DHK-4-53 as yellow oil. MS: 406.0 (M+H$^+$).

Preparation of DHK-4-55: CB-18

General experimental procedure for carbazole formation using P(OEt)$_3$ was followed. Reaction was performed on a 0.07 g scale. Product eluted out in 40% EtOAc:Hexanes mixture in a gradient elution on a Combiflash purification system. Isolated 0.05 g (78%) of CB-18 as colorless oil. MS: 374.0 (M+H$^+$).

Synthesis of CB-22 Std

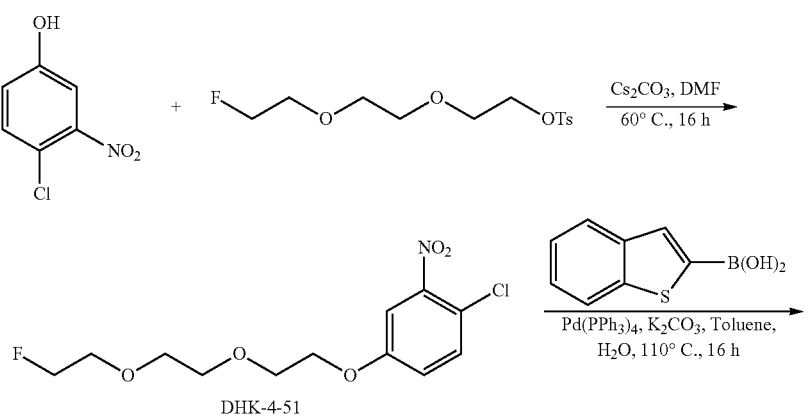

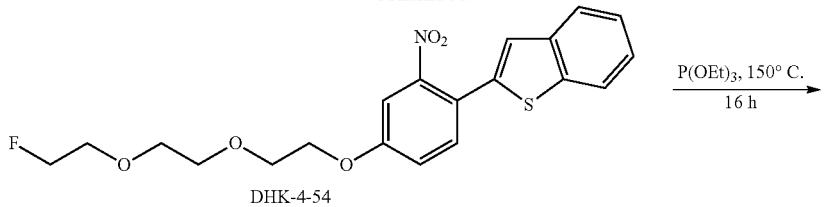

Preparation of 1-chloro-4-(2-(2-(2-fluoroethoxy)ethoxy)ethoxy)-2-nitrobenzene: DHK-4-51

General experimental procedure for phenolic alkylation was followed. Reaction was performed on a 0.25 g scale. Product eluted out in 20-30% EtOAc:Hexanes mixture in a gradient elution on a Combiflash purification system. Isolated 0.44 g (99%) of DHK-4-51 as yellow oil. MS: 308 0 (M+H$^+$).

Preparation of 3-(4-(2-(2-(2-fluoroethoxy)ethoxy)ethoxy)-2-nitrophenyl)benzo[b]thiophene: DHK-4-54

General experimental procedure for Suzuki coupling reaction was followed. Reaction was performed on a 0.10 g scale. Product eluted out in 40-50% EtOAc:Hexanes mixture in a gradient elution on a Combiflash purification system. Isolated 0.07 g (53%) of DHK-4-54 as yellow oil. MS: 406 0 (M+H$^+$).

Preparation of DHK-4-57: CB-22

General experimental procedure for carbazole formation using P(OEt)$_3$ was followed. Reaction was performed on a 0.07 g scale. Product eluted out in 50% EtOAc:Hexanes mixture in a gradient elution on a Combiflash purification system. Isolated 0.01 g (16%) of CB-22 as white solid. MS: 374.0 (M+H$^+$).

AD-OX-001S-WZ02005

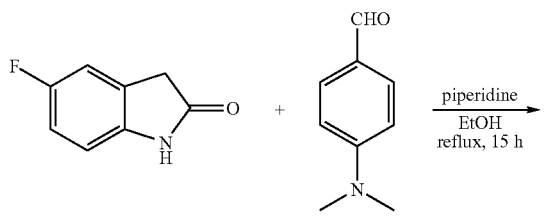

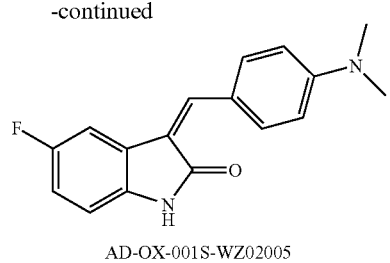

AD-OX-001S-WZ02005

A general procedure for the preparation of 3-benzylideneindolin-2-ones: A mixture of 5-fluoroindolin-2-one (151 mg, 1 mmol), 4-(dimethylamino)benzaldehyde (149 mg, 1 mmol), and piperidine (12.7 mg, 0.15 mmol) in 4 mL EtOH was heated at reflux for 15 h and cooled to rt. The solid was collected via filtration and washed with ether (10 mL), and dried under vacuum. The crude product was further purified with silica chromatography (hexane/EtOAc) to afford 3-(4-(dimethylamino)benzylidene)-5-fluoroindolin-2-one as a orange solid (220 mg, 78%, E/Z ratio 7:1). For the major E/Z isomer: $^1$H NMR (400 MHz, acetone-d6) δ 9.41 (s, 1 H), 7.68-7.64 (m, 3 H), 7.58 (dd, J=9.6, 2.4 Hz, 1 H), 6.98-6.86 (m, 4 H), 3.09 (s, 6 H); MS (ESI) m/z 283 (M+H$^+$).

AD-OX-001P-WZ02007

AD-OX-001P-WZ02007

Compound 3-(4-(dimethylamino)benzylidene)-5-nitroindolin-2-one (AD-OX-001P-WZ02007) was prepared using the general procedure for the preparation of 3-benzylideneindolin-2-ones. For the major E/Z isomer: $^1$H NMR (400 MHz, acetone-d6) δ 11.13 (s, 1 H), 8.56 (d, J=2.4 Hz, 1 H), 8.50 (d, J=8.8 Hz, 2 H), 8.03 (dd, J=8.4, 2.0 Hz, 1 H), 8.00 (s, 1 H), 6.93 (d, J=8.4 Hz, 1 H), 6.77 (d, J=8.8 Hz, 2 H), 3.04 (s, 6 H); MS (ESI) m/z 310 (M+H$^+$).

AD-OX-003S-WZ02017

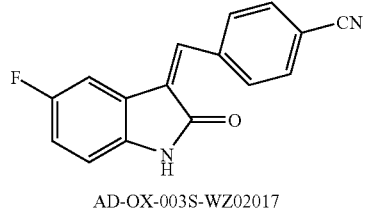

AD-OX-003S-WZ02017

Compound 4-((5-fluoro-2-oxoindolin-3-ylidene)methyl)benzonitrile (AD-OX-003S-WZ02017) was prepared using the general procedure for the preparation of 3-benzylideneindolin-2-ones. For the major E/Z isomer: $^1$H NMR (400 MHz, acetone-d6) δ 9.63 (s, 1 H), 7.94 (m, 4 H), 7.73 (s, 1 H), 7.17 (dd, J=9.2, 2.8 Hz, 1 H), 7.06 (td, J=8.8, 2.4 Hz, 1 H), 6.95 (dd, J=8.8, 4.8 Hz, 1 H); MS (ESI) m/z 265 (M+H$^+$).

AD-OX-003P-WZ02031

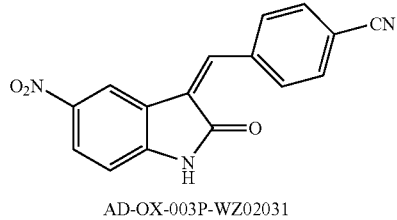

AD-OX-003P-WZ02031

Compound 4-((5-nitro-2-oxoindolin-3-ylidene)methyl)benzonitrile (AD-OX-003P-WZ02031) was prepared using the general procedure for the preparation of 3-benzylideneindolin-2-ones. $^1$H NMR (400 MHz, DMSO-d6) δ 11.39 (s, 1 H), 8.72 (d, J=2.4 Hz, 0.5 H), 8.49 (d, J=8.4 Hz, 1 H), 8.28 (s, 0.5 H), 8.21 (td, J=8.8, 2.4 Hz, 1 H), 8.14 (d, J=2.4 Hz, 0.5 H), 8.05 (d, J=8.0 Hz, 1 H), 7.96 (m, 2 H), 7.87 (s, 0.5 H), 7.03 (d, J=8.8 Hz, 0.5 H), 7.02 (d, J=8.4 Hz, 0.5 H); MS (ESI) m/z 292 (M+H$^+$).

AD-OX-004S-WZ02021

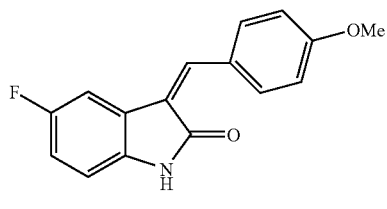

AD-OX-004S-WZ02021

Compound 5-fluoro-3-(4-methoxybenzylidene)indolin-2-one (AD-OX-004S-WZ02021) was prepared using the general procedure for the preparation of 3-benzylideneindolin-2-ones. For the major E/Z isomer: $^1$H NMR (400 MHz, acetone-d6) δ 9.52 (s, 1 H), 7.71 (m, 3 H), 7.43 (dd, J=9.6, 2.4 Hz, 1 H), 7.11 (m, 2 H), 7.02-6.97 (m, 1 H), 6.94-6.90 (m, 1 H), 3.90 (s, 3 H); MS (ESI) m/z 270 (M+H$^+$).

AD-OX-004P-WZ02023

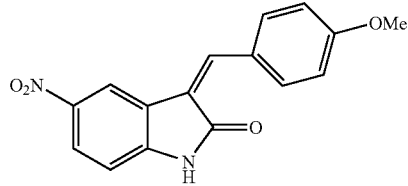

AD-OX-004P-WZ02023

Compound 3-(4-methoxybenzylidene)-5-nitroindolin-2-one (AD-OX-004P-WZ02023) was prepared using the general procedure for the preparation of 3-benzylideneindolin-2-ones. For the major E/Z isomer: $^1$H NMR (400 MHz, DMSO-d6) δ 11.32 (s, 1 H), 8.48 (d, J=2.0 Hz, 1 H), 8.18 (dd, J=8.4, 2.4 Hz, 1 H), 7.81-7.78 9 (m, 3 H), 7.14 (d, J=8.8 Hz, 2 H), 7.06 (d, J=8.8 Hz, 1 H), 3.88 (s, 3 H); MS (ESI) m/z 297 (M+H$^+$).

AD-TZ-001S-WZ02019

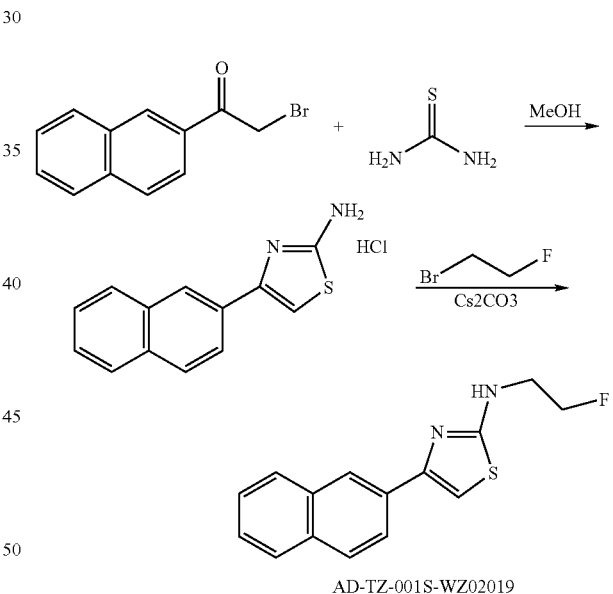

AD-TZ-001S-WZ02019

A solution of 2-bromo-1-(naphthalen-2-yl)ethanone (498 mg, 2 mmol) and thiourea (144 mg, 2.4 mmol) in 8 mL of MeOH was stirred at rt for 1 h and then heated at reflux for 30 min. After cooling to rt, solid was collected via filtration and washed with water (2×10 mL) and dried under high vacuum to afford 4-(naphthalen-2-yl)thiazol-2-amine hydrochloride salt as a white solid (410 mg, 78%). $^1$H NMR (400 MHz, DMSO-d6) δ 8.25 (d, J=2.0 Hz, 1 H), 7.98 (d, J=8.8 Hz, 1 H), 7.93-7.91 (m, 2 H), 7.84 (dd, J=8.4, 2.0 Hz, 1 H), 7.57-7.55 (m, 2 H), 7.33 (s, 1 H); MS (ESI) m/z 227 (M+H$^+$).

A mixture of 4-(naphthalen-2-yl)thiazol-2-amine hydrochloride (113 mg, 0.5 mmol), 1-bromo-2-fluoroethane (127 mg, 1 mmol), Cs$_2$CO$_3$ (326 mg, 1 mmol), and 15 mg KI in 2 mL of NMP was heated at 80 C for 20 min in a microwave reactor. After cooling to rt, the mixture was taken up to 50 mL EtOAc and washed with water (3×80 mL) and dried over MgSO₄ and concentrated. The residue was chromatographed (hexane/EtOAc) to afford N-(2-fluoroethyl)-4-(naphthalen-2-yl)thiazol-2-amine as a white solid (10 mg, 18%). $^1$H NMR (400 MHz, CDCl$_3$) δ 12.32 (s, 1 H), 8.29 (d, J=1.6 Hz, 1 H), 7.95-7.91 (m, 2 H), 7.86-7.83 (m, 1 H), 7.67 (dd, J=8.4, 2.0 Hz, 1 H), 7.57-7.54 (m, 2 H), 6.70 (s, 1 H), 4.79 (t, J=4.8 Hz, 1 H), 4.67 (t, J=4.8 Hz, 1 H), 3.71 (m, 1 H), 3.65 (m, 1 H); MS (ESI) m/z 273 (M+H$^+$).

Synthetic Scheme of OX-02

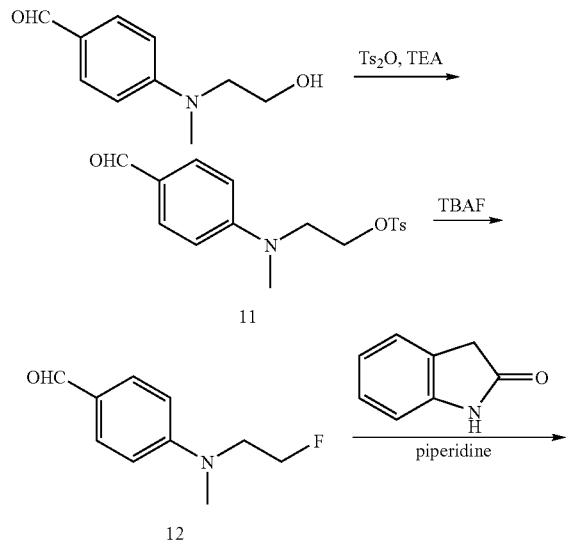

2-((4-formylphenyl)(methyl)amino)ethyl 4-methyl-benzenesulfonate (Compound 11)

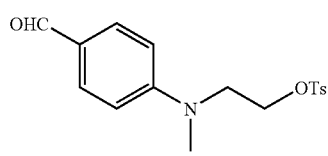 [SMILES: Cc1ccc(S(=O)(=O)OCCN(C)c2ccc(C=O)cc2)cc1]

To a round bottom flask containing 4-((2-hydroxyethyl)(methyl)amino)benzaldehyde (7.0 g, 39 mmol) and tosyl anhydride (15.3 g, 47 mmol) in DCM (50 ml) at ice bath temperature, was added triethylamine (13.7 mL, 98 mmol) dropwise. The reaction was allowed to rt and stirred for 72 h. The reaction was diluted with brine (150 mL) and extracted with DCM (100 mL×3). The combined organic layer was concentrated in vacuo. The residue was purified on a silica gel column to afford Compound 11 as a red solid (1.5 g, 4.5 mmol, 12% yield). $^1$H NMR (400 MHz, CDCl$_3$) δ: 9.75 (s, 1H), 7.70-7.67 (m, 4H), 7.24 (d, J=8.0 Hz, 2H), 6.59 (d, J=5.6 Hz, 1H), 4.21 (t, J=5.6 Hz, 2H), 3.74 (t, J=5.6 Hz, 2H), 3.01 (s, 3H), 2.40 (s, 3H).

4-((2-fluoroethyl)(methyl)amino)benzaldehyde (Compound 12)

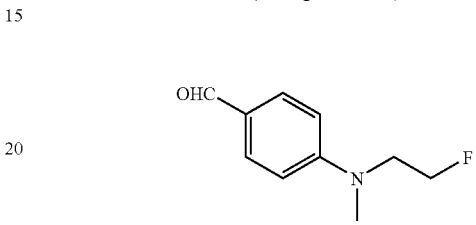

To a round bottom flask containing Compound 11 (150 mg, 0.45 mmol) in THF (1 mL), was added tetrabutylammonium fluoride (1.0 M solution in THF, 0.54 mL, 0.54 mmol). The reaction mixture was heated at 100° C. for 30 min. The reaction was then concentrated in vacuo and purified on a silica gel column to afford Compound 12 as a white solid (72 mg, 0.40 mmol, 88% yield). $^1$H-NMR (400 MHz, CDCl$_3$) δ: 9.76 (s, 1H), 7.75 (d, J=8.8 Hz, 2H), 6.73 (d, J=8.8 Hz, 2H), 4.70 (m, 1H), 4.58 (m, 1H), 3.80-3.74 (m, 2H), 3.14 (s, 3H).

(E)-3-(4-((2-fluoroethyl)(methyl)amino)benzylidene)indolin-2-one (OX-02)

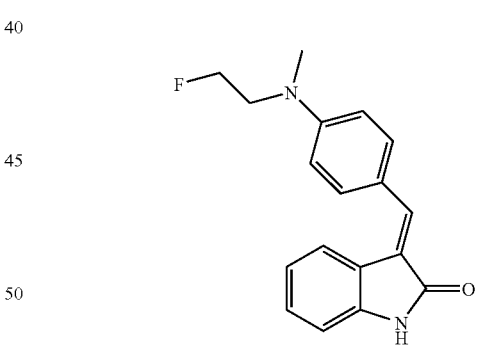

To a round bottom flask containing Compound 12 (72 mg, 0.40 mmol) and 2-oxoindole (54 mg, 0.40 mmol) in ethanol (2 mL), was added piperidine (39 uL, 0.40 mL). The reaction was heated at 80° C. for 15 min and then allowed to rt for 72 h. A yellow precipitate formed in the solution and was collected via vacuum filtration. The yellow solid was dried via lypholization to afford OX-02 (94 mg, 0.32 mmol, 80% yield). $^1$H NMR (400 MHz, CDCl$_3$) δ: 10.41 (br, 1H), 7.73 (d, J=8.40 Hz, 1H), 7.59 (d, J=8.40 Hz, 2H), 7.46 (s, 1H), 7.15-7.11 (m, 1H), 6.85-6.80 (m, 4H), 4.65-4.62 (m, 1H), 4.53-4.50 (m, 1H), 3.77-3.69 (m, 2H), 3.00 (s, 3H); LRMS for C$_{18}$H$_{17}$N$_2$O+H$^+$, calc'd: 297.1, found: 297.1 (M+H$^+$)

Experimental Section for Indolizine Derivatives

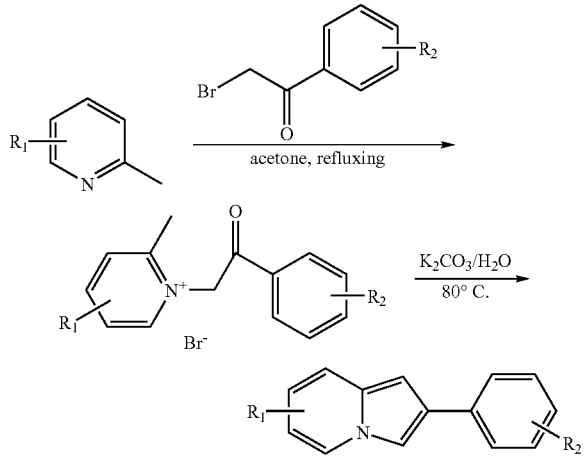

General procedures for the preparation of indolizine derivatives: A mixture of 2-picoline (1 eq) and α-bromoketones (1 eq.) in acetone (50 mL) was refluxed for 3 h, then cooled and filtered. The solid was washed with acetone and dried. It was redissolved in water (50 mL). To this solution was added $K_2CO_3$ (1 eq.). The resulting mixture was heated at 80° C. for 4 hrs, then cooled and filtered. The solid collected was washed with $H_2O$ (2×30 mL) and dried in vacuo to give the desired indolizine derivatives.

2-(3-Methoxyphenyl)indolizine: (1.84 g, 86%). $^1$H NMR (CDCl$_3$, 400 MHz) 7.89 (dd, J=6.8, 1.2 Hz, 1H), 7.57 (d, J=1.2 Hz, 1H), 7.18-7.36 (m, 4H), 6.82 (dq, J=8, 2.4, 1.2 Hz, 1H), 6.68 (s, 1H), 6.61-6.68 (m, 1H), 6.45 (td, J=6.8, 1.2 Hz, 1H), 3.87 (s, 3H). MS: m/z=224 (M+H$^+$).

2-(4-Nitrophenyl)indolizine: (0.2 g, 10%). $^1$H NMR (Acetone-d$_6$, 400 MHz) δ: 8.13 (d, J=8.8 Hz, 2H), 8.09 (dd, J=6.8, 0.8 Hz, 1H), 7.97 (d, J=0.8 Hz, 1H), 7.87 (d, J=9.2 Hz, 2H), 7.31 (d, J=8.8 Hz, 1H), 6.78 (s, 1H), 6.62 (dd, J=4.6, 1.2 Hz, 1H), 6.46 (td, J=6.8, 1.2 Hz, 1H). MS: m/z=239 (M+H$^+$).

2-(4-Methoxyphenyl)indolizine: (0.8 g, 36%). $^1$H NMR (CDCl$_3$, 400 MHz) δ: 7.88 (dd, J=6.8, 0.8 Hz, 1H), 7.58 (d, J=8.8 Hz, 2H), 7.51 (d, J=1.6 Hz, 1H), 7.33 (d, J=4.4 Hz, 1H), 6.94 (d, J=8.8 Hz, 2H), 6.63 (t, J=4.8 Hz, 2H), 6.43 (td, J=6.8, 1.2 Hz, 1H), 3.84 (s, 3H). MS: m/z=224 (M+H$^+$).

2-(4-Cyanophenyl)indolizine: (0.92 g, 67%). $^1$H NMR (CDCl$_3$, 400 MHz) δ: 7.90 (dd, J=6.8, 0.8 Hz, 1H), 7.72 (d, J=8.4 Hz, 2H), 7.65 (d, J=8.4 Hz, 2H), 7.61 (d, J=1.2 Hz, 1H), 7.36 (d, J=9.2 Hz, 1H), 6.70 (t, J=6.8 Hz, 1H), 6.50 (td, J=6.8, 1.2 Hz, 1H). MS: m/z=219 (M+H$^+$).

2-(3-Nitrophenyl)indolizine-6-carboxamide: (0.76 g, 64%). $^1$H NMR (CDCl$_3$, 400 MHz) δ: 8.69 (s, 1H), 8.50 (s, 1H), 8.13 (d, J=8.4 Hz, 1H), 7.97 (d, J=8.8 Hz, 1H), 7.76 (s, 1H), 7.58 (t, J=8.0 Hz, 1H), 7.42 (d, J=8.4 Hz, 1H), 6.92 (d, J=7.6 Hz, 1H), 6.84 (s, 1H). MS: m/z=282 (M+H$^+$).

2-(4-Methoxyphenyl)indolizine-6-carboxamide: (1.8 g, 87%). $^1$H NMR (DMSO-d$_6$, 400 MHz) δ: 8.79 (s, 1H), 7.97 (d, J=1.2 Hz, 1H), 7.84 (br s, 1H), 7.63 (d, J=8.8 Hz, 2H), 7.36 (d, J=9.2 Hz, 1H), 7.26 (br s, 1H), 7.10 (dd, J=9.2, 1.6 Hz, 1H), 6.96 (d, J=8.8 Hz, 2H), 6.75 (s, 1H), 3.76 (s, 3H). MS: m/z=282 (M+H$^+$).

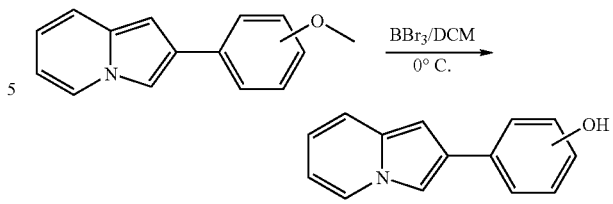

General procedures for the demethylation reaction: To a cooled solution of 2-(4-methoxyphenyl)indolizine (1.0 mmol) in dichloromethane (20 mL) was added dropwise a solution of BBr$_3$ in dichloromethane (1.0 M, 4.0 mL, 4.0 mmol). The resulting mixture was stirred under Ar at 0° C. and warmed gradually to room temperature. After stirring at room temperature overnight, LCMS results show that no starting material was present. It was cooled in an ice-bath. Water was added slowly. The resulting mixture was transferred to a separatory funnel. The layers were separated. The organic layer was washed with $H_2O$ (2×20 mL), dried (MgSO$_4$), and filtered. The filtrate was concentrated in vacuo to give the desired product.

2-(3-Hydroxyphenyl)indolizine: (1.0 g, 97%). NMR (acetone-d$_6$, 400 MHz) δ: 8.14 (d, J=7.2 Hz, 1H), 7.82 (d, J=1.6 Hz, 1H), 7.46 (d, J=8.8 Hz, 1H), 7.24-7.34 (m, 2H), 7.22-7.25 (m, 1H), 7.03 (br s, 1H), 6.75-6.83 (m, 3H), 6.60 (td, J=7.6, 1.2 Hz, 1H). MS: m/z=210 (M+H$^+$).

2-(4-Hydroxyphenyl)indolizine: (0.58 g, 77%). $^1$H NMR (CDCl$_3$, 400 MHz) 6; 7.88 (d, J=6.8 Hz, 1H), 7.54 (d, J=8.4 Hz, 2H), 7.50 (d, J=1.6 Hz, 1H), 7.33 (d, J=10 Hz, 1H), 6.87 (d, J=8.4 Hz, 2H), 6.63-6.66 (m, 1H), 6.62 (s, 1H), 6.44 (t, J=6.8 Hz, 1H). MS: m/z=210 (M+H$^+$).

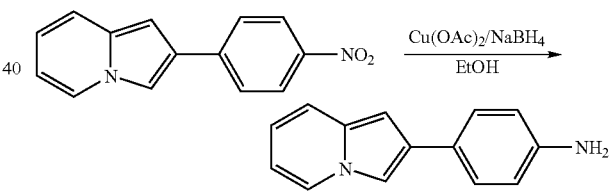

2-(4-Aminophenyl)indolizine: To a suspension of 2-(4-nitrophenyl)indolizine (0.2 g, 0.84 mmol) and Cu(OAc)$_2$ (0.16 g, 0.88 mmol) in EtOH (50 mL) was added NaBH$_4$ (0.64 g, 16.8 mmol). The resulting mixture was stirred at room temperature for 3 hrs and concentrated in vacuo. The residue was dissolved in H$_2$O (20 mL) and extracted with EtOAc (3×20 mL). The combined organic layers were dried (MgSO$_4$), filtered. The filtrate was concentrated in vacuo to give a solid (0.092 g, 53%). $^1$H NMR (CDCl$_3$, 400 MHz) δ: 7.87 (dd, J=6.8, 1.2 Hz, 1H), 7.44-7.95 (m, 3H), 7.31 (d, J=8.4 Hz, 1H), 6.73 (d, J=8.4 Hz, 2H), 6.59-6.64 (m, 2H), 6.42 (td, J=6.8, 1.2 Hz, 1H), 3.67 (br s, 2H). MS: m/z=209 (M+H$^+$).

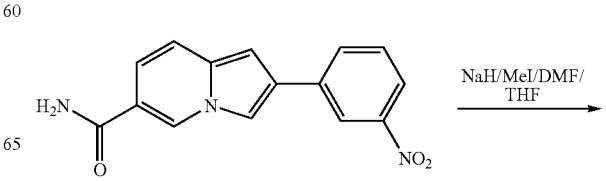

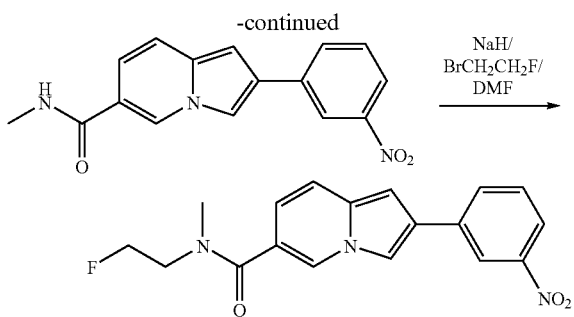

N-Methyl-2-(3-nitrophenyl)indolizine-6-carboxamide: To a cooled solution of 2-(3-nitrophenyl)indolizine-6-carboxamide (0.4 g, 1.42 mmol) in DMF/THF (20/10 ml) was added NaH (60% in mineral oil, 58 mg, 1.45 mmol). The resulting mixture was stirred under Ar at 0° C. for 5 min, and then MeI (0.13 mL, 2.08 mmol) was added. The reaction mixture was stirred under Ar at 0° C. and warmed gradually to room temperature and stirred at room temperature overnight. It was concentrated in vacuo. The residue was recrystallized from $CH_2Cl_2$/acetone/EtOAc to give a white solid (0.1 g, 24%). $^1$H NMR (CDCl$_3$, 400 MHz) δ: 8.78 (s, 1H), 8.48 (t, J=2.0 Hz, 1H), 8.42 (br s, 1H), 8.30 (d, J=1.6 Hz, 1H), 8.18 (d, J=7.6 Hz, 1H), 8.09 (dd, J=8.0, 1.6 Hz, 1H), 7.69 (t, J=8.0 Hz, 1H), 7.45 (d, J=9.2 Hz, 1H), 7.13 (dd, J=9.6, 1.6 Hz, 1H), 6.99 (s, 1H), 2.77 (d, J=4.4 Hz, 3H). MS: m/z=296 (M+H$^+$).

N-(2-Fluoroethyl)-N-methyl-2-(3-nitrophenyl)indolizine-6-carboxamide: To a cooled solution of N-methyl-2-(3-nitrophenyl)indolizine-6-carboxamide (100 mg, 0.34 mmol) in DMF (4 mL) was added NaH (60% in mineral oil, 20 mg, 0.5 mmol). After stirring at 0° C. under Ar for 5 min, 2-fluoroethyl bromide (excess) was added. The resulting mixture was stirred under Ar at 0° C. and warmed gradually to room temperature, then stirred at room temperature overnight. It was concentrated in vacuo. The residue was purified via column chromatography (silica gel, 0-5% EtOAc/CH$_2$Cl$_2$) to give an orange solid (59 mg, 51%). $^1$H NMR (acetone-d$_6$, 400 MHz) δ: 8.53 (t, J=2.4 Hz, 1H), 8.42 (s, 1H), 8.17-8.22 (m, 2H), 8.12 (dd, J=7.6, 1.6 Hz, 1H), 7.71 (t, J=8.0 Hz, 1H), 7.50 (d, J=9.6 Hz, 1H), 7.00 (s, 1H), 6.83 (d, J=8.0 Hz, 1H), 4.69 (dt, J=47.6, 4.8 Hz, 2H), 3.83 (dt, J=26.4, 4.8 Hz, 2H), 3.18 (s, 3H). MS: m/z=342 (M+H$^+$).

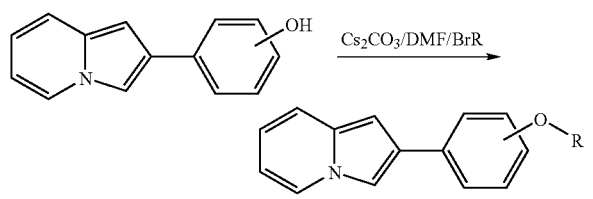

General procedures for the preparation of O-alkylated indolizine derivatives: To a solution of 2-(hydroxyphenyl)indolizine (1.0 eq.) and Cs$_2$CO$_3$ (1.0 eq) in DMF (4 mL) was added w-fluoroalkyl bromide (1.1 eq.). The reaction mixture was stirred at room temperature overnight, and then concentrated in vacuo. The residue was purified via column chromatography (silica gel, 0-5% EtOAc/CH$_2$Cl$_2$) to give the desired compound.

2-[3-(2-Fluoroethoxyphenyl)]indolizine: (150 mg, 95%). $^1$H NMR (CDCl$_3$, 400 MHz) δ: 7.88 (d, J=6.8 Hz, 1H), 7.56 (s, 1H), 7.21-7.36 (m, 4H), 6.82 (dt, J=8.0, 1.8 Hz, 1H), 6.67 (s, 1H), 6.62-6.66 (m, 1H), 6.45 (td, J=6.8, 1.2 Hz, 1H), 4.79 (dt, J=47.6, 4.0 Hz, 2H), 4.28 (dt, J=28.0, 4.0 Hz, 2H). MS: m/z=256 (M+H$^+$).

2-[3-(4-Fluorobutoxyphenyl)]indolizine: (90 mg, 59%). $^1$H NMR (CDCl$_3$, 400 MHz) δ: 7.87 (d, J=6.8 Hz, 1H), 7.55 (d, J=1.2 Hz, 1H), 7.16-7.38 (m, 4H), 6.79 (d, J=7.6 Hz, 1H), 6.67 (1H), 6.60-6.67 (m, 1H), 6.44 (t, J=6.8 Hz, 1H), 4.54 (dt, J=47.2, 5.6 Hz, 2H), 4.07 (t, J=5.6 Hz, 2H), 1.85-2.01 (m, 4H). MS: m/z=284 (M+H$^+$).

2-{3-[2-(2-(2-Fluoroethoxy)ethoxy)ethoxy]phenyl}indolizine: (150 mg, 88%). $^1$H NMR (acetone-d$_6$, 400 MHz) δ: 8.45 (d, J=6.8 Hz, 1H), 8.14 (d, J=1.6 Hz, 1H), 7.81-7.94 (m, 4H), 7.40 (dt, J=7.6, 1.6 Hz, 1H), 7.26 (s, 1H), 7.19-7.24 (m, 1H), 7.02 (td, J=6.8, 1.2 Hz, 1H), 5.15 (dt, J=47.6, 4.4 Hz, 2H), 4.79 (t, J=4.8 Hz, 2H), 4.48 (t, J=4.8 Hz, 2H), 4.29-4.42 (m, 6H). MS: m/z=344 (M+H$^+$).

2-[4-(2-Fluoroethoxyphenyl)]indolizine: (30 mg, 27%). $^1$H NMR (CDCl$_3$, 400 MHz) δ: 7.88 (d, J=7.2 Hz, 1H), 7.58 (d, J=8.8 Hz, 2H), 7.51 (s, 1H), 7.32 (d, J=8.8 Hz, 1H), 6.96 (d, J=8.8 Hz, 2H), 6.60-6.68 (m, 2H), 6.44 (t, J=3.2 Hz, 1H), 4.78 (dt, J=47.6, 4.0 Hz, 2H), 4.25 (dt, J=28, 4.4 Hz, 214). MS: m/z=256 (M+H$^+$).

2-[4-(4-Fluorobutoxyphenyl)]indolizine: (16 mg). $^1$H NMR (CDCl$_3$, 400 MHz) δ: 7.88 (dd, J=6.8, 1.2 Hz, 1H), 7.57 (d, J=8.8 Hz, 2H), 7.50 (d, J=1.2 Hz, 1H), 7.32 (d, J=9.2 Hz, 1H), 6.93 (d, J=8.8 Hz, 2H), 6.60-6.67 (m, 2H), 6.43 (td, J=6.8, 1.2 Hz, 1H), 4.54 (dt, J=47.2, 5.6 Hz, 2H), 4.04 (t, J=5.6 Hz, 2H), 1.84-2.01 (m, 4H). MS: m/z=284 (M+H$^+$).

Preparation of W119

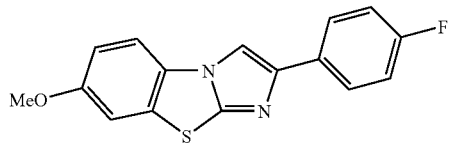 [SMILES: COc1ccc2c(c1)sc1nc(-c3ccc(F)cc3)cn12]

Compound W119 was prepared using the general procedure for cyclization between 6-methoxybenzo[d]thiazol-2-amine (90 mg, 0.5 mmol) and 2-bromo-1-(4-fluorophenyl)ethanone (119 mg, 0.55 mmol), as a white solid (132 mg, 69%). $^1$H NMR (400 MHz, DMSO-d6) δ 8.74 (s, 1 H), 7.91 (d, J=8.8 Hz, 1 H), 7.85 (m, 2 H), 7.70 (d, J=2.4 Hz, 1 H), 7.27 (t, J=9.2 Hz, 2 H), 7.17 (m, J=8.8, 2.4 Hz, 1 H), 3.82 (s, 3 H); MS (ESI) m/z 299 (M+H)$^+$.

Preparation of W120

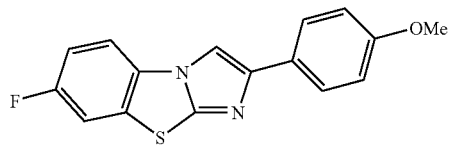 [SMILES: COc1ccc(-c2cn3c(n2)sc2cc(F)ccc23)cc1]

Compound W120 was prepared using the general procedure for cyclization between 6-fluorobenzo[d]thiazol-2-amine (84 mg, 0.5 mmol) and 2-bromo-1-(4-methoxyphenyl)ethanone (115 mg, 0.55 mmol), as a white solid (82 mg, 43%). $^1$H NMR (400 MHz, DMSO-d6) δ 8.60 (s, 1 H), 8.00-7.94 (m, 2 H), 7.75 (d, J=8.8 Hz, 2 H), 7.42 (td, J=9.2 Hz, 1 H), 6.98 (d, J=8.8 Hz, 1 H), 3.76 (s, 3 H); MS (ESI) m/z 299 (M+H$^+$).

Preparation of 4-(benzo[d]thiazol-5-yl)-2-fluorophenol: W121

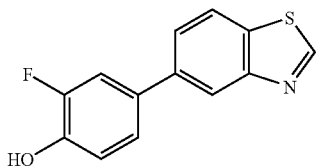 [SMILES: Oc1ccc(-c2ccc3scnc3c2)cc1F]

Compound 4-(benzo[d]thiazol-5-yl)-2-fluorophenol (W121) was prepared using the general procedure for Suzuki coupling reaction between 4-bromo-2-fluorophenol (57 mg, 0.3 mmol) and 5-(4,4,5,5-tetramethyl-1,3,2-dioxaborolan-2-yl)benzo[d]thiazole (78 mg, 0.3 mmol), as a white solid (45 mg, 61%). $^1$H NMR (400 MHz, acetone-d6) δ 9.27 (s, 1 H), 8.85 (s, 1 H), 8.28 (d, J=1.6 Hz, 1 H), 8.15 (d, J=8.4 Hz, 1 H), 7.75 (dd, J=8.4, 1.6 Hz 1 H), 7.55 (dd, J=12.4, 2.4 Hz, 1 H), 7.45 (m, 1 H), 7.12 (t, 9.2 Hz, 1 H); MS (ESI) m/z 246 (M+H$^+$).

Preparation of 6-(3-fluoro-4-methoxyphenyl)benzo[d]thiazol-2-amine: W143

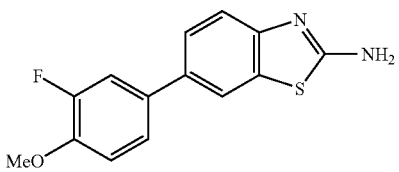 [SMILES: COc1ccc(-c2ccc3nc(N)sc3c2)cc1F]

Compound 6-(3-fluoro-4-methoxyphenyl)benzo[d]thiazol-2-amine (W143) was prepared using the general procedure for Suzuki coupling reaction between 6-bromobenzo[d]thiazol-2-amine (75 mg, 0.3 mmol) and 2-(3-fluoro-4-methoxyphenyl)-4,4,5,5-tetramethyl-1,3,2-dioxaborolane (69 mg, 0.3 mmol), as a white solid (30 mg, 36%). $^1$H NMR (400 MHz, acetone-d6) δ 7.92 (d, J=2.0 Hz, 1 H), 7.52 (dd, J=8.4, 2.0 Hz, 1 H), 7.47-7.24 (m, 3 H), 7.20 (t, J=8.4 Hz, 1 H), 6.86 (brs, 2 H), 3.92 (s, 3 H); MS (ESI) m/z 275 (M+H$^+$).

Preparation of 6-(4-(benzyloxy)-3-fluorophenyl)benzo[d]thiazol-2-amine (W146)

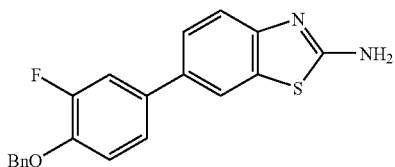 [SMILES: Nc1nc2ccc(-c3ccc(OCc4ccccc4)c(F)c3)cc2s1]

Compound 6-(4-(benzyloxy)-3-fluorophenyl)benzo[d]thiazol-2-amine (W146) was prepared using the general procedure for Suzuki coupling reaction between 4-(benzyloxy)-3-fluorophenylboronic acid (100 mg, 0.4 mmol) and 6-bromobenzo[d]thiazol-2-amine (92 mg, 0.4 mmol), as a white solid (65 mg, 58%). $^1$H NMR (400 MHz, acetone-d6) δ 7.92 (d, J=2.0 Hz, 1 H), 7.54-7.51 (m, 3 H), 7.49-7.46 (m, 1 H), 7.46-7.40 (m, 4 H), 7.37-7.33 (m, 1 H), 7.30-7.26 (m, 1 H), 6.86 (brs, 2 H), 5.25 (s, 2 H); MS (ESI) m/z 351 (M+H$^+$).

Preparation of 3-(benzo[d]thiazol-5-yl)-5-fluorophenol: W190

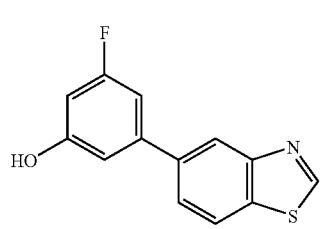 [SMILES: Oc1cc(F)cc(-c2ccc3scnc3c2)c1]

Compound 3-(benzo[d]thiazol-5-yl)-5-fluorophenol (W190) was prepared using the general procedure for Suzuki coupling reaction between 3-bromo-5-fluorophenol (57 mg, 0.3 mmol) and 5-(4,4,5,5-tetramethyl-1,3,2-dioxaborolan-2-yl)benzo[d]thiazole (78 mg, 0.3 mmol), as a white solid (60 mg, 81%). $^1$H NMR (400 MHz, acetone-d6) δ 9.30 (s, 1 H), 9.02 (brs, 1 H), 8.30 (d, J=1.6 Hz, 1 H), 8.19 (d, J=8.4 Hz, 1 H), 7.45 (dd, J=8.4, 2.0 Hz, 1 H), 7.07 (t, J=1.6 Hz, 1 H), 7.02 (dt, J=10.0, 2.0 Hz, 1 H), 6.64 (dt, J=10.4, 2.4 Hz, 1 H); MS (ESI) m/z 275 (M+H$^+$).

Preparation of 4-(benzo[d]thiazol-5-yl)-N-methylaniline: W189

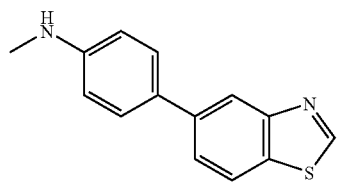 [SMILES: CNc1ccc(-c2ccc3scnc3c2)cc1]

Compound 4-(benzo[d]thiazol-5-yl)-N-methylaniline (W189) was prepared using the general procedure for Suzuki coupling reaction between 4-bromo-N-methylaniline (56 mg, 0.3 mmol) and 5-(4,4,5,5-tetramethyl-1,3,2-dioxaborolan-2-yl)benzo[d]thiazole (78 mg, 0.3 mmol), as a white solid (20 mg, 28%). $^1$H NMR (400 MHz, acetone-d6) δ 9.22 (s, 1 H), 8.22 (d, J=1.6 Hz, 1 H), 8.08 (d, J=8.4 Hz, 1 H), 7.71 (dd, J=8.4, 1.6 Hz, 1 H), 7.56 (m, 2 H), 6.72 (m, 2 H), 5.14 (brs, 1 H), 2.83 (s, 0.5 H), 2.82 (s, 0.5 H); MS (ESI) m/z 241 (M+H$^+$).

Preparation of W200

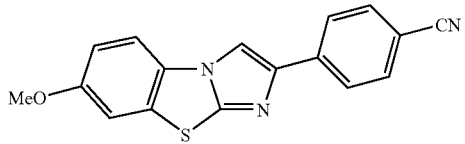 [SMILES: COc1ccc2c(c1)sc1nc(-c3ccc(C#N)cc3)cn12]

Compound W200 was prepared using the general procedure for cyclization between 6-methoxybenzo[d]thiazol-2- amine (90 mg, 0.5 mmol) and 4-(2-bromoacetyl)benzonitrile (123 mg, 0.55 mmol), as an off-white solid (60 mg, 39%). $^1$H NMR (400 MHz, DMSO-d6) δ 8.89 (s, 1 H), 7.97 (d, J=8.4 Hz, 1 H), 7.87-7.83 (m, 3 H), 7.66 (d, J=2.8 Hz, 1 H), 7.14 (dd, J=9.2, 2.4 Hz, 1 H), 3.79 (s, 3 H); MS (ESI) m/z 305 (M+H$^+$).

Preparation of (E)-6-(4-methoxystyryl)benzo[d]thiazol-2-amine: W201

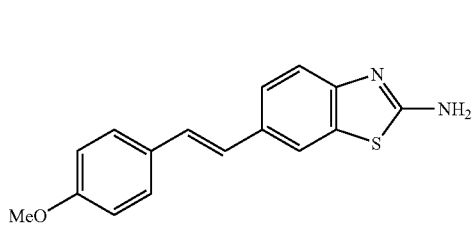 [SMILES: COc1ccc(/C=C/c2ccc3nc(N)sc3c2)cc1]

Compound (E)-6-(4-methoxystyryl)benzo[d]thiazol-2-amine (W201) was prepared using the general procedure for Suzuki coupling reaction between 6-bromobenzo[d]thiazol-2-amine (69 mg, 0.3 mmol) and (E)-4-methoxystyrylboronic acid (53 mg, 0.3 mmol), as a white solid (80 mg, 94%). $^1$H NMR (400 MHz, DMSO-d6) δ 7.80 (d, J=1.6 Hz, 1 H), 7.46 (s, 2 H), 7.45 (d, J=8.8 Hz, 2 H), 7.36 (dd, J=8.4, 1.6 Hz, 1 H), 7.24 (d, J=8.0 Hz, 1 H), 7.03 (d, J=2.0 Hz, 2 H), 6.89 (d, J=9.2 Hz, 1 H), 3.71 (s, 3 H); MS (ESI) m/z 283 (M+H$^+$).

Preparation of 5-(5-fluoropyridin-2-yl)benzo[d]thiazole: W208

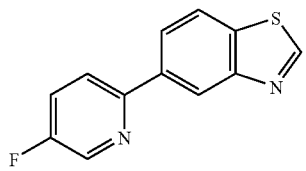 [SMILES: Fc1ccc(-c2ccc3scnc3c2)nc1]

Compound 5-(5-fluoropyridin-2-yl)benzo[d]thiazole (W208) was prepared using the general procedure for Suzuki coupling reaction between 2-bromo-5-fluoropyridine (39 mg, 0.22 mmol) and 5-(4,4,5,5-tetramethyl-1,3,2-dioxaborolan-2-yl)benzo[d]thiazole (53 mg, 0.2 mmol), as a white solid (20 mg, 43%). $^1$H NMR (400 MHz, CDCl$_3$) δ 9.05 (s, 1 H), 8.65 (d, J=1.6 Hz, 1 H), 8.59 (d, J=2.8 Hz, 1 H), 8.14 (dd, J=8.4, 2.0 Hz, 1 H), 8.06 (d, J=8.4 Hz, 1 H), 7.85 (dd, J=8.8, 4.0 Hz, 1 H), 7.52 (td, J=8.4, 2.8 Hz, 1 H); MS (ESI) m/z 231 (M+H$^+$).

Preparation of W209

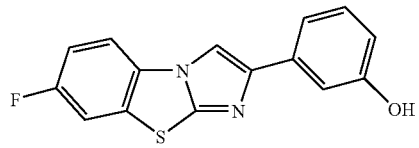 [SMILES: Oc1cccc(-c2cn3c(n2)sc2cc(F)ccc23)c1]

Compound W209 was prepared using the general procedure for cyclization between 6-fluorobenzo[d]thiazol-2-amine (84 mg, 0.5 mmol) and 2-bromo-1-(3-hydroxyphenyl)ethanone (113 mg, 0.55 mmol), as an off-white solid (100 mg, 70%). $^1$H NMR (400 MHz, DMSO-d6) δ 8.77 (s, 1 H), 8.10-8.04 (m, 2 H), 7.49 (td, J=8.8, 2.8 Hz, 1 H), 7.28-7.22 (m, 3 H), 6.73 (dt, J=7.6, 2.0 Hz, 1 H); MS (ESI) m/z 284 (M+H$^+$).

Preparation of W210

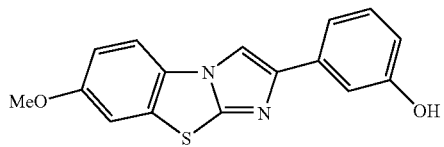 [SMILES: COc1ccc2c(c1)sc1nc(-c3cccc(O)c3)cn12]

Compound W210 was prepared using the general procedure for cyclization between 6-methoxybenzo[d]thiazol-2-amine (90 mg, 0.5 mmol) and 2-bromo-1-(3-hydroxyphenyl)ethanone (113 mg, 0.55 mmol), as an off-white solid (100 mg, 67%). $^1$H NMR (400 MHz, DMSO-d6) δ 8.67 (s, 1 H), 7.95 (d, J=8.8 Hz, 1 H) 7.70 (d, J=2.8 Hz, 1 H), 7.27-7.25 (m, 2 H), 7.22 (t, J=8.0 Hz, 1 H), 7.17 (dd, J=8.8 Hz, 1 H), 6.71-6.68 (m, 1 H), 3.84 (s, 3 H); MS (ESI) m/z 297 (M+H$^+$).

Preparation of W239

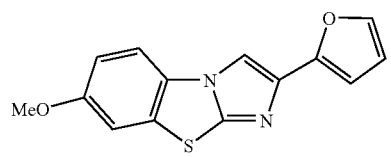

Compound W239 was prepared using the general procedure for cyclization between 6-methoxybenzo[d]thiazol-2-amine (54 mg, 0.3 mmol) and 2-bromo-1-(furan-2-yl)ethanone (63 mg, 0.33 mmol), as a white solid (3 mg, 4%). $^1$H NMR (400 MHz, CDCl$_3$) δ 7.84 (s, 1 H), 7.51 (d, J=8.8 Hz, 1 H), 7.43 (dd, J=1.6, 0.8 Hz, 1 H), 7.22 (d, J=2.0 Hz, 1 H), 7.03 (dd, J=8.8, 2.4 Hz, 1 H), 6.77 (d, J=3.2 Hz, 1 H), 6.49 (dd, J=3.6, 2.0 Hz, 1 H), 3.88 (s, 3 H); MS (ESI) m/z 271 (M+H$^+$).

Preparation of W247

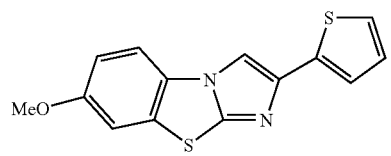 [SMILES: COc1ccc2c(c1)sc1nc(-c3ccco3)cn12]

Compound W247 was prepared using the general procedure for cyclization between 6-methoxybenzo[d]thiazol-2-amine (54 mg, 0.3 mmol) and 2-bromo-1-(thiophen-2-yl)ethanone (68 mg, 0.33 mmol), as a white solid (50 mg, 58%). $^1$H NMR (400 MHz, DMSO-d6) δ 8.62 (s, 1 H), 7.95 (d, J=8.8 Hz, 1 H), 7.70 (d, J=2.4 Hz, 1 H), 7.48 (dd, J=5.2, 1.2 Hz, 1 H), 7.40 (dd, J=3.6, 1.2 Hz, 1 H), 7.17 (dd, J=9.2, 2.8 Hz, 1 H), 7.12 (dd, J=4.8, 3.2 Hz, 1 H), 3.84 (s, 3 H); MS (ESI) m/z 286 (M+H⁺).

Preparation of W248

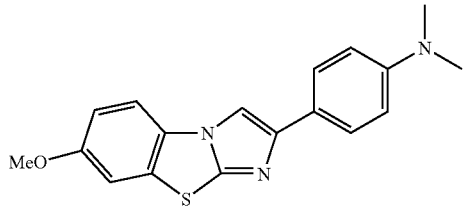 [SMILES: COc1ccc2c(c1)sc1nc(-c3ccc(N(C)C)cc3)cn12]

Compound W248 was prepared using the general procedure for cyclization between 6-methoxybenzo[d]thiazol-2-amine (90 mg, 0.5 mmol) and 2-bromo-1-(4-(dimethylamino)phenyl)ethanone (127 mg, 0.52 mmol), as an off-white solid (150 mg, 74%). ¹H NMR (400 MHz, DMSO-d6) δ 8.69 (s, 1 H), 7.95 (d, J=8.8 Hz, 1 H), 7.75 (d, J=7.76-7.73 (m, 3 H), 7.21 (dd, J=8.8, 2.4 Hz, 1 H), 7.08 (m, 2 H), 3.85 (s, 3 H), 3.03 (s, 6 H); MS (ESI) m/z 324 (M+H⁺).

Preparation of W270

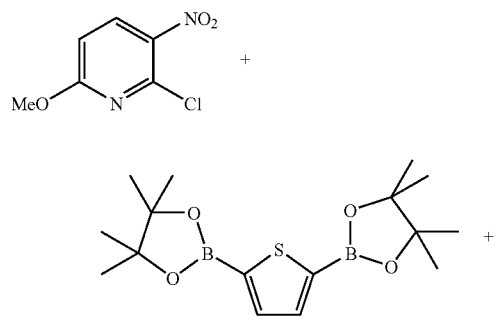

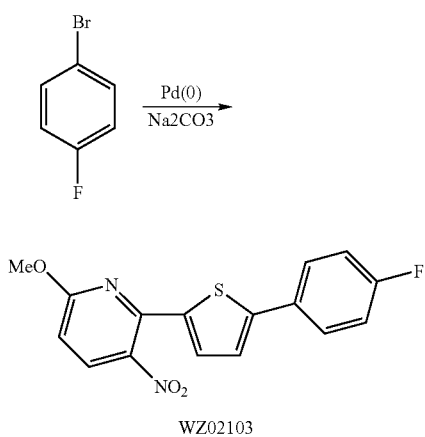

-continued

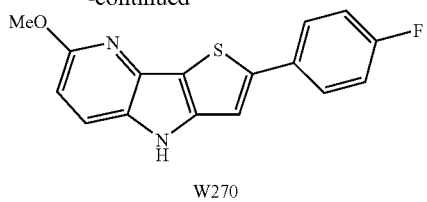

W270

Preparation of 2-(5-(4-fluorophenyl)thiophen-2-yl)-6-methoxy-3-nitropyridine (WZ02103)

A suspension of 2-chloro-6-methoxy-3-nitropyridine (94 mg, 0.5 mmol), 2,5-bis(4,4,5,5-tetramethyl-1,3,2-dioxaborolan-2-yl)thiophene (168 mg, 0.5 mmol), 1-bromo-4-fluorobenzene (105 mg, 0.6 mmol), 1.5 mL of dioxane, 1.5 mL of 1 M Na₂CO₃, and tetrakis(triphenylphosphine)palladium (29 mg, 0.025 mmol) was heated in a microwave reactor at 95 C for 10 min. It was concentrated under reduced pressure and the residue was chromatographed (EtOAc/hexane) to afford 2-(5-(4-fluorophenyl)thiophen-2-yl)-6-methoxy-3-nitropyridine (WZ02103) as a yellow solid (20 mg, 12%). MS (ESI) m/z 330 (M+H⁺).

Preparation of W270

The above compound (20 mg, 0.6 mmol) in 0.5 mL of triethyl phosphite was heated at 147 C for 5 h and cooled to rt. The volatiles were removed under reduced pressure and the crude product was purified by silica chromatography (EtOAc/hexane) to afford W270 as a yellow solid (6 mg, 33%). ¹H NMR (400 MHz, acetone-d6) δ 10.22 (brs, 1 H), 7.71-7.67 9m, 3 H), 7.34 (s, 1 H), 7.13 (t, J=8.4 Hz, 2 H), 6.63 (d, J=8.8 Hz, 1 H), 3.99 (s, 3 H); MS (ESI) m/z 299 (M+H⁺).

Preparation of W281

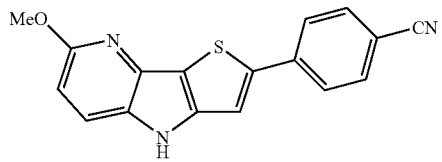 [SMILES: COc1ccc2[nH]c3cc(-c4ccc(C#N)cc4)sc3c2n1]

Compound W281 was synthesized using the same procedure for the preparation of W270 from 2-chloro-6-methoxy-3-nitropyridine (94 mg, 0.5 mmol), 2,5-bis(4,4,5,5-tetramethyl-1,3,2-dioxaborolan-2-yl)thiophene (168 mg, 0.5 mmol), and 4-bromobenzonitrile (91 mg, 0.6 mmol), as a yellow solid (5 mg, total yield 3.2%). ¹H NMR (400 MHz, acetone-d6) δ 10.34 (brs, 1 H), 7.86-7.84 (m, 2 H), 7.43-7.72 (m, 3 H), 7.65 (s, 1 H), 6.68 (d, J=8.8 Hz, 1 H), 4.00 (s, 3 H); MS (ESI) m/z 306 (M+H⁺).

Preparation of 2-(4-fluorophenyl)-7-methoxy-5H-imidazo[1,2-b]indazole (W289)

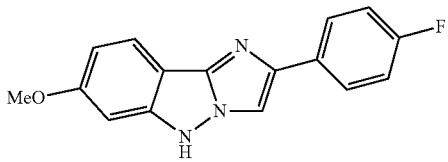 [SMILES: COc1ccc2c(c1)[nH]n1cc(-c3ccc(F)cc3)nc21]

Compound 2-(4-fluorophenyl)-7-methoxy-5H-imidazo[1,2-b]indazole (W289) was prepared using the general procedure for cyclization between 6-methoxy-1H-indazol-3-amine (80 mg, 0.5 mmol) and 2-bromo-1-(4-fluorophenyl)ethanone (119 mg, 0.55 mmol), as an off-white solid (30 mg, 16%). $^1$H NMR (400 MHz, DMSO-d6) δ 8.64 (s, 1 H), 7.94-7.91 (m, 2 H), 7.83 (d, J=8.8 Hz, 1 H), 7.44 (m, 2 H), 7.11 (d, J=2.4 Hz, 1 H), 6.96 (dd, J=9.2, 2.0 Hz, 1 H), 3.89 (s, 3 H); MS (ESI) m/z 282 (M+H$^+$).

Preparation of 3-(7-methoxy-5H-imidazo[1,2-b]indazol-2-yl)phenol: W298

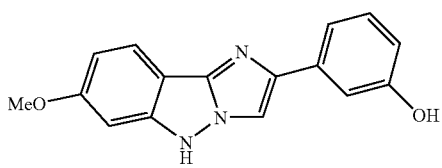 [SMILES: COc1ccc2c(c1)[nH]n1cc(-c3cccc(O)c3)nc21]

Compound 3-(7-methoxy-5H-imidazo[1,2-b]indazol-2-yl)phenol (W298) was prepared using the general procedure for cyclization between 6-methoxy-1H-indazol-3-amine (80 mg, 0.5 mmol) and 2-bromo-1-(3-hydroxyphenyl)ethanone (107 mg, 0.55 mmol), as a white solid (40 mg, 22%). $^1$H NMR (400 MHz, DMSO-d6) δ 9.84 (brs, 1 H), 8.63 (s, 1 H), 7.85 (d, J=9.2 Hz, 1 H), 7.36 (t, J=8.0 Hz, 1 H), 7.31-7.29 (m, 1 H), 7.24 (t, J=2.0 Hz, 1 H), 7.13 (d, J=2.0 Hz, 1 H), 6.99 (dd, J=9.2, 2.0 Hz, 1 H), 6.88 (m, 1 H), 3.90 (s, 3 H); MS (ESI) m/z 280 (M+H$^+$).

Preparation of 7-methoxy-2-(4-methoxyphenyl)-5H-imidazo[1,2-b]indazole (W302)

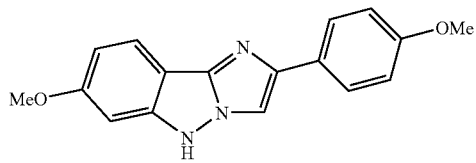 [SMILES: COc1ccc(-c2cn3[nH]c4cc(OC)ccc4c3n2)cc1]

Compound 7-methoxy-2-(4-methoxyphenyl)-5H-imidazo[1,2-b]indazole (W302) was prepared using the general procedure for cyclization between 6-methoxy-1H-indazol-3-amine (90 mg, 0.3 mmol) and 2-bromo-1-(4-methoxyphenyl)ethanone (72 mg, 0.31 mmol), as white solid (50 mg, 57%). $^1$H NMR (400 MHz, DMSO-d6) δ 8.57 (s, 1 HO, 7.85-7.81 (m, 3 H), 7.16-7.12 (m, 3 H), 6.99 (dd, J=8.8, 2.4 Hz, 1 H), 3.90 (s, 3 H), 3.84 (s, 3 H); MS (ESI) m/z 294 (M+H$^+$).

Preparation of 2-(5-fluoropyridin-3-yl)-6-methoxy-4H-thieno[3,2-b]indole: W309

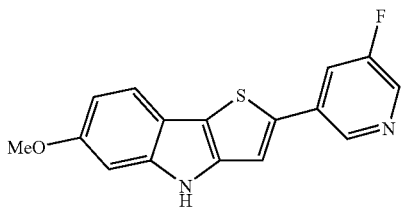 [SMILES: COc1ccc2c(c1)[nH]c1cc(-c3cncc(F)c3)sc12]

Compound 2-(5-fluoropyridin-3-yl)-6-methoxy-4H-thieno[3,2-b]indole (W309) was synthesized using the same procedure for the preparation of W270 from 1-bromo-4-methoxy-2-nitrobenzene (104 mg, 0.45 mmol), 2,5-bis(4,4,5,5-tetramethyl-1,3,2-dioxaborolan-2-yl)thiophene (168 mg, 0.5 mmol), and 3-bromo-5-fluoropyridine (105 mg, 0.6 mmol), as a yellow solid (10 mg, total yield 6.7%). $^1$H NMR (400 MHz, acetone-d6) δ 10.36 (brs, 1 H), 8.76 (s, 1 H), 8.33 (s, 1 H), 7.83 (m, 2 H), 7.77 (m, 1 H), 7.62-7.60 (m, 1 H), 7.02 (s, 1 H), 6.80 (d, J=8.8 Hz, 1 H), 3.86 (s, 3 H); MS (ESI) m/z 299 (M+H$^+$).

Preparation of W328

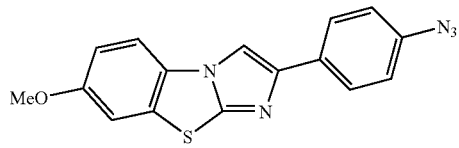 [SMILES: COc1ccc2c(c1)sc1nc(-c3ccc(N=[N+]=[N-])cc3)cn12]

Compound W328 was prepared using the general procedure for cyclization between 6-methoxybenzo[d]thiazol-2-amine (54 mg, 0.3 mmol) and 1-(4-azidophenyl)-2-bromoethanone (74 mg, 0.31 mmol), as an off-white solid (35 mg, 29%). $^1$H NMR (400 MHz, DMSO-d6) δ 8.78 (s, 1 H), 7.92 (d, J=8.8 Hz, 1 H), 7.87 (d, J=8.4 Hz, 2 H), 7.72 (d, J=2.0 Hz, 1 H), 7.21 (d, J=8.4 Hz, 2 H), 7.19 (dd, J=8.8, 2.8 Hz, 1 H), 3.84 (s, 3 H); MS (ESI) m/z 322 (M+H$^+$).

Preparation of W331

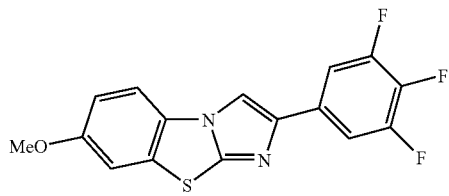 [SMILES: COc1ccc2c(c1)sc1nc(-c3cc(F)c(F)c(F)c3)cn12]

Compound W331 was prepared using the general procedure for cyclization between 6-methoxybenzo[d]thiazol-2-amine (90 mg, 0.5 mmol) and 2-bromo-1-(3,4,5-trifluorophenyl)ethanone (134 mg, 0.52 mmol), as an off-white solid (45 mg, 21%). $^1$H NMR (400 MHz, DMSO-d6) δ 8.80 (s, 1 H), 7.80 (d, J=8.8 Hz, 1 H), 7.70 (m, 3 H), 7.17 (dd, J=8.8 Hz, 1 H), 3.83 (s, 1 H); MS (ESI) m/z 335 (M+H⁺).

Preparation of W332

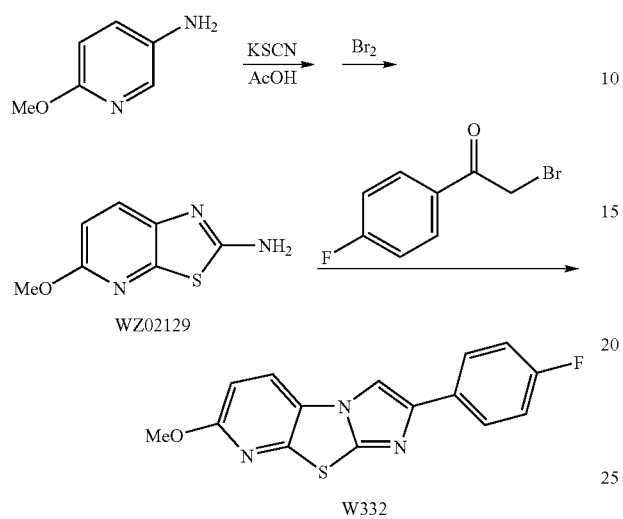

Preparation of WZ02129

A solution of 6-methoxypyridin-3-amine (2.5 g, 20 mmol) in 5 mL of AcOH was slowly added to a solution of KSCN in 50 mL of AcOH with vigorously stirring at 0 C, followed by a solution of bromine in 3 mL of AcOH. The mixture was stirring at 0 C for 1 h and slowly warmed to rt and stirring was continued for 30 min at rt. Solid was collected via filtration and washed with AcOH (2×20 mL), and partitioned between EtOAc (100 mL) and NaHCO₃ (sat. 80 mL). Organic phase was dried over MgSO4 and filtered and the filtrate was concentrated to afford 5-methoxythiazolo[5,4-b]pyridin-2-amine (WZ02129) as a tan solid (2.5 g, 69%). MS (ESI) m/z 182 (M+H⁺).

Preparation of W332

A mixture of the above compound (90 mg, 0.5 mmol) and 2-bromo-1-(4-fluorophenyl)ethanone (114 mg, 0.52 mmol) in 1.5 mL of EtOH was heated at 85 C for 5 h and cooled to rt. Solid was collected via filtration and washed with EtOAc (4 mL), and dried under high vacuum to afford W332 as a white solid (70 mg, 37%). ¹H NMR (400 MHz, DMSO-d6) δ 8.73 (s, 1 H), 8.34 (d, J=8.8H, 1 H), 7.89-7.85 (m, 2 H), 7.28 (m, 2 H), 7.08 (d, J=8.8 Hz, 1 H), 3.94 (s, 3 H); MS (ESI) m/z 300 (M+H⁺).

Preparation of W333

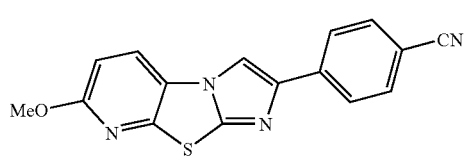 [SMILES: COc1ccc2c(n1)sc1nc(-c3ccc(C#N)cc3)cn12]

Compound W333 was prepared using the general procedure for the synthesis of W332 from 5-methoxythiazolo[5,4-b]pyridin-2-amine (90 mg, 0.5 mmol) and 4-(2-bromoacetyl)benzonitrile (117 mg, 0.52 mmol), as a white solid (73 mg, 38%). ¹H NMR (400 MHz, DMSO-d6) δ 8.93 (s, 1 H), 8.33 (d, J=8.8 Hz, 1 H), 8.01-7.99 (m, 2 H), 7.90-7.88 (m, 2 H), 7.08 (d, J=8.8 Hz, 1 H), 3.95 (s, 3 H); MS (ESI) m/z 307 (M+H⁺).

Preparation of W353

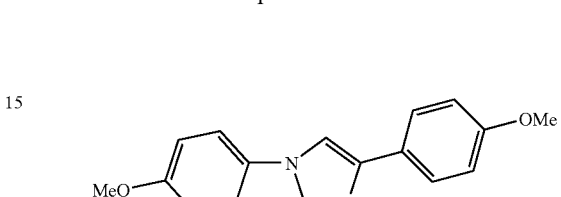

Compound W353 was prepared using the general procedure for the synthesis of W332 from 5-methoxythiazolo[5,4-b]pyridin-2-amine (90 mg, 0.5 mmol) and 2-bromo-1-(4-methoxyphenyl)ethanone (119 mg, 0.52 mmol), as a white solid (62 mg, 31%). ¹H NMR (400 MHz, DMSO-d6) δ 8.62 (s, 1 H), 8.33 (d, J=8.8 Hz, 1 H), 7.77 (m, 2 H), 7.07 (d, J=8.8 Hz, 1 H), 7.02 (m, 2 H), 3.94 (s, 3 H), 3.79 (s, 3 H); MS (ESI) m/z 312 (M+H⁺).

Preparation of W354

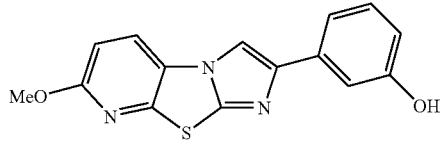 [SMILES: COc1ccc2c(n1)sc1nc(-c3cccc(O)c3)cn12]

Compound W354 was prepared using the general procedure for the synthesis of W332 from 5-methoxythiazolo[5,4-b]pyridin-2-amine (90 mg, 0.5 mmol) and 2-bromo-1-(3-hydroxyphenyl)ethanone (112 mg, 0.52 mmol), as a white solid (70 mg, 37%). ¹H NMR (400 MHz, DMSO-d6) δ 8.70 (s, 1 H), 8.38 (d, J=8.8 Hz, 1 H), 7.27-7.21 (m, 3 H), 7.09 (d, J=8.8 Hz, 1 H), 6.71 (dt, J=8.0, 2.0 Hz, 1 H), 3.95 (s, 3 H); MS (ESI) m/z 298 (M+H⁺).

Preparation of W355

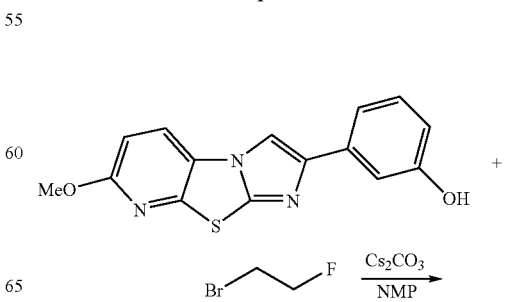

-continued

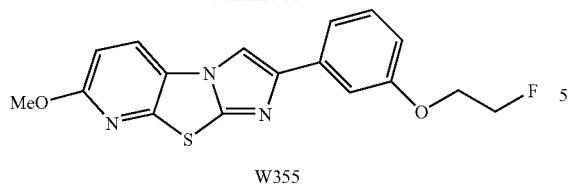

W355

To W354 (38 mg, 0.1 mmol) and 1-bromo-2-fluoroethane (50 mg, 0.4 mmol) in 0.4 mL of NMP was added $Cs_2CO_3$ (98 mg, 0.3 mmol). The mixture was stirred at rt for 5 hours and quenched by adding 10 mL water. Solid was collected by filtration and washed with ether (2×3 mL) and dried under high vacuum to afford a white solid. (31 mg, 90%). $^1$H NMR (400 MHz, DMSO-d6) δ 8.75 (s, 1 H), 8.31 (d, J=8.8 Hz, 1 H), 7.46-7.44 (m, 2 H), 7.36 (t, J=8.4 Hz, 1 H), 7.08 (d, J=8.8 Hz, 1 H), 6.90 (m, 1 H), 4.84 (m, 1 H), 4.72 (m, 1 H), 4.34 (m, 1 H), 4.26 (m, 1 H) 3.95 (s, 3 H); MS (ESI) /z 344 (M+H$^+$).

Preparation of W356

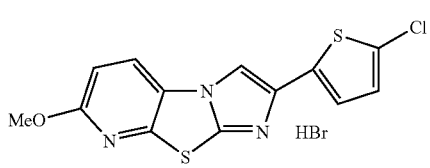

Compound W354 was prepared using the general procedure for the synthesis of W332 from 5-methoxythiazolo[5,4-b]pyridin-2-amine (90 mg, 0.5 mmol) and 2-bromo-1-(5-chlorothiophen-2-yl)ethanone (124 mg, 0.52 mmol), as a yellow solid (60 mg, 30%). $^1$H NMR (400 MHz, DMSO-d6) δ 8.63 (s, 1 H), 8.34 (d, J=8.8 Hz, 1 H), 7.25 (d, J=4.0 1 H), 7.13 (d, J=4.0 Hz, 1 H), 7.07 (d, J=8.8 Hz, 1 H), 3.94 (s, 3 H); MS (ESI) m/z 322 (M+H$^+$).

Preparation of W357

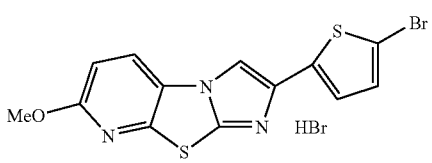 [SMILES: COc1ccc2c(n1)sc1nc(-c3ccc(Br)s3)cn12 ; Br]

Compound W357 was prepared using the general procedure for the synthesis of W332 from 5-methoxythiazolo[5,4-b]pyridin-2-amine (90 mg, 0.5 mmol) and 2-bromo-1-(5-bromothiophen-2-yl)ethanone (48 mg, 0.52 mmol), as a yellow solid (73 mg, 32%). $^1$H NMR (400 MHz, DMSO-d6) δ 8.63 (s, 1 H), 8.34 (d, J=8.8 Hz, 1 H), 7.22 (s, 2 H), 7.07 (d, J=8.8 Hz, 1 H), 3.94 (s, 3 H); MS (ESI) m/z 367.9 (M+H$^+$).

Preparation of W357

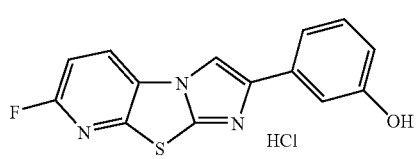 [SMILES: Oc1cccc(-c2cn3c(n2)sc2nc(F)ccc23)c1 ; Cl]

Compound W357 was prepared using the general procedure for the synthesis of W332 from 5-fluorothiazolo[5,4-b]pyridin-2-amine (60 mg, 0.35 mmol) and 2-bromo-1-(3-hydroxyphenyl)ethanone (80 mg, 0.37 mmol), as a yellow solid (33 mg, 29%). $^1$H NMR (400 MHz, DMSO-d6) δ 9.51 (brs, 1 H), 8.73 (s, 1 H), 8.58 (dd, J=8.8, 6.8 Hz, 1 H), 7.47 (dd, J=8.8, 1.6 Hz, 1 H), 7.29-7.21 (m, 3 H), 6.70 (m, 1 H); MS (ESI) m/z 286 (M+H$^+$).

N-(2-fluoroethyl)-6-(4-(methylamino)phenyl)benzo [d]thiazol-2-amine (W368)

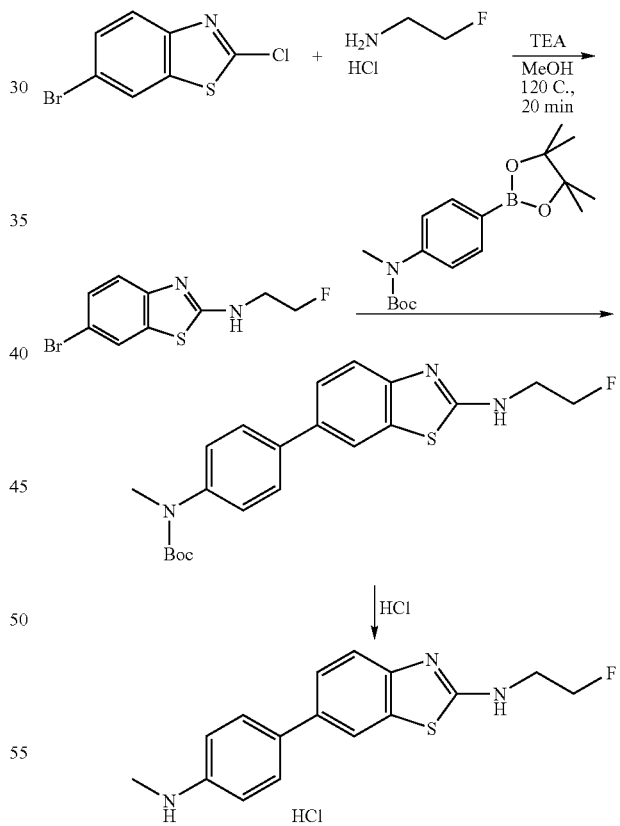

6-Bromo-N-(2-fluoroethyl)benzo[d]thiazol-2-amine

A mixture of 6-bromo-2-chlorobenzo[d]thiazole (248 mg, 1 mmol), 2-fluoroethanamine hydrochloride (200 mg, 2 mmol), and TEA (303 mg, 3 mmol) in 3 mL MeOH was heated at 120° C. in a microwave reactor for 20 min. After cooling to rt, the mixture was concentrated and chromatographed (6% to 60% EtOAc in hexane) to afford 6-bromo-N-(2-fluoroethyl)benzo[d]thiazol-2-amine as a white solid (150 mg, 54%). MS (ESI) m/z 276.9 (M+H⁺).

tert-butyl 4-(2-(2-fluoroethylamino)benzo[d]thiazol-6-yl)phenyl(methyl)carbamate A mixture of afford 6-bromo-N-(2-fluoroethyl)benzo[d]thiazol-2-amine (55 mg, 0.2 mmol), tert-butyl methyl(4-(4,4,5,5-tetramethyl-1,3,2-dioxaborolan-2-yl)phenyl)carbamate (66 mg, 0.2 mmol), and tetrakis(triphenylphosphine)palladium (7 mg, 0.006 mmol) in 2 mL dioxane and 0.5 mL of a 1 M Na₂CO₃ aqueous solution was heated at 100° C. in a microwave reactor for 10 min. After cooling to rt, it was diluted with EtOAc (30 mL) and washed with brine (30 mL), dried over MgSO₄ and concentrated. The crude product was purified with silica chromatography (5% to 30% EtOAc in hexane) to afford tert-butyl 4-(2-(2-fluoroethylamino)benzo[d]thiazol-6-yl)phenyl(methyl)carbamate as a clear wax (25 mg, 31%). MS (ESI) m/z 402 (M+H⁺).

N-(2-Fluoroethyl)-6-(4-(methylamino)phenyl)benzo[d]thiazol-2-amine hydrochloride (W368)

Tert-butyl 4-(2-(2-fluoroethylamino)benzo[d]thiazol-6-yl)phenyl(methyl)carbamate (25 mg, 0.06 mmol) was treated with 4 mL of 4 M HCl dioxane solution for 2 h and concentrated. The residue was washed with ether (2×3 mL) and dried under high vacuum to afford N-(2-fluoroethyl)-6-(4-(methylamino)phenyl)benzo[d]thiazol-2-amine hydrochloride as a yellow solid (15 mg, 74%). ¹H NMR (400 MHz, methanol-d4) δ 8.18 (s, 1 H), 7.91-7.88 (m, 2 H), 7.86-7.84 (m, 1 H), 7.67 (m, 3 H), 4.82 (t, J=4.8 Hz, 1 H), 4.70 (t, J=4/8 Hz, 1 H), 3.99 (t, J=4.4 Hz, 1 H), 3.93 (t, J=4.4 Hz, 1 H), 3.13 (s, 3 H); MS (ESI) m/z 302 (M+H⁺).

Preparation of 4-(2-(2-fluoroethylthio)benzo[d]thiazol-6-yl)-N-methylaniline (W382)

6-Bromobenzo[d]thiazole-2-thiol

A mixture of 6-bromo-2-chlorobenzo[d]thiazole (250 mg, 1 mmol) and thiourea (228 mg, 3 mmol) in 2 mL of MeOH in a microwave tube was heated in a microwave reactor for 10 min at 120° C. The mixture was concentrated and the solid was collected through filtration and washed with water and dried under high vacuum to afford 6-bromobenzo[d]thiazole-2-thiol as a yellow solid (200 mg, 81%). MS (ESI) m/z 247.9 (M+H⁺).

6-Bromo-2-(2-fluoroethylthio)benzo[d]thiazole

To 6-bromobenzo[d]thiazole-2-thiol (160 mg, 0.65 mmol) and 1-bromo-2-fluoroethane (165 mg, 1.3 mmol) in 5 mL of NMP was added Cs₂CO₃ (635 mg, 1.95 mmol). The mixture was stirred at rt for 5 hours. It was added water (20 mL) and precipitate was collected through filtration and washed with water (10 mL) and dried under high vacuum. The crude product was purified with silica chromatography (5% to 30% EtOAc in hexane) to afford 6-Bromo-2-(2-fluoroethylthio)benzo[d]thiazole as a yellow solid (88 mg, 46%). MS (ESI) m/z 291.9, 293.9 (M+H⁺).

Tert-butyl 4-(2-(2-fluoroethylthio)benzo[d]thiazol-6-yl)phenyl(methyl)carbamate

A mixture of 6-Bromo-2-(2-fluoroethylthio)benzo[d]thiazole (60 mg, 0.2 mmol), tert-butyl methyl(4-(4,4,5,5-tetramethyl-1,3,2-dioxaborolan-2-yl)phenyl)carbamate (68 mg, 0.2 mmol), and tetrakis(triphenylphosphine)palladium (11 mg, 0.01 mmol) in 2 mL dioxane and 0.5 mL of a 1 M Na₂CO₃ aqueous solution was heated at 95° C. in a microwave reactor for 10 min. After cooling to rt, it was diluted with EtOAc (30 mL) and washed with brine (30 mL), dried over MgSO₄ and concentrated. The crude product was purified with silica chromatography (5% to 30% EtOAc in hexane) to afford tert-butyl 4-(2-(2-fluoroethylthio)benzo[d]thiazol-6-yl)phenyl(methyl)carbamate as a clear wax (15 mg, 18%). MS (ESI) m/z 419 (M+H⁺).

4-(2-(2-Fluoroethylthio)benzo[d]thiazol-6-yl)-N-methylaniline (W382)

Tert-butyl 4-(2-(2-fluoroethylthio)benzo[d]thiazol-6-yl)phenyl(methyl)carbamate (15 mg, 0.036 mmol) was treated with 3 mL of 4 M HCl dioxane solution for 2 h and concentrated. The crude product was purified with RP-HPLC (20% to 80% TFA buffered MeCN in water) to afford 4-(2-(2-fluoroethylthio)benzo[d]thiazol-6-yl)-N-methylaniline as a yellow wax (4 mg, 25%). ¹H NMR (400 MHz, CDCl₃) δ 7.84

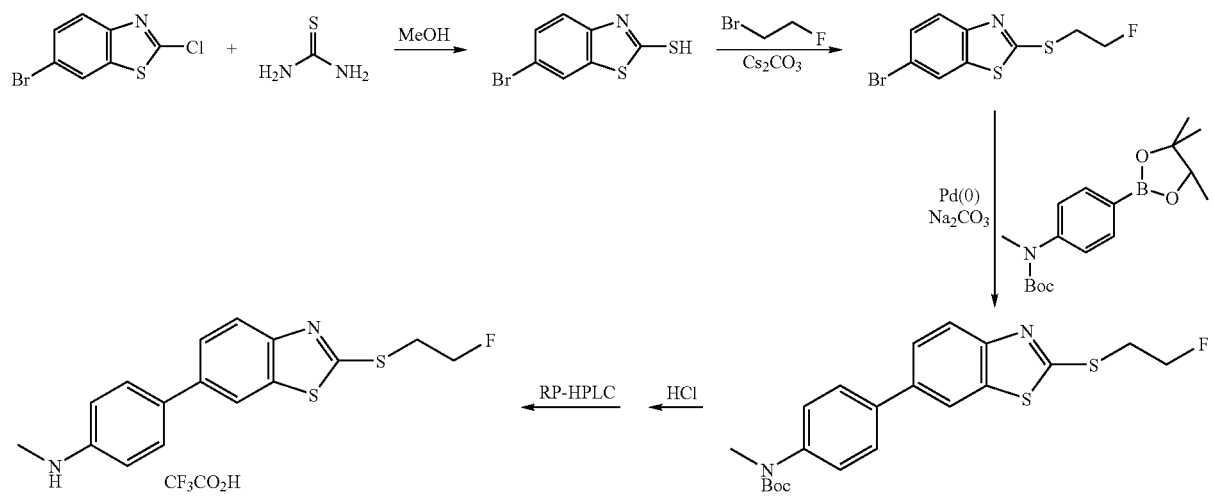

(d, J=8.4 Hz, 1 H), 7.81 (d, J=1.6 Hz, 1 H), 7.58-7.56 (m, 2 H), 7.53 (dd, J=8.8, 2.0 Hz, 1 H), 7.34-7.32 (m, 2 H), 4.86 (t, J=6.4 Hz, 11 H), 4.74 (t, J=6.4 Hz, 1 H), 3.73 (t, J=6.4 Hz, 1 H), 3.68 (t, J=6.4 Hz, 1 H), 3.02 (s, 3 H); MS (ESI) m/z 319 (M+H$^+$).

N-(2-fluoroethyl)-5-(4-(methylamino)phenyl)benzo[d]thiazol-2-amine hydrochloride (W390)

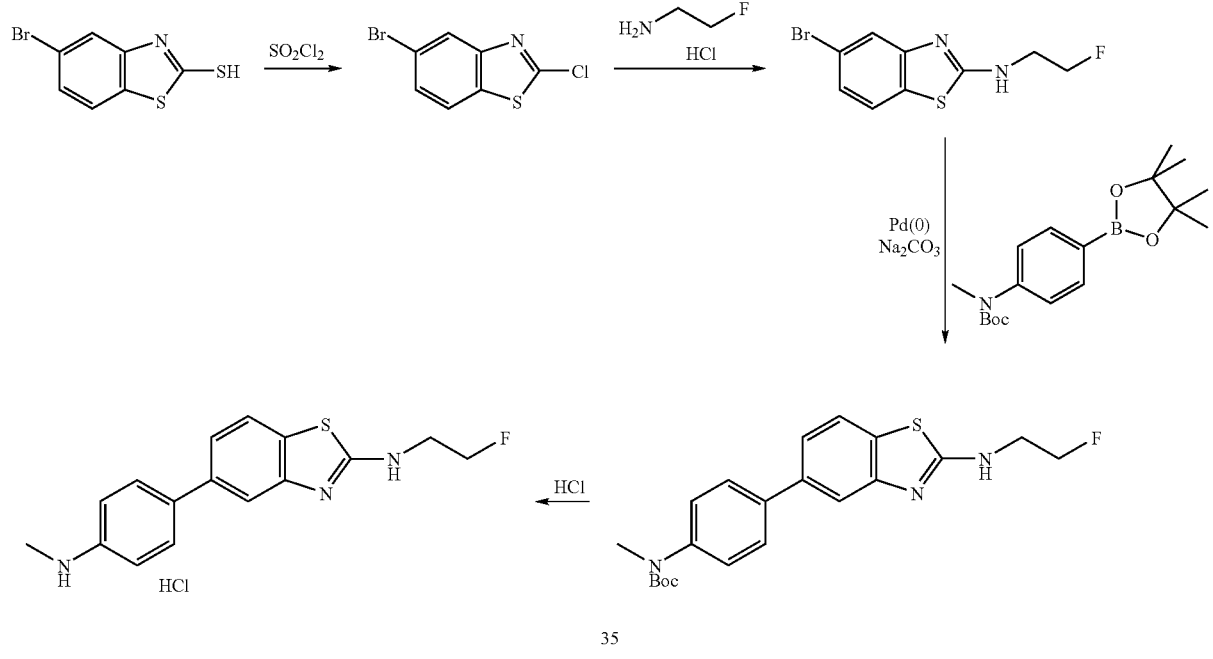

5-bromo-2-chlorobenzo[d]thiazole

To sulfuryl dichloride (5 mL) was added 5-bromobenzo[d]thiazole-2-thiol (450 mg, 1.8 mmol) portionwise. The mixture was stirred at rt for 1 hour and heated at 50° C. for 15 min. After cooling to rt, the reaction mixture was slowly poured onto ice (50 g) and the resulting suspension was stirred for 30 min. Solid was collected through filtration and washed with water (10 mL) and dried under high vacuum to afford 5-bromo-2-chlorobenzo[d]thiazole as a pink solid (470 mg, 100%). MS (ESI) m/z 248 (M+H$^+$).

5-Bromo-N-(2-fluoroethyl)benzo[d]thiazol-2-amine

To bromo-2-chlorobenzo[d]thiazole (400 mg, 1.6 mmol) and 2-fluoroethanamine hydrochloride (318 mg, 3.2 mmol), and TEA (565 mg, 5.6 mmol) in 3 mL MeOH was heated at 120° C. in a microwave reactor for 20 min. After cooling to rt, the mixture was concentrated and chromatographed (6% to 60% EtOAc in hexane) to afford 5-Bromo-N-(2-fluoroethyl)benzo[d]thiazol-2-amine as a yellow solid (140 mg, 32%). MS (ESI) m/z 274.9 (M+H$^+$).

Tert-butyl 4-(2-(2-fluoroethylamino)benzo[d]thiazol-5-yl)phenyl(methyl)carbamate A mixture of 5-Bromo-N-(2-fluoroethyl)benzo[d]thiazol-2-amine (60 mg, 0.2 mmol), tert-butyl methyl(4-(4,4,5,5-tetramethyl-1,3,2-dioxaborolan-2-yl)phenyl)carbamate (68 mg, 0.2 mmol), and tetrakis(triphenylphosphine)palladium (11 mg, 0.01 mmol) in 2 mL dioxane and 0.5 mL of a 1 M Na$_2$CO$_3$ aqueous solution was heated at 95° C. in a microwave reactor for 10 min. After cooling to rt, it was diluted with EtOAc (30 mL) and washed with brine (30 mL), dried over MgSO$_4$ and concentrated. The crude product was purified with silica chromatography (5% to 50% EtOAc in hexane) to afford tert-butyl 44242-fluoroethylamino)benzo[d]thiazol-5-yl)phenyl(methyl)carbamate as a white solid (60 mg, 75%). MS (ESI) m/z 402 (M+H$^+$).

N-(2-fluoroethyl)-5-(4-(methylamino)phenyl)benzo[d]thiazol-2-amine hydrochloride (W390)

Tert-butyl tert-butyl 4-(2-(2-fluoroethylamino)benzo[d]thiazol-5-yl)phenyl(methyl)carbamate (60 mg, 0.15 mmol) was treated with 5 mL of 4 M HCl dioxane solution for 2 h and concentrated. The residue was washed with ether (2×5 mL) and dried under high vacuum to afford N-(2-fluoroethyl)-5-(4-(methylamino)phenyl)benzo[d]thiazol-2-amine hydrochloride (W390) as a yellow solid (40 mg, 88%). $^1$H NMR (400 MHz, methanol-d4) δ 7.94 (d, J=8.4 Hz, 1 H), 7.91-7.87 (m, 2 H), 7.79 (d, J=1.6 Hz, 1 H), 7.79 (dd, J=8.4, 1.6 Hz, 1 H), 7.64-7.61 (m, 2 H), 4.81 (t, J=4.8 Hz, 1 H), 4.69 (t, J=4.8 Hz, 1 H), 3.97 (t, J=4.8 Hz, 1 H), 3.91 (t, J=4.8 Hz, 1 H), 3.13 (s, 3 H); MS (ESI) m/z 302 (M+H$^+$).

General Procedure for N-Arylation

To a 50 mL round bottomed flask equipped with a magnetic stir bar containing DCM (100 vol) was placed benzothiazolinone (1 equiv). To this solution was added boronic acid (2 equiv). Cu(OAc)$_2$ (1.1 equiv), TEMPO (1.1 equiv), MS ( ), Et$_3$N (2 equiv) and the reaction was allowed to stir at RT for 24-48 h. After the reaction was complete, DCM was removed in vacuo. The residue was purified over silica gel using Hexanes-EtOAC as the eluent to afford the final compound

General Procedure for Demethylation

To a 50 mL round bottomed flask equipped with a magnetic stir bar containing DCM (100 vl) was placed methoxy compound (1 equiv). To this reaction mixture at 0° C., added 1.0 M BBr$_3$ in DCM (4-5 equiv) and stir from 0° C. to room temp for 1-2 h. After reaction was complete, DCM was removed in vacuo. The residue was neutralized with sat NaHCO₃ solution and extracted with EtOAC. The EtOAc layer was dried over Na₂SO4 and evaporated to dryness. To this residue, ether and hexane was added and demethylated compounds as a solid was filtered.

3-Benzyl-6-methoxybenzothiazol-2(3H)-one W-124

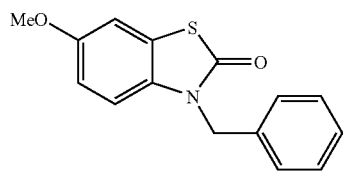 [SMILES: COc1ccc2c(c1)sc(=O)n2Cc1ccccc1]

A solution of 6-methoxybenzthiazol-2-one (1, 0.036 g, 0.2 mmol), anhydrous K₂CO₃ (0.110 g, 0.8 mmol, 4 eq) and benzyl bromide (0.035 L, 0.3 mmol, 1.5 eq) was stirred in anhydrous DMF (2 mL) at 120° C. for 2 h. The reaction mixture was cooled and poured in to water, extracted with EtOAc. The EtOAc layer washed with water (2×10 mL), dried over Na₂SO₄ and evaporated to dryness. The crude mixture was purified by Combiflash, using hexane-ethylacetate (7:3) as a solvent afforded W-124 as a solid (0.037 g, 68%) as colorless oil; ¹H NMR (CDCl₃): δ 7.36-7.25 (5H, m), 7.0 (1H, d, J=2.4 Hz), 6.85 (1H, d, J=8.8 Hz), 6.77 (1H, dd, J=8.8 and 2.8 Hz), 5.12 (2H, s), 3.79 (3H, s); MS: 274.0 (M+H⁺).

3-Benzyl-6-hydroxybenzothiazol-2(3H)-one W-128

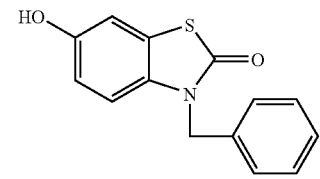 [SMILES: O=c1sc2cc(O)ccc2n1Cc1ccccc1]

General experimental procedure for demethylation was followed. Reaction was performed on a 0.030 g. Isolated 0.015 g (52%) of W-128 as off white solid. ¹H NMR (Acetone-d₆): δ 8.44 (1H, br s), 7.33 (2H, d, J=4.8 Hz), 7.29 (1H, m), 7.09 (1H, d, J=2.8 Hz), 7.0 (1H, d, J=8.0 Hz), 6.76 (1H, dd. J=8.8 and 3.2 Hz), 5.18 (2H, s), 2.82 (3H, s); MS: 258 (M+H⁺).

3-(4-Dimethylamino)-phenyl-6-methoxybenzothiazole-2(3H)-one W-125

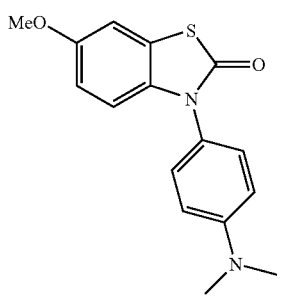 [SMILES: COc1ccc2c(c1)sc(=O)n2-c1ccc(N(C)C)cc1]

General experimental procedure for N-arylation was followed. Reaction was performed on a 0.1 g scale. Product eluted out in 20-30% EtOAc:Hexanes mixture in a gradient elution on a Combiflash purification system. Isolated 0.117 g (70%) of W-125 as off white solid. ¹H NMR (CDCl₃): δ 7.26 (1H, br s), 7.21 (2H, dt, J=9.2 and 2.4 Hz), 7.05 (1H, d, J=2.8 Hz), 6.82 (2H, dt, J=9.2 and 2.4 Hz), 6.76 (1H, dd, J=9.2 and 2.4 Hz), 6.71 (1H, d, J=9.2 Hz), 3.81 (3H, s), 3.03 (6H, s); MS: 301 (M+H⁺).

(E)-3-(4-Fluorostyryl)-6-methoxybenzo[d]thiazol-2(3H)-one W-147

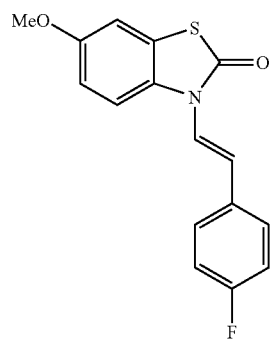 [SMILES: COc1ccc2c(c1)sc(=O)n2/C=C/c1ccc(F)cc1]

General experimental procedure for N-arylation was followed. Reaction was performed on a 0.1 g scale. Product eluted out in 20-30% EtOAc:hexanes mixture in a gradient elution on a Combiflash purification system. Isolated 0.068 g (41%) of W-147 as of white solid. ¹H NMR (CDCl₃): δ 7.44 (2H, tt, J=8.8 and 2.4 Hz), 7.2 (2H, dd, J=4.8 and 4.0 Hz), 7.07 (2H, td, J=8.8 and 2.4 Hz), 7.05 (1H, d, J=6.8 Hz), 7.01 (1H, d, J=2.4 Hz), 6.90 (1H, dd, J=8.8 and 2.4 Hz), 3.85 (3H, s); MS: 302 (M+H⁺).

(E)-3-(3-Fluorostyryl)-6-methoxybenzo[d]thiazol-2(3H)-one W-149

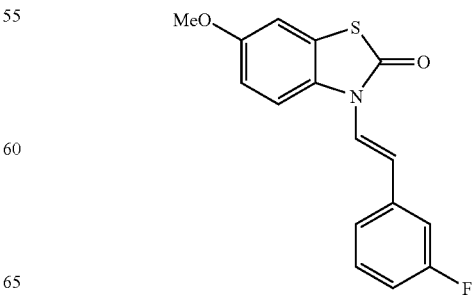

General experimental procedure for N-arylation was followed. Reaction was performed on a 0.053 g scale. Product eluted out in 20-30% EtOAc:hexanes mixture in a gradient elution on a Combiflash purification system. Isolated 0.047 g (96%) of W-149 as solid. $^1$H NMR (CDCl$_3$): δ 7.3 (2H, m), 7.24 (3H, m), 7.16 (1H, dt, J=11.6 and 2.4 Hz), 7.15 (1H, d, J=14.8 Hz), 6.91 (1H, dd, J=8.8 and 2.4 Hz), 3.84 (3H, s); 302 (M+H$^+$).

(E)-3-(4-Methoxystyryl)-6-nitrobenzo[d]thiazol-2(3H)-one W 129

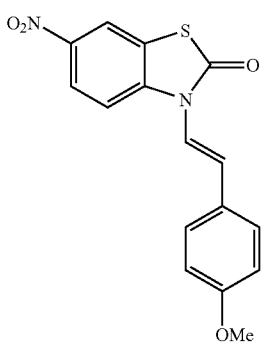 [SMILES: COc1ccc(/C=C/n2c(=O)sc3cc([N+](=O)[O-])ccc32)cc1]

General experimental procedure for N-arylation was followed. Reaction was performed on a 0.1 g scale. Product eluted out in 20-30% EtOAc-hexanes mixture in a gradient elution on a Combiflash purification system. Isolated 0.12 g (45%) of W-129 as yellow solid. $^1$H NMR (Acetone-d$_6$): δ 8.39 (1H, d, J=2.4 Hz), 8.24 (1H, dd, J=9.2 and 2.4), 7.44 (1H, m), 7.43 (1H, d, J=8.8 Hz), 7.38 (1H, d, J=8.8 Hz), 7.17 (1H, d, J=14.4 Hz), 6.93 (1H, d, J=14.4 Hz), 6.93 (1H, m), 6.92 (1H, d, J=8.0 Hz), 3.86 (3H, s); MS: 329 (M+H$^+$).

(E)-6-Nitro-3-styrylbenzo[d]thiazol-2(3H)-one W-148

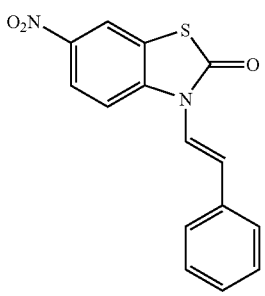 [SMILES: O=c1sc2cc([N+](=O)[O-])ccc2n1/C=C/c1ccccc1]

General experimental procedure for N-arylation was followed. Reaction was performed on a 0.185 g scale. Product eluted out in 20-40% EtOAc-hexanes mixture in a gradient elution on a Combiflash purification system. Isolated 0.088 g (60%) of W-148 as yellow solid; $^1$H NMR (CDCl$_3$): δ 8.40 (1H, t, J=2.0 Hz), 8.27 (1H, dt, J=9.2 and 2.0 Hz), 7.50 (2H, d, J=8.0 Hz), 7.45-7.35 (4H, m), 7.26 (1H, d, J=14.4 Hz), 7.08 (1H, d, J=14.4 Hz); MS: 299 (M+H$^+$).

(E)-6-Methoxy-3-styrylbenzo[d]thiazol-2(3H)-one W-161

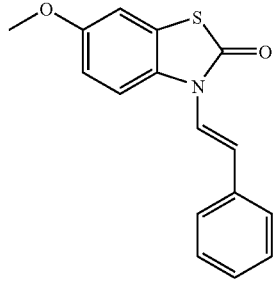 [SMILES: COc1ccc2c(c1)sc(=O)n2/C=C/c1ccccc1]

General experimental procedure for N-arylation was followed. Reaction was performed on a 0.185 g scale. Product eluted out in 20-30% EtOAc-hexanes mixture in a gradient elution on a Combiflash purification system. Isolated 0.267 g (92%) of W-161 as white solid. $^1$H NMR (CDCl$_3$): δ 7.47 (1H, dq, J=7.2 and 1.6 Hz), 7.38 (1H, tt, J=8.0 and 1.6 Hz), 7.30 (1H, tt, J=8.0 and 1.6 Hz), 7.24 (1H, d, J=6.0 Hz), 7.135 (1H, d, J=14.4 Hz), 7.01 (1H, d, J=2.8 Hz), 6.90 (1H, dd, J=8.8 and 2.4 Hz), 3.84 (3H, s); MS: 284 (M+H$^+$).

3-(4-Dimethylamino)phenyl)-6-hydroxybenzo[d]thiazol-2(3H)-one W-127

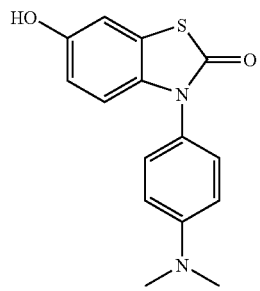 [SMILES: CN(C)c1ccc(-n2c(=O)sc3cc(O)ccc32)cc1]

General experimental procedure for demethylation was followed. Reaction was performed on a 0.040 g. Isolated 0.023 g (80%) of W-127 as white solid. $^1$H NMR (CDCl$_3$): δ 8.04 (1H, s), 7.20 (2H, dt, J=8.8 and 3.6 Hz), 7.07 (1H, d, J=2.4 Hz), 6.86 (2H, dt, J=8.8 and 3.6 Hz), 6.75 (1H, dd, J=8.8 and 2.8 Hz), 6.57 (1H, d, J=8.8 Hz), 3.01 (6H, s); MS: 287 (M+H$^+$).

(E)-3-(4-Fluorostyryl)-6-hydroxybenzo[d]thiazol-2(3H)-one W 150

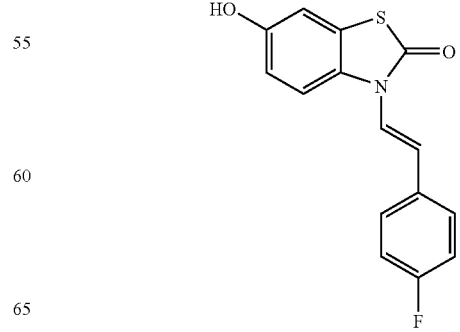

General experimental procedure for demethylation was followed. Reaction was performed on a 0.058 g. Isolated 0.030 g (55%) of W-150 as white solid. $^1$H NMR (Acetone-$d_6$): δ 8.57 (1H, s), 7.65 (2H, dd, J=8.8 and 5.6 Hz), 7.44 (1H, d, J=4.8 Hz), 7.41 (1H, d, J=14.8 Hz), 7.34 (1H, d, J=14.8 Hz), 7.15 (2H, t, J=8.8 Hz), 7.11 (1H, d, J=2.8 Hz), 6.90 (1H, dd, J=8.8 and 2.4 Hz); MS: 288 (M+H$^+$).

(E)-3-(3-Fluorostyryl)-6-hydroxybenzo[d]thiazol-2(3H)-one W 151

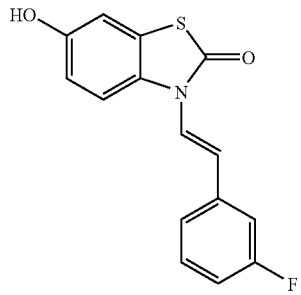 [SMILES: O=c1sc2cc(O)ccc2n1/C=C/c1cccc(F)c1]

General experimental procedure for demethylation was followed. Reaction was performed on a 0.053 g. Isolated 0.047 g (96%) of W-151 as white solid. $^1$H NMR (Acetone-$d_6$): δ 8.60 (1H, s), 7.51 (1H, d, J=8.8 Hz), 7.48-7.39 (5H, m), 7.13 (1H, d, J=2.4 Hz), 7.08-7.02 (1H, m), 6.90 (1H, dd, J=9.2 and 2.8 Hz); MS: 288 (M+H$^+$).

(E)-6-Hydroxy-3-styrylbenzo[d]thiazol-2(3H)-one W-152

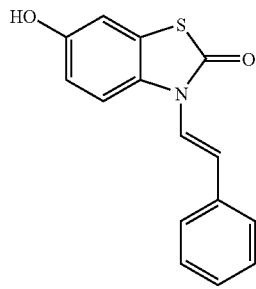 [SMILES: O=c1sc2cc(O)ccc2n1/C=C/c1ccccc1]

General experimental procedure for demethylation was followed. Reaction was performed on a 0.267 g. Isolated 0.187 g (74%) of W-152 as off-white solid. $^1$H NMR (CDCl$_3$): δ 8.57 (1H, s), 7.60 (2H, dq, J=7.2 and 1.6 Hz), 7.45 (1H, d, J=8.8 Hz), 7.42-7.35 (4H, m), 7.30 (1H, tt, J=7.2 and 2.0 Hz), 7.12 (1H, d, J=2.4 Hz), 6.90 (1H, dd, J=8.8 and 2.4 Hz); MS: 270 (M+H$^+$).

General Experimental Procedure for Suzuki Coupling

A 5 mL microwave tube was charged with aryl halide (1 equiv), boronic acid or ester (1-1.1 equiv) Pd(PPh$_3$)$_4$ (0.01-0.03 equiv) and K$_2$CO$_3$ or NaHCO$_3$ (2-3 equiv) in isopropanol or 1,4-dioxane (10 vol) and H$_2$O (10 vol). The suspension was irradiated in a Biotage Emrys Optimizer microwave reactor (250 W) at 100° C. for 10-30 min. After cooling to room temperature the solvent was evaporated in vacuo. The residue was purified over silica gel using Hexanes:EtOAc as the eluent to afford the biaryl.

General Experimental Procedure for Cyclization

A 5 mL microwave tube was charged with benzothiazolylamine (1 equiv), and bromoketone (1-2 equiv) in ethanol (20 vol). The suspension was irradiated in a Biotage Emrys Optimizer microwave reactor (250 W) at 100° C. for 10-30 min. After cooling to room temperature the solid was filtered, washed with EtOH and ether, dried in vacuo to afford the desired cyclized product.

Method B for Cyclization

A 50 mL flask was charged with pyridinothiazolylamine (1 equiv), and bromoketone (1-2 equiv) in ethanol (20 vol). The suspension was refluxed at 85° C. for 16 h. After cooling to room temperature the solid was filtered, washed with EtOH and ether, dried in vacuo to afford the desired cyclized product.

General Experimental Procedure for N-Alkylation of Benzimidazole

Method A

A 5 mL microwave tube was charged with 2-chloro-5-methoxy-1H-benzo[d]imidazole (1 equiv), bromoketone (1.1 equiv), Cs$_2$CO$_3$ (1 equiv) in DMF (20 vol). The suspension was irradiated in a Biotage Emrys Optimizer microwave reactor (250 W) at 100° C. for 15 min. After cooling to room temperature water was added and the yellow solid was filtered, washed with water and ether, dried in vacuo to afford the desired N-alkylated product.

General Experimental Procedure for Thiourea Reaction

Method B

The N-alkylated-benzo[d]imidazol-1-yl)ethanone (1 equiv), thiourea (1.2 equiv) in MeOH (20 vol) was stirred at 50° C. for 2.5 h, After cooling to room temperature, the solid was filtered, washed with MeOH and ether, dried in vacuo.

General Experimental Procedure for Acid Catalyzed Cyclization

Method C

A mixture of benzo[d]imidazo-1-yl)ethanonethiol (1 equiv) and Ac$_2$O (25 vol) was refluxed for 30 min, to that 2-3 drops of concentrated H$_2$SO$_4$ was added and mixture was refluxed for 30 min. The residue was cooled, added to ice-H$_2$O and extracted with EtOAc. The EtOAc layer was washed with aq. NaHCO$_3$ and water, dried over Na$_2$SO$_4$ and evaporated. The residue was purified by Combiflash to afford the cyclized product.

General Experimental Procedure for Sonogashira Coupling

A 5 mL microwave tube was charged with aryl halide (1-2 equiv), alkyne (1 equiv) [Pd(PPh$_3$)$_4$] (0.1 equiv), CuI (0.15 equiv) and NH(C$_2$H$_5$)$_2$ or TEA (3 equiv) in DMF or ACN (1-5 vol). The suspension was either irradiated in a Biotage Emrys Optimizer microwave reactor (250 W) at 100-130° C. for 10-30 min or the reaction is carried out at RT for 2-4 hrs. After cooling to room temperature the solvent was evaporated in vacuo. The residue was purified over silica gel using hexanes: EtOAc as the eluent to afford the coupling product.

General Experimental Procedure for Desilylation

To a round bottomed flask equipped with a magnetic stir bar and TMS protected alkyne (1 equiv), MeOH (10 vol) and $K_2CO_3$ (1.2 equiv) were added and was stirred at RT for 30 min. To the reaction mixture silica added and concentrated in vacuo. The residue was purified over silica gel using EtOAc: Hexanes as an eluent to afford alkyne.

2-(2-Chloro-5-methoxy-1H-benzo[d]imidazo-1-yl)-1-(4-fluorophenyl)ethanone W253

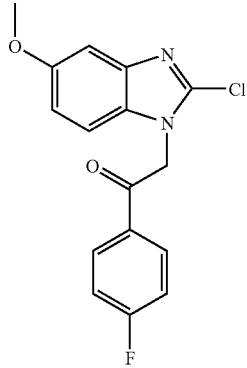 [SMILES: COc1ccc2c(c1)nc(Cl)n2CC(=O)c1ccc(F)cc1]

General experimental procedure for N-alkylation (Method A) was followed. Reaction performed on a 0.092 g scale. Isolated 0.120 g (75%) W 253 as yellow solid. NMR is assigned as a mixture of two isomer. $^1$H NMR (DMSO-$d_6$): δ 8.09 (2H, m), 7.61 and 7.0 (1H, d, J=8.8 Hz), 7.25 (3H, m), 6.90 (1H, m), 5.52 and 5.51 (2H, s each), 3.85 and 3.80 (3H, s each); MS: 319 (M+H$^+$).

1-(4-Fluorophenyl)-2-(2-mercapto-5-methoxy-1H-benzo[d]imidazo-1-yl)ethanone: W299

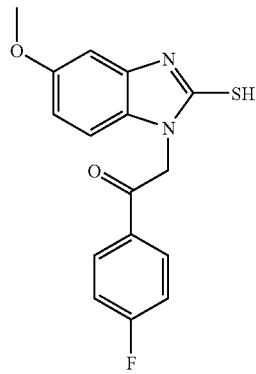 [SMILES: COc1ccc2c(c1)nc(S)n2CC(=O)c1ccc(F)cc1]

General experimental procedure for thiourea reaction (Method B) was followed. Reaction performed on a 0.115 g scale. Isolated 0.100 g (88%) W299 as yellow solid. NMR is assigned as a mixture of two isomer. $^1$H NMR (DMSO-$d_6$): δ 10.45 (1H, br s), 8.27 (2H, m), 7.37 (2H, m), 7.28 (1H, d, J=8.8 Hz), 6.91 (2H, m), 5.83 and 5.81 (2H, s each), 3.91 and 3.86 (3H, s each); MS: 317 (M+H$^+$).

2-(4-Fluorophenyl)-6-methoxybenzo[d]thiazolo[3,2-a]imidazole: W255

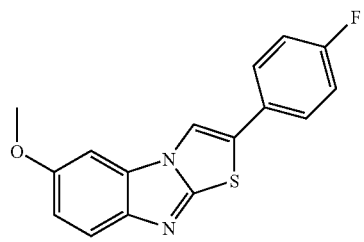 [SMILES: COc1ccc2nc3sc(-c4ccc(F)cc4)cn3c2c1]

General experimental procedure for acid catalyzed cyclization reaction (Method C) was followed. Reaction performed on a 0.0.023 g scale. Isolated 0.0.08 g (37%) W255 as yellow solid. NMR is assigned as a mixture of two isomer. $^1$H NMR (DMSO-$d_6$): δ 7.78 (1H, d, J=4.0 Hz), 7.67 (1H, d, J=9.2 Hz), 7.54 (2H, m), 7.26 (1H, d, J=3.2 Hz), 7.15 (2H, m), 7.01 (1H, dd, J=8.8 and 2.4 Hz), 6.91 (1H, dd, J=8.8 and 2.4 Hz), 3.90 and 3.89 (3H, s each); MS: 299 [(M+H$^+$).

1-(2-Chloro-5-methoxy-1H-benzo[d]imidazol-1yl-2-(4-nitrophenyl)ethanone: AS-119

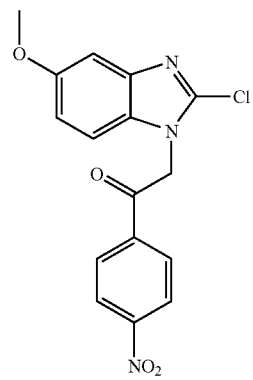 [SMILES: COc1ccc2c(c1)nc(Cl)n2CC(=O)c1ccc([N+](=O)[O-])cc1]

General experimental procedure for N-alkylation (Method A) was followed. Reaction performed on a 0.092 g scale. Isolated 0.128 g (74%) of AS-119 as yellow solid: MS: 346 (M+H$^+$).

1-(2-Mercapto-5-methoxy-1H-benzo[d]imidazol-1yl-2-(4-nitrophenyl)ethanone: AS-134

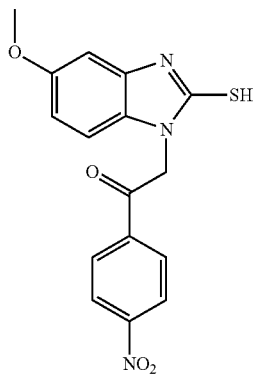 [SMILES: COc1ccc2c(c1)nc(S)n2CC(=O)c1ccc([N+](=O)[O-])cc1]

General experimental procedure for thiourea reaction (Method B) was followed. Reaction performed on a 0.110 g scale. Isolated 0.094 g (86%) of AS-134 as yellow solid: MS: 344 (M+H⁺).

6-Methoxy-2-(4-nitrophenyl)benzolo[d]thiazolo[3,2-a]imidazole: AS-135

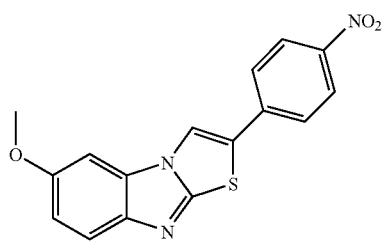 [SMILES: COc1ccc2nc3sc(-c4ccc([N+](=O)[O-])cc4)cn3c2c1]

General experimental procedure for acid catalyzed cyclization reaction (Method C) was followed. Reaction performed on a 0.0.062 g scale. Isolated 0.060 g (100%) of AS-135 as yellow solid: MS: 326 (M+H⁺).

1-(2-Chloro-5-methoxy-1H-benzo[d]imidazol-1yl)-2-(4-(dimethylamino)phenyl)ethanone: AS-125

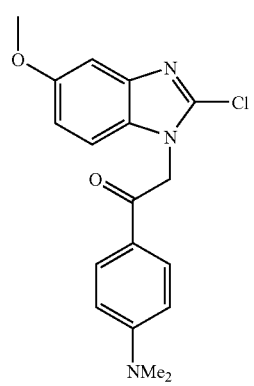 [SMILES: COc1ccc2c(c1)nc(Cl)n2CC(=O)c1ccc(N(C)C)cc1]

General experimental procedure for alkylation (Method A) was followed. Reaction performed on a 0.092 g scale and purified by combiflash (Hex-EtOAc (55:45) yielded AS-125 0.104 g (60%) as yellow solid. NMR is assigned as mixture of isomer. NMR is assigned as a mixture of two isomer. ¹H NMR (DMSO-d₆): δ 7.92 (2H, m), 7.58 (1H, d, J=8.8 Hz), 7.20 (1H, d, J=2.4 Hz), 7.02 (1H, d, J=8.8 Hz), 6.88 (1H, dt, J=8.4, 4.4 and 2.4 Hz), 6.69 (1H, dd, J=8.8 and 3.6 Hz), 6.59 (1H, d, J=2.4 Hz), 5.44 (2H, s), 3.83 and 3.782 (3H, s each); MS: 344 (M+H⁺).

2-(4-Dimethylamino)phenyl)-1-(2-mercapto-5-methoxy-1H-benzo[d]imidazol-1-yl) ethanone: AS-127A

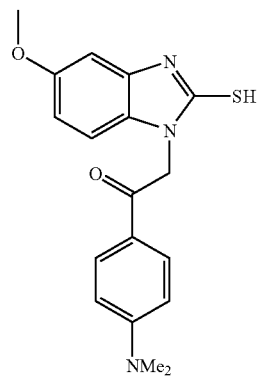

General experimental procedure for thiourea reaction (Method B) was followed. Reaction performed on a 0.052 g scale. Isolated 0.050 g (100%) of AS-127A as yellow solid. NMR is assigned as a mixture of two isomer. ¹H NMR (CDCl₃): δ 9.56 and 9.50 (1H, br s each), 8.08 (1H, br s), 8.0 (1H, m), 7.09 (1H, d, J=8.8 Hz), 6.90 (1H, t, J=4.8 Hz), 6.76 (1H, m), 6.68 (1H, dd, J=8.8 and 3.6 Hz), 6.64 (1H, d, J=4.0 Hz), 5.65 and 5.64 (2H s each), 3.08 and 3.77 (3H, s each); MS: 342 (M+H⁺).

4-(6-Methoxy-benzolo[d]thiazolo[3,2-a]imidazol-2-yl)-N,N-dimethylaniline: W274

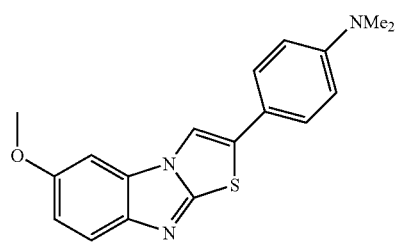 [SMILES: COc1ccc2nc3sc(-c4ccc(N(C)C)cc4)cn3c2c1]

General experimental procedure for acid catalyzed cyclization reaction (Method C) was followed. Reaction performed on a 0.054 g scale. Isolated 0.04 g (8%) of W274 as light yellow solid after purification through Combiflash (hexane-EtOAc (6:4). NMR is assigned as a mixture of two isomer. ¹H NMR (CDCl₃): δ 7.65 (1H, s), 7.64 (1H, dd, J=2.4 Hz), 7.50 (1H, d, J=8.8 Hz), 7.42 (2H, m), 7.24 (1H, d, J=2.4

Hz) 7.12 (1H, d, J=2.4 Hz), 6.98 and 6.88 (1H, dd, J=8.4 and 2.4 Hz), 6.75 (2H, dt, J=8.8 and 1.6 Hz), 3.90 and 3.89 (3H s each); MS: 324 (M+H⁺).

4-(6-Methoxy-benzolo[d]thiazolo[3,2-a]imidazol-2-yl)-N-methylaniline: W334

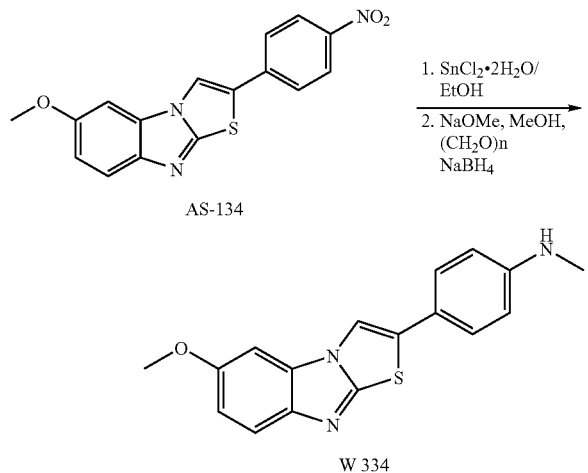

Compound AS-134 (0.0.060 g, 0.18 mmol) was reduced with SnCl₂·2H₂O (0.250 g, 1.08, 6.0 eq) in EtOH (10 ml) for 4 h. After usual work-up it yielded the amine 0.041 g, (77%). To a solution amine (0.041 g, 0.14 mmol) in MeOH (2 ml), paraformaldehyde (0.025 mg, 0.83 mmol, 6 eq) and NaOMe (0.070 g, 10 eq) was added heated at 65° C. for 1 h. The reaction mixture was cooled to ice-bath and NaBH₄ (0.032 g, 0.86 mmol, 6.0 eq) was added and heated for another 65° C. for 2 h. The reaction mixture was adsorbed over SiO₂ gel and Combiflash. The compound W334 was eluted with hexane-EtOAc (4:6) 0.07 g, (16%). NMR is assigned as mix of two isomers. ¹H NMR (DMSO-d₆): δ 8.20 (1H, s), 7.52 (1H, d, J=8.8 Hz), 7.43 (2H, dd, J=5.2 and 2.4 Hz), 7.40 (1H, t, J=2.4 Hz), 6.97 MS: 310 (M+H⁺).

Synthesis of W256

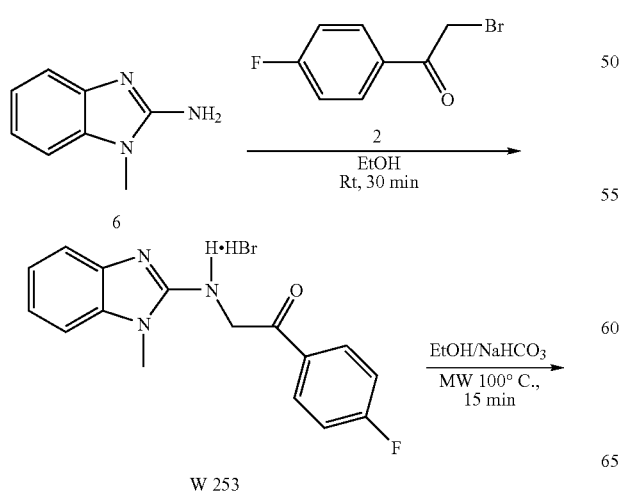

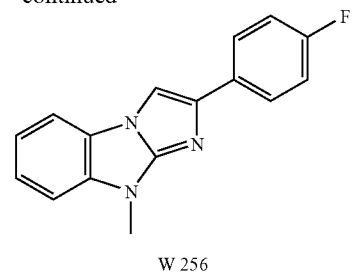

1-(4-Fluorophenyl)-2-(1-methyl-1H[d]imidazo-2-ylaminoethanone: W253

A solution of 1-methyl-1H-benzo[d]imidazole-2-amine (6, 0.074 g, 0.5 mmol) and 2-bromo-4-fluoroacetophenone (0.130 g, 0.6 mmol, 1.2 eq) in EtOH (2 mL) stirred at rt for 30 min, the off white hydro bromide salt W253 was filtered and washed with EtOH (0.182 g, 100%). NMR is assigned as a mixture of two isomer. ¹H NMR (DMSO-d₆): δ 8.83 (1H, s), 8.15 (2H, m), 7.58 (2H, d, J=8.8 Hz), 7.46 (2H, t, J=8.8 Hz), 7.33 (1H, t, J=8.0 Hz), 7.26 (1H, t, J=8.0 Hz), MS: 284 (M+H⁺).

Preparation of W256

A solution of compound W253 (0.072 g, 0.19 mmol), NaHCO₃ (0.032 g, 0.38 mmol) in EtOH (2 ml) was irradiated in a Biotage Emrys Optimizer microwave reactor (250 W) at 100° C. for 15 min. After cooling the reaction mixture, was adsorbed over SiO₂ gel and Combiflash. The W256 was eluted with hexane-EtOAC (1:1) (0.024 g, 47%) as white colorless solid. NMR is assigned as a mixture of two isomer. ¹H NMR (CDCl₃): δ 7.81 (2H, m), 7.57 (1H, s), 7.52 (1H, d J=8.0 Hz), 7.29 (2H, m), 7.18 (1H, m), 7.07 (1H, tt, J=8.8 and 2.0 Hz), 3.01 (3H, s); MS: 266 (M+H⁺).

7-Methoxy-2(furanyl-2-yl)imidazo[2,1-b]8-pyridinothiazole: W335

General experimental procedure for cyclization was followed. Reaction was performed on a 0.045 g scale. Isolated 0.045 g (70%) of W335 as a colorless solid after purification through Combiflash (hexane-EtOAc (6:4). ¹H NMR (DMSO-d₆): δ 8.30 (1H, d, J=8.8 Hz), 8.29 (1H, s), 7.57 (1H, t, J=0.8 Hz), 6.99 (1H, d, J=8.8 Hz), 6.71 (1H, d, J=3.6 Hz), 6.54 (1H, dd, J=3.6 and 2.0 Hz), 3.99 (3H, s); MS: 272 (M+H⁺)

7-Methoxy-2(thiophen-2-Aimidazo[2,1-b]8-pyridinothiazole: W336

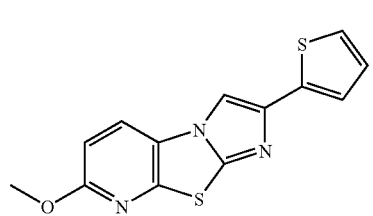 [SMILES: COc1ccc2c(n1)sc1nc(-c3cccs3)cn12]

General experimental procedure for cyclization was followed. Reaction was performed on a 0.050 g scale. Isolated 0.013 g (17%) after purification through Combiflash (hexane-EtOAc (6:4) of W336 as a colorless solid. $^1$H NMR (DMSO-$d_6$): δ 8.38 (1H, s), 8.26 (1H, d, J=8.8 Hz), 7.42 (1H, dd, J=3.2 and 1.2 Hz), 7.38 (1H, dd, J=5.2 and 1.2 Hz), 7.08 (1H, dd, J=9.2 and 0.4 Hz) 3.99 (3H, s); MS: 288 (M+H$^+$)

7-Methoxy-2(4-dimethylaminophenyl)imidazo[2,1-b]8-pyridinothiazole: W337

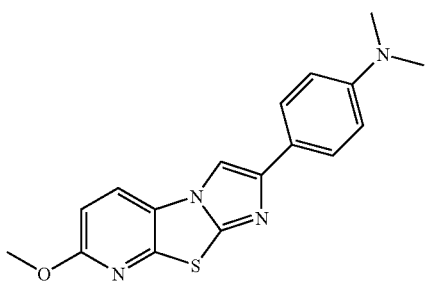

General experimental procedure for cyclization was followed. Reaction was performed on a 0.091 g scale. Isolated 0.035 g (20%) of W337 as a off white solid. $^1$H NMR (DMSO-$d_6$): δ 8.53 (1H, s), 8.28 (1H, d, J=8.8 Hz), 7.70 (2H, d, J=8.8 Hz), 7.03 (1H, d, J=8.8 Hz), 6.95 (1H, br d, J=8.4 Hz) 3.91 (3H, s), 2.96 (6H, s); MS: 325 (M+H$^+$).

7-Methoxy-2(4-nitrophenyl)imidazo[2,1-b]8-pyridinothiazole: W347 (W332 Precursor)

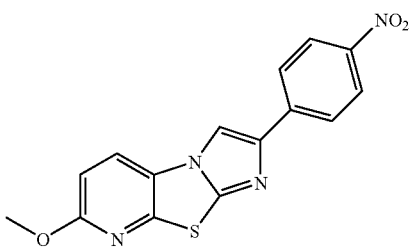 [SMILES: COc1ccc2c(n1)sc1nc(-c3ccc([N+](=O)[O-])cc3)cn12]

General experimental procedure for cyclization was followed. Reaction was performed on a 0.138 g scale. Isolated 0.086 g (34%) of W347 as a yellow solid. $^1$H NMR (DMSO-$d_6$): δ 8.79 (1H, s), 8.30 (3H, dd, J=9.2 and 2.4 Hz), 8.17 (1H, dd, J=9.2 Hz), 4.0 (3H, s); MS: 327 (M+H$^+$).

7-Fluoro-2(4-methoxyphenyl)imidazo[2,1-b]8-pyridinothiazole: W348

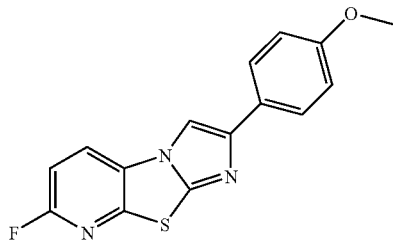 [SMILES: COc1ccc(-c2cn3c(n2)sc2nc(F)ccc23)cc1]

General experimental procedure for cyclization was followed. Reaction was performed on a 0.085 g scale. Isolated 0.039 g (26%) of W348 as a yellow solid. $^1$H NMR (DMSO-$d_6$): δ 8.65 (1H, s), 8.52 (1H, dd J=8.8 and 6.8 Hz), 7.75 (1H, d, J=8.8 Hz), 7.43 (1H, dd, J=8.8 and 1.6 Hz), 6.99 (1H, dd, J=8.8 Hz), 3.76 (3H, s); MS: 300 (M+H$^+$).

7-Fluoro-2(furanyl-2-yl)imidazo[2,1-b]8-pyridinothiazole: W349

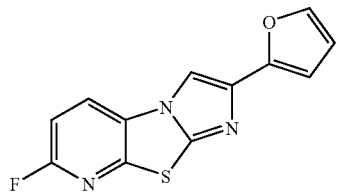 [SMILES: Fc1ccc2c(n1)sc1nc(-c3ccco3)cn12]

General experimental procedure for cyclization was followed. Reaction was performed on a 0.095 g scale. Isolated 0.018 g (12%) after purification through Combiflash (hexane-EtOAc (6:4) of W349 as a brown solid. $^1$H NMR (DMSO-$d_6$): δ 8.56 (1H, dd, J=8.8 and 6.8 Hz), 8.39 (1H, s), 7.59 (1H, dd, J=2.0 and 0.8 Hz), 7.34 (1H, dd, J=8.8 and 2.0 Hz), 6.75 (1H, dd, J=3.2 and 0.4 Hz), MS: 260 (M+H$^+$).

7-Fluoroethyl-2(furanyl-2-yl)imidazo[2,1-b]8-pyridinothiazole: W350

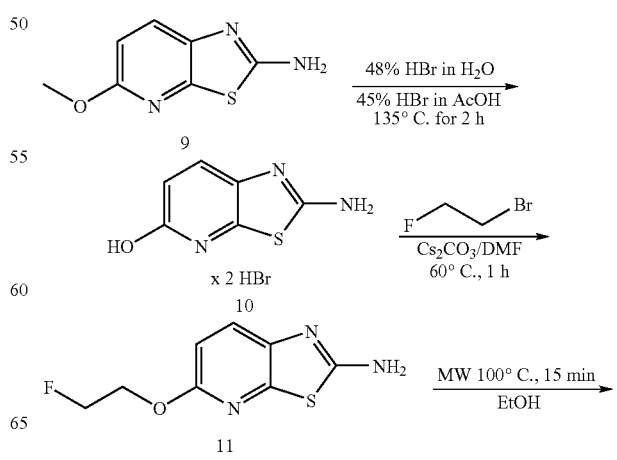

-continued

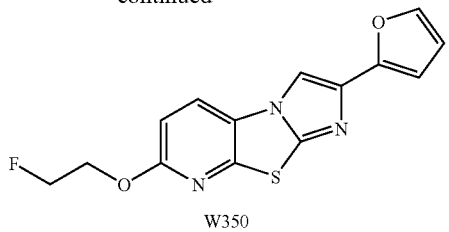

W350

Preparation of 2-aminothiazolo[5,4-b]pyridine-5-ol-dihydrobromide 10

5-Methoxythiazolo[5,4-b]pyridin-2-amine (9, 1.0 g, 5.5 mmol) was hydrolyzed with mixture of 48% HBr in water and 45% HBr in acetic acid (4 ml, 1:1) at 135° C. in a pressure bottle for 2 h. The white dihydrobromide salt 10 was filtered and washed with diethyl ether, dried in vacuo 1.7 g (92%). $^1$H NMR (DMSO-$d_6$): δ 7.64 (1H, m), 6.64 (1H, m); MS: 168 (M+H$^+$).

Preparation of 5-(2-fluoroethoxy)thiazolo[5,4-b]pyridine-2-amine 11

General experimental procedure for phenolic alkylation was followed to prepare compound 11. Reaction was performed on 0.130 g scale. Isolated crude brown oily product 0.085 g (100%) used as is for next step. MS: 214 (M+H$^+$).

7-Fluoroethyl-2(furanyl-2-yl)imidazo[2,1-b]8-pyridinothiazole: W350

General experimental procedure for cyclization of 11 to W350 was followed. Reaction was performed on a 0.085 g scale. Isolated 0.08 g (7%) of W350 as white solid after Combiflash (hexane-EtOAc, 6:4). $^1$H NMR (DMSO-$d_6$): δ 8.34 (1H, d, J=8.8 Hz), 8.31 (1H, s), 7.57 (1H, dd, J=2.0 and 0.8 Hz), 7.05 (1H, d, J=8.8 Hz), 6.72 (1H, d, J=3.2 Hz), 6.54 (1H, dd, J=3.2 and 1.6 Hz), 4.88 (1H, t, J=4.0 Hz), 4.76 (1H, t, J=4.0 Hz), 4.69 (1H, t, J=4.0 Hz), 4.61 (1H, t, J=4.0 Hz); MS: 304 (M+H$^+$).

7-Fluoro-2(4-fluorophenyl)imidazo[2,1-b]8-pyridinothiazole: W358

General experimental procedure for cyclization was followed. Reaction was performed on a 0.169 g scale. Isolated 0.060 g (20%) of W 358 as a off white solid. NMR (DMSO-$d_6$): δ 8.76 (1H, s), 8.53 (1H, dd, J=6.8 and 8.8 Hz), 7.85 (1H, m), 7.43 (1H, dd, J=8.8 and 1.6 Hz), 7.25 (1H, tt, J=8.8 and 2.0 Hz); MS: 288 (M+H$^+$).

7-Fluoro-2(thiophen-2-yl)imidazo[2,1-b]8-pyridinothiazole: W364

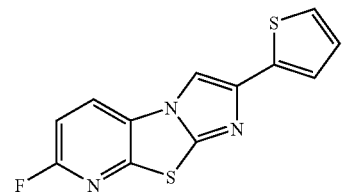 [SMILES: Fc1ccc2c(n1)sc1nc(-c3cccs3)cn12]

General experimental procedure for cyclization was followed. Reaction was performed on a 0.085 g scale. Isolated 0.008 g (6%) of W 364 as brown solid after Combiflash (hexane-EtOAc, 2:3); $^1$H NMR (DMSO-$d_6$): δ 8.33 (1H, s), 8.31 (1H, dd, J=8.4 and 6.4 Hz), 7.51 (1H, dd, J=3.6 and 1.2 Hz), 7.29 (1H, dd, J=8.8 and 1.6 Hz), 7.20 (1H, dd, J=5.4 and 3.6 Hz); MS: 277 (M+H$^+$).

7-Methoxy-2(6-fluoropyridin-3-yl)imidazo[2,1-b]8-pyridinothiazole: W372

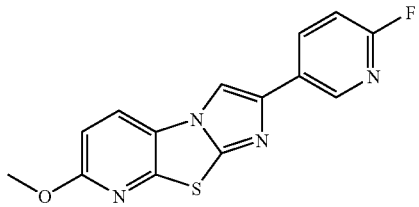

General experimental procedure for cyclization B was followed. Reaction was performed on a 0.033 g scale. Isolated 0.007 g (15%) of W372 as off white solid; $^1$H NMR (DMSO-$d_6$): δ 8.79 (1H, s), 8.66 (1H, d, J=2.4 Hz), 8.31 (1H, dt, J=2.4 and 8.4 Hz), 8.29 (1H, d, J=8.8 Hz), 7.25 (1H, dd, J=8.8 and 2.8 Hz), 7.05 (1H, d, J=8.8 Hz), 3.91 (3H, s), Calcd for $C_{14}H_9FN_4OS$: C, 55.99; H, 3.02; N, 18.66; S, 10.68. Found: C, 56.01; H, 3.34; N, 18.64; S, 10.31. MS: 301 (M+H$^+$).

7-Chloro-2(furanyl-2-yl)imidazo[2,1-b]8-pyridinothiazole: W376

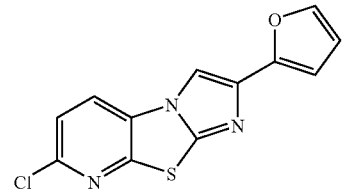 [SMILES: Clc1ccc2c(n1)sc1nc(-c3ccco3)cn12]

General experimental procedure for cyclization was followed. Reaction was performed on a 0.169 g scale. Isolated 0.060 g (20%) of W376 as a brown solid. $^1$H NMR (DMSO- $d_6$): δ 8.59 (1H, s), 8.47 (1H, d J=8.4 Hz), 7.74 (1H, d, J=0.8 Hz), 6.70 (1H, dd, J=3.2 and 0.8 Hz), 6.56 (1H, dd, J=3.2 and 1.6 Hz); MS: 277 (M+H⁺).

7-Methoxy-2(6-chloropyridin-3-yl)imidazo[2,1-b]8-pyridinothiazole: W384

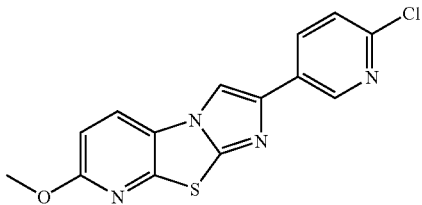 [SMILES: COc1ccc2c(n1)sc1nc(-c3ccc(Cl)nc3)cn12]

General experimental procedure for cyclization B was followed. Reaction was performed on a 0.070 g scale. Isolated 0.030 g (32%) of W384 as off white solid; ¹H NMR (DMSO-$d_6$): δ 8.85 (1H, s), 8.44 (1H, dt, J=3.6 and 7.2 Hz), 8.29 (1H, d J=8.4 Hz), 8.20 (1H, dd, J=8.4 and 2.8 Hz), 7.56 (1H, d, J=8.8 Hz), 7.05 (1H, d, J=8.8 Hz), 3.91 (3H, s); MS: 317 (M+H⁺).

7-Methoxy-2(6-fluoro-2-methylpyridin-3-yl)imidazo[2,1-b]8-pyridinothiazole: W385

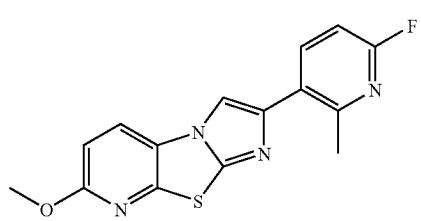 [SMILES: COc1ccc2c(n1)sc1nc(-c3ccc(F)nc3C)cn12]

General experimental procedure for cyclization B was followed. Reaction was performed on a 0.182 g scale. Isolated 0.030 g (9.5%) of W385 as off white solid; ¹H NMR (DMSO-$d_6$): δ 8.61 (1H, s), 8.41 (1H, d, J=8.8 Hz), 8.35 (1H, m), 7.06 (1H, m), 7.04 (1H, d, J=8.8 Hz), 3.91 (3H, s), 2.65 (3H, s); MS: 315 (M+H⁺).

7-Methoxy-2(4-fluorophenyl)imidazo[2,1-b]8-pyridino-oxazole W386

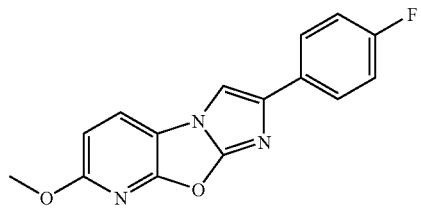

General experimental procedure for oxazole synthesis was followed. Reaction was performed on a 0.020 g scale. Isolated 0.0012 g (8%) of W386 as off white solid after combiflash (hexane:EtOAc 7:3); ¹H NMR (CDCl₃): δ 7.80 (2H, dd, J=9.2 and 5.6 Hz), 7.74 (1H, dt, J=8.4 Hz), 7.46 (1H, s), 7.09 (2H, t, J=8.0 Hz), 6.78 (1H, d, J=8.4 Hz), 4.01 (3H, s); MS: 284 (M+H⁺).

7-Chloro-2(4-fluorophenyl)imidazo[2,1-b]8-pyridinothiazole: W387

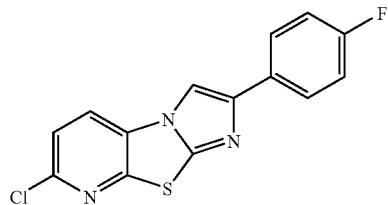 [SMILES: Fc1ccc(-c2cn3c(n2)sc2nc(Cl)ccc23)cc1]

General experimental procedure for cyclization B was followed. Reaction was performed on a 0.070 g scale. Isolated 0.030 g (32%) of W387 as off white solid; ¹H NMR (DMSO-$d_6$): δ 8.77 (1H, s), 8.38 (1H, d, J=8.8 Hz), 7.86 (2H, d, J=8.8 and 5.6 Hz), 7.74 (1H, d, J=8.4 Hz), 7.26 (2H, t, J=9.2 Hz); MS: 304 (M+H⁺).

7-Methoxy-2 (6-dimethylaminopyridin-3-yl)imidazo[2,1-b]8-pyridinothiazole: AS-184

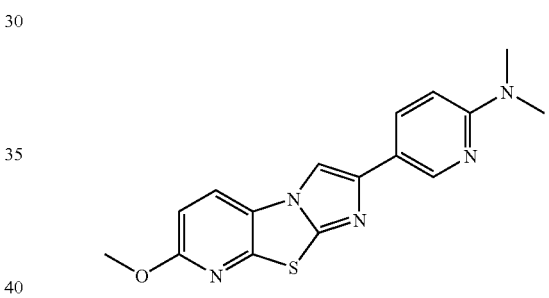

General experimental procedure for cyclization B was followed. Reaction was performed on a 0.182 g scale. Isolated 0.180 g (55%) of AS-184 as off white solid; ¹H NMR (DMSO-$d_6$): δ 8.62 (1H, d, J=2.0 Hz), 7.98 (1H, dd, J=8.8 and 2.8 Hz), 7.77 (2H, t, J=5.2 Hz), 6.82 (1H, d, J=8.8 Hz), 6.60 (1H, d, J=9.2 Hz), 4.00 (3H, s), 3.14 (6H, s); MS: 326 (M+H⁺).

7-Methoxy-2 (6-nitropyridin-3-yl)imidazo[2,1-b]8-pyridinothiazole: AS-168

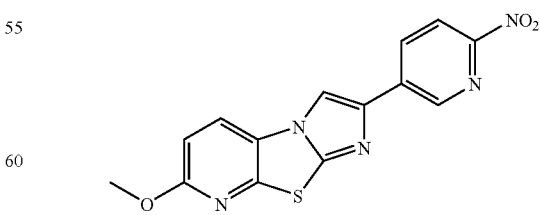

General experimental procedure for cyclization B was followed. Reaction was performed on a 0.181 g scale. Isolated 0.118 g (36%) of AS-168 as yellow solid; ¹H NMR (DMSO-$d_6$): δ 9.087 and 9.081 (1H, s each), 8.53 (1H, dd, J=8.8 and 4.0 Hz), 8.39 (1H, d, J=8.8 Hz), 8.33 (1H, d, J=8.8 Hz), 7.08 (1H, d, J=8.8 Hz), 3.93 (3H, s); MS: 328 (M+H⁺).

5-(5-Fluoropyridin-3-yl)benzo[d]thiazole: W234

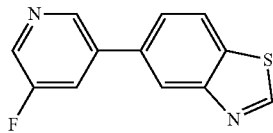 [SMILES: Fc1cncc(-c2ccc3scnc3c2)c1]

General experimental procedure for Suzuki coupling was followed. Reaction was performed on a 65 mg scale. Product was purified on a Biotage purification system eluting out in 40% EtOAc:Hexanes mixture in a gradient elution to give title compound (15 mg, 26%). ¹H NMR (Acetone-$d_6$, 400 MHz) δ 9.36 (s, 1H), 8.90 (t, J=1.6 Hz, 1H), 8.55 (d, J=2.4 Hz, 1H), 8.47 (d, J=1.6 Hz, 1H), 8.31 (d, J=8.4 Hz, 1H), 8.05 (dt, J=10.4, 1.6 Hz, 1H), 7.90 (dd, J=8.0, 2.0 Hz, 1H). MS: m/z=231 (M+H⁺).

5-(5-Cyanopyridin-2-yl)benzo[d]thiazole: W243

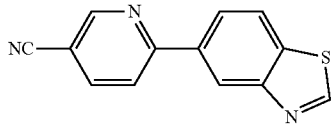 [SMILES: N#Cc1ccc(-c2ccc3scnc3c2)nc1]

General experimental procedure for Suzuki coupling was followed. Reaction was performed on a 65 mg scale. Product was purified on a Biotage purification system eluting out in 40% EtOAc:Hexanes mixture in a gradient elution to give title compound (30 mg, 51%). ¹H NMR (Acetone-$d_6$, 400 MHz) δ 9.37 (s, 1H), 9.09 (t, J=1.2 Hz, 1H), 8.90 (d, J=2.0 Hz, 1H), 8.34-8.38 (m, 3H), 8.31 (d, J=8.4 Hz, 1H). MS: m/z=238 (M+H⁺).

2-Methyl-5,5'-bibenzo[d]thiazole: W244

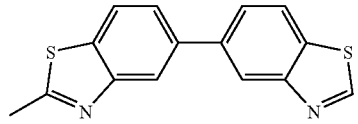

General experimental procedure for Suzuki coupling was followed. Reaction was performed on a 65 mg scale. Product was purified on a Biotage purification system eluting out in 40% EtOAc:Hexanes mixture in a gradient elution to give title compound (41 mg, 58%). ¹H NMR (Acetone-$d_6$, 400 MHz) δ 9.33 (s, 1H), 8.44 (d, J=1.2 Hz, 1H), 8.28 (d, J=2.0 Hz, 1H), 8.26 (d, J=8.0 Hz, 1H), 8.11 (d, J=8.4 Hz, 1H), 7.91 (dd, J=8.4, 1.6 Hz, 1H), 7.83 (dd, J=8.0, 1.6 Hz, 1H). MS: m/z=283 (M+H⁺).

5-(6-(1H-Pyrrol-1-yl)pyridin-3-yl)benzo[d]thiazole: W245

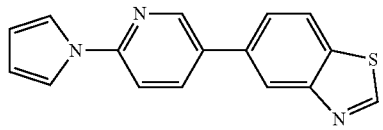 [SMILES: c1ccn(-c2ccc(-c3ccc4scnc4c3)cn2)c1]

General experimental procedure for Suzuki coupling was followed. Reaction was performed on a 65 mg scale. Product was purified on a Biotage purification system eluting out in 40% EtOAc:Hexanes mixture in a gradient elution to give title compound (30 mg, 43%). ¹H NMR (CDCl₃, 400 MHz) δ 9.08 (s, 1H), 8.75 (d, J=2.0 Hz, 1H), 8.36 (d, J=1.6 Hz, 1H), 8.07 (d, J=8.4 Hz, 1H), 8.04 (dd, J=8.8, 2.4 Hz, 1H), 7.69 (dd, J=8.4, 1.6 Hz, 1H), 7.58 (t, J=2.4 Hz, 2H), 7.44 (d, J=8.4 Hz, 1H), 6.40 (t, J=2.4 Hz, 2H). MS: m/z=278 (M+H⁺).

5-(6-Cyanopyridin-3-yl)benzo[d]thiazole: W250

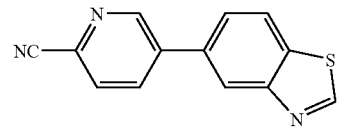

General experimental procedure for Suzuki coupling was followed. Reaction was performed on a 65 mg scale. Product was purified on a Biotage purification system eluting out in 40% EtOAc:Hexanes mixture in a gradient elution to give title compound (31 mg, 54%). ¹H NMR (DMSO-$d_6$, 400 MHz) δ 9.50 (s, 1H), 9.26 (d, J=2.0 Hz, 1H), 8.60 (d, J=1.6 Hz, 1H), 8.51 (dd, J=8.0, 2.4 Hz, 1H), 8.37 (d, J=8.4 Hz, 1H), 8.17 (d, J=8.4 Hz, 1H), 7.97 (dd, J=8.4, 2.0 Hz, 1H). MS: m/z=231 (M+H⁺).

5-(7-Nitro-1H-indol-5-yl)benzo[d]thiazole: W251

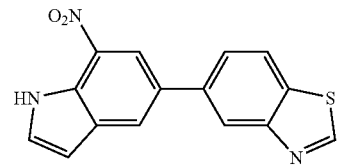 [SMILES: O=[N+]([O-])c1cc(-c2ccc3scnc3c2)cc2cc[nH]c12]

General experimental procedure for Suzuki coupling was followed. Reaction was performed on a 65 mg scale. Product was purified on a Biotage purification system eluting out in 40% EtOAc:Hexanes mixture in a gradient elution to give title compound (35 mg, 47%). ¹H NMR (CDCl₃, 400 MHz) δ 9.96 (br s, 1H), 9.08 (s, 1H), 8.51 (d, J=1.6 Hz, 1H), 8.42 (d, J=2.0 Hz, 1H), 8.29 (d, J=1.2 Hz, 1H), 8.07 (d, J=8.4 Hz, 1H), 7.78 (dd, J=8.4, 2.0 Hz, 1H), 7.47 (t, J=2.4 Hz, 1H), 6.80 (dd, J=3.2, 2.0 Hz, 1H). MS: m/z=296 (M+H⁺).

5-[4-Nitro-3-(trifluoromethyl)phenyl]benzo[d]thiazole: W252

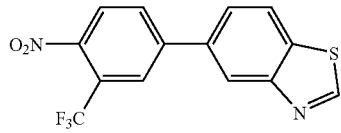 [SMILES: O=[N+]([O-])c1ccc(-c2ccc3scnc3c2)cc1C(F)(F)F]

General experimental procedure for Suzuki coupling was followed. Reaction was performed on a 65 mg scale. Product was purified on a Biotage purification system eluting out in 40% EtOAc:Hexanes mixture in a gradient elution to give title compound (37 mg, 46%). $^1$H NMR (CDCl$_3$, 400 MHz) δ 9.11 (s, 1H), 8.39 (d, J=1.2 Hz, 1H), 8.09-8.16 (m, 2H), 8.06 (d, J=8.4 Hz, 1H), 8.00 (dd, J=8.4, 1.6 Hz, 1H), 7.71 (dd, J=8.4, 2.0 Hz, 1H). MS: m/z=325 (M+H$^+$).

5-(7-Nitroindolin-5-yl)benzo[d]thiazole: W276

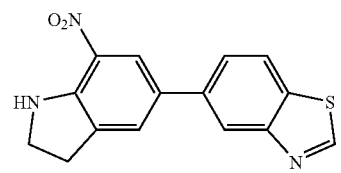 [SMILES: O=[N+]([O-])c1cc(-c2ccc3scnc3c2)cc2c1NCC2]

General experimental procedure for Suzuki coupling was followed. Reaction was performed on a 65 mg scale. Product was purified on a Biotage purification system eluting out in 40% EtOAc:Hexanes mixture in a gradient elution to give title compound (32 mg, 43%). $^1$H NMR (Acetone-d$_6$, 400 MHz) δ 9.29 (s, 1H), 8.31 (d, J=2.0 Hz, 1H), 8.19 (d, J=8.4 Hz, 1H), 8.09 (d, J=1.2 Hz, 1H), 7.76-8.11 (m, 2H), 7.49 (br s, 1H), 3.98 (t, J=8.4 Hz, 2H), 3.30 (t, J=8.4 Hz, 2H). MS: m/z=298 (M+H$^+$).

5-(5-Cyanopyridin-3-yl)benzo[d]thiazole: W277

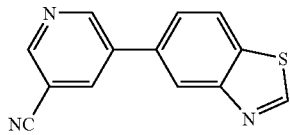

General experimental procedure for Suzuki coupling was followed. Reaction was performed on a 65 mg scale. Product was purified on a Biotage purification system eluting out in 40% EtOAc:Hexanes mixture in a gradient elution to give title compound (30 mg, 51%). $^1$H NMR (CDCl$_3$, 400 MHz) δ 9.13 (d, J=2.4 Hz, 1H), 9.12 (s, 1H), 8.91 (d, J=2.0 Hz, 2H), 8.35 (d, J=2.0 Hz, 1H), 8.23 (t, J=2.0 Hz, 1H), 8.13 (d, J=8.4 Hz, 1H), 7.66 (dd, J=8.0, 2.0 Hz, 1H). MS: m/z=238 (M+H$^+$).

5-(2-Nitropyridin-5-yl)benzo[d]thiazole: W278

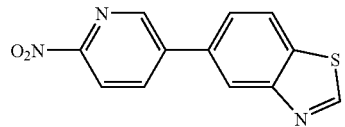

General experimental procedure for Suzuki coupling was followed. Reaction was performed on a 65 mg scale. Product was purified on a Biotage purification system eluting out in 40% EtOAc:Hexanes mixture in a gradient elution to give title compound (31 mg, 48%). $^1$H NMR (DMSO-d$_6$, 400 MHz) δ 9.52 (s, 1H), 9.16 (d, J=2.4 Hz, 1H), 8.68 (dd, J=8.4, 2.0 Hz, 1H), 8.65 (d, J=2.0 Hz, 1H), 8.43 (d, J=8.4 Hz, 1H), 8.39 (d, J=8.4 Hz, 1H), 8.01 (dd, J=8.0, 1.6 Hz, 1H). MS: m/z=258 (M+H$^+$).

5-(Pyrimidin-5-yl)benzo[d]thiazole: W290

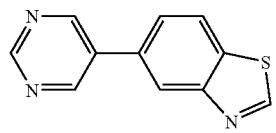

General experimental procedure for Suzuki coupling was followed. Reaction was performed on a 65 mg scale. Product was purified on a Biotage purification system eluting out in 40% EtOAc:Hexanes mixture in a gradient elution to give title compound (38 mg, 71%). $^1$H NMR (Acetone-d$_6$, 400 MHz) δ 9.37 (s, 1H), 9.21 (s, 2H), 9.19 (s, 1H), 8.50 (d, J=1.6 Hz, 1H), 8.34 (d, J=8.4 Hz, 1H), 7.92 (dd, J=8.4, 2.0 Hz, 1H). MS: m/z=214 (M+H$^+$).

4-(Benzo[d]thiazol-5-yl)benzenesulfonamide: W306

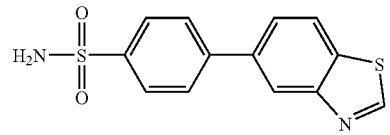 [SMILES: NS(=O)(=O)c1ccc(-c2ccc3scnc3c2)cc1]

General experimental procedure for Suzuki coupling was followed. Reaction was performed on a 65 mg scale. Product was purified on a Biotage purification system eluting out in 40% EtOAc:Hexanes mixture in a gradient elution to give title compound (55 mg, 76%). $^1$H NMR (CDCl$_3$, 400 MHz) δ 9.30 (s, 1H), 8.35 (d, J=1.6 Hz, 1H), 8.17 (d, J=8.4 Hz, 1H), 8.01 (d, J=2.0 Hz, 1H), 8.00 (d, J=1.6 Hz, 1H), 7.90 (d, J=8.4 Hz, 1H), 7.82 (dd, J=8.4, 2.0 Hz, 1H). MS: m/z=291 (M+H$^+$).

5-(4-Cyanopyridin-2-yl)benzo[d]thiazole: W291

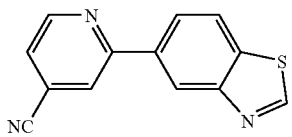

General experimental procedure for Suzuki coupling was followed. Reaction was performed on a 65 mg scale. Product was purified on a Biotage purification system eluting out in 40% EtOAc:Hexanes mixture in a gradient elution to give title compound (45 mg, 76%). $^1$H NMR (CDCl$_3$, 400 MHz) δ 9.09 (s, 1H), 8.91 (dd, J=6.0, 0.8 Hz, 1H), 8.75 (d, J=1.6 Hz, 1H), 8.16 (dd, J=8.4, 1.6 Hz, 1H), 8.10 (d, J=8.4 Hz, 1H), 8.06 (t, J=0.8 Hz, 1H), 7.50 (dd, J=4.8, 1.6 Hz, 1H). MS: m/z=238 (M+H$^+$).

5-(4-(Benzo[d]thiazol-5-yl)phenyl)furan-2-carbonitrile: W292

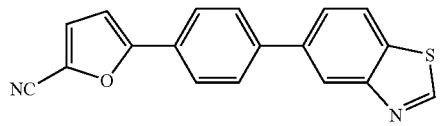

General experimental procedure for Suzuki coupling was followed. Reaction was performed on a 65 mg scale. Product was purified on a Biotage purification system eluting out in 40% EtOAc:Hexanes mixture in a gradient elution to give title compound (37 mg, 49%). $^1$H NMR (CDCl$_3$, 400 MHz) δ 9.06 (s, 1H), 8.38 (d, J=1.6 Hz, 1H), 8.05 (d, J=8.4 Hz, 1H), 7.68-7.88 (m, 5H), 7.20 (d, J=4.0 Hz, 1H), 6.79 (d, J=4.0 Hz, 1H). MS: m/z=303 (M+H$^+$).

5-(4-(Imidazo[1,2-a]pyridin-2-yl)phenyl)benzo[d]thiazole: W307

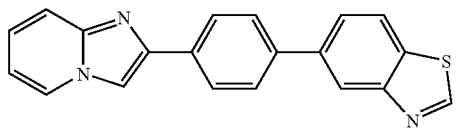

General experimental procedure for Suzuki coupling was followed. Reaction was performed on a 65 mg scale. Product was purified on a Biotage purification system eluting out in 40% EtOAc:Hexanes mixture in a gradient elution to give title compound (15 mg, 26%). $^1$H NMR (CDCl$_3$, 400 MHz) δ 9.05 (s, 1H), 8.42 (d, J=1.2 Hz, 1H), 8.15 (dt, J=6.8, 1.2 Hz, 1H), 8.09 (dd, J=6.8, 2.0 Hz, 2H), 8.04 (d, J=8.4 Hz, 1H), 7.94 (s, 1H), 7.74-7.81 (m, 3H), 7.66 (d, J=9.2 Hz, 1H), 7.16-7.21 (m, 1H), 6.81 (td, J=6.8, 1.2 Hz, 1H). MS: m/z=328 (M+H$^+$).

5-(4-Trifluoromethylpyridin-2-yl)benzo[d]thiazole: W319

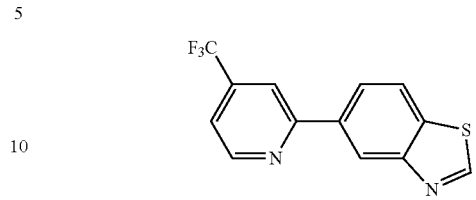

General experimental procedure for Suzuki coupling was followed. Reaction was performed on a 65 mg scale. Product was purified on a Biotage purification system eluting out in 40% EtOAc:Hexanes mixture in a gradient elution to give title compound (35 mg, 50%). $^1$HNMR (CDCl$_3$, 400 MHz) δ 9.08 (s, 1H), 8.92 (d, J=4.8 Hz, 1H), 8.78 (d, J=2.4 Hz, 1H), 8.20 (dd, J=8.4, 1.6 Hz, 1H), 8.10 (d, J=8.4 Hz, 1H), 8.05 (br s, 1H), 7.50 (dd, J=5.2, 0.8 Hz, 1H). MS: m/z=281 (M+H$^+$).

5-(5-Trifluoromethylpyridin-3-yl)benzo[d]thiazole: W293

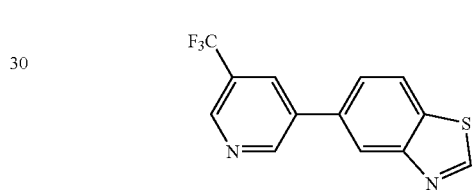

General experimental procedure for Suzuki coupling was followed. Reaction was performed on a 65 mg scale. Product was purified on a Biotage purification system eluting out in 40% EtOAc:Hexanes mixture in a gradient elution to give title compound (50 mg, 67%). $^1$H NMR (CDCl$_3$, 400 MHz) δ 9.13 (d, J=2.4 Hz, 1H), 9.10 (s, 1H), 8.92 (d, J=1.2 Hz, 1H), 8.38 (d, J=1.6 Hz, 1H), 8.20 (br s, 1H), 8.13 (d, J=8.4 Hz, 1H), 7.70 (dd, J=8.4, 2.0 Hz, 1H). MS: m/z=281 (M+H$^+$).

5-(6-Trifluoromethylpyridin-3-yl)benzo[d]thiazole: W320

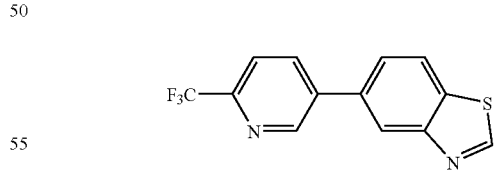

General experimental procedure for Suzuki coupling was followed. Reaction was performed on a 65 mg scale. Product was purified on a Biotage purification system eluting out in 40% EtOAc:Hexanes mixture in a gradient elution to give title compound (57 mg, 76%). $^1$H NMR (CDCl$_3$, 400 MHz) δ 9.11 (s, 1H), 9.05 (d, J=2.0 Hz, 1H), 8.39 (d, J=1.6 Hz, 1H), 8.13-8.17 (m, 1H), 8.12 (d, J=8.4 Hz, 1H), 7.82 (d, J=8.4 Hz, 1H), 7.70 (dd, J=8.4, 1.6 Hz, 1H). MS: m/z=281 (M+H$^+$).

5-(6-Trifluoromethylpyridin-2-yl)benzo[d]thiazole: W321

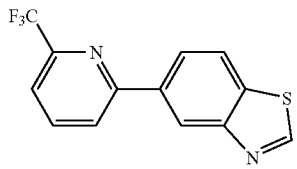 [SMILES: FC(F)(F)c1cccc(-c2ccc3scnc3c2)n1]

General experimental procedure for Suzuki coupling was followed. Reaction was performed on a 65 mg scale. Product was purified on a Biotage purification system eluting out in 40% EtOAc:Hexanes mixture in a gradient elution to give title compound (54 mg, 75%). $^1$H NMR (CDCl$_3$, 400 MHz) δ 9.08 (s, 1H), 8.78 (d, J=1.2 Hz, 1H), 8.27 (dd, J=8.4, 1.6 Hz, 1H), 8.08 (d, J=8.4 Hz, 1H), 8.04 (d, J=7.6 Hz, 1H), 7.97 (t, J=7.6 Hz, 1H), 7.65 (d, J=8.4 Hz, 1H). MS: m/z=281 (M+H$^+$).

5-(5-Trifluoromethylpyridin-2-yl)benzo[d]thiazole: W322

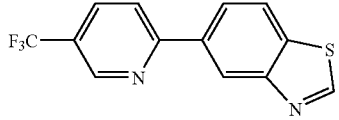 [SMILES: FC(F)(F)c1ccc(-c2ccc3scnc3c2)nc1]

General experimental procedure for Suzuki coupling was followed. Reaction was performed on a 65 mg scale. Product was purified on a Biotage purification system eluting out in 40% EtOAc:Hexanes mixture in a gradient elution to give title compound (68 mg, 91%). $^1$H NMR (CDCl$_3$, 400 MHz) δ 9.09 (s, 1H), 8.99 (br s, 1H), 8.23 (dd, J=8.4, 1.6 Hz, 1H), 8.10 (d, J=8.4 Hz, 1H), 8.04 (dd, J=8.4, 2.4 Hz, 1H). MS: m/z=281 (M+H$^+$).

5-(4-(Methylsulfonyl)phenyl)benzo[d]thiazole: W308

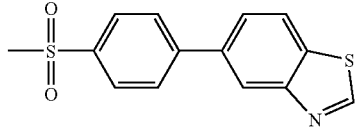

General experimental procedure for Suzuki coupling was followed. Reaction was performed on a 65 mg scale. Product was purified on a Biotage purification system eluting out in 40% EtOAc:Hexanes mixture in a gradient elution to give title compound (30 mg, 41%). $^1$H NMR (CDCl$_3$, 400 MHz) δ 9.18 (s, 1H), 8.38 (d, J=1.6 Hz, 1H), 8.05-8.12 (m, 3H), 7.88 (d, J=8.8 Hz, 2H), 7.71 (dd, J=8.4, 1.6 Hz, 2H), 3.13 (s, 3H). MS: m/z=290 (M+H$^+$).

5-(3,4-Dichlorophenyl)benzo[d]thiazole: W323

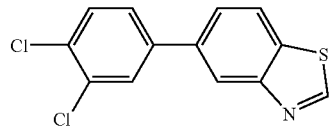 [SMILES: Clc1ccc(-c2ccc3scnc3c2)cc1Cl]

General experimental procedure for Suzuki coupling was followed. Reaction was performed on a 65 mg scale. Product was purified on a Biotage purification system eluting out in 40% EtOAc:Hexanes mixture in a gradient elution to give title compound (55 mg, 79%). $^1$H NMR (CDCl$_3$, 400 MHz) δ 9.66 (s, 1H), 8.33 (s, 1H), 8.03 (d, J=8.4 Hz, 1H), 7.76 (d, J=2.0 Hz, 1H), 7.63 (dd, J=8.4, 1.6 Hz, 1H), 7.45-7.58 (m, 2H). MS: m/z=279.9 (M+H$^+$).

2-[4-(4-(Benzo[d]thiazol-5-yl)phenyl)thiazol-2-yl]acetonitrile: W351

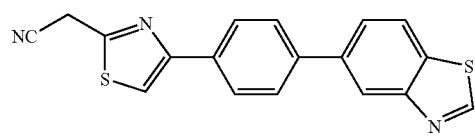

General experimental procedure for Suzuki coupling was followed. Reaction was performed on a 65 mg scale. Product was purified on a Biotage purification system eluting out in 40% EtOAc:Hexanes mixture in a gradient elution to give title compound (48 mg, 58%). $^1$H NMR (CDCl$_3$, 400 MHz) δ 9.05 (s, 1H), 8.40 (d, J=1.2 Hz, 1H), 7.98-8.09 (m, 3H), 7.71-7.82 (m, 3H), 7.55 (s, 1H), 4.21 (s, 2H). MS: m/z=334 (M+H$^+$).

5-(3,5-Difluorophenyl)benzo[d]thiazole: W352

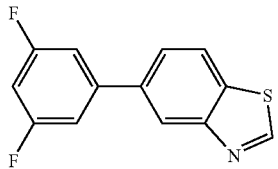 [SMILES: Fc1cc(F)cc(-c2ccc3scnc3c2)c1]

General experimental procedure for Suzuki coupling was followed. Reaction was performed on a 65 mg scale. Product was purified on a Biotage purification system eluting out in 40% EtOAc:Hexanes mixture in a gradient elution to give title compound (54 mg, 87%). $^1$H NMR (CDCl$_3$, 400 MHz) δ 9.07 (s, 1H), 8.31 (d, J=2.0 Hz, 1H), 8.04 (d, J=8.4 Hz, 1H), 7.64 (dd, J=8.4, 1.6 Hz, 1H), 7.16-7.25 (m, 2H), 6.79-6.88 (m, 1H). MS: m/z=248 (M+H$^+$).

5-(2,3,5,6-Tetrafluoro-4-trifluoromethylphenyl)benzo[d]thiazole: W324

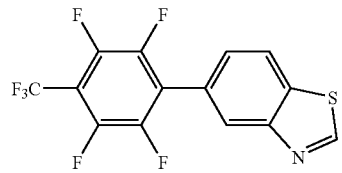 [SMILES: Fc1c(F)c(C(F)(F)F)c(F)c(F)c1-c1ccc2scnc2c1]

General experimental procedure for Suzuki coupling was followed. Reaction was performed on a 65 mg scale. Product was purified on a Biotage purification system eluting out in 40% EtOAc:Hexanes mixture in a gradient elution to give title compound (68 mg, 77%). $^1$H NMR (CDCl$_3$, 400 MHz) δ 9.11 (s, 1H), 9.05 (d, J=2.0 Hz, 1H), 8.27 (s, 1H), 8.13 (d, J=8.0 Hz, 1H), 7.54 (d, J=8.0 Hz, 1H). MS: m/z=352 (M+H$^+$).

5-[3-(4-Fluorophenoxy)phenyl]benzo[d]thiazole: W325

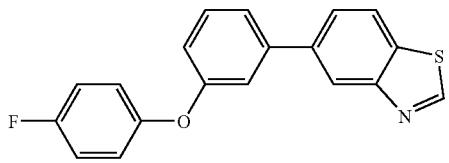 [SMILES: Fc1ccc(Oc2cccc(-c3ccc4scnc4c3)c2)cc1]

General experimental procedure for Suzuki coupling was followed. Reaction was performed on a 65 mg scale. Product was purified on a Biotage purification system eluting out in 10% EtOAc:Hexanes mixture in a gradient elution to give title compound (20 mg, 25%). $^1$H NMR (CDCl$_3$, 400 MHz) δ 9.03 (s, 1H), 9.31 (d, J=1.2 Hz, 1H), 8.00 (d, J=8.4 Hz, 1H), 7.65 (dd, J=8.4, 1.2 Hz, 1H), 7.36-7.46 (m, 2H), 7.27 (d, J=9.2 Hz, 1H), 6.94-7.12 (m, 5H). MS: m/z=322 (M+H$^+$).

5-(2,4-Dichloropyrimidin-5-yl)benzo[d]thiazole: W326

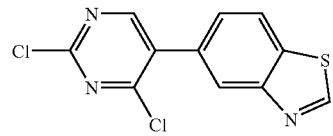 [SMILES: Clc1ncc(-c2ccc3scnc3c2)c(Cl)n1]

General experimental procedure for Suzuki coupling was followed. Reaction was performed on a 65 mg scale. Product was purified on a Biotage purification system eluting out in 0-20% EtOAc:Hexanes mixture in a gradient elution to give title compound (32 mg, 46%). $^1$H NMR (CDCl$_3$, 400 MHz) δ 9.12 (s, 1H), 8.64 (s, 1H), 8.23 (d, J=1.2 Hz, 1H), 8.12 (d, J=8.4 Hz, 1H), 8.12 (d, J=8.4 Hz, 1H), 7.54 (dd, J=8.4, 1.6 Hz, 1H). MS: m/z=281 (M+H$^+$).

5,5'-(4-Chloropyrimidine-2,5-diyl)dibenzo[d]thiazole: W327

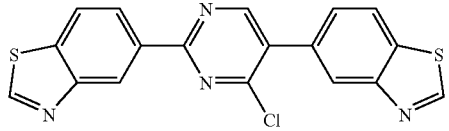 [SMILES: Clc1nc(-c2ccc3scnc3c2)ncc1-c1ccc2scnc2c1]

General experimental procedure for Suzuki coupling was followed. Reaction was performed on a 65 mg scale. Product was purified on a Biotage purification system eluting out in 0-20% EtOAc:Hexanes mixture in a gradient elution to give title compound (32 mg, 46%). $^1$H NMR (CDCl$_3$, 400 MHz) δ 9.05 (s, 1H), 8.98 (s, 1H), 8.73 (s, 1H), 8.24 (s, J=1.6 Hz, 1H), 8.11 (d, J=2.0 Hz, 1H), 7.90 (d, J=8.4 Hz, 1H), 7.88 (d, J=8.4 Hz, 1H), 7.60 (dd, J=8.8, 1.6 Hz, 1H), 7.23 (dd, J=8.8, 1.6 Hz, 1H). MS: m/z=281 (M+H$^+$).

5-(4-Fluoro-5-trifluoromethylphenyl)benzo[d]thiazole: W338

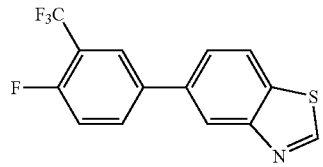 [SMILES: Fc1ccc(-c2ccc3scnc3c2)cc1C(F)(F)F]

General experimental procedure for Suzuki coupling was followed. Reaction was performed on a 65 mg scale. Product was purified on a Biotage purification system eluting out in 0-20% EtOAc:Hexanes mixture in a gradient elution to give title compound (60 mg, 81%). $^1$H NMR (CDCl$_3$, 400 MHz) δ 9.07 (s, 1H), 8.30 (d, J=1.2 Hz, 1H), 8.05 (d, J=8.4 Hz, 1H), 7.78-7.82 (m, 2H), 7.64 (dd, J=8.4, 1.6 Hz, 1H), 7.31 (t, J=9.2 Hz, 1H). MS: m/z=298 (M+H$^+$).

5-(3-Fluoro-5-trifluoromethylphenyl)benzo[d]thiazole: W339

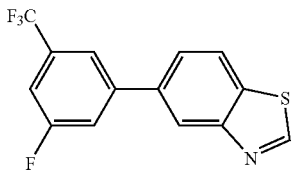 [SMILES: Fc1cc(-c2ccc3scnc3c2)cc(C(F)(F)F)c1]

General experimental procedure for Suzuki coupling was followed. Reaction was performed on a 65 mg scale. Product was purified on a Biotage purification system eluting out in 0-20% EtOAc:Hexanes mixture in a gradient elution to give title compound (54 mg, 73%). NMR (CDCl$_3$, 400 MHz) δ 9.09 (s, 1H), 8.35 (d, J=1.6 Hz, 1H), 8.07 (d, J=8.4 Hz, 1H), 7.73 (s, 1H), 7.68 (dd, J=8.4, 2.0 Hz, 1H), 7.57 (d, J=9.2 Hz, 1H), 7.35 (d, J=8.4 Hz, 1H). MS: m/z=298 (M+H$^+$).

5-(3-Fluoro-4-trifluoromethylphenyl)benzo[d]thiazole: W340

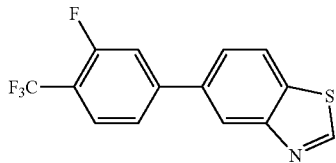 [SMILES: Fc1cc(-c2ccc3scnc3c2)ccc1C(F)(F)F]

General experimental procedure for Suzuki coupling was followed. Reaction was performed on a 65 mg scale. Product was purified on a Biotage purification system eluting out in 0-20% EtOAc:Hexanes mixture in a gradient elution to give title compound (58 mg, 78%). $^1$HNMR (CDCl$_3$, 400 MHz) δ 9.08 (s, 1H), 8.35 (d, J=1.2 Hz, 1H), 8.07 (d, J=8.0 Hz, 1H), 7.62-7.78 (m, 2H), 7.44-7.58 (m, 2H). MS: m/z=298 (M+H$^+$).

5-(2,3,5,6-Tetrafluoropyridin-4-yl)benzo[d]thiazole: W341

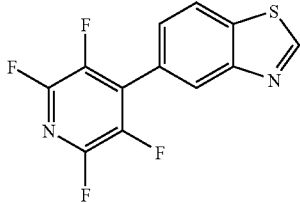 [SMILES: Fc1nc(F)c(F)c(-c2ccc3scnc3c2)c1F]

General experimental procedure for Suzuki coupling was followed. Reaction was performed on a 65 mg scale. Product was purified on a Biotage purification system eluting out in 0-20% EtOAc:Hexanes mixture in a gradient elution to give title compound (54 mg, 46%). $^1$H NMR (CDCl$_3$, 400 MHz) δ 9.13 (s, 1H), 8.34 (d, J=0.8 Hz, 1H), 8.15 (d, J=8.4 Hz, 1H), 7.60 (dd, J=8.4, 1.2 Hz, 1H). MS: m/z=285 (M+H$^+$).

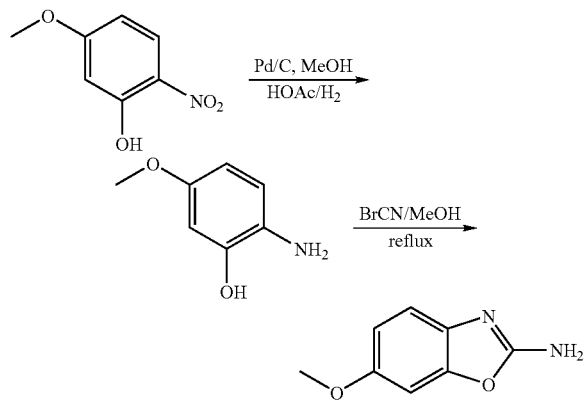

General experimental procedure for the preparation of 6-methoxybenzo[d]oxazol-2-amine: A mixture of 5-methoxy-2-nitrophenol (0.51 g, 3.02 mmol), Pd/C (10% by weight, 70 mg), and HOAc (cat. amount) in MeOH (30 mL) was hydrogenated under H$_2$ at room temperature for 2 hrs, and then was filtered through a short Celite pad. The filtrate was concentrated in vacuo to provide 2-amino-5-methoxyphenol as a brown solid (0.42 g, 100%). $^1$H NMR (CDCl$_3$, 400 MHz) δ 6.79 (d, J=8.4 Hz, 1H), 6.44 (d, J=2.8 Hz, 1H), 6.35 (dd, J=8.4, 2.8 Hz, 1H), 3.74 (s, 3H). This product was used directly in the next step without any further purification.

A mixture of 2-amino-5-methoxyphenol (0.42 g, 3.17 mmol) and cyanogen bromide (0.34 g, 3.17 mmol) in MeOH (40 mL) was refluxed for 1 h, and concentrated in vacuo. The residue was neutralized with sat. NaHCO$_3$ aqueous solution and diluted with H$_2$O (20 mL). The resulting mixture was extracted with EtOAc (3×20 mL). The combined organic layers were dried (MgSO$_4$) and decolorized with activated carbon, filtered and concentrated. The residue was purified on column chromatography (silica gel, 0-40% EtOAc/hexanes) to give a light red solid (0.25 g, 50%). $^1$H NMR (CDCl$_3$, 400 MHz) δ 7.24 (d, J=8.4 Hz, 1H), 6.89 (d, J=2.4 Hz, 1H), 6.78 (dd, J=8.4, 2.4 Hz, 1H), 5.26 (br s, 2H), 3.82 (s, 3H).

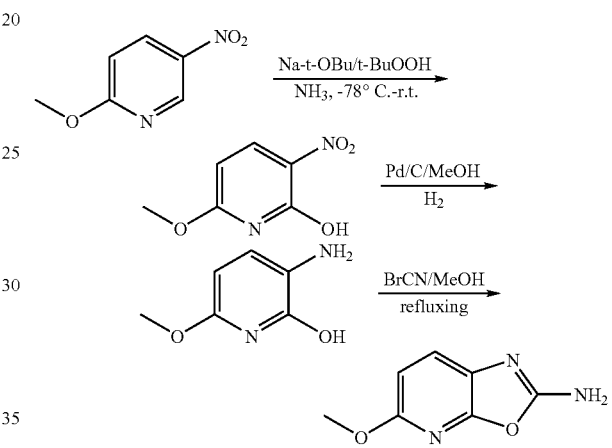

General Procedures for the Preparation of 5-methoxyoxazolo[5,4-b]pyridin-2-amine Preparation of 2-hydroxy-6-methoxy-3-nitropyridine: To a cooled suspension of Na t-OBu (6.24 g, 64.9 mmol) in liquid ammonia was added dropwise a solution of 6-methoxy-3-nitropyridine (2.0 g, 12.98 mmol) and t-butyl hydrogenperoxide (1.53 mL, 14.31 mmol) in THF (20 mL). After the completion of addition, the resulting mixture was stirred at −78° C. under Ar and warmed gradually to room temperature, and then stirred at room temperature overnight, which gave a yellow solid. It was diluted with H$_2$O (30 mL). The resulting mixture was neutralized with the addition of 1N HCl solution. The solid formed was collected and washed with H$_2$O and DCM, and then dried (1.18 g). The filtrate was extracted with DCM (2×20 mL). The combined organic layers were dried (MgSO$_4$), filtered and concentrated to give the second portion (0.59 g, total 1.77 g, 80%). NMR (MeOD-d$_3$, 400 MHz) □ 8.20 (d, J=8.8 Hz, 1H), 5.79 (d, J=8.8 Hz, 1H), 4.87 (s, 3H). MS: m/z=171 (M+H$^+$).

Preparation of 3-amino-2-hydroxy-6-methoxypyridine: A mixture of 2-hydroxy-6-methoxy-3-nitropyridine (0.59 g, 3.44 mmol), Pd/C (10%, 80 mg), and HOAc (cat. amount) in MeOH (40 mL) was hydrogenated under H$_2$ at room temperature for 2 hrs. It was passed through a short Celite pad. The filtrate was concentrated in vacuo to give a brown solid (0.473 g, 98%). NMR (CDCl$_3$, 400 MHz) □ 6.65 (d, J=8.0 Hz, 1H), 5.37 (d, J=8.0 Hz, 1H), 3.77 (s, 3H). This product was used directly in the next step without any further purification.

A mixture of 3-amino-2-hydroxy-6-methoxypyridine (0.473 g, 3.38 mmol) and cyanogen bromide (0.37 g, 3.49 mmol) in MeOH (30 mL) was refluxed for 1 hr, and cooled to room temperature and neutralized with sat. NaHCO$_3$ aqueous solution, and then concentrated. The residue was diluted with H$_2$O, filtered, and dried (0.325 g, 58%). $^1$H NMR (MeOD-d3, 400 MHz) δ 7.49 (d, J=8.0 Hz, 1H), 6.61 (d, J=8.0 Hz, 1H), 3.87 (s, 3H). MS: m/z=166 (M+H$^+$).

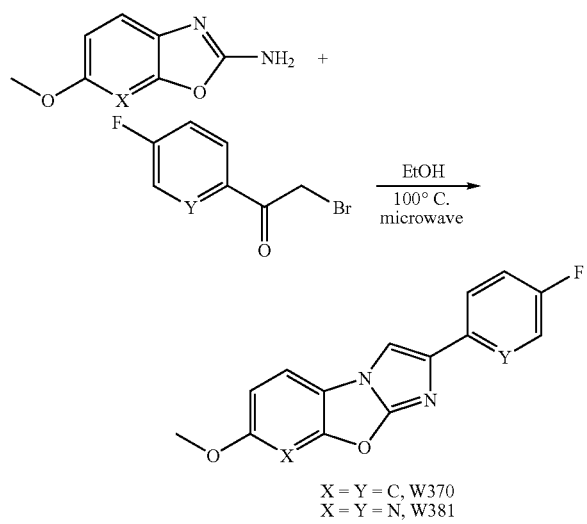

X = Y = C, W370
X = Y = N, W381

General Procedures for the Preparation of 6-methoxy-2-aryl-imidazo[2',1':2,3]oxazolo[5,4-b]pyridine A mixture of 2-aminooxazole derivative (1.0 eq.) and a proper α-bromoketone (1.0 eq.) in EtOH (2.0 mL) was microwaved at 100° C. for 1.5 hrs, cooled to room temperature, and filtered. The solid collected was washed with H$_2$O, EtOH, EtOAc, DCM, and ether to give the desired product as HBr salt. The salt was stirred with 5% Na$_2$CO$_3$ solution overnight. The mixture was filtered, washed with H$_2$O, ether. The solid collected was then dried to give the desired product.

7-methoxy-2-(4-fluorophenyl)-imidazo[2,1-b]benzoxazole: W 370

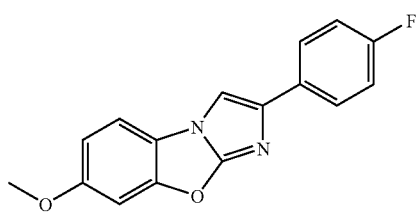

General experimental procedure for the preparation of oxazolopyridine derivatives was followed. Reaction was performed on a 53 mg scale. A solid (3.5 mg, 5%) was obtained. $^1$H NMR (CDCl$_3$, 400 MHz) δ 7.79 (d, J=8.8 Hz, 1H), 7.78 (d, J=8.8 Hz, 1H), 7.45 (s, 1H), 7.38 (d, J=8.8 Hz, 1H), 7.06-7.14 (m, 3H), 6.89 (d, J=8.8, 2.4 Hz, 1H), 3.88 (s, 3H). MS: m/z=283 (M+H$^+$).

6-methoxy-2-(5-fluoro-2-pyridyl)-imidazo[2',1':2,3]oxazolo[5,4-b]pyridine: W 381

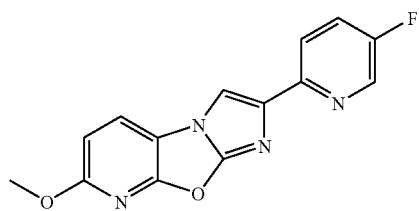 [SMILES: COc1ccc2c(n1)oc1nc(-c3ccc(F)cn3)cn12]

General experimental procedure for the preparation of oxazolopyridine derivatives was followed. Reaction was performed on a 57 mg scale. A solid (3.6 mg, 4%) was obtained. $^1$H NMR (CDCl$_3$, 400 MHz) δ 7.79 (d, J=8.8 Hz, 1H), 7.78 (d, J=8.8 Hz, 1H), 7.45 (s, 1H), 7.38 (d, J=8.8 Hz, 1H), 7.06-7.14 (m, 3H), 6.89 (d, J=8.8, 2.4 Hz, 1H), 3.88 (s, 3H). MS: m/z=285 (M+H$^+$).

7-methoxy-2-(5-fluoro-2-pyridyl)-imidazo[2,1-b]benzoxazole: W 380

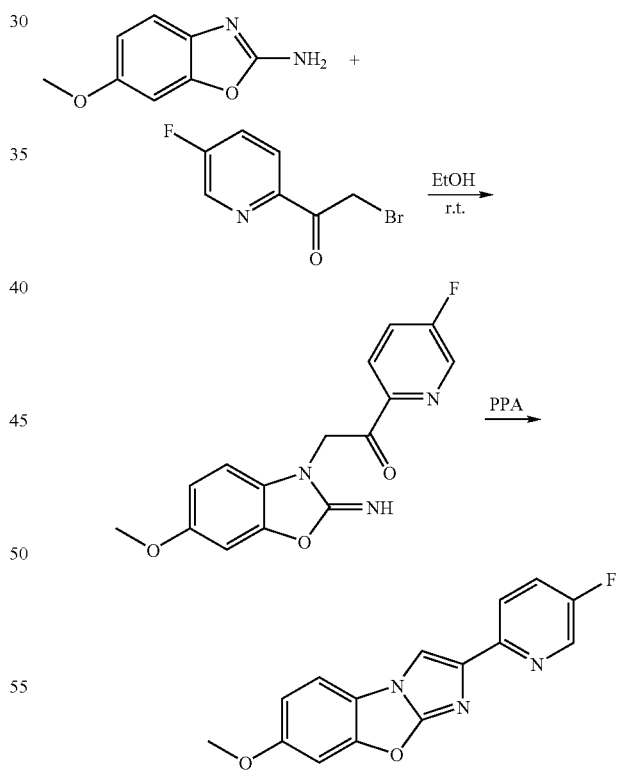

General procedure for the preparation of W380: A mixture of 2-amino-6-methoxybenzoxazole (75 mg, 0.46 mmol) and 2-bromo-1-(5-fluoropyridin-2-yl)ethanone (102 mg, 0.47 mmol) was stirred at room temperature for 3 days, and then filtered. The solid was washed with ether and dried in vacuo (70 mg, 50%). This product was used directly in the next step without any further purification.

To a heated solution of PPA (1.9 g) at 125° C. was added the intermediate obtained above (60 mg). The resulting mixture was heated at 125° C. for 2 hrs. The mixture was cooled and neutralized with NaHCO$_3$ solution, extracted with EtOAc (2×10 mL). The combined organic layers were dried (MgSO$_4$), filtered, and concentrated. The residue was purified on column chromatography (silica gel, 5-30% EtOAc/hexanes) to give the desired product (7.0 mg, 12%). $^1$H NMR (CDCl$_3$, 400 MHz) δ 8.42 (d, J=2.1 Hz, 1H), 7.99 (dd, J=8.8, 0.8 Hz, 1H), 7.85 (s, 1H), 7.46 (dd, J=8.4, 2.8 Hz, 1H), 7.43 (d, J=8.8 Hz, 1H), 7.13 (d, J=2.4 Hz, 1H), 6.91 (dd, J=8.4, 2.0 Hz, 1H), 3.89 (s, 3H). MS: m/z=284 (M+H$^+$).

Synthesis of OX-02

Synthetic Scheme of OX-02

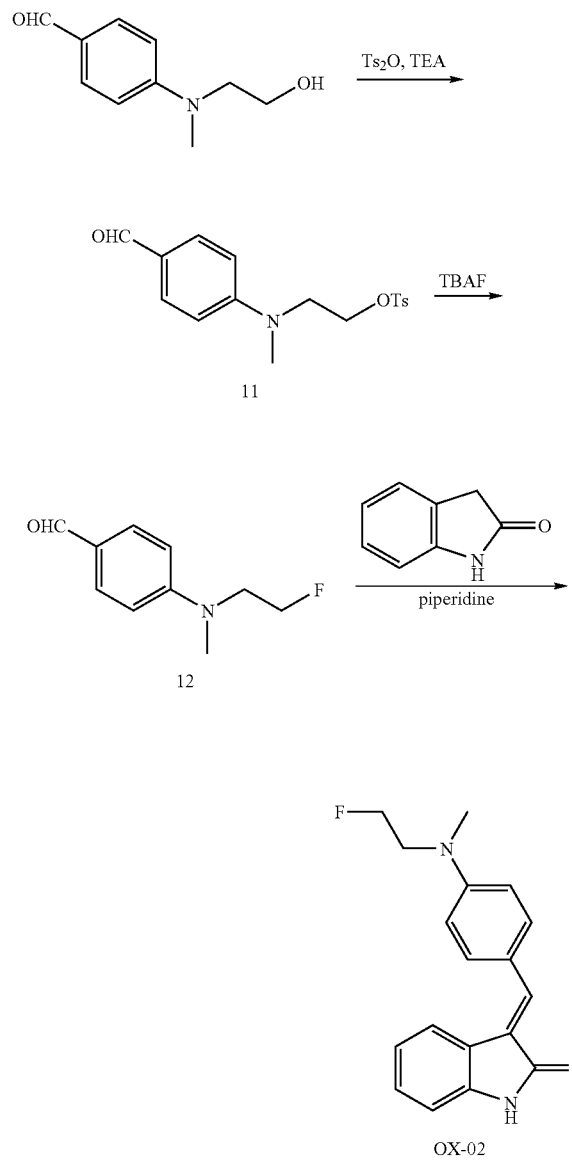

Preparation of 2-((4-formylphenyl)(methyl)amino) ethyl 4-methylbenzenesulfonate (Compound 11)

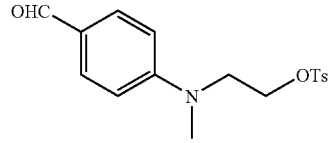 [SMILES: Cc1ccc(S(=O)(=O)OCCN(C)c2ccc(C=O)cc2)cc1]

To a round bottom flask containing 4-((2-hydroxyethyl)(methyl)amino)benzaldehyde (7.0 g, 39 mmol) and tosyl anhydride (15.3 g, 47 mmol) in DCM (50 ml) at ice bath temperature, was added triethylamine (13.7 mL, 98 mmol) dropwise. The reaction was allowed to rt and stirred for 72 h. The reaction was diluted with brine (150 mL) and extracted with DCM (100 mL×3). The combined organic layer was concentrated in vacuo. The residue was purified on a silica gel column to afford Compound 11 as a red solid (1.5 g, 4.5 mmol, 12% yield). $^1$H-NMR (400 MHz, CDCl$_3$) δ: 9.75 (s, 1H), 7.70-7.67 (m, 4H), 7.24 (d, J=8.0 Hz, 2H), 6.59 (d, J=5.6 Hz, 1H), 4.21 (t, J=5.6 Hz, 2H), 3.74 (t, J=5.6 Hz, 2H), 3.01 (s, 3H), 2.40 (s, 3H).

Preparation of 4-((2-fluoroethyl)(methyl)amino)benzaldehyde (Compound 12)

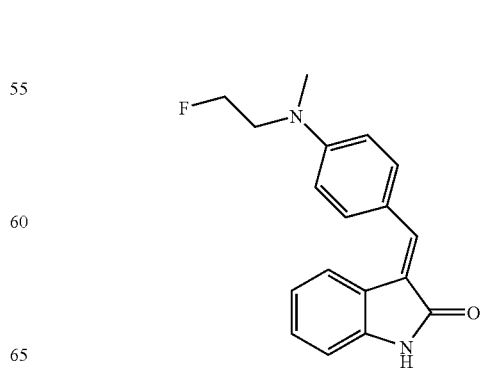

To a round bottom flask containing Compound 11 (150 mg, 0.45 mmol) in THF (1 mL), was added tetrabutylammonium fluoride (1.0 M solution in THF, 0.54 mL, 0.54 mmol). The reaction mixture was heated at 100° C. for 30 min. The reaction was then concentrated in vacuo and purified on a silica gel column to afford Compound 12 as a white solid (72 mg, 0.40 mmol, 88% yield). $^1$H-NMR (400 MHz, CDCl$_3$) δ: 9.76 (s, 1H), 7.75 (d, J=8.8 Hz, 2H), 6.73 (d, J=8.8 Hz, 2H), 4.70 (m, 1H), 4.58 (m, 1H), 3.80-3.74 (m, 2H), 3.14 (s, 3H).

Preparation of (E)-3-(4-((2-fluoroethyl)(methyl)amino)benzylidene)indolin-2-one (OX-02)

To a round bottom flask containing Compound 12 (72 mg, 0.40 mmol) and 2-oxoindole (54 mg, 0.40 mmol) in ethanol (2 mL), was added piperidine (39 uL, 0.40 mL). The reaction was heated at 80° C. for 15 min and then allowed to rt for 72 h. A yellow precipitate formed in the solution and was collected via vacuum filtration. The yellow solid was dried via lypholization to afford OX-02 (94 mg, 0.32 mmol, 80% yield). $^1$H NMR (400 MHz, CDCl$_3$) δ: 10.41 (br, 1H), 7.73 (d, J=8.40 Hz, 1H), 7.59 (d, J=8.40 Hz, 2H), 7.46 (s, 1H), 7.15-7.11 (m, 1H), 6.85-6.80 (m, 4H), 4.65-4.62 (m, 1H), 4.53-4.50 (m, 1H), 3.77-3.69 (m, 2H), 3.00 (s, 3H); LRMS for C$_{18}$H$_{17}$N$_2$O+H$^+$, calc'd: 297.1, found: 297.1 (M+H$^+$)

Synthesis of W213, W279, W280, W283, W342 and W343

Synthesis of W213

Preparation of 7-hydroxy-(2-(4-fluorophenyl)imidazo[2,1-b]8-benzothiazole) (W198)

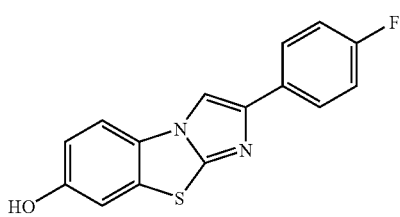 [SMILES: Oc1ccc2c(c1)sc1nc(-c3ccc(F)cc3)cn12]

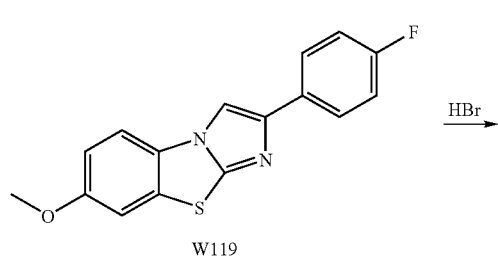

To a vial equipped with a magnetic stir bar, was added W119 (0.023 g, 0.077 mmol, 1.0 equiv). To the vial, was added 48% HBr in AcOH (0.3 mL) and 45% HBr aqueous solution (0.3 mL). The vial was sealed and heated to 135° C. for 5 h until LCMS indicated completion of the reaction. The mixture was allowed to rt and cooled in the ice bath. The solid precipitate was filtered, washed with diethyl ether (2 mL×2) and dried in vacuo to afford an off white solid W198 (0.012 g, 55%). $^1$H-NMR (400 MHz, DMSO) δ: 8.59 (s, 1H), 7.85-7.81 (m, 2H), 7.73 (d, J=8.8 Hz, 1H), 7.34 (d, J=2.4 Hz, 1H), 7.25-7.22 (m, 2H), 6.93 (dd, J=8.8 Hz, 2.0 Hz, 2H); MS: 285 [M+H$^+$—HBr].

Preparation of 7-(2-fluoroethoxy)-(2-(4-fluorophenyl)imidazo[2,1-b]8-benzothiazole) (W213)

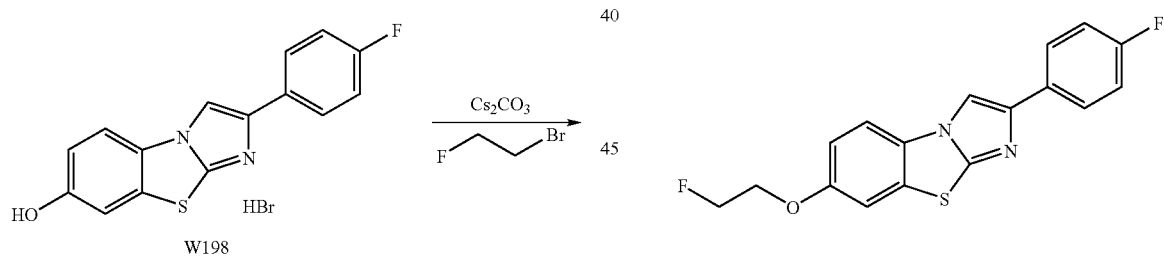

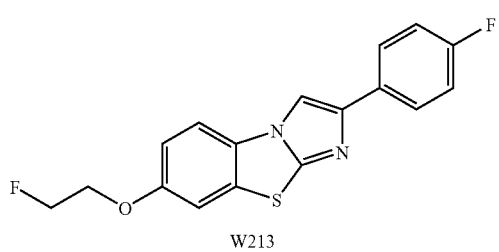

To a vial equipped with a magnetic stir bar, was added W198 (0.056 g, 0.15 mmol, 1.0 equiv). To the vial, was added cesium carbonate (0.150 g, 0.46 mmol, 3 equiv) and DMF (0.5 mL). To the solution, was added 2-bromofluoroethane (195 mg, 1.53 mmol, 10 equiv). The mixture was stirred at rt for 15 h. LCMS indicated completion of the reaction. The mixture was diluted with water (15 mL). The solid precipitates were collected via vacuum filtration. The product was washed with water (5 mL) and ether (5 mL×2) and dried in vacuo to afford W213 (50 mg, 99%) as a white solid. $^1$H-NMR (400 MHz, Acetone-D$_6$) δ: 8.47 (s, 1H), 7.96 (dd, J=8.8 Hz, 5.6 Hz, 2H), 7.85 (d, J=8.8 Hz, 1H), 7.63 (d, J=2.4 Hz, 1H), 7.21-7.18 (m, 2H), 4.87-4.75 (m, 2H), 4.44-4.37 (m, 2H); MS: 331.0 (M+H$^+$).

Synthesis of W279, W280, W283

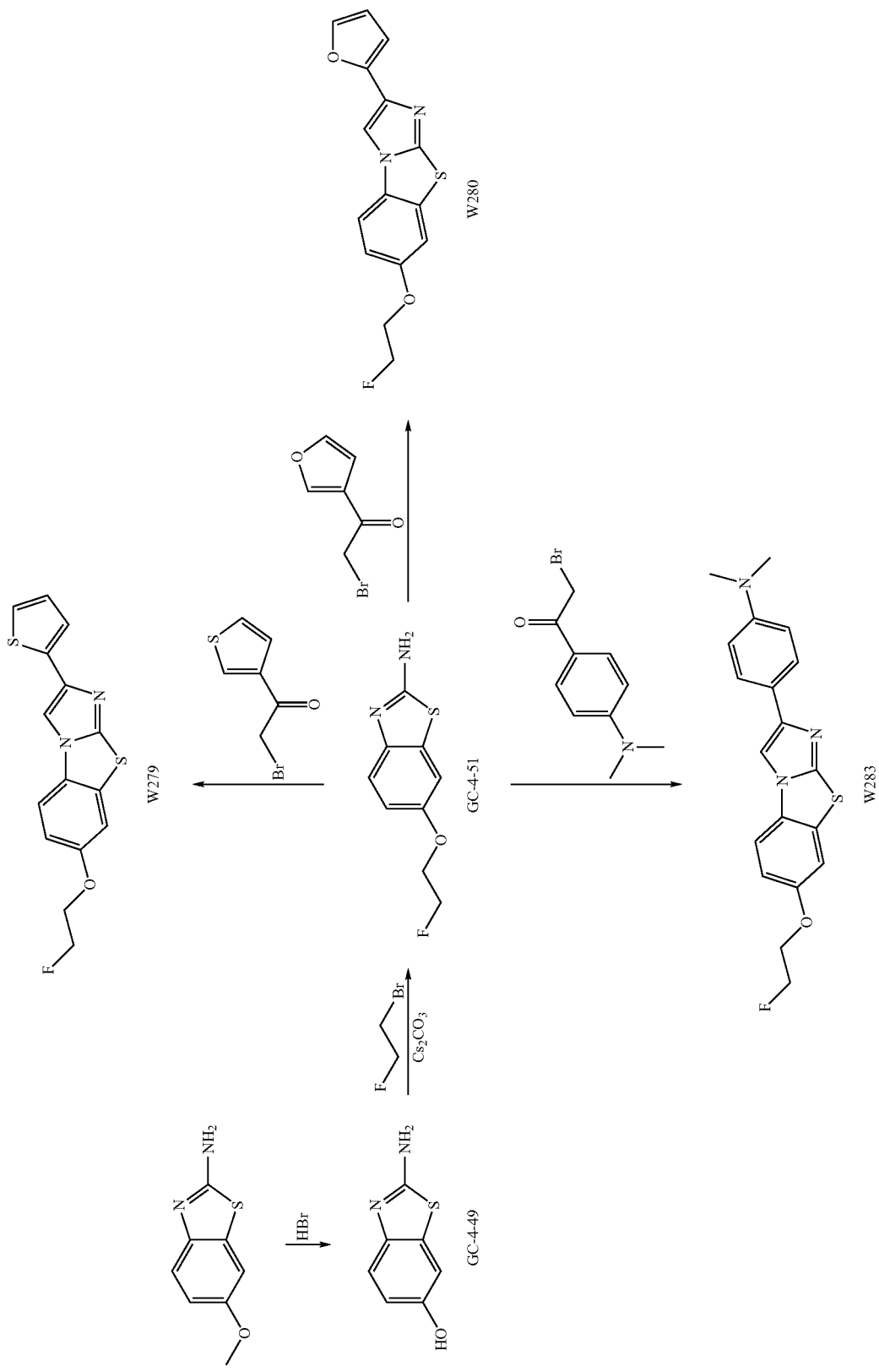

Preparation of 2-aminobenzo[d]thiazol-6-ol: GC-4-49

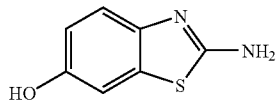 [SMILES: Nc1nc2ccc(O)cc2s1]

To a vial equipped with a magnetic stir bar, was added 2-amino-6-methoxybenzthiazole (1.0 g, 5.55 mmol, 1.0 equiv). To the vial, was added 48% HBr in AcOH (1.5 mL) and 45% HBr aqueous solution (1.5 mL). The vial was sealed and heated to 135° C. for 3 h until LCMS indicated completion of the reaction. The mixture was allowed to rt. The solid precipitate was filtered, washed with water (2 mL), diethyl ether (2 mL×2) and dried in vacuo to afford an off white solid GC-4-49 (1.0 g, 73%). $^1$H-NMR (400 MHz, DMSO) δ: 9.42 (br, 2H), 7.31 (m, 2H), 6.87 (dd, J=8.8 Hz, 2.4 Hz, 1H); MS: 248.1 [M+H$^+$—HBr].

Preparation of 6-(2-fluoroethoxy)benzo[d]thiazol-2-amine: GC-4-51

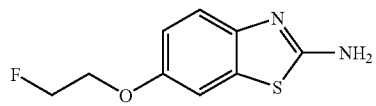 [SMILES: Nc1nc2ccc(OCCF)cc2s1]

To a vial equipped with a magnetic stir bar, was added GC-4-49 (0.400 g, 1.62 mmol, 1.0 equiv). To the vial, was added cesium carbonate (1.06 g, 3.32 mmol, 2 equiv) and DMF (2 mL). To the solution, was added 2-bromofluoroethane (1.03 g, 8.07 mmol, 5 equiv). The mixture was stirred at rt for 48 h until LCMS indicated completion of the reaction. The mixture was diluted with water (20 mL), extracted with EtOAc (15 mL×2). The combined organic layers were dried and concentrated. The residue was purified on a Biotage silica gel column (Hexanes:EtOAc=3:1) to afford GC-4-51 (250 mg, 73%) as a white solid. $^1$H-NMR (400 MHz, DMSO) δ: 7.32 (d, J=2.8 Hz, 1H), 7.24 (br, 2H), 7.23 (d, J=8.8 Hz, 1H), 6.84 (d, J=8.8 Hz, 2.4 Hz, 1H), 4.80-4.68 (m, 2H), 4.24-4.16 (, 2H); MS: 213.2 (M+H$^+$).

Preparation of 7-(2-fluoroethoxy)-2-(thiophene-2-yl)imidazo[2,1-b]8-benzothiazole (W279)

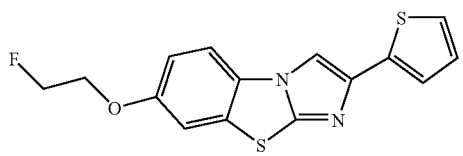

General experimental procedure for cyclization was followed. Reaction was performed on a 0.01 g scale. The reaction mixture was concentrated and loaded onto a silica gel column on a Biotage purification system. The product eluted out in 50% EtOAc:Hexanes mixture in a gradient elution. Isolated 0.007 g (45%) of W279 as a white solid. $^1$H-NMR (400 MHz, Acetone-D$_6$) δ: 8.31 (s, 1H), 7.84 (d, J=8.8 Hz, 1H), 7.61 (d, J=2.4 Hz, 1H), 7.40 (dd, J=3.6, 1.2 Hz, 1H), 7.35 (dd, J=5.2, 1.2 Hz, 1H) 7.18 (dd, J=8.8 Hz, 2.4 Hz, 1H), 7.06 (dd, J=5.2 Hz, 3.6 Hz, 1H), 4.87-4.73 (m, 2H), 4.42-4.35 (m, 2H); MS: 318.9 (M+H$^+$).

Preparation of 7-(2-fluoroethoxy)-2-(furan-2-yl)imidazo[2,1-b]8-benzothiazole (W280)

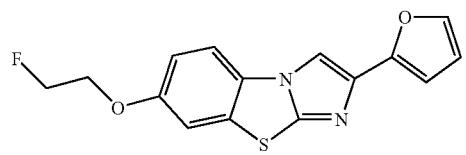 [SMILES: FCCOc1ccc2c(c1)sc1nc(-c3ccco3)cn12]

General experimental procedure for cyclization was followed. Reaction was performed on a 0.015 g scale. The reaction mixture was concentrated, diluted with water/MeOH (1:1, 20 mL). The product was purified on HPLC using MeCN/Water mixture in a gradient elution on a Phenomenex-Luna column to afford W280 as a white solid. MS: $^1$H-NMR (400 MHz, Acetone-D$_6$) δ: 8.24 (s, 1H), 7.89 (d, J=8.8 Hz, 1H), 7.61 (d, J=2.4 Hz, 1H), 7.54 (dd, J=2.0 Hz, 0.8 Hz, 1H), 7.19 (d, J=1.6 Hz, 1H), 7.18 (dd, J=8.8 Hz, 2.4 Hz, 1H), 7.06 (dd, J=5.2 Hz, 3.6 Hz, 1H), 4.87-4.73 (m, 2H), 4.42-4.35 (m, 2H); MS: 303.0 (M+H$^+$).

Preparation of 7-(2-fluoroethoxy)-2-(4-dimethylaminophenyl)imidazo[2,1-b]8-benzothiazole W283

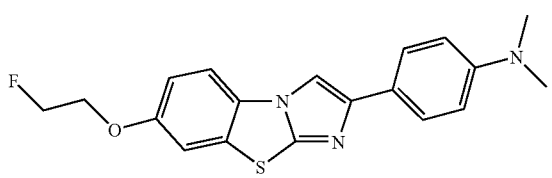 [SMILES: CN(C)c1ccc(-c2cn3c(n2)sc2cc(OCCF)ccc23)cc1]

General experimental procedure for cyclization was followed. Reaction was performed on a 0.018 g scale. The reaction mixture was concentrated and loaded onto a silica gel column on a Biotage purification system. The product eluted out in 50% EtOAc:Hexanes mixture in a gradient elution. Isolated 0.005 g (17%) of W283 as a white solid. $^1$H-NMR (400 MHz, Acetone-D$_6$) δ: 8.25 (s, 1H), 7.80 (d, J=8.8 Hz, 1H), 7.75 (s, 1H), 7.72 (s, 1H), 7.58 (d, J=2.4 Hz, 1H), 7.15 (dd, J=8.8 Hz, 2.8 Hz, 1H), 6.77 (d, J=8.8 Hz, 1H), 4.87-4.72 (m, 2H), 4.42-4.35 (m, 2H), 2.96 (s, 6H); MS: 356.1 (M+H$^+$).

Synthesis of W342 and W343

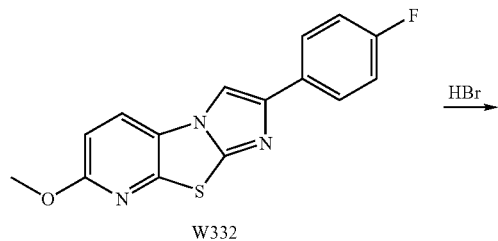

W332

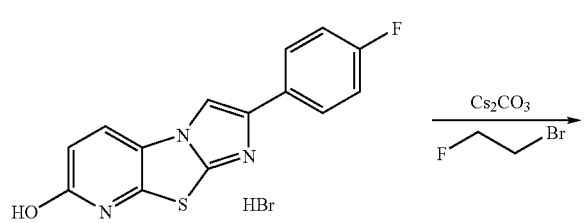

W342

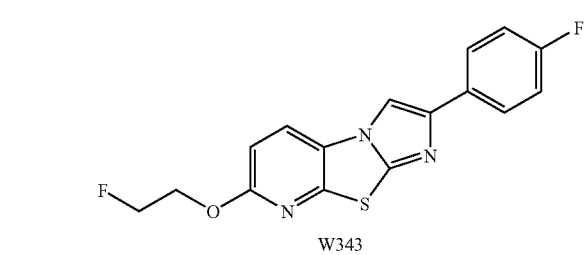

W343

Preparation of 2-hydroxy-2-(4-fluorophenyl)imidazo[2,1-b]8-pyridinothiazole W342

To a vial equipped with a magnetic stir bar, was added W332 (0.050 g, 0.17 mmol, 1.0 equiv). To the vial, was added 48% HBr in AcOH (0.5 mL) and 45% HBr aqueous solution (0.5 mL). The vial was sealed and heated to 135° C. for 3 h until LCMS indicated completion of the reaction. The mixture was allowed to rt and cooled in the ice bath. The solid precipitate was filtered, washed with diethyl ether (2 mL×2) and dried in vacuo to afford an off white solid W342 (0.049 g, 80%). $^1$H-NMR (400 MHz, DMSO) δ: 8.63 (s, 1H), 7.84-7.74 (m, 3H), 7.37 (d, J=2.4 Hz, 1H), 7.27-7.24 (m, 3H), 6.90 (d, J=8.8 Hz, 1H); MS: 286.0 [M+H$^+$—HBr].

Preparation of 7-(2-fluoroethoxy)-2-(4-fluorophenyl)imidazol[2,1-b]8-pyridinothiazole W343

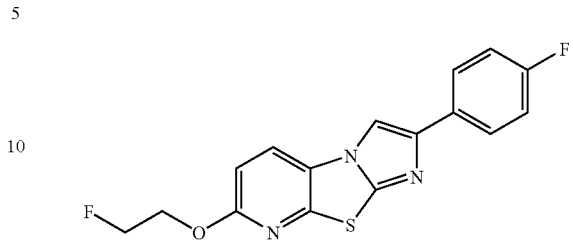

To a vial equipped with a magnetic stir bar, was added W342 (0.040 g, 0.11 mmol, 1.0 equiv). To the vial, was added cesium carbonate (0.107 g, 0.33 mmol, 3 equiv) and DMF (0.5 mL). To the solution, was added 2-bromofluoroethane (111 mg, 0.87 mmol, 8 equiv). The mixture was stirred at rt for 1 h until LCMS indicated completion of the reaction. The mixture was diluted with water (20 mL). The solid precipitates were collected via vacuum filtration. The product was washed with water (5 mL) and ether (5 mL×2) and dried in vacuo to afford W343 (30 mg, 83%) as a white solid. $^1$H-NMR (400 MHz, DMSO-D$_6$) δ: 8.71 (s, 1H), 8.34 (d, J=8.8 Hz, 1H), 7.89-7.86 (m, 2H), 7.30-7.27 (m, 2H), 7.12 (d, J=8.8 Hz, 1H), 4.92-4.73 (m, 2H), 4.60-4.50 (m, 2H); MS: 332.0 (M+H$^+$).

Synthesis of Bi-Aryl Compounds (W305, W284, W268, W231, W239, W240, W241, W246, W238, W232, W222, W216, W237, W212, W215, W217, W214, W193, W194, W199, W181, W203)

Synthesis of 5-(benzo[d]thiazol-5-yl)-N-methylpyridin-2-amine TFA salt: W305

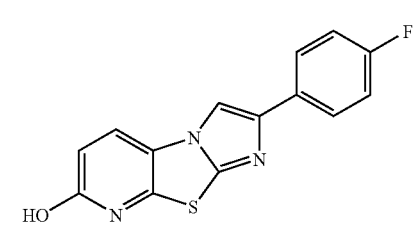 [SMILES: Oc1ccc2c(n1)sc1nc(-c3ccc(F)cc3)cn12]

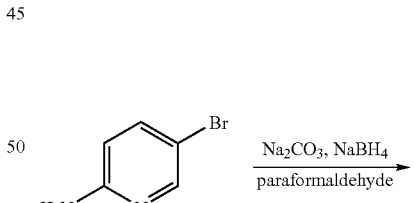

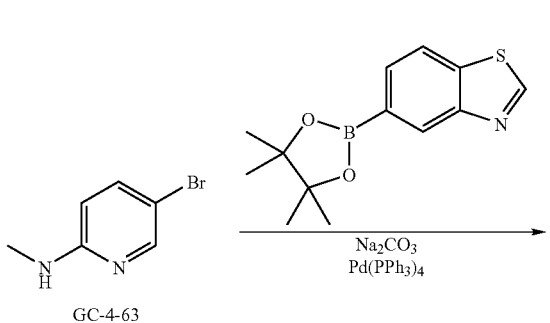

GC-4-63

-continued

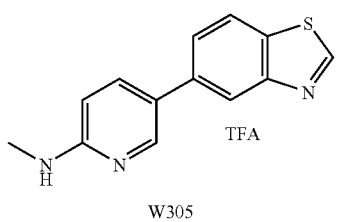

W305

Preparation of 5-bromo-N-methylpyridin-2-amine: GC-4-63

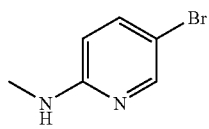

To a round bottomed flask equipped with a magnetic stir bar and a condenser, was placed 2-amino-4-bromo-pyridine (0.100 g, 0.578 mmol, 1.0 equiv). To this solution was added paraformaldehyde (0.104 g, 3.47 mmol, 6 equiv) and 25% NaOMe solution in MeOH (1.25 g, 5.78 mmol, 10 equiv). The reaction was allowed to stir at 65° C. for 1 h. The mixture was allowed to rt. To this reaction was added NaBH$_4$ (0.131 g, 3.47 mmol, 6 equiv) and the reaction was allowed to stir at 70° C. for 2 h. After the reaction was complete by LCMS, the reaction mixture was concentrated, diluted with brine (20 mL) and extracted with EtOAc (10 mL×2). The combined organic layers was dried, concentrated and purified on a Biotage silica gel column (Hexanes/EtOAc=4:1) to afford GC-4-63 (70 mg, 65%) as a white solid. $^1$H-NMR (400 MHz, CDCl$_3$) δ: 8.11 (d, J=2.0 Hz, 1H), 7.48 (dd, J=8.8 Hz, 2.8 Hz, 1H), 6.30 (dd, J=8.8 Hz, 0.8 Hz, 1H), 4.60 (br, 1H), 2.89 (d, J=5.2 Hz, 3H); MS: 187.0 (M+H$^+$).

Preparation of 5-(benzo[d]thiazol-5-yl)-N-methylpyridin-2-amine TFA salt: W305

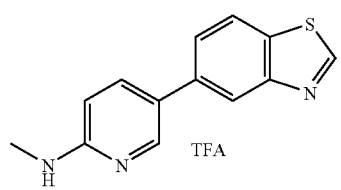 [SMILES: "TFA" ; CNc1ccc(-c2ccc3scnc3c2)cn1]

General experimental procedure for Suzuki coupling was followed. The reaction was performed on a 0.070 g scale. The reaction was concentrated, diluted with MeOH/water (1:1, 20 mL) and filtered through micro filter. The product was purified on HPLC using MeCN/Water mixture in a gradient elution on a Phenomenex-Luna column to afford W305 as TFA salt (0.020 g, 22%). $^1$H-NMR (400 MHz, Acetone-D$_6$) δ: 9.31 (s, 1H), 8.44 (d, J=2.4 Hz, 1H), 8.39 (s, 1H), 8.38 (s, 1H), 8.23 (d, J=8.4 Hz, 1H), 7.83 (dd, J=8.4 Hz, 2.0 Hz, 1H), 7.14 (d, J=8.4 Hz, 1H), 3.10 (br, 1H), 3.05 (s, J=5.2 Hz, 3H); MS: 242.0 [M+H$^+$-TFA].

Preparation of 5-(3-fluoro-4-methoxyphenyl)-2-(1H-pyrrol-1-yl)pyridine TFA salt: W284

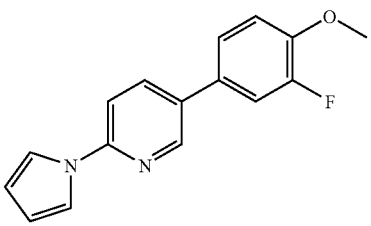 [SMILES: COc1ccc(-c2ccc(-n3cccc3)nc2)cc1F]

General experimental procedure for Suzuki coupling was followed. Reaction was performed on a 0.10 g scale. Product eluted out in EtOAc and Hexanes (1:1) mixture in a gradient elution on a Biotage purification system. Isolated 0.50 g (50%) of W284 as a white solid. %). $^1$H-NMR (400 MHz, Acetone-D$_6$) δ: 8.69 (d, J=2.0 Hz, 1H), 8.13 (dd, J=8.8 Hz, 2.8 Hz, 1H), 7.68-7.66 (m, 3H), 7.56-7.53 (m, 2H), 7.28 (t, J=8.8 Hz, 1H), 6.30 (m, 2H), 3.94 (s, 3H); MS: 269.1 (M+H$^+$).

Preparation of 5-(6-(1H-pyrrol-1-yl)pyridin-3-yl)-2-methylbenzo[d]thiazole: W268

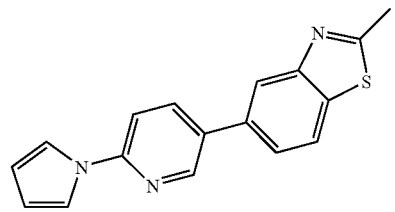 [SMILES: Cc1nc2cc(-c3ccc(-n4cccc4)nc3)ccc2s1]

To a microwave reaction vial equipped with a magnetic stir bar, were added 5-bromo-2-methylbenzo[d]thiazole (100 mg, 0.44 mmol, 1.0 equiv), potassium acetate (129 mg, 1.32 mmol, 3 equiv), pinacol diborane (117 mg, 0.46 mmol, 1.05 equiv) and palladium acetate (20 mg, 0.04 mmol, 0.1 equiv) in DMF (2 mL). The mixture was stirred at 80° C. for 3 h. 5-iodo-2-(1H-pyrrol-1-yl)pyridine (118 mg, 0.44 mmol, 1.0 equiv), Pd(PPh$_3$)$_4$ (36 mg, 0.04 mmol, 0.1 equiv) and cesium carbonate (280 mg, 0.88 mmol, 2 equiv). The mixture was heated in microwave at 100° C. for 10 min. The mixture was diluted with water (20 mL), extracted with EtOAc (15 mL×2). The combined organic layers were dried and concentrated. The residue was diluted with MeOH/water (1:1, 20 mL). The product was purified on HPLC using MeCN/Water mixture in a gradient elution on a Phenomenex-Luna column to afford W268 (5 mg, 4%) as the TFA salt. $^1$H-NMR (400 MHz, CDCl$_3$) δ: 8.73 (d, J=2.0 Hz, 1H), 8.16 (d, J=2.0 Hz, 1H), 8.03 (dd, J=8.4 Hz, 2.4 Hz, 1H), 7.93 (dd, J=8.4 Hz, 1H), 7.59-7.57 (m, 3H), 7.44 (d, J=8.4 Hz, 1H), 6.39 (m, 2H), 2.88 (s, 3H); MS: 292.0 (M+H$^+$).

Preparation of 5-(benzo[d]thiazol-5-yl)-N-benzyl-N-methylpyridin-2-amine: W249

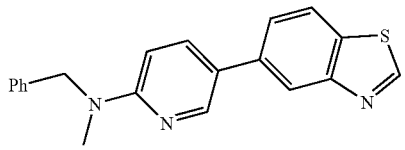 [SMILES: CN(Cc1ccccc1)c1ccc(-c2ccc3scnc3c2)cn1]

General experimental procedure for Suzuki coupling was followed. Reaction was performed on a 0.09 g scale. Product eluted out in 30% EtOAc:Hexanes mixture in a gradient elution on a Biotage purification system. Isolated 0.070 g (51%) of W249 as a white solid. $^1$H-NMR (400 MHz, CDCl$_3$) δ: 9.02 (s, 1H), 8.54 (d, J=2.0 Hz, 1H), 8.27 (d, J=1.6 Hz, 1H), 7.98 (d, J=8.4 Hz, 1H), 7.90-7.65 (m, 2H), 7.33-7.26 (m, 5H), 6.63 (dd, J=8.8 Hz, 0.8 Hz, 1H), 4.87 (s, 2H), 3.15 (s, 3H); MS: 332.2 (M+H$^+$).

Synthesis of 3-(benzo[d]thiazol-5-yl)-N-methylaniline TFA salt: W240

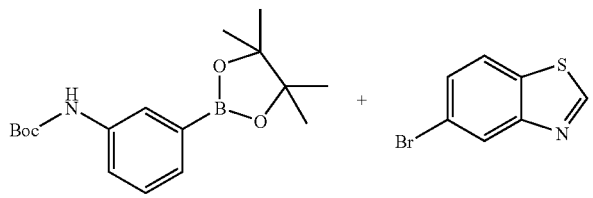

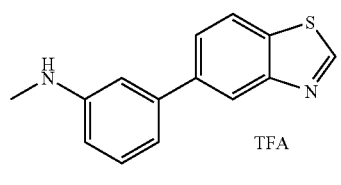

Preparation of tert-butyl 3-(benzo[d]thiazol-5-yl)phenylcarbamate: GC-4-11

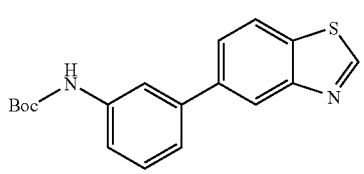 [SMILES: CC(C)(C)OC(=O)Nc1cccc(-c2ccc3scnc3c2)c1]

General experimental procedure for Suzuki coupling was followed. Reaction was performed on a 0.067 g scale. Product eluted out in 50% EtOAc:Hexanes mixture in a gradient elution on a Combiflash purification system. Isolated 0.066 g (65%) of GC-4-11 as a white solid. $^1$H-NMR (400 MHz, CDCl$_3$) δ: 9.03 (s, 1H), 8.33 (s, J=1.6 Hz, 1H), 7.97 (d, J=8.4 Hz, 1H), 7.96-7.68 (m, 2H), 7.38-7.34 (m, 3H), 6.79 (br, 1H), 1.54 (s, 9H); MS: 327.0 (M+H$^+$).

Preparation of 3-(benzo[d]thiazol-5-yl)aniline hydrochloride: W231

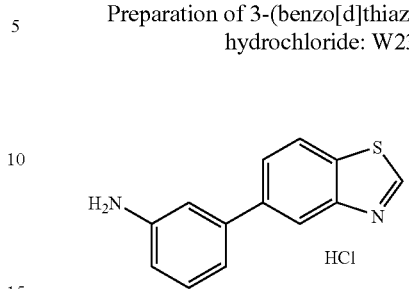

To a 50 mL round bottomed flask equipped with a magnetic stir bar was placed GC-4-11 (0.07 g, 0.213 mmol, 1 equiv). To this compound was added HCl (4M solution in dioxane) (3 mL) and the reaction was allowed to stir at room temperature for 16 h. After the reaction was complete, the product was collected via filtration. The solid was washed with ether (5 mL) and dried in vacuo to afford W231 (0.05 g, 89%) as a yellow solid. $^1$H-NMR (400 MHz, DMSO-D$_6$) δ: 9.44 (s, 1H), 8.31 (s, 1H), 8.26 (d, J=8.4 Hz, 1H), 7.76 (dd, J=8.4 Hz, 1.6 Hz, 1H), 7.74 (s, 1H), 7.58 (t, J=8.0 Hz, 1H), 7.55 (d, J=8.0 Hz, 1H); MS: 263.0 [M+H$^+$—HCl].

Preparation of 3-(benzo[d]thiazol-5-yl)-N-methylaniline TFA salt: W240

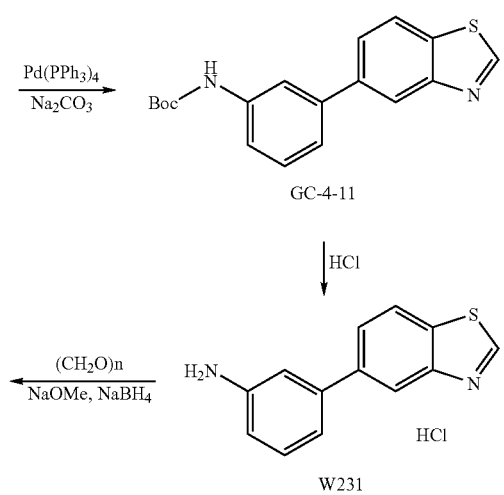

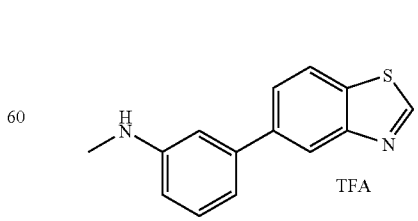

To a round bottomed flask equipped with a magnetic stir bar, was placed W231 (0.030 g, 0.13 mmol, 1.0 equiv) and 25% NaOMe solution in MeOH (286 mg, 1.32 mmol, 10 equiv). To this solution was added parafomaldehyde (0.024 g, 0.80 mmol, 6 equiv). The reaction was allowed to stir at 70° C. for 1 h. After allowed to rt, this reaction was added NaBH$_4$ (0.030 g, 0.80 mmol, 6 equiv) and the reaction was allowed to stir at 70° C. for 2 h. After the reaction was complete by LCMS, the reaction mixture was diluted with MeOH/H$_2$O (1:1, 5 ml) and purified by HPLC to afford 0.025 g (78%) of the methylamine W240 as a white solid, the TFA salt. $^1$H-NMR (400 MHz, Aceton-D$_6$) δ: 9.28 (s, 1H), 8.29 (s, 1H), 8.17 (d, J=8.4 Hz, 1H), 7.77 (dd, J=8.4 Hz, 1.6 Hz, 1H), 7.25 (td, J=8.0 Hz, 1.6 Hz, 1H), 7.02 (s, 1H), 7.01 (d, J=1.6 Hz, 1H), 6.70 (dd, J=8.8 Hz, 1.6 Hz, 1H), 3.61 (br, 1H), 2.89 (3H); MS: 241.0 [M+H$^+$-TFA].

Synthesis of W246

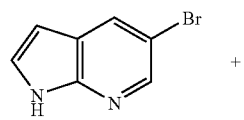

+

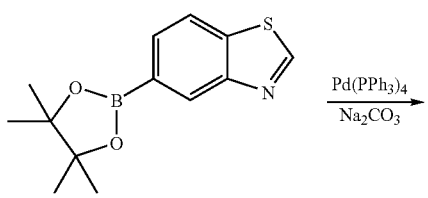

Pd(PPh$_3$)$_4$
Na$_2$CO$_3$

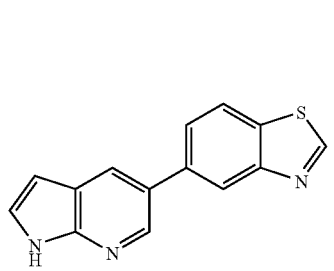 [SMILES: c1cc2cc(-c3ccc4scnc4c3)cnc2[nH]1]

W241

NaH
MeI

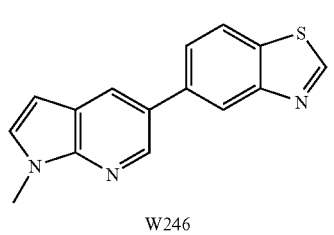

W246

Preparation of 5-(1H-pyrrolo[2,3-b]pyridin-5-yl)benzo[d]thiazole: W241

General experimental procedure for Suzuki coupling was followed. Reaction was performed on a 45 mg scale. Product eluted out in 30% EtOAc:Hexanes mixture in a gradient elution on a Biotage purification system. Isolated 50 mg (88%) of W241 as a white solid. $^1$H-NMR (400 MHz, CD$_3$CN) δ: 12.00 (s, 1H), 9.20 (s, 1H), 8.69 (s, 2H), 8.42 (d, J=2.0 Hz, 1H), 8.21 (d, J=8.4 Hz, 1H), 7.83 (t, J=1.6 Hz, 1H), 7.63 (d, J=1.6 Hz, 1H), 6.76 (d, J=2.8 Hz, 1H); MS: 252.0 (M+H$^+$).

Preparation of 5-(1-methyl-1H-pyrrolo[2,3-b]pyridin-5-yl)benzo[d]thiazole TFA salt: W246

To an oven-dried vial equipped with a magnetic stir bar, was added sodium hydride 60% suspension in mineral oil (2.4 mg, 0.06 mmol, 1 equiv). To the solid, was added W241 (15 mg, 0.060 mmol, 1 equiv) in DMF (0.5 mL). After stirred at rt for 30 min, was added iodomethane (8.5 mg, 0.06 mmol, 1 equiv). The reaction was stirred overnight, diluted with water (5 mL), extracted with EtOAc (5 mL×3). The combined organic layers was dried, concentrated and re-diluted with MeOH/Water (1:1, 10 mL). The solution was filtered through a micro filter. The product was purified on HPLC using MeCN/Water mixture in a gradient elution on a Phenomenex-Luna column to afford W246 (8 mg, 51%) as the TFA salt. $^1$H-NMR (400 MHz, CD$_3$CN) δ: 9.17 (s, 1H), 8.66 (d, J=2.0 Hz, 1H), 8.39 (d, J=1.6 Hz, 1H), 8.30 (d, J=2.0 Hz, 1H), 8.17 (d, J=8.0 Hz, 1H), 7.85 (d, J=8.0 Hz, 1H), 7.41 (d, J=3.6 Hz, 1H), 6.56 (d, J=3.6 Hz, 1H), 3.89 (s, 3H); MS: 266 [M+H$^+$-TFA].

Synthesis of 6-(benzo[d]thiazol-5-yl)-N-methylpyridin-3-amine TFA salt: W238

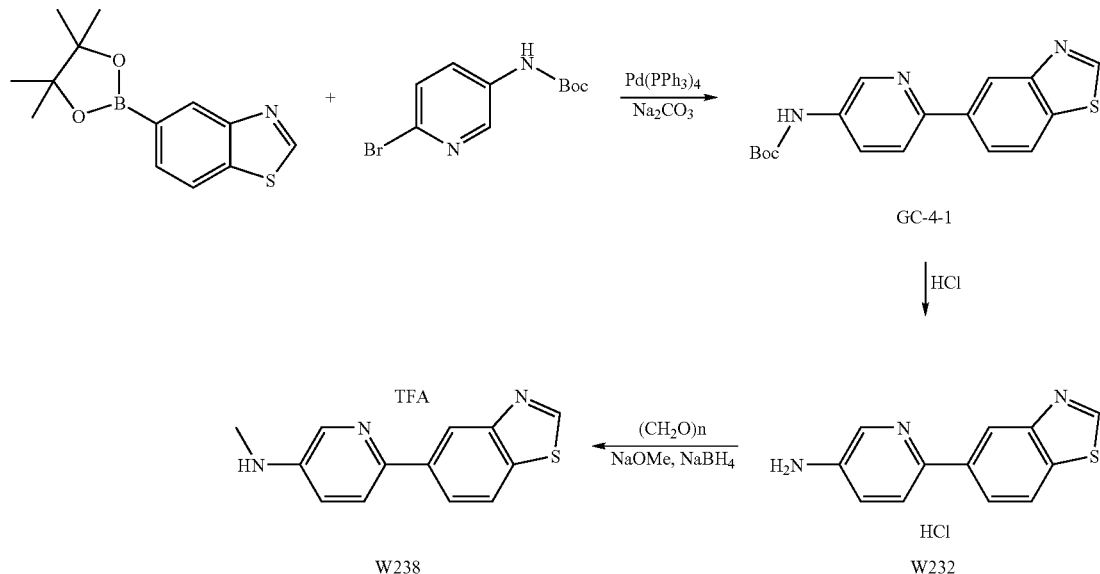

Preparation of tert-butyl 6-(benzo[d]thiazol-5-yl)pyridin-3-ylcarbamate: GC-4-1

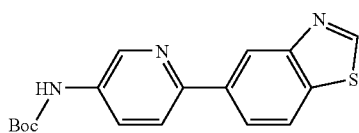

General experimental procedure for Suzuki coupling was followed. Reaction was performed on a 60 mg scale. Product eluted out in 20-80% EtOAc:Hexanes mixture in a gradient elution on a Biotage purification system. Isolated 0.018 g (24%) of GC-4-1 as a white solid. $^1$H-NMR (400 MHz, CDCl$_3$) δ: 9.04 (s, 1H), 8.67 (d, J=2.0 Hz, 1H), 8.52 (d, J=2.4 Hz, 1H), 8.14 (s, 1H), 8.12 (s, 1H), 8.04 (d, J=8.4 Hz, 1H), 7.84 (d, J=8.4 Hz, 1H), 6.76 (br, 1H), 1.55 (s, 9H); MS: 328.1 (M+H$^+$).

Preparation of 6-(benzo[d]thiazol-5-yl)pyridin-3-amine hydrochloride: W232

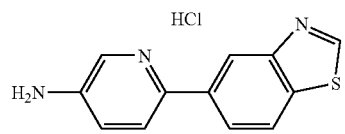

To a 10 mL round bottomed flask equipped with a magnetic stir bar was placed GC-4-1 (18 mg, 0.055 mmol, 1 equiv). To this compound was added HCl (4M solution in dioxane) (4 mL) and the reaction was allowed to stir at room temperature for 16 h. After the reaction was complete, the reaction was concentrated. The solid was washed with ether (2 mL) and dried in vacuo to afford W232 (0.015 g, 100%) as a yellow solid. $^1$H-NMR (400 MHz, CDCl$_3$) δ: 9.50 (s, 1H), 8.62 (d, J=1.6 Hz, 1H), 8.35 (d, J=8.4 Hz, 1H), 8.17 (d, J=8.8 Hz, 1H), 8.08 (s, 1H), 8.00 (d, J=1.6H, 1H), 7.71 (dd, J=8.8 Hz, 2.4 Hz, 1H); MS: 228.0 [M+H$^+$—HCl].

Preparation of 6-(benzo[d]thiazol-5-yl)-N-methylpyridin-3-amine TFA salt: W238

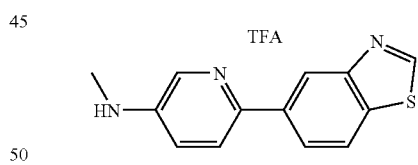

To a round bottomed flask equipped with a magnetic stir bar, was placed W232 (0.010 g, 0.044 mmol, 1.0 equiv) and 25% NaOMe solution in MeOH (95 mg, 0.44 mmol, 10 equiv). To this solution was added parafomaldehyde (8 mg, 0.264 mmol, 6 equiv). The reaction was allowed to stir at 65° C. for 1 h. After allowed to rt, to the reaction was added NaBH$_4$ (10 mg, 0.264 mmol, 6 equiv) and the reaction was allowed to stir at 65° C. for 2 h. After the reaction was complete by LCMS, the reaction mixture was diluted with MeOH/H$_2$O (1:1, 5 ml). The product was purified on HPLC using MeCN/Water mixture in a gradient elution on a Phenomenex-Luna column to afford W238 (10 mg, 94%) as the TFA salt. $^1$H-NMR (400 MHz, CDCl$_3$) δ: 9.34 (s, 1H), 8.64 (d, J=1.6 Hz, 1H), 8.36 (d, J=2.8 Hz, 1H), 8.25 (d, J=8.4 Hz, 1H), 8.11 (d, J=2.0 Hz, 1H), 8.09 (s, 1H), 7.58 (dd, J=8.4 Hz, 1.6 Hz, 1H), 2.99 (s, 3H); MS: 242.1 [M+H$^+$-TFA].

Synthesis of
4-(benzo[d]thiazol-5-yl)-N-(2-fluoroethyl)aniline
TFA salt: W237

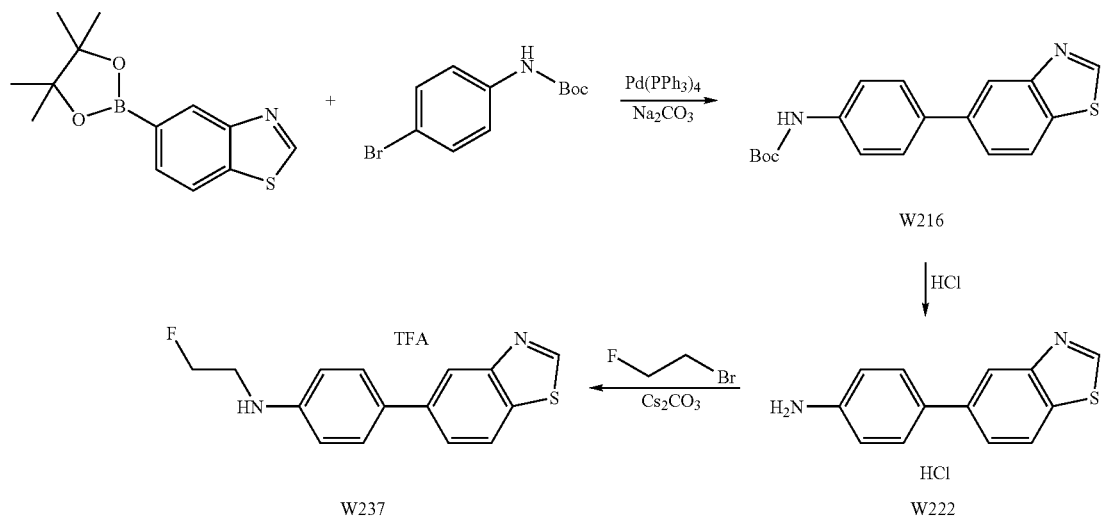

Preparation of tert-butyl 4-(benzo[d]thiazol-5-yl)phenylcarbamate: W216

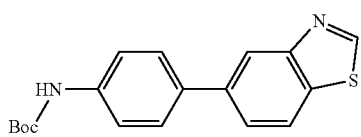 [SMILES: CC(C)(C)OC(=O)Nc1ccc(-c2ccc3scnc3c2)nc1]

General experimental procedure for Suzuki coupling was followed. Reaction was performed on a 67 mg scale. Product eluted out in 10-50% EtOAc:Hexanes mixture in a gradient elution on a Biotage purification system. Isolated 0.11 g (73%) of W216 as a white solid. $^1$H-NMR (400 MHz, CDCl$_3$) δ: 9.02 (s, 1H), 8.32 (s, 1H), 7.99 (d, J=8.4 Hz, 1H), 7.68-7.70 (m, 3H), 7.48 (d, J=8.4 Hz, 2H), 6.63 (br, 1H), 1.54 (s, 9H); MS: 327.0 (M+H).

Preparation of 4-(benzo[d]thiazol-5-yl)aniline hydrochloride: W222

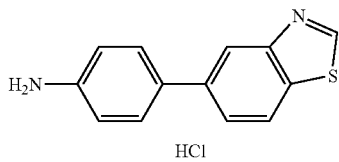

To a 25 mL round bottomed flask equipped with a magnetic stir bar was placed W216 (60 mg, 0.184 mmol, 1 equiv). To this compound was added HCl (4M solution in dioxane) (4 mL) and the reaction was allowed to stir at room temperature for 16 h. After the reaction was complete, the reaction was concentrated. The solid was washed with ether (2 mL) and dried in vacuo to afford W222 (50 mg, 100%) as a yellow solid. $^1$H-NMR (400 MHz, CDCl$_3$) δ: 9.02 (s, 1H), 8.32 (s, 1H), 7.99 (d, J=8.4 Hz, 1H), 7.68-7.70 (m, 3H), 7.48 (d, J=8.4 Hz, 2H); MS: 263.0 [M+H$^+$—HCl].

Preparation of 4-(benzo[d]thiazol-5-yl)-N-(2-fluoroethyl)aniline TFA salt: W237

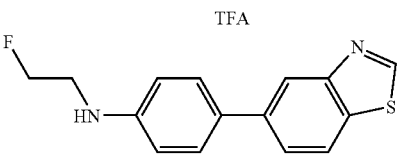 [SMILES: FCCNc1ccc(-c2ccc3scnc3c2)cc1]

To a vial equipped with a magnetic stir bar, was added W222 (0.030 g, 0.11 mmol, 1.0 equiv). To the vial, was added cesium carbonate (0.074 g, 0.228 mmol, 2 equiv) and DMF (0.5 mL). To the solution, was added 2-bromofluoroethane (73 mg, 0.571 mmol, 5 equiv). The mixture was stirred at 95° C. for 15 h. LCMS indicated 60% of conversion. No selectivity between the monoalkylation and dialkylation reaction. The mixture was diluted with water (5 mL), extracted with EtOAc (5 mL×3). Organic layers were concentrated and diluted with MeOH/water (1:1, 15 mL). The product was purified on HPLC using MeCN/Water mixture in a gradient elution on a Phenomenex-Luna column to afford W237 (8 mg, 26%) as the TFA salt. $^1$H-NMR (400 MHz, CDCl$_3$) δ: 9.24 (s, 1H), 8.24 (d, J=2.0 Hz, 1H), 8.13 (d, J=8.4 Hz, 1H), 7.74 (d, J=8.4 Hz, 1H), 7.59 (d, J=8.4 Hz, 2H), 6.84 (d, J=8.4 Hz, 2H), 4.71-4.59 (m, 2H), 3.57-3.51 (m, 2H), 3.10 (br, 1H); MS: 273.0 [M+H$^+$-TFA].

Preparation of 4-(benzo[d]thiazol-5-yl)benzonitrile: W217

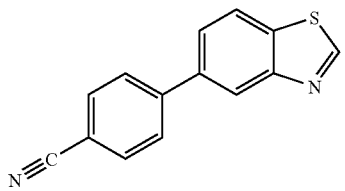 [SMILES: N#Cc1ccc(-c2ccc3scnc3c2)cc1]

General experimental procedure for Suzuki coupling was followed. Reaction was performed on a 0.067 g scale. Product eluted out in 10-60% EtOAc:Hexanes mixture in a gradient elution on a Biotage purification system. Isolated 0.018 g (25%) of W217 as a white solid. $^1$H-NMR (400 MHz, CDCl$_3$) δ: 9.08 (s, 1H), 8.36 (d, J=2.0 Hz, 1H), 8.07 (d, J=8.4 Hz, 1H), 7.74 (s, 4H), 7.68 (d, J=8.4 Hz, 1H), MS: 237.0 (M+H$^+$).

Synthesis of 6-(4-(2-fluoroethoxy)phenyl)benzo[d]thiazol-2-amine: W215

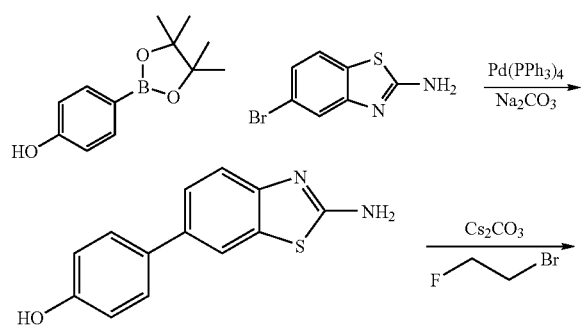

Preparation of 4-(2-aminobenzo[d]thiazol-6-yl)phenol: W212

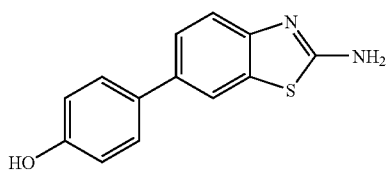 [SMILES: Nc1nc2ccc(-c3ccc(O)cc3)cc2s1]

General experimental procedure for Suzuki coupling was followed. Reaction was performed on a 0.080 g scale. Product eluted out in 10-60% EtOAc:Hexanes mixture in a gradient elution on a Biotage purification system. Isolated 0.035 g (40%) of W212 as a white solid. $^1$H-NMR (400 MHz, Acetone-D$_6$) δ: 9.78 (br, 2H), 8.00 (s, 1H), 7.45 (d, J=8.4 Hz, 1H), 7.54-7.48 (m, 3H), 6.95-6.93 (m, 2H); MS: 243.0 (M+H$^+$).

Preparation of 6-(4-(2-fluoroethoxy)phenyl)benzo[d]thiazol-2-amine: W215

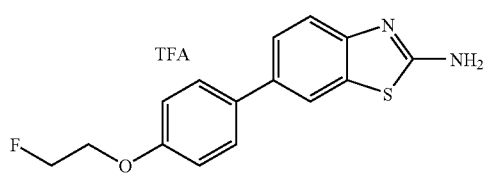 [SMILES: Nc1nc2ccc(-c3ccc(OCCF)cc3)cc2s1]

To a vial equipped with a magnetic stir bar, was added W212 (5 mg, 0.021 mmol, 1.0 equiv). To the vial, was added cesium carbonate (7 mg, 0.021 mmol, 1 equiv) and DMF (0.2 mL). To the solution, was added 2-bromofluoroethane (13 mg, 0.10 mmol, 5 equiv). The mixture was stirred at rt for 15 h. LCMS indicated completion of the reaction. The mixture was diluted with water (5 mL), extracted with EtOAc (5 mL×3). Organic layers were concentrated and diluted with MeOH/water (1:1, 10 mL). The product was purified on HPLC using MeCN/Water mixture in a gradient elution on a Phenomenex-Luna column to afford W215 (2 mg, 34%) as the TFA salt. $^1$H-NMR (400 MHz, CDCl$_3$) δ: 7.93 (s, 1H), 7.62-7.45 (m, 4H), 7.06 (d, J=8.8 Hz, 1H), 4.87-4.72 (m, 2H), 4.38-4.28 (m, 2H); MS: 289.0 [M+H$^+$-TFA].

Preparation of 4-(benzo[d]thiazol-5-yl)-N-(2-fluoroethyl)-N-methylaniline TFA salt: W214

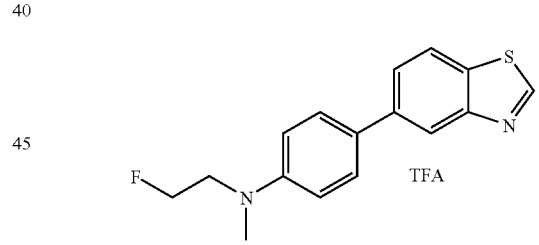

To a vial equipped with a magnetic stir bar, was added W189 (0.020 g, 0.083 mmol, 1.0 equiv). To the vial, was added cesium carbonate (0.027 g, 0.083 mmol, 1.0 equiv) and DMF (0.5 mL). To the solution, was added 2-bromofluoroethane (106 mg, 0.83 mmol, 10.0 equiv). The mixture was stirred at 95° C. for 4 h. LCMS indicated 40% of conversion. The mixture was diluted with water (5 mL), extracted with EtOAc (5 mL×3). Organic layers were concentrated and diluted with MeOH/water (1:1, 15 mL). The product was purified on HPLC using MeCN/Water mixture in a gradient elution on a Phenomenex-Luna column to afford W237 (4 mg, 17%) as the TFA salt. $^1$H-NMR (400 MHz, CDCl$_3$) δ: 9.25 (s, 1H), 8.26 (d, J=1.6 Hz, 1H), 8.12 (d, J=8.4 Hz, 1H), 7.75 (d, J=8.8 Hz, 1H), 7.65 (d, J=8.4 Hz, 1H), 6.91 (d, J=8.8 Hz, 1H), 4.74-4.62 (m, 2H), 3.81-3.72 (m, 2H), 3.08 (s, 3H); MS: 287.0 [M+H$^+$-TFA].

Preparation of 5,6'-bibenzo[d]thiazol-2'-amine: W203

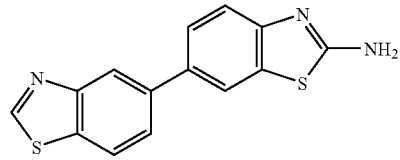 [SMILES: Nc1nc2ccc(-c3ccc4scnc4c3)cc2s1]

General experimental procedure for Suzuki coupling was followed. Reaction was performed on a 0.068 g scale. Product was purified by recrystallized from DCM/Hexanes. Isolated 0.015 g (20%) of W203 as a white solid. $^1$H-NMR (400 MHz, DMSO) δ: 9.35 (s, 1H), 8.26 (d, J=1.2 Hz, 1H), 8.14 (d, J=8.8 Hz, 1H), 8.06 (d, J=1.6 Hz, 1H), 7.65 (d, J=8.4 Hz, 1H), 7.57 (d, J=8.4 Hz, 1H), 7.35 (d, J=8.4 Hz, 1H); MS: 284.0 (M+H$^+$).

Preparation of 6-(6-(benzyloxy)naphthalen-2-yl)benzo[d]thiazol-2-amine: W199

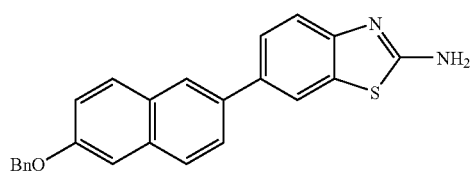 [SMILES: Nc1nc2ccc(-c3ccc4cc(OCc5ccccc5)ccc4c3)cc2s1]

General experimental procedure for Suzuki coupling was followed. Reaction was performed on a 0.050 g scale. Product eluted out in 5-20% MeOH:DCM mixture in a gradient elution on a Biotage purification system. Isolated 0.11 g (6%) of W199 as a white solid. $^1$H-NMR (400 MHz, DMSO) δ: 8.08 (d, J=11.6 Hz, 2H), 7.88-7.78 (m, 3H), 7.54 (d, J=8.4 Hz, 1H), 7.53-7.38 (m, 8H), 7.35 (d, J=5.4 Hz, 1H), 7.23 (d, J=8.8 Hz, 1H), 5.21 (s, 2H); MS: 383.0 (M+H$^+$).

Synthesis of 6-(6-(benzyloxy)pyridin-3-yl)-N-methylbenzo[d]thiazol-2-amine: W194

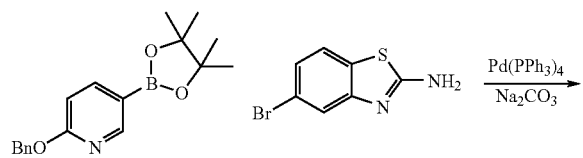

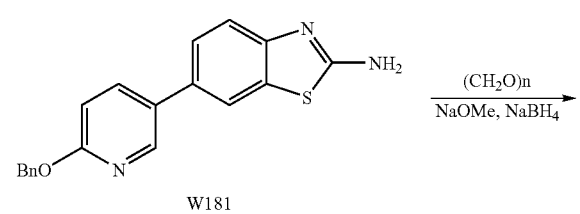

Preparation of 6-(6-(benzyloxy)pyridin-3-yl)benzo[d]thiazol-2-amine: W181

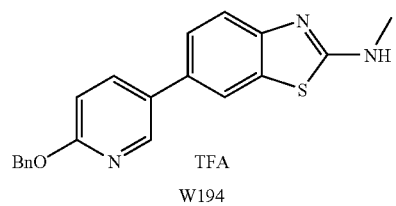

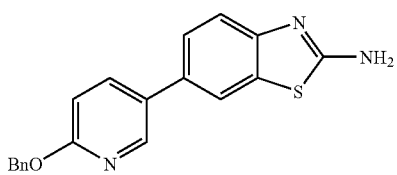 [SMILES: Nc1nc2ccc(-c3ccc(OCc4ccccc4)nc3)cc2s1]

General experimental procedure for Suzuki coupling was followed. Reaction was performed on a 0.074 g scale. Product was purified by recrystallization from EtOAc/DCM. Isolated 0.065 g (61%) of W181 as a yellow solid. $^1$H-NMR (400 MHz, DMSO) δ: 8.44 (d, J=2.0 Hz, 1H), 8.00-7.95 (m, 2H), 7.52-7.35 (m, 10H), 6.92 (d, J=8.8 Hz, 1H), 5.37 (s, 2H); MS: 268.1 (M+H$^+$).

Preparation of 6-(6-(benzyloxy)pyridin-3-yl)-N-methylbenzo[d]thiazol-2-amine: W194

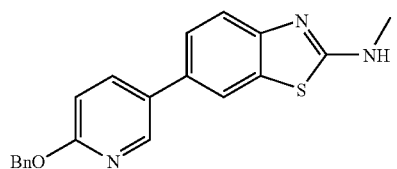 [SMILES: CNc1nc2ccc(-c3ccc(OCc4ccccc4)nc3)cc2s1]

To a 10 mL round bottomed flask equipped with a magnetic stir bar, was placed W232 (0.010 g, 0.030 mmol, 1.0 equiv) and 25% NaOMe solution in MeOH (130 mg, 0.60 mmol, 20 equiv). To this solution was added parafomaldehyde (9 mg, 0.3 mmol, 10 equiv). The reaction was allowed to stir at 65° C. for 1 h. After allowed to rt, to the reaction was added NaBH$_4$ (11 mg, 0.30 mmol, 10 equiv) and the reaction was allowed to stir at 65° C. for 1 h. After the reaction was complete by LCMS, the reaction mixture was diluted with water (5 ml) and extracted with EtOAc (5 mL×3). The organic layers were dried and concentrated to afford 194 (8 mg, 77%). $^1$H-NMR (400 MHz, DMSO) δ: 8.44 (d, J=2.8 Hz, 1H), 8.00 (dd, J=8.4 Hz, 2.4 Hz, 1H), 7.93 (d, J=2.0 Hz, 1H), 7.53-7.50 (m, 4H), 7.39-7.34 (m, 3H), 7.06 (br, 1H), 6.92 (d, J=8.8 Hz, 1H), 5.44 (s, 2H), 3.09 (d, J=4.4 Hz, 3H); MS: 348.0 (M+H$^+$).

Preparation of 6-(6-(benzyloxy)pyridin-3-yl)benzo[d]thiazol-2(3H)-one: W193

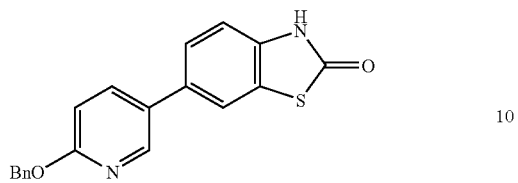

General experimental procedure for Suzuki coupling was followed. Reaction was performed on a 0.074 g scale. Product was purified by recrystallization from Hexanes/EtOAc. Isolated 0.035 g (33%) of W193 as a white solid. $^1$H-NMR (400 MHz, DMSO) δ: 11.90, (br, 1H), 8.42 (d, J=2.8 Hz, 1H), 8.00 (dd, J=8.4 Hz, 2.4 Hz, 1H), 7.90 (d, J=2.4 Hz, 1H), 7.53 (d, J=8.8 Hz, 1H), 7.50-7.30 (m, 5H), 7.17 (d, J=8.4 Hz, 1H), 6.95 (d, J=8.4 Hz, 1H), 5.37 (s, 2H); MS: 335.0 (M+H$^+$).

Synthesis of W369, W379 and W392

Synthesis of W369 and W379

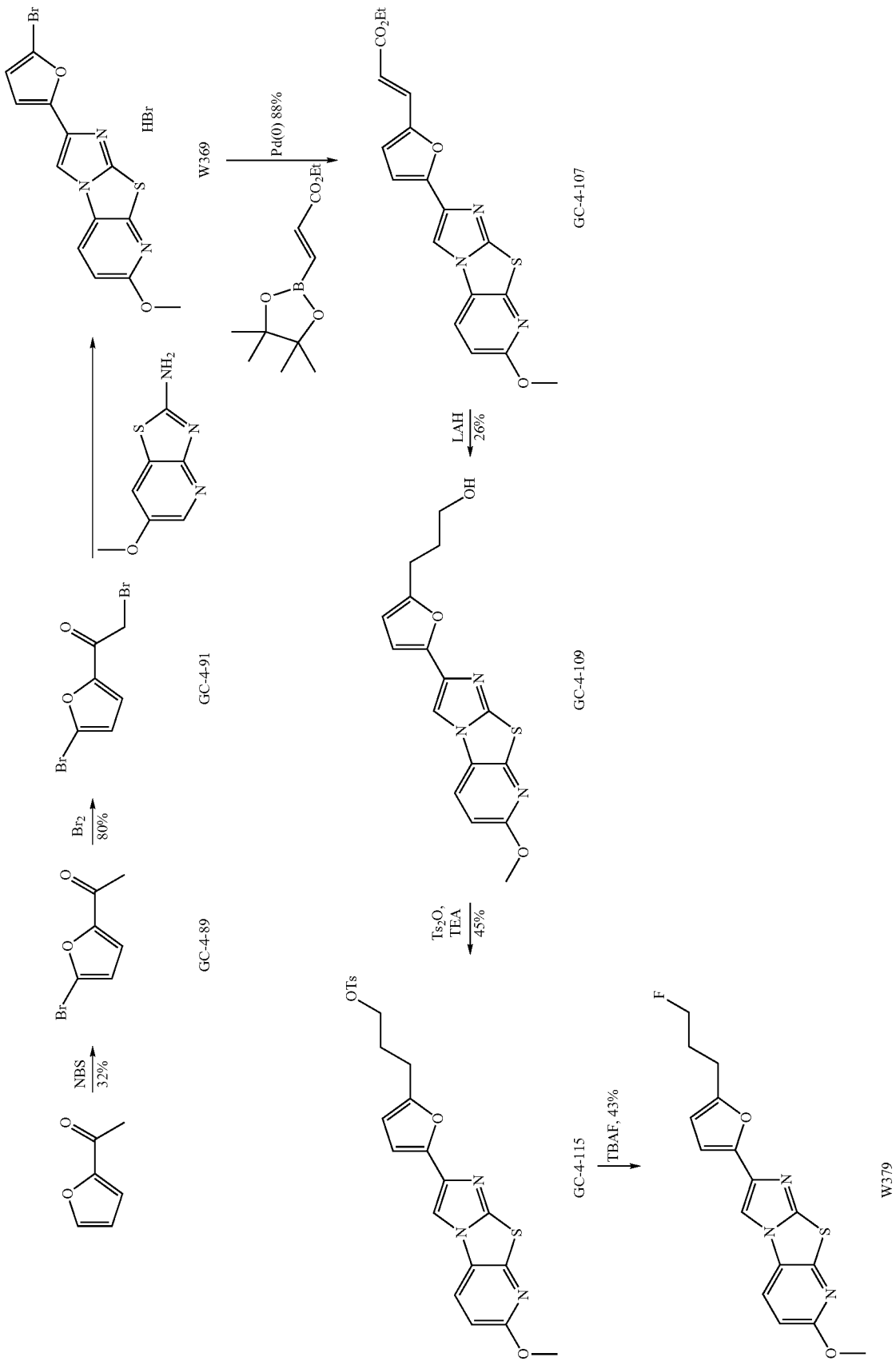

Preparation of 1-(5-bromofuran-2-yl)ethanone (GC-4-89)

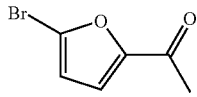

To a one-neck-flask charged with 2-acetylfuran (5.51 g, 50 mmol) in DMF (40 ml) at 0° C., was added N-Bromosuccinimide (9.79 g, 55.0 mmol) portionwise with stirring. The reaction mixture was stirred at rt overnight. The reaction mixture was poured into water (400 mL), extracted with ether (150 mL×3). The combined organic layers was dried, concentrated and purified on a silica gel column (Hexanes:EtOAc=4:1) to afford a white solid GC-4-89 (3 g, 31.7%). $^1$H-NMR (400 MHz, CDCl$_3$) δ: 7.12 (d, J=3.6 Hz, 1H), 6.49 (d, J=3.2 Hz, 1H), 2.46 (s, 3H)

Preparation of 2-bromo-1-(5-bromofuran-2-yl)ethanone (GC-4-91)

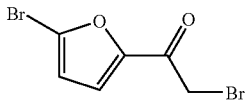

To a one-neck-flask containing GC-4-89 (1.5 g, 7.94 mmol) in AcOH (15 ml), was added hydrobromic acid (30%, 1.586 ml, 7.94 mmol). The mixture was cooled down to 5-10° C.; Bromine (0.409 ml, 7.94 mmol) was added dropwise with vigorous stirring. The mixture was stirred over 1.5 h. neutralized with NaHCO$_3$ (aq, 100 mL). The solid was filtered, washed with water, redissloved in EtOAc, washed with brine. The organic layer was concentrated to afford GC-4-91 (2.2 g, 6.57 mmol, 83% yield, purity 80%) as a orange-pink solid. $^1$H-NMR (400 MHz, CDCl$_3$) δ: 7.25 (d, J=3.6 Hz, 1H), 6.51 (d, J=3.2 Hz, 1H), 4.29 (s, 2H).

Preparation of 7-methoxy-2(5-bromofuran-2-Aimidazo[2,1-b]8-pyridinothiazole (W369)

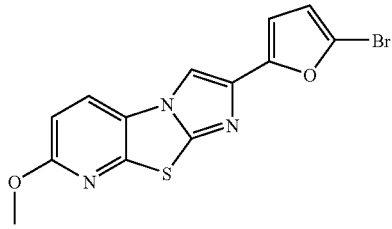 [SMILES: COc1ccc2c(n1)sc1nc(-c3ccc(Br)o3)cn12]

General experimental procedure for cyclization was followed. Reaction was performed on a 2 g scale. Product was isolated via filtration after precipitation from the reaction mixture and free based using NaHCO$_3$ (57% yield) of W369 as an off-white solid. $^1$H-NMR (400 MHz, CDCl$_3$) δ: 7.85 (s, 1H), 7.76 (d, J=8.8 Hz, 1H), 6.84 (d, J=8.4 Hz, 1H), 6.72 (d, J=3.2 Hz, 1H), 6.41 (d, J=3.2 Hz, 1H), 4.00 (s, 1H). MS: 351.9 (M+H$^+$).

Preparation of (E)-ethyl 3-(5-(7-methoxy-imidazo[2,1-b]8-pyridinothiazol-2-yl)furan-2-yl)acrylate (GC-4-107)

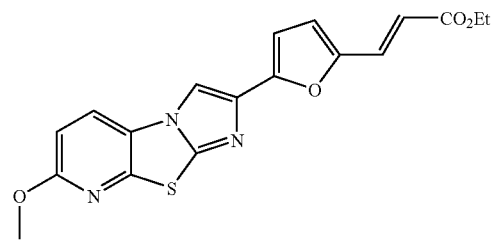 [SMILES: CCOC(=O)/C=C/c1ccc(-c2cn3c(n2)sc2nc(OC)ccc23)o1]

To a vial charged with tetrakis(triphenylphosphine) palladium(0) (46.2 mg, 0.040 mmol), was added W389 (200 mg, 0.571 mmol) and (E)-ethyl 3-(4,4,5,5-tetramethyl-1,3,2-dioxaborolan-2-yl)acrylate (387 mg, 1.713 mmol) and Dioxane (4 ml). Sodium carbonate (1M, 1.713 ml, 1.713 mmol) solution was added with stirring at rt. The reaction mixture was heated to 90° C. in microwave for 50 min. The reaction top layer was diluted with EtOAc/DCM/MeCN (20 mL), filtered through a filter pad. The organic layer was concentrated to afford a yellow solid. The solid was washed with hexanes (30 mL) thoroughly filtered again and dried to afford GC-4-107 (185 mg, 88% yield). $^1$H-NMR (400 MHz, DMSO) δ: 8.75 (s, 1H), 8.38 (d, J=8.8 Hz, 1H), 7.49 (d, J=15.6 Hz, 1H), 7.11-7.08 (m, 2H), 6.85 (d, J=3.6 Hz, 1H), 6.32 (d, J=15.6 Hz, 1H), 4.18 (q, J=7.2 Hz, 2H), 3.95 (s, 3H), 1.26 (t, J=7.2 Hz, 3H). MS: 370.1 (M+H$^+$).

Preparation of 3-(5-(7-methoxy-imidazo[2,1-b]8-pyridinothiazol-2-yl)furan-2-yl)propan-1-ol (GC-4-109)

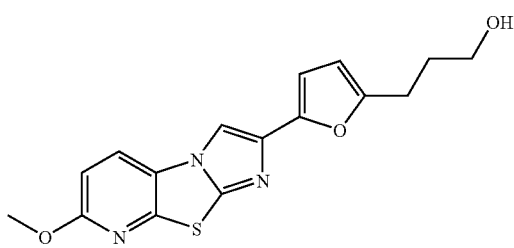 [SMILES: COc1ccc2c(n1)sc1nc(-c3ccc(CCCO)o3)cn12]

To a vial charged with GC-4-107 (65 mg, 0.176 mmol), was added THF (3 ml). The mixture was cooled down to 0° C. LiAlH$_4$ (1M, 0.387 ml, 0.387 mmol) in solution (THF) was added to the solution dropwise. The reaction was diluted with water (15 mL), extracted with EtOAc (30 mL×3), the organic layers were concentrated and purified on a silica gel column to afford GC-4-109 (15 mg, 26% yield) as yellow oil. $^1$H-NMR (400 MHz, CDCl$_3$) δ: 7.75 (s, 1H), 7.76 (d, J=8.8 Hz, 1H), 6.81 (d, J=8.8 Hz, 1H), 6.60 (d, J=3.2 Hz, 1H), 6.10 (d, J=3.2 Hz, 1H), 3.97 (s, 3H), 3.70 (t, J=6.8 Hz, 2H), 2.80 (t, J=7.2 Hz, 2H), 1.95 (m, 2H); MS: 330.2 (M+H$^+$).

117
Preparation of 3-(5-(7-methoxy-imidazo[2,1-b]8-pyridinothizol-2-yl)furan-2-yl)prop-1-yl toluenesulfonate (GC-4-115)

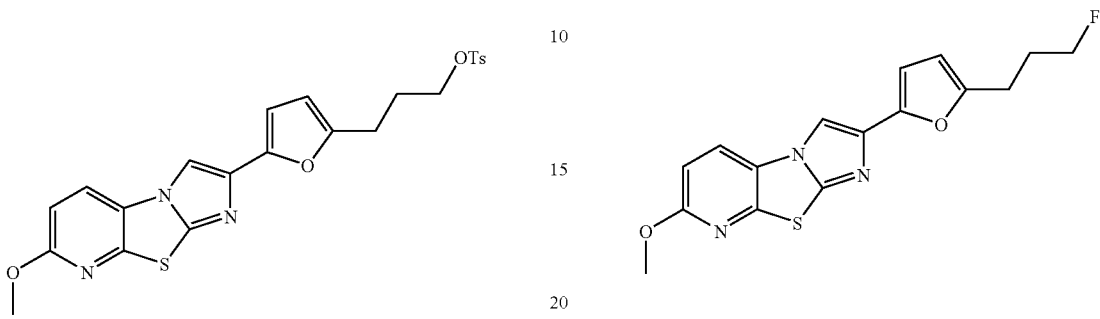

To a vial containing GC-4-109 (25 mg, 0.076 mmol in DCM (2 ml), was added triethylamine (0.023 ml, 0.167 mmol) and tosylate anhydride (29.7 mg, 0.091 mmol). The reaction was stirred overnight. LCMS indicates completion of the reaction. The reaction was concentrated, dried in vacuo and loaded onto a silica gel column (DCM:EtOAc=10:1) to afford a colorless oil GC-4-115 (22 mg, 59.9% yield) $^1$H-NMR (400 MHz, CDCl$_3$) δ: 7.79-7.71 (m, 4H), 7.31 (d, J=8.0 Hz, 2H), 6.80 (d, J=8.8 Hz, 1H), 6.60 (d, J=3.2 Hz, 1H), 5.99 (d, J=3.2 Hz, 1H), 4.10 (t, J=6.8 Hz, 2H), 3.98 (s, 3H), 2.73 (t, J=7.2 Hz, 2H), 2.42 (s, 3H), 1.95 (m, 2H); MS: 484.0 (M+H$^+$).

118
Preparation of 7-methoxy-2(5-(3-fluoropropyl)furan-2-yl)imidazo[2,1-b]8-pyridinothiazole (W379)

To a vial containing GC-4-115 (10 mg, 0.021 mmol) in THF (0.5 ml), was added TBAF (Tetrabutyl ammonium fluoride 1M THF) (0.030 ml, 0.103 mmol). The reaction was heated at 50° C. overnight. The reaction mixture was diluted with water (10 mL), extracted with DCM (15 mL) and washed with brine (10 mL). The organic layer was dried and concentrated. The residue mixture was purified on HPLC (phanomax LUNA, MeCN/H2O w/0.05% TFA, gradient elusion 12% to 85% in 30 min) to afford W379 as a white solid (3 mg, 9.05 mmol, 43.8% yield)) $^1$H-NMR (400 MHz, Acetone-D$_6$) δ: 8.31 (d, J=8.8 Hz, 1H), 8.25 (s, 1H), 6.99 (d, J=8.8 Hz, 1H), 6.61 (d, J=3.2 Hz, 1H), 6.13 (d, J=3.2 Hz, 1H), 4.58 (dt, J=48.8, 6.8 Hz, 2H), 3.99 (s, 3H), 2.82 (t, J=7.2 Hz, 2H), 2.05 (m, 21-1); MS: 332.0 (M+H$^+$).

Synthesis of W392

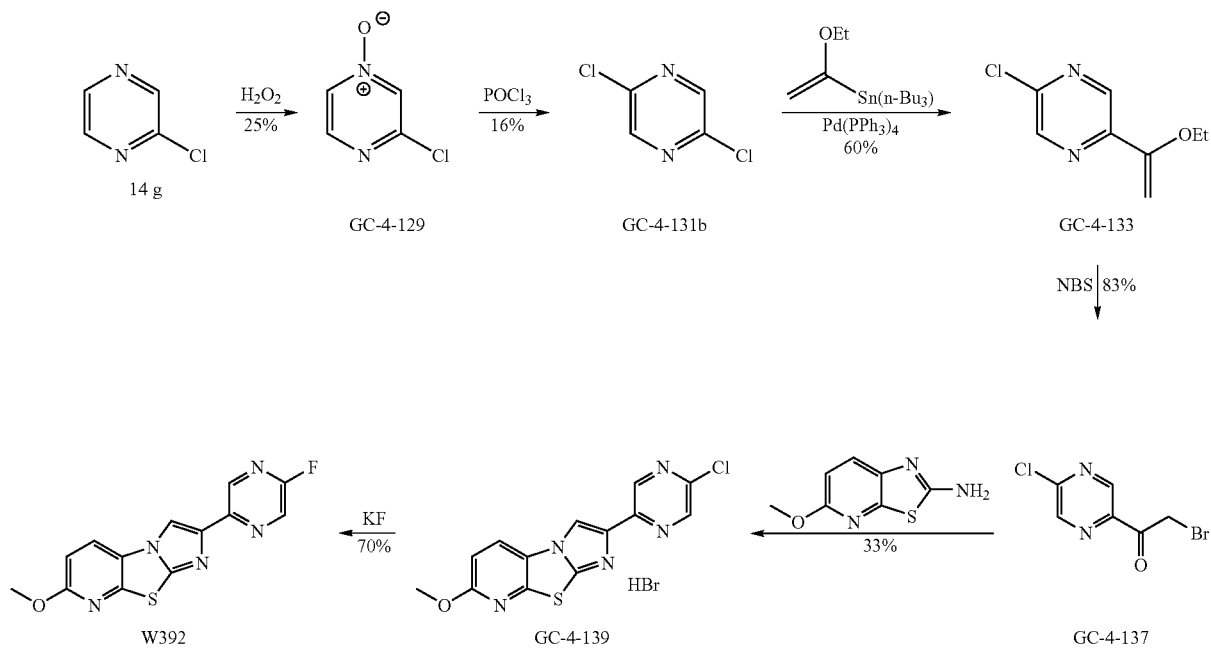

Preparation of 3-chloropyrazine 1-oxide (GC-4-129)

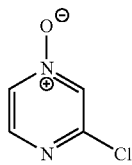

To a solution of 2-chloropyrazine (13.8 g, 120 mmol) in AcOH (36 ml), was added hydrogen peroxide 30% (23.26 ml, 759 mmol). The reaction mixture was stirred at 75° C. for 5 hour then at 55° C. overnight. The reaction was concentrated, diluted with water (20 mL) and concentrated again. The reaction was diluted with NaHCO$_3$ (aq, 150 mL), The pH was adjusted to 9.0. The aqueous layers were extracted with DCM (50 mL×3). The organic layer was concentrated, washed with hexanes/Ether. GC-4-129 was isolated as a white solid (4 g, 30.6 mmol, 25.4% yield) $^1$H-NMR (400 MHz, CDCl$_3$) δ: 8.25 (d, J=4.0 Hz, 1H), 8.15 (s, 1H), 8.02 (d, J=4.0 Hz, 1H) MS: 131.0 (M+H$^+$).

Preparation of 2,5-dichloropyrazine (GC-4-131b)

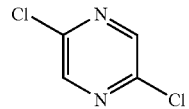

The solution of GC-4-129 (2.6 g, 19.92 mmol) in phosphorus oxychloride (8.7 g, 56.7 mmol) was heated to reflux for 1 h. The reaction mixture was allowed to rt and poured into ice (80 g) in a beaker (500 mL). The mixture was stirred vigorously to allow all of the oil dissolved in water. The solution was then extracted with DCM (50 mL×3). The organic layers was washed with Water (20 mL), Sodium Bicarbonate (aq, 20 mL), and water (20 mL) again. The extracts was dried, concentrated and purified in a silica gel column (EtOAc:Hex=1:10). GC-4-131b (480 mg, 3.22 mmol, 16.18% yield) was isolated as colorless oil. $^1$H-NMR (400 MHz, CDCl$_3$) δ: 8.52 (s, 1H).

Preparation of 2-chloro-5-(1-ethoxyvinyl)pyrazine (GC-4-133)

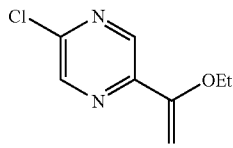

To flask charged with Tetrakis(triphenylphosphine) palladium(0) (298 mg, 0.258 mmol), was added Tributyl(1-ethoxyvinyl)tin (1.471 ml, 4.32 mmol) and GC-4-131b (480 mg, 3.22 mmol). The reaction was heated in Toluene (7 ml) at 100° C. for 4 h. The reaction was concentrated, diluted with hexane (50 mL), washed with water (25 mL), brine (25 mL) and water (25 mL) again. The organic layers were concentrated and purified on a silica gel column (Hexane:EtOAc=9:1) to afford a white solid GC-4-133 (360 mg, 60% yield) $^1$H-NMR (400 MHz, CDCl$_3$) δ: 8.80 (s, 1H), 8.48 (s, 1H), 5.45 (s, 1H), 4.50 (s, 1H), 3.97 (q, J=6.8 Hz, 2H), 1.40 (t, J=6.8 Hz, 3H).

Preparation of 2-bromo-1-(5-chloropyrazin-2-yl)ethanone (GC-4-137)

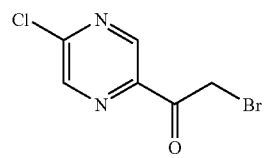 [SMILES: O=C(CBr)c1cnc(Cl)cn1]

NBS (N-Bromosuccinimide) (297 mg, 1.667 mmol) was added into a solution of GC-4-133 (360 mg, 1.852 mmol) in THF (6 ml) and Water (1.200 ml) at 0° C. After addition, the solution was stirred at for 5 min. The reaction was concentrated in vacuo, extracted with Hexanes (25 mL), washed with water (25 mL). The organic layer was concentrated and loaded onto a silica gel column (Hex:EtOAc=9:1) to afford GC-4-137 (360 mg, 1.529 mmol, 83% yield) as a yellow liquid. $^1$H-NMR (400 MHz, CDCl$_3$) δ: 9.19 (s, 1H), 8.80 (s, 1H), 4.70 (s, 2H).

Preparation of 7-methoxy-2(2-chloropyrazin-5-yl)imidazo[2,1-b]8-pyridinothiazole (GC-4-139/W392 precursor)

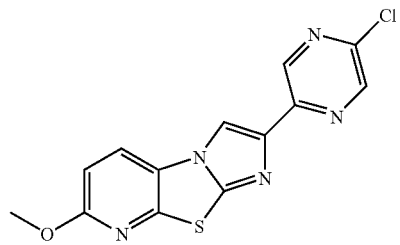 [SMILES: COc1ccc2c(n1)sc1nc(-c3cnc(Cl)cn3)cn12]

GC-4-137 (360 mg, 1.529 mmol) and 2-amino-6-methoxy-7-azabenzothiazole (277 mg, 1.529 mmol) was dissolved in EtOH (5 ml). The solution was added into a sealed vial and heated to 90° C. for 2 h. The reaction mixture was allowed to rt. Solid was filtered and washed with Ether (2 mL×2) to afford a brown solid GC-4-139 (160 mg, 0.504 mmol, 32.9% yield) as HBr salt. The crude product was stirred in NaHCO$_3$ (aq, 15 mL) overnight at rt. The solid was filtered and dried to afford free base product as an off-white solid (78 mg). $^1$H-NMR (400 MHz, CDCl$_3$) δ: 9.13 (d, J=6.0 Hz, 1H), 8.68 (s, 1H), 8.53 (d, J=8.8 Hz, 1H), 7.11 (d, J=8.8 Hz, 2H), 3.96 (s, 3H). MS: 318.0 (M+H$^+$).

Preparation of 7-methoxy-2(2-fluoropyrazin-5-yl) imidazo[2,1-b]8-pyridinothiazole (W392)

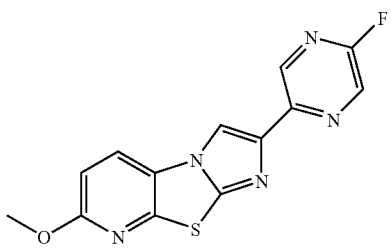 [SMILES: COc1ccc2c(n1)sc1nc(-c3cnc(F)cn3)cn12]

To a solution of GC-4-139 (30 mg, 0.094 mmol) in DMSO (2 ml), was added potassium fluoride (110 mg, 1.888 mmol). The mixture was heated in microwave reaction to 140-145° C. for 45 min. Water (10 mL) was added to the reaction solution, solid ppt was collected via filtration. The solid was washed with water and ether, dried in vacuo to afford a brown solid as W392 (20 mg, 0.066 mmol, 70.3% yield). $^1$H-NMR (400 MHz, CDCl$_3$) δ: 9.15 (d, J=6.0 Hz, 1H), 9.05 (s, 1H), 8.55 (d, J=6.0 Hz, 1H), 8.50 (d, J=8.8 Hz, 1H), 7.11 (d, J=8.8 Hz, 2H), 3.96 (s, 3H). MS: 302.0 (M+H$^+$).

General Procedure for Carbazole N-Boc Protection

To a round bottomed flask equipped with a magnetic stir bar, rubber septum, and argon inlet containing THF (40 vol) was placed carbazole (1.0 equiv). To this solution was added NaH (60% dispersion in oil, 3 equiv) at 0° C. and the reaction was allowed to stir at 0° C. for 30 min. To this reaction was added (Boc)$_2$O (1.2 equiv) at 0° C. and the reaction was allowed to stir for 1 h. After the reaction was complete by LCMS, poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Procedure for Carbazole N-Methylation

To a round bottomed flask equipped with a magnetic stir bar, rubber septum, and argon inlet containing THF (50 vol) was placed carbazole (1.0 equiv). To this solution was added NaH (60% dispersion in oil, 3 equiv) at 0° C. and the reaction was allowed to stir at 0° C. for 30 min. To this reaction was added MeOTf (1.0 equiv) at 0° C. and the reaction was allowed to stir for 1 h. After the reaction was complete by LCMS, poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Experimental Procedure for Phenolic Alkylation

To a round bottomed flask equipped with a magnetic stir bar containing DMF (20 vol) was placed phenol (1 equiv). To this solution was added alkylating agent (1.0 equiv), Cs$_2$CO$_3$ (1.2 equiv) and the reaction was allowed to stir at 60° C. for 16 h. The reaction was then poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Experimental Procedure for Suzuki Coupling Reaction

To a round bottomed flask equipped with a magnetic stir bar rubber septum, and argon inlet containing toluene:H$_2$O (1:1, 40 vol) was placed chloro compound (1 equiv). To this solution was added boronic acid (1.5 equiv), Pd(PPh$_3$)$_4$ (0.02 equiv), K$_2$CO$_3$ and the reaction was allowed to stir at 110° C. for 16 h. The reaction was then poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Experimental Procedure for Carbazole Formation Using P(OEt)$_3$

To a round bottomed flask equipped with a magnetic stir bar containing P(OEt)$_3$ (25 vol) was placed biaryl (1 equiv). The reaction was allowed to stir at 150° C. for 16 h. After the reaction was complete, P(OEt)$_3$ was removed in vacuo. The residue was purified over silica gel using Hexanes:EtOAc as the eluent to afford the final compound.

Benzothiazolinone Compounds

General Procedure for N-Arylation

To a 50 mL round bottomed flask equipped with a magnetic stir bar containing DCM (100 vol) was placed benzothiazolinone (1 equiv). To this solution was added boronic acid (2 equiv). Cu(OAc)$_2$ (1.1 equiv), TEMPO (1.1 equiv), MS ( ), Et$_3$N (2 equiv) and the reaction was allowed to stir at RT for 24-48 h. After the reaction was complete, DCM was removed in vacuo. The residue was purified over silica gel using Hexanes:EtOAc as the eluent to afford the final compound.

Preparation of 3-(4-(dimethylamino)phenyl)benzo[d]thiazol-2(3H)-one: DHK-4-61

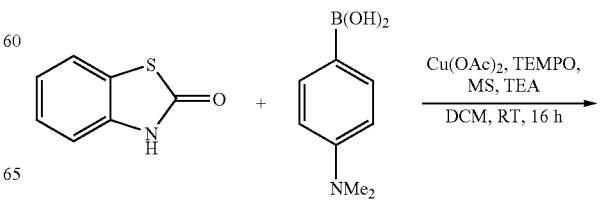

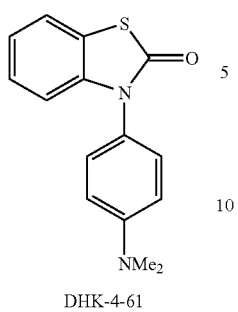

DHK-4-61

General experimental procedure for N-arylation was followed. Reaction was performed on a 0.1 g scale. Product eluted out in 20-30% EtOAc:Hexanes mixture in a gradient elution on a Combiflash purification system. Isolated 0.12 g (67%) of DHK-4-61 as colorless oil.

$^1$H NMR (400 MHz, CDCl$_3$) δ: 7.44-7.42 (m, 1H), 7.23-7.12 (m, 4H), 6.83-6.77 (m, 3H), 3.01 (s, 6H). MS: 271.0 (M+H$^+$).

Preparation of 3-(pyridin-2-yl)benzo[d]thiazol-2(3H)-one: DHK-4-62

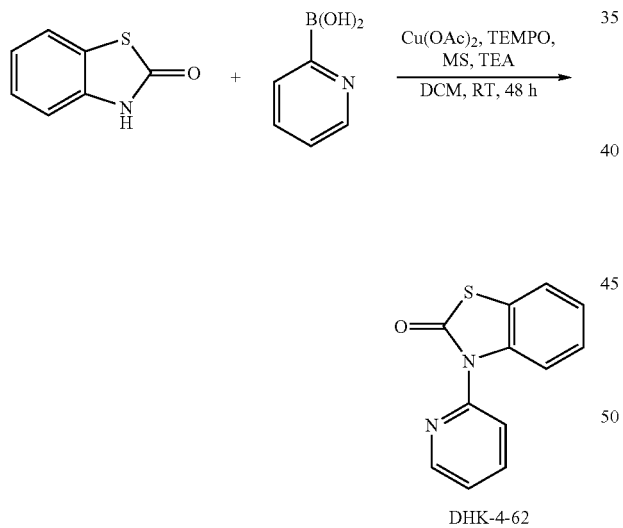

DHK-4-62

General experimental procedure for N-arylation was followed. Reaction was performed on a 0.1 g scale. Product eluted out in 20-30% EtOAc:Hexanes mixture in a gradient elution on a Combiflash purification system. Isolated 0.004 g (3%) of DHK-4-62 as white solid. $^1$H NMR (400 MHz, CDCl$_3$) δ: 8.67 (dd, J=4.8, 1.6 Hz, 1H), 7.94 (dd, J=7.6, 2 Hz, 1H), 7.61 (d, J=8.4 Hz, 1H), 7.44 (d, J=7.2 Hz, 1H), 7.40 (dddd, J=12.4, 7.2, 4.8, 0.4 Hz, 1H), 7.24-7.17 (m, 3H). MS: 229.0 (M+H$^+$).

Preparation of (E)-5-(4-methoxystyryl)benzo[d]thiazole: W205

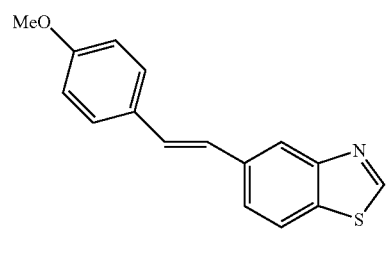 [SMILES: COc1ccc(/C=C/c2ccc3scnc3c2)cc1]

General experimental procedure for Suzuki coupling was followed. Reaction was performed on a 0.1 g scale. Product eluted out in 30% EtOAc:Hexanes mixture in a gradient elution on a Combiflash purification system. Isolated 0.11 g (88%) of W205 as a white solid. $^1$H NMR (400 MHz, CDCl$_3$) δ: 8.90 (s, 1H), 8.21 (d, J=8.2 Hz, 1H), 7.92 (d, J=8.0 Hz, 1H), 7.64 (dd, J=7.6, 1.6 Hz, 1H), 7.50 (d, J=8.8 Hz, 1H), 7.19 (d, J=16.4 Hz, 1H), 7.12 (d, J=16.4 Hz, 1H), 6.93 (d, J=8.8 Hz, 2H), 3.85 (s, 3H). MS: 268.1 (M+H$^+$).

Preparation of (E)-5-(4-fluorostyryl)benzo[d]thiazole: W206

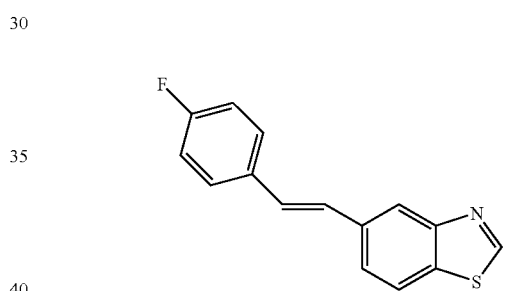

General experimental procedure for Suzuki coupling was followed. Reaction was performed on a 0.1 g scale. Product eluted out in 25% EtOAc:Hexanes mixture in a gradient elution on a Combiflash purification system. Isolated 0.05 g (42%) of W206 as a white solid. $^1$H NMR (400 MHz, CDCl$_3$) δ: 9.01 (s, 1H), 8.22 (d, J=1.6 Hz, 1H), 7.94 (d, J=8.4 Hz, 1H), 7.64 (dd, J=8.4, 1.6 Hz, 1H), 7.55-7.51 (m, 2H), 7.18 (d, J=1.2 Hz, 2H), 7.08 (t, J=8.4 Hz, 2H). MS: 256.0 (M+H$^+$).

Preparation of (E)-3-fluoro-5-(4-methoxystyryl)pyridine: W207

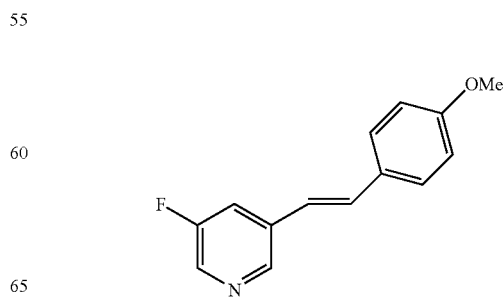

General experimental procedure for Suzuki coupling was followed. Reaction was performed on a 0.11 g scale. Product eluted out in 25% EtOAc:Hexanes mixture in a gradient elution on a Combiflash purification system. Isolated 0.135 g (94%) of W207 as a white solid. MS: 230.1 (M+H$^+$).

Preparation of 4-(benzo[d]thiazol-5-yl)phenol: W261

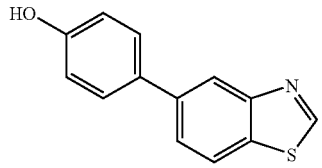 [SMILES: Oc1ccc(-c2ccc3scnc3c2)cc1]

General experimental procedure for Suzuki coupling was followed. Reaction was performed on a 0.1 g scale. Product eluted out in 37% EtOAc:Hexanes mixture in a gradient elution on a Combiflash purification system. Isolated 0.066 g (62%) of W261 as a white solid. MS: 228.0 (M+H$^+$).

Preparation of 5-(6-fluoropyridin-3-yl)benzo[d]thiazole: W262

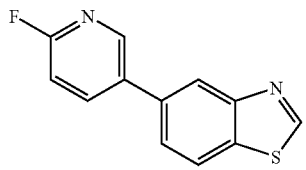 [SMILES: Fc1ccc(-c2ccc3scnc3c2)cn1]

General experimental procedure for Suzuki coupling was followed. Reaction was performed on a 0.1 g scale. Product eluted out in 30% EtOAc:Hexanes mixture in a gradient elution on a Combiflash purification system. Isolated 0.09 g (84%) of W262 as a white solid. $^1$H NMR (400 MHz, Acetone-d$_6$) δ: 9.33 (s, 1H), 8.62 (d, J=2.8 Hz, 1H), 8.38-8.34 (m, 2H), 8.26 (d, J=8.4 Hz, 1H), 7.82 (dd, J=8.4, 1.6 Hz, 1H), 7.22 (dd, J=8.4, 2.8 Hz, 1H). MS: 231.0 (M+H$^+$).

Preparation of 5-(5-methoxypyridin-3-yl)benzo[d]thiazole: W263

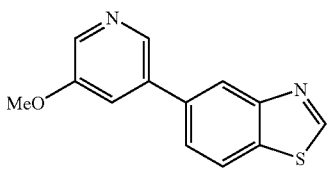 [SMILES: COc1cncc(-c2ccc3scnc3c2)c1]

General experimental procedure for Suzuki coupling was followed. Reaction was performed on a 0.1 g scale. Product eluted out in 50% EtOAc:Hexanes mixture in a gradient elution on a Combiflash purification system. Isolated 0.11 g (97%) of W263 as a white solid. $^1$H NMR (400 MHz, Acetone-d$_6$) δ: 9.33 (s, 1H), 8.57 (d, J=2.0 Hz, 1H), 8.40 (d, J=1.6 Hz, 1H), 8.31 (d, J=3.2 Hz, 1H), 8.25 (d, J=8.4 Hz, 1H), 7.85 (dd, J=8.4, 2.0 Hz, 1H), 7.70 (dd, J=2.8, 2.0 Hz, 1H), 3.99 (s, 3H). MS: 243.0 (M+H$^+$).

Preparation of 5-(5-methoxypyridin-3-yl)-2-methyl-benzo[d]thiazole: W264

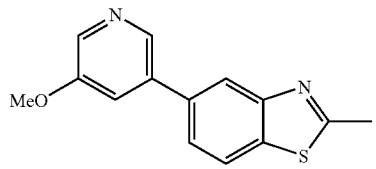 [SMILES: COc1cncc(-c2ccc3sc(C)nc3c2)c1]

General experimental procedure for Suzuki coupling was followed. Reaction was performed on a 0.1 g scale. Product eluted out in 40% EtOAc:Hexanes mixture in a gradient elution on a Combiflash purification system. Isolated 0.092 g (82%) of W264 as a white solid. $^1$H NMR (400 MHz, Acetone-d$_6$) δ: 8.56 (d, J=1.6 Hz, 1H), 8.31 (d, J=2.8 Hz, 1H), 8.22 (d, J=1.6 Hz, 1H), 8.10 (d, J=8.4 Hz, 1H), 7.75 (dd, J=8.4, 2.0 Hz, 1H), 7.68 (dd, J=2.8, 2.0 Hz, 1H), 4.00 (s, 3H), 2.79 (s, 3H). MS: 257.0 (M+H$^+$).

Preparation of 4-(2-methylbenzo[d]thiazol-5-yl)phenol: W266

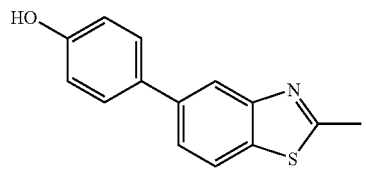

General experimental procedure for Suzuki coupling was followed. Reaction was performed on a 0.15 g scale. Product eluted out in 30% EtOAc:Hexanes mixture in a gradient elution on a Combiflash purification system. Isolated 0.16 g (100%) of W266 as a white solid. $^1$H NMR (400 MHz, CDCl$_3$) δ: 8.49 (s, 1H), 8.08 (d, J=1.6 Hz, 1H), 8.00 (d, J=8.8 Hz, 1H), 7.63 (dd, J=8.4, 1.9 Hz, 1H), 7.60 (d, J=8.4 Hz, 2H), 6.97 (d, J=8.8 Hz, 2H), 2.82 (s, 3H). MS: 242.0 (M+H$^+$).

Preparation of 5-(6-fluoropyridin-3-yl)-2-methylbenzo[d]thiazole: W267

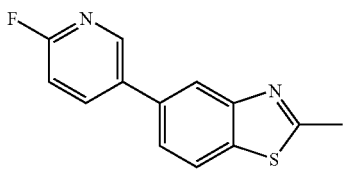 [SMILES: Cc1nc2cc(-c3ccc(F)nc3)ccc2s1]

General experimental procedure for Suzuki coupling was followed. Reaction was performed on a 0.11 g scale. Product eluted out in 30% EtOAc:Hexanes mixture in a gradient elution on a Combiflash purification system. Isolated 0.11 g (100%) of W267 as a white solid. $^1$H NMR (400 MHz, Acetone-d$_6$) δ: 8.49 (s, 1H), 8.60 (d, J=1.6 Hz, 1H), 8.34 (dt, J=8.3, 2.8 Hz, 1H), 8.21 (d, J=2.0 Hz, 1H), 8.11 (d, J=8.4 Hz, 1H), 7.73 (dd, J=8.4, 2 Hz, 2H), 7.22 (dd, J=8.4, 3.2 Hz, 1H), 2.82 (s, 3H). MS: 245.0 (M+H⁺).

Preparation of 4-(2-methylbenzo[d]thiazol-5-yl)benzonitrile: W285

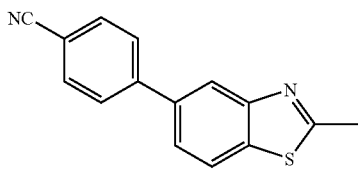

General experimental procedure for Suzuki coupling was followed. Reaction was performed on a 0.1 g scale. Product eluted out in 30% EtOAc:Hexanes mixture in a gradient elution on a Combiflash purification system. Isolated 0.1 g (92%) of W285 as a white solid. ¹H NMR (400 MHz, Acetone-d₆) δ: 8.25 (d, J=2 Hz, 1H), 8.13 (d, J=8.4 Hz, 1H), 8.00 (d, J=8.0 Hz, 2H), 7.92 (d, J=8.0 Hz, 2H), 7.78 (dd, J=8.4, 1.6 Hz, 1H), 2.85 (s, 3H). MS: 251.0 (M+H⁺).

Preparation of N,N-dimethyl-4-(2-methylbenzo[d]thiazol-5-yl)aniline: W362

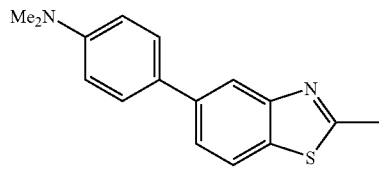 [SMILES: Cc1nc2cc(-c3ccc(N(C)C)cc3)ccc2s1]

General experimental procedure for Suzuki coupling was followed. Reaction was performed on a 0.1 g scale. Product eluted out in 50% EtOAc:Hexanes mixture in a gradient elution on a Combiflash purification system. Isolated 0.12 g (100%) of W362 as a white solid. ¹H NMR (400 MHz, CDCl₃) δ: 8.12 (d, J=1.6 Hz, 1H), 7.82 (d, J=8.4 Hz, 1H), 7.58 (d, J=8.4 Hz, 2H), 7.56 (s, 1H), 6.84 (d, J=8.8 Hz, 2H), 3.01 (s, 6H), 2.85 (s, 3H). MS: 269.1 (M+H⁺).

Preparation of 4-(benzo[d]thiazol-5-yl)-N,N-dimethylaniline: W363

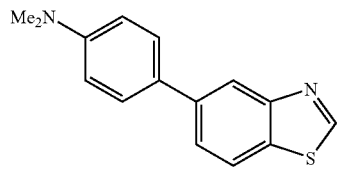 [SMILES: CN(C)c1ccc(-c2ccc3scnc3c2)cc1]

General experimental procedure for Suzuki coupling was followed. Reaction was performed on a 0.1 g scale. Product eluted out in 59% EtOAc:Hexanes mixture in a gradient elution on a Combiflash purification system. Isolated 0.11 g (93%) of W363 as a white solid. MS: 255.1 (M+H⁺).

Preparation of 5-(4-(2-fluoroethoxy)phenyl)benzo[d]thiazole: W265

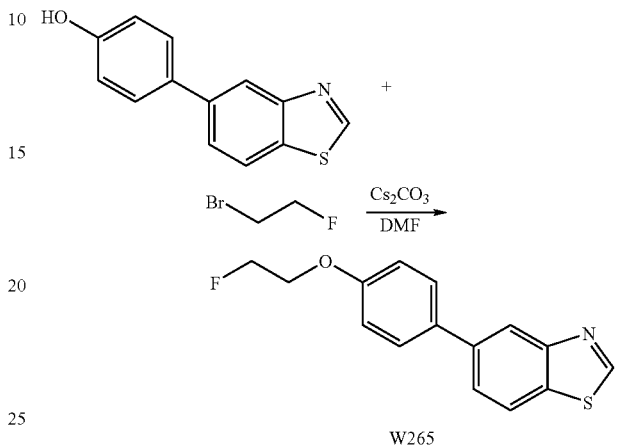

General experimental procedure for phenolic alkylation was followed. Reaction was performed on a 0.05 g scale at room temperature. Isolated 0.06 g (100%) of W265 as a white solid. ¹H NMR (400 MHz, CDCl₃) δ: 9.03 (s, 1H), 8.31 (d, J=2.0 Hz, 1H), 8.00 (d, J=8.4 Hz, 1H), 7.66 (dd, J=8.4, 2.0 Hz, 1H), 7.63 (d, J=8.8 Hz, 2H), 7.05 (dd, J=8.8 Hz, 2H), 4.86 (t, J=4.0 Hz, 1H), 4.74 (t, J=4.4 Hz, 1H), 4.32 (t, J=4.4 Hz, 1H), 4.26 (t, J=4.0 Hz, 1H). MS: 274.0 (M+H⁺).

Preparation of 5-(4-(2-fluoroethoxy)phenyl)-2-methylbenzo[d]thiazole: W288

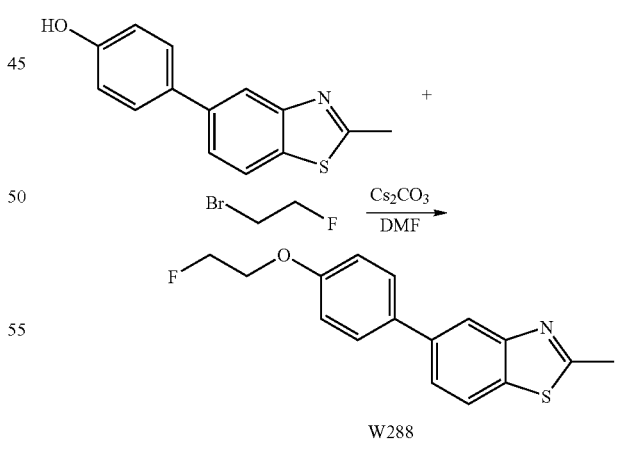

General experimental procedure for phenolic alkylation was followed. Reaction was performed on a 0.09 g scale at room temperature. Isolated 0.105 g (98%) of W288 as a white solid. ¹H NMR (400 MHz, Acetone-d₆) δ: 8.11 (d, J=2.0 Hz, 1H), 8.02 (d, J=8.4 Hz, 1H), 7.71 (d, J=8.8 Hz, 2H), 7.66 (dd, J=8.4, 2.0 Hz, 1H), 7.11 (d, J=8.8 Hz, 2H), 4.87 (t, J=5.2 Hz, 1H), 4.75 (t, J=3.6 Hz, 1H), 4.39 (t, J=4.0 Hz, 1H), 4.32 (t, J=4.0 Hz, 1H), 2.83 (s, 3H). MS: 288.0 (M+H$^+$).

Preparation of N-(2-fluoroethyl)-4-(2-methylbenzo[d]thiazol-5-yl)aniline: W317

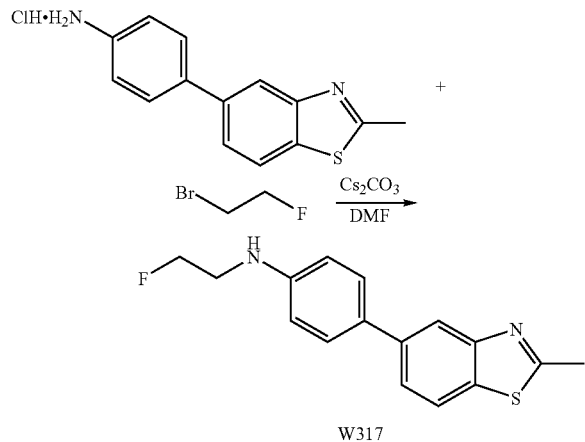

General experimental procedure for phenolic alkylation was followed for the N-alkylation reaction. Reaction was performed on a 0.077 g scale at 70° C. Isolated 0.035 g (44%) of W317 as a white solid. MS: 287.1 (M+H$^+$).

Synthesis of N-methyl-4-(2-methylbenzo[d]thiazol-5-yl)aniline: W287

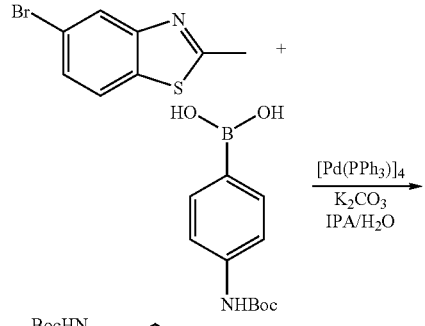

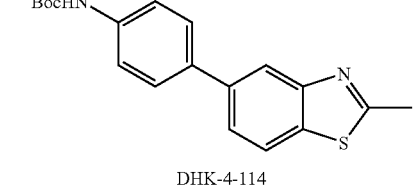

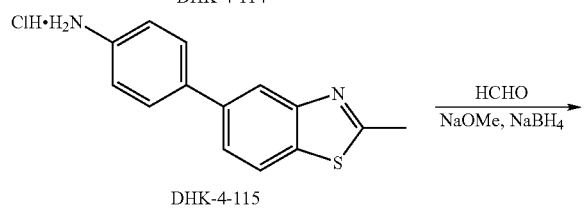

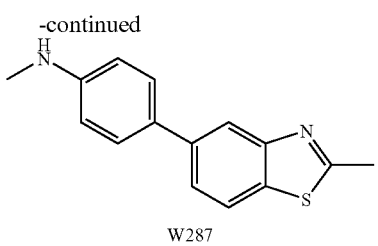

Preparation of tert-butyl 4-(2-methylbenzo[d]thiazol-5-yl)phenylcarbamate: DHK-4-114

General experimental procedure for Suzuki coupling was followed. Reaction was performed on a 0.15 g scale. Product eluted out in 30-40% EtOAc:Hexanes mixture in a gradient elution on a Combiflash purification system. Isolated 0.2 g (93%) of DHK-4-114 as a tan solid. $^1$H NMR (400 MHz, Acetone-d$_6$) δ: 8.54 (s, 1H), 8.13 (d, J=2.0 Hz, 1H), 8.02 (d, J=8.4 Hz, 1H), 7.68 (s, 5H), 7.67 (d, J=2.0 Hz, 1H), 2.82 (s, 3H), 1.51 (s, 9H). MS: 341.1 (M+H$^+$).

Preparation of 4-(2-methylbenzo[d]thiazol-5-yl)aniline hydrochloride: DHK-4-115

To a 50 mL round bottomed flask equipped with a magnetic stir bar was placed DHK-4-114 (0.2 g, 0.59 mmol, 1 equiv). To this compound was added HCl (4M solution in dioxane) (2 mL) and the reaction was allowed to stir at room temperature for 16 h. After the reaction was complete, solvent was removed in vacuo to afford DHK-4-115 (0.18 g, 100%) as a white solid. MS: 241.0 (M+H$^+$).

Preparation of N-methyl-4-(2-methylbenzo[d]thiazol-5-yl)aniline: DHK-4-117

To a round bottomed flask equipped with a magnetic stir bar, rubber septum, and argon inlet containing MeOH (2 mL) was placed DHK-4-115 (0.046 g, 0.17 mmol, 1.0 equiv). To this solution was added HCHO (0.025 g, 0.83 mmol, 5 equiv) and NaOMe (0.054 g, 1.0 mmol, 6 equiv) and the reaction was allowed to stir at 70° C. for 1 h. To this reaction was added NaBH$_4$ (0.063 g, 1.6 mmol, 10 equiv) and the reaction was allowed to stir at 70° C. for 16 h. After the reaction was complete by LCMS, the reaction mixture was diluted with MeOH/H$_2$O (1:1, 2 ml) and purified by HPLC to afford 0.04 g (100%) of the methylamine W287 as a white solid. MS: 255.1 (M+H$^+$).

Preparation of W228

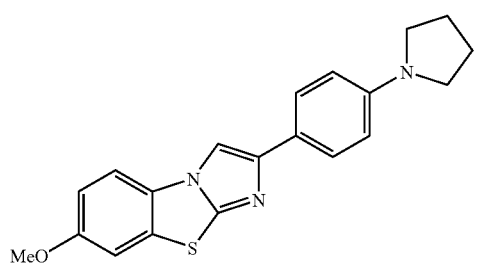 [SMILES: COc1ccc2c(c1)sc1nc(-c3ccc(N4CCCC4)cc3)cn12]

General experimental procedure for cyclization was followed. Reaction was performed on a 0.1 g scale. Isolated 0.05 g (26%) of W228 as a tan colored solid. $^1$H NMR (400 MHz, DMSO-d$_6$) δ: 8.58 (s, 1H), 7.94 (d, J=8.8 Hz, 1H), 7.72 (d, J=2.4 Hz, 1H), 7.60 (d, J=8.8 Hz, 2H), 7.19 (dd, J=9.2, 2.8 Hz, 1H), 6.62 (d, J=8.8 Hz, 2H), 3.82 (s, 3H), 3.25 (t, J=6.4 Hz, 4H), 1.94 (t, J=6.4 Hz, 4H). MS: 350.1 (M+H$^+$).

Preparation of W229

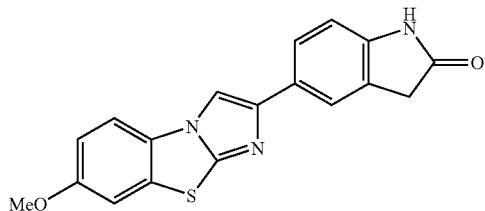 [SMILES: COc1ccc2c(c1)sc1nc(-c3ccc4c(c3)CC(=O)N4)cn12]

General experimental procedure for cyclization was followed. Reaction was performed on a 0.1 g scale. Isolated 0.084 g (45%) of W229 as a tan colored solid. $^1$H NMR (400 MHz, DMSO-d$_6$) δ: 8.53 (s, 1H), 7.85 (dd, J=8.0, 1.6 Hz, 2H), 7.80 (s, 2H), 7.65-7.63 (m, 1H), 6.90 (d, J=8.0 Hz, 2H), 5.05 (s, 2H), 3.54 (s, 3H). MS: 336.0 (M+H$^+$).

Preparation of W230

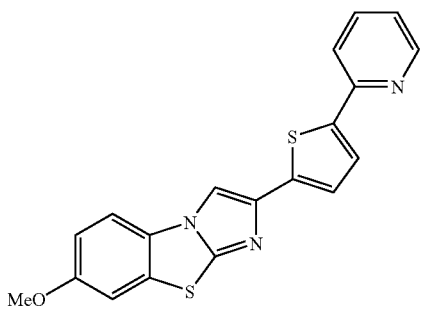 [SMILES: COc1ccc2c(c1)sc1nc(-c3ccc(-c4ccccn4)s3)cn12]

General experimental procedure for cyclization was followed. Reaction was performed on a 0.1 g scale. Isolated 0.13 g (65%) of W230 as a yellow solid. $^1$H NMR (400 MHz, DMSO-d$_6$) δ: 8.63 (s, 1H), 8.51-8.50 (m, 1H), 7.89 (d, J=8.4 Hz, 2H), 7.2 (dt, J=7.2, 1.6 Hz, 1H), 7.75 (d, J=3.6 Hz, 1H), 7.66 (d, J=2.4 Hz, 1H), 7.39 (d, J=4.0 Hz, 1H), 7.25-7.22 (m, 1H), 7.13 (dd, J=9.2, 2.8 Hz, 1H), 3.81 (s, 3H). MS: 364.0 (M+H$^+$).

Preparation of W318

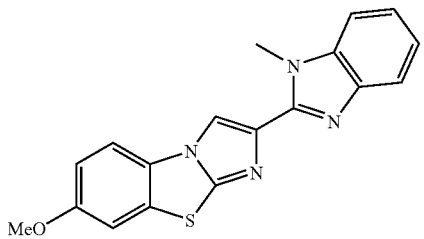 [SMILES: COc1ccc2c(c1)sc1nc(-c3nc4ccccc4n3C)cn12]

General experimental procedure for cyclization was followed. Reaction was performed on a 0.1 g scale. Isolated 0.18 g (97%) of W318 as a white solid. MS: 335.0 (M+H$^+$).

Preparation of W360

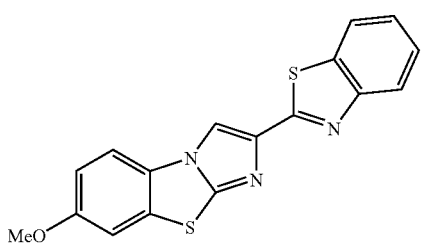 [SMILES: COc1ccc2c(c1)sc1nc(-c3nc4ccccc4s3)cn12]

General experimental procedure for cyclization was followed. Reaction was performed on a 0.1 g scale. Isolated 0.1 g (53%) of W360 as an yellow solid. MS: 338.0 (M+H$^+$).

Preparation of W361

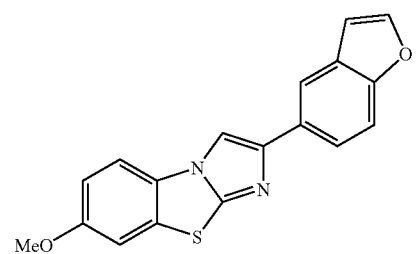 [SMILES: COc1ccc2c(c1)sc1nc(-c3ccc4occc4c3)cn12]

General experimental procedure for cyclization was followed. Reaction was performed on a 0.1 g scale. Isolated 0.11 g (62%) of W361 as a white solid. MS: 321.0 (M+H$^+$).

Preparation of W388

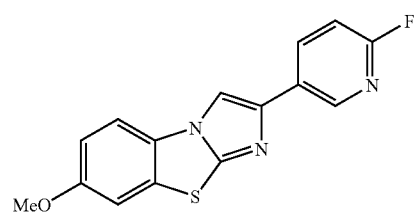 [SMILES: COc1ccc2c(c1)sc1nc(-c3ccc(F)nc3)cn12]

General experimental procedure for cyclization was followed. Reaction was performed on a 0.1 g scale. Isolated 0.095 g (57%) of W388 as a brown solid. $^1$H NMR (400 MHz, DMSO-$d_6$) δ: 8.77 (d, J=0.8 Hz, 1H), 8.65 (s, 1H), 8.32 (dt, J=8.8, 2.0 Hz, 1H), 7.67 (d, J=1.6 Hz, 1H), 7.84 (dd, J=8.8, 0.8 Hz, 1H), 7.24 (dd, J=8.8, 2.4 Hz, 1H), 7.14 (ddd, J=8.8, 2.4, 0.8 Hz, 1H) 3.80 (s, 3H). MS: 300.0 (M+H$^+$).

Preparation of DHK-4-157

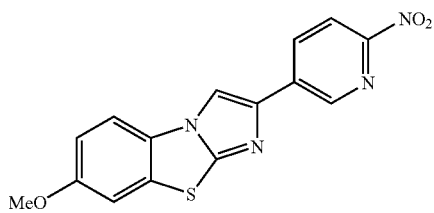 [SMILES: COc1ccc2c(c1)sc1nc(-c3ccc([N+](=O)[O-])nc3)cn12]

General experimental procedure for cyclization was followed. Reaction was performed on a 0.1 g scale. Isolated 0.08 g (44%) of DHK-4-157 as an yellow solid. MS: 327.0 (M+H$^+$).

Preparation of W393

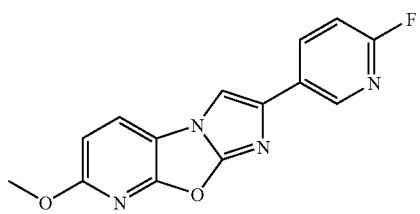

General experimental procedure for cyclization was followed. Reaction was performed on a 0.1 g scale. Isolated 0.08 g (44%) of W393 as a white solid. $^1$H NMR (400 MHz, CDCl$_3$) δ: 8.63 (s, 1H), 8.25 (dt, J=8.4, 2.8 Hz, 1H), 8.32 (dt, J=8.8, 2.0 Hz, 1H), 7.78 (d, J=8.4 Hz, 1H), 7.57 (s, 1H), 6.99 (dd, J=8.8, 2.4 Hz, 1H), 6.81 (d, J=8.4 Hz, 1H), 4.03 (s, 3H). MS: 285.1 (M+H$^+$).

Synthesis of W286

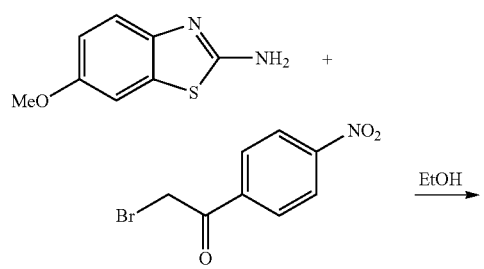

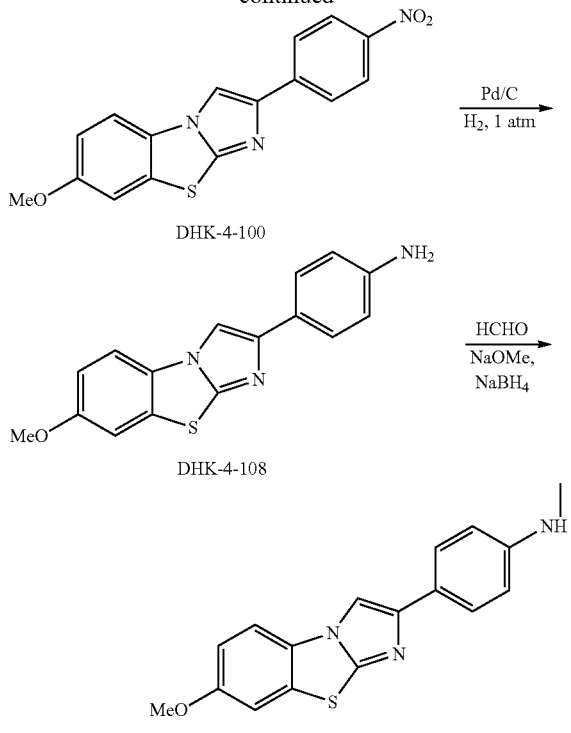

Preparation of DHK-4-100

General experimental procedure for cyclization was followed. Reaction was performed on a 1 g scale. Isolated 0.7 g (39%) of DHK-4-123 as a white solid. $^1$H NMR (400 MHz, DMSO-$d_6$) δ: 8.98 (s, 1H), 8.27 (d, J=8.8 Hz, 2H), 8.05 (d, J=9.2 Hz, 2H), 7.89 (d, J=8.8 Hz, 1H), 7.68 (d, J=2.4 Hz, 1H), 7.15 (dd, J=8.8, 2.4 Hz, 2H), 3.81 (s, 3H). MS: 326.0 (M+H$^+$).

Preparation of DHK-4-108

To a 250 mL round bottomed flask equipped with a magnetic stir bar containing EtOH (200 mL) was placed DHK-4-100 (0.2 g, 0.61 mmol). To this solution was added Pd/C (10%, 20 mg) and the reaction was allowed to stir under H$_2$ (1 atm) at RT for 16 h. After the reaction was complete, the reaction mixture was filtered through celite and the volatiles were removed in vacuo to afford DHK-4-108 (0.04 g, 22%) as a brown solid. $^1$H NMR (400 MHz, Acetone-$d_6$) δ: 8.21 (s, 1H), 7.79 (d, J=8.8 Hz, 1H), 7.63 (d, J=8.4 Hz, 2H), 7.54 (d, J=2.8 Hz, 1H), 7.11 (d, J=9.2, 2.8 Hz, 1H), 6.71 (d, J=8.4 Hz, 2H), 3.90 (s, 3H). MS: 296.0 (M+H$^+$).

Preparation of W286

To a round bottomed flask equipped with a magnetic stir bar, rubber septum, and argon inlet containing MeOH (2 mL) was placed DHK-4-108 (0.038 g, 0.13 mmol, 1.0 equiv). To this solution was added HCHO (0.019 g, 0.64 mmol, 5 equiv) and NaOMe (0.035 g, 0.64 mmol, 5 equiv) and the reaction was allowed to stir at 70° C. for 1 h. To this reaction was added NaBH$_4$ (0.024 g, 0.64 mmol, 5 equiv) and the reaction was allowed to stir at 70° C. for 16 h. After the reaction was complete by LCMS, the reaction mixture was diluted with MeOH/H₂O (1:1, 2 ml) and purified by HPLC to afford 0.02 g (50%) of the methylamine W286 as a white solid. MS: 310.1 (M+H⁺).

Synthesis of W204 and W211

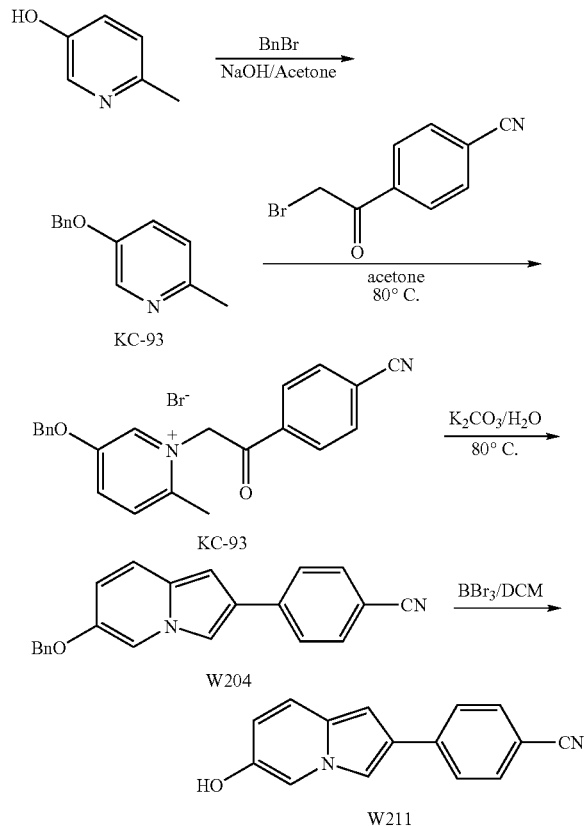

Preparation of KC-93

A mixture of 6-methylpyridin-3-ol (10 mmol, 1.09 g), benzyl bromide (10.5 mmol, 1.8 g), and sodium hydroxide (20 mmol, 0.8 g) was refluxed in acetone (30 mL) for 2 h, then cooled to room temperature. After evaporating the solvent, water (50 mL) was added into the residue. The mixture was extracted with dichloromethane (2×30 mL), dried over Na₂SO₄, and concentrated in vacuo. The residue was purified on a silica gel column (EtOAc:Hexanes=3:7) to afford KC-93 as a yellow oil (1.39 g, 70% yield). ¹H NMR (CDCl₃, 400 MHz), δ: 8.25 (s, 1H), 7.33-7.43 (m, 5H), 7.14-7.17 (dd, J=3.2 Hz, J=8.4 Hz, 1H), 7.03-7.05 (d, J=8.8 Hz, 1H), 5.07 (s, 2H), 2.48 (s, 3H). MS: 200.1 (M+H⁺).

Preparation of W204

A mixture of KC-93 (1.26 mmol, 0.25 g) and 4-(2-bromoacetyl)benzonitrile (1.32 mmol, 0.3 g) in acetone (25 mL) was refluxed for 3 h, then cooled and filtered. The solid was washed with acetone and dried. It was redissolved in water (25 mL). To this solution was added K₂CO₃ (1.18 mmol, 0.164 g). The resulting mixture was heated at 80° C. for 4 h, then cooled and filtered. The solid collected was washed with H₂O (2×15 mL) and dried in vacuo to give W204 (0.326 g, 80%) as a brown solid. ¹H NMR (CDCl₃, 400 MHz), δ: 7.63-7.70 (q, J=2 Hz, J=6.4 Hz, 4H), 7.52-7.55 (dd, J=1.6 Hz, J=10.4 Hz, 2H), 7.34-7.46 (m, 6H), 7.27-7.30 (d, J=10 Hz, 2H), 6.66 (s, 1H), 6.61-6.64 (dd, J=2 Hz, J=9.6 Hz, 1H). MS: 325.0 (M+H⁺).

Preparation of W211

To a cooled solution of W204 (0.309 mmol, 0.1 g) in dichloromethane (10 mL) was added dropwise a solution of BBr₃ in dichloromethane (1.0 M, 1.23 mL). The resulting mixture was stirred under Ar at 0° C. and warmed gradually to room temperature. After stirring at room temperature overnight, LCMS results show that no starting material was present. It was cooled in an ice-bath. Water was added slowly. The resulting mixture was transferred to a separatory funnel. The layers were separated. The organic layer was washed with H₂O (2×20 mL), dried (MgSO₄), and filtered. The filtrate was concentrated in vacuo. The residue was purified on a silica gel column (EtOAc:Hexanes=1:3) to afford W211 as a red brown solid (47 mg, 65% yield). ¹H NMR (CD₃OD, 400 MHz), δ: 8.73-8.74 (t, J=1.6 Hz, 1H), 7.97 (d, J=1.6 Hz, 2H), 7.94 (s, 1H), 7.92 (d, J=2.4 Hz, 2H), 7.88-7.89 (d, J=2.4 Hz, 2H), 7.86 (s, 1H). MS: 235.0 (M+H⁺).

General Experimental Procedure for Suzuki Coupling

A 5 mL microwave tube was charged with aryl halide (1 equiv), boronic acid or ester (1-1.1 equiv) [Pd(PPh₃)₄ (0.01-0.03 equiv) and Na₂CO₃ or NaHCO₃ (2-3 equiv) in isopropanol or 1,4-dioxane (10 vol) and H₂O (10 vol). The suspension was irradiated in a Biotage Emrys Optimizer microwave reactor (250 W) at 100° C. for 10-30 min. After cooling to room temperature the solvent was evaporated in vacuo. The residue was purified over silica gel using Hexanes:EtOAc as the eluent to afford the biaryl derivatives.

Synthesis of W223

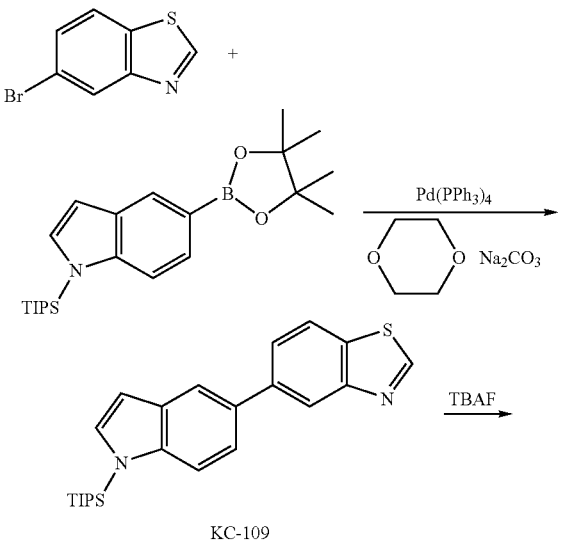

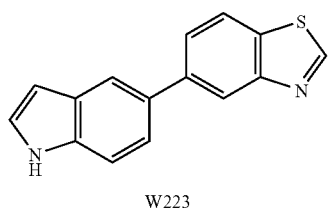

W223

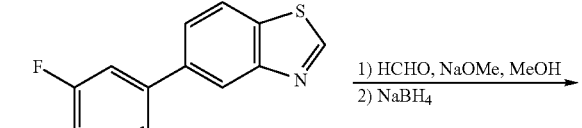

W224

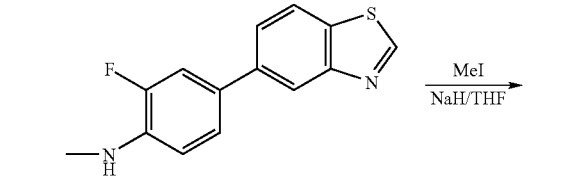

W225

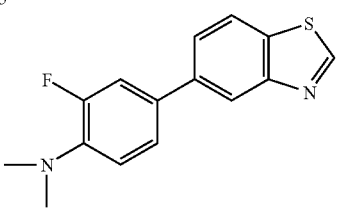

KC-181

Preparation of KC-109

General experimental procedure for Suzuki coupling was followed. Reaction was performed on a 54 mg scale. Product eluted out in 25% EtOAc:Hexanes mixture in a gradient elution on a Combiflash purification system. Isolated 71 mg (70%) of KC-109 as a light yellow syrup. MS: 407.1 (M+H$^+$).

Preparation of W223

To a round bottom flask equipped with a magnetic stir bar, rubber septum, and argon inlet containing THF (5 mL) was placed KC-109 (0.1 g, 0.246 mmol). To this solution was added TBAF (1M in THF, 0.49 mL) and the reaction was allowed to stir at room temperature for 2 h. After the reaction was completed, the solvent was evaporated. To the residue, water (15 mL) was added. The mixture was extracted with dichloromethane (3×20 mL), dried over Na$_2$SO$_4$, and concentrated in vacuo. The residue was purified on a silica gel column (EtOAc:Hexanes=1:4) to afford W223 as a white solid (40 mg, 65% yield). $^1$H NMR (CDCl$_3$, 400 MHz), δ: 9.03 (s, 1H), 8.41 (d, J=2.0 Hz, 1H), 8.25 (s, 1H), 8.00-8.02 (d, J=8.4 Hz, 1H), 7.96 (s, 1H), 7.77-7.79 (dd, J=1.6 Hz, J=8 Hz, 1H), 7.50-7.57 (qq, J=1.6 Hz, J=8.8 Hz, 2H), 7.27-7.29 (t, J=3.2 Hz, 1H), 6.64-6.66 (q, J=2.8 Hz, 1H). MS: 251.0 (M+H$^+$).

Synthesis of W224, W225, and KC-181

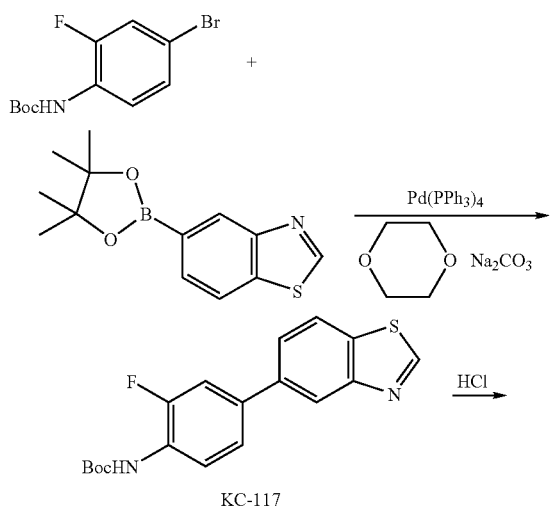

Preparation of KC-117

General experimental procedure for Suzuki coupling was followed. Reaction was performed on a 73 mg scale. Product eluted out in 25% EtOAc:Hexanes mixture in a gradient elution on a Combiflash purification system. Isolated 56 mg (65%) of KC-117 as a white solid. $^1$H NMR (CDCl$_3$, 400 MHz), δ: 9.04 (s, 1H), 8.30 (q, J=1.6 Hz, J=0.4 Hz, 1H), 8.18-8.22 (t, J=7.6 Hz, 1H), 7.99-8.01 (dd, J=0.4 Hz, J=8.4 Hz, 1H), 7.64-7.66 (dd, J=1.2 Hz, J=8 Hz, 1H), 7.43-7.46 (dd, J=2.0 Hz, J=8.4 Hz, 1H), 7.38-7.42 (dd, J=1.6 Hz, J=12 Hz, 2H), 6.77 (s, 1H). $^{19}$F NMR (CDCl$_3$, 376 MHz), δ: −132.61. MS: 345.0 (WO.

Preparation of W224

To a round bottom flask equipped with a magnetic stir bar, rubber septum, and argon inlet containing 1,4-dioxane (5 mL) was placed KC-117 (50 mg, 0.145 mmol). To this solution was added HCl in 1,4-dioxane (4M, 5 mL) and the reaction was allowed to stir at room temperature for 5 h. After the reaction was completed, the precipitate was washed with ether (10 mL). The solid was then suspended in EtOAc (10 mL). To the solution wss added saturated NaHCO$_3$ solution (5 mL) and stirred for 10 min. The mixture was extracted with EtOAc (2×20 mL), dried over Na$_2$SO$_4$, and concentrated in vacuo to afford W224 as a white solid (34 mg, 97% yield). $^1$H NMR (CDCl$_3$, 400 MHz), δ: 9.02 (s, 1H), 8.27 (d, J=1.6 Hz, 1H), 7.97-7.99 (d, J=8.4 Hz, 1H), 7.61-7.64 (dd, J=1.6 Hz, J=8.8 Hz, 1H), 7.33-7.36 (dd, J=2.0 Hz, J=12 Hz, 1H), 7.28-7.31 (dd, J=2.0 Hz, J=8.0 Hz, 1H), 6.86-6.91 (q, J=1.2 Hz, J=8 Hz, 1H), 3.83 (s, 2H). $^{19}$F NMR (CDCl$_3$, 376 MHz), δ: −135.29. MS: 245.0 (M+H$^+$).

Preparation of W225

To a round bottom flask equipped with a magnetic stir bar, rubber septum, and argon inlet containing CH$_3$OH (5 mL) was placed W224 (28 mg, 0.115 mmol). To this solution was added HCHO (17 mg, 0.574 mmol) and sodium methoxide solution (25% wt. % in methanol, 200 mg). The reaction was allowed to stir at 70° C. for 1 h. To the solution was then added NaBH$_4$ (22 mg, 0.574 mmol). The reaction was allowed stir at 70° C. for 12 h. After the reaction was completed, the solvent was evaporated. The residue was purified on a silica gel column (EtOAc:Hexanes=1:3) to afford W225 as a yellow solid (15 mg, 50% yield). $^1$H NMR (CDCl$_3$, 400 MHz), δ: 9.01 (s, 1H), 8.27 (d, J=1.6 Hz, 1H), 7.96-7.98 (d, J=8.8 Hz, 1H), 7.62-7.65 (dd, J=2.0 Hz, J=8.4 Hz, 1H), 7.38-7.40 (dt, J=2.4 Hz, J=7.6 Hz, 1H), 7.26-7.36 (dd, J=2.0 Hz, J=12.8 Hz, 1H), 6.78-6.81 (t, J=8.8 Hz, 1H), 4.05 (s, 1H), 2.94-2.95 (d, J=4.8 Hz, 3H). $^{19}$F NMR (CDCl$_3$, 376 MHz), δ: −137.20. MS: 259.0 (M+H$^+$).

Preparation of KC-181

To a round bottom flask equipped with a magnetic stir bar, rubber septum, and argon inlet containing THF (5 mL) was placed NaH (8 mg, 0.194 mmol) and W225 (50 mg, 0.194 mmol). The reaction was allowed to stir at room temperature for 30 min. To this solution was added CH$_3$I (30 mg, 0.213 mmol) dropwise and the reaction was allowed to stir at room temperature for 3 h. After the reaction was completed, the solvent was evaporated. The residue was purified on a silica gel column (EtOAc:Hexanes=1:3) to afford KC-181 as a brown solid (36 mg, 68% yield). $^1$H NMR (CDCl$_3$, 400 MHz), δ: 9.03 (s, 1H), 8.30 (d, J=1.6 Hz, 1H), 7.98-8.00 (d, J=8.4 Hz, 1H), 7.63-7.66 (dd, J=1.6 Hz, J=8.4 Hz, 1H), 7.35-7.41 (m, 2H), 7.00 (s, 1H), 2.93 (s, 6H). $^{19}$F NMR (CDCl$_3$, 376 MHz), δ: −122.44. MS: 273.0 (M+H$^+$).

Synthesis of W226

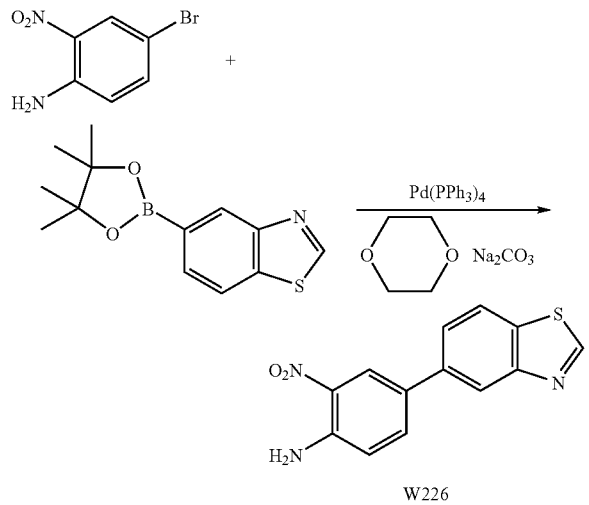

W226

General experimental procedure for Suzuki coupling was followed. Reaction was performed on a 54 mg scale. Product eluted out in 25% EtOAc:Hexanes mixture in a gradient elution on a Combiflash purification system. Isolated 35 mg (52%) of W226 as a yellow solid. $^1$H NMR (CDCl$_3$, 400 MHz), δ: 9.06 (s, 1H), 8.48 (d, J=2.0 Hz, 1H), 8.31-8.32 (q, J=1.2 Hz, 1H), 8.01-8.04 (d, J=8.4 Hz, 1H), 7.74-7.76 (dd, J=2.4 Hz, J=8.4 Hz, 1H), 7.67-7.69 (dd, J=1.6 Hz, J=8.4 Hz, 1H), 6.94-6.97 (d, J=8.4 Hz, 1H), 6.17 (s, 2H). MS: 272.0 (M+H$^+$).

Synthesis of W257 and W275

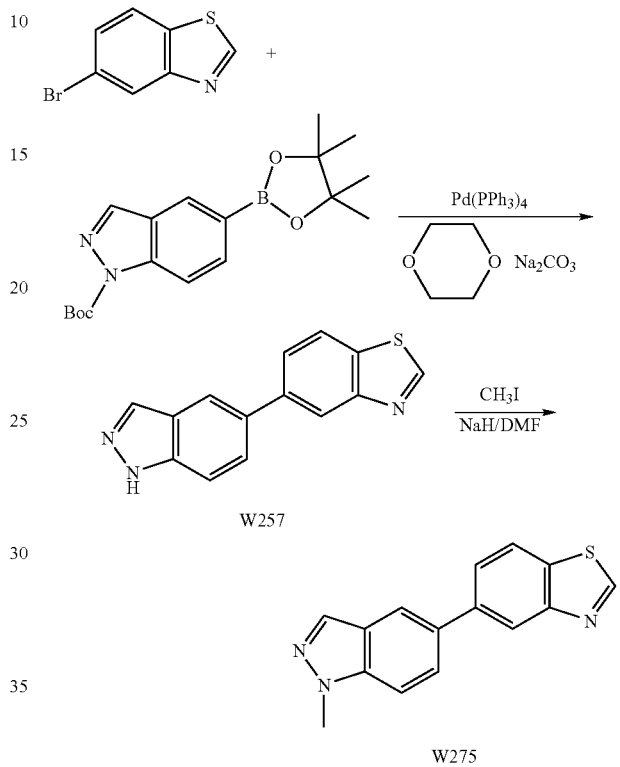

W257

W275

Preparation of W257

General experimental procedure for Suzuki coupling was followed. Reaction was performed on a 54 mg scale. Product eluted out in 25% EtOAc:Hexanes mixture in a gradient elution on a Combiflash purification system. Isolated 32 mg (51%) of W257 as a white solid. $^1$H NMR (d$_6$-DMSO, 400 MHz), δ: 13.15 (s, 1H), 9.44 (s, 1H), 8.37 (d, J=2.0 Hz, 1H), 8.24-8.26 (d, J=8.4 Hz, 1H), 8.15-8.16 (m, 2H), 7.84-7.86 (dd, J=1.6 Hz, J=8.4 Hz, 1H), 7.78-7.81 (dd, J=2.0 Hz, J=8.4 Hz, 1H), 7.65-7.67 (d, J=8.4 Hz, 1H). MS: 252.0 (M+H$^+$).

Preparation of W275

To a round bottom flask equipped with a magnetic stir bar, rubber septum, and argon inlet containing THF (3 mL) was placed NaH (2 mg, 0.048 mmol) and W257 (10 mg, 0.04 mmol). The reaction was allowed to stir at room temperature for 30 min. To this solution was added CH$_3$I (7 mg, 0.048 mmol) and the reaction was allowed to stir at room temperature for 3 h. After the reaction was completed, the solvent was evaporated. The residue was purified on a silica gel column (EtOAc:Hexanes=2:3) to afford W275 as a light yellow solid (5 mg, 43% yield). $^1$H NMR (CD$_2$Cl$_2$, 400 MHz), δ: 9.05 (s, 1H), 8.38 (s, 1H), 8.05-8.07 (d, J=8.4 Hz, 1H), 8.03 (s, 2H), 7.76-7.79 (d, J=8.8 Hz, 2H), 7.53-7.55 (d, J=8.8 Hz, 1H), 5.32 (s, 3H). MS: 266.0 (M+H$^+$).

Synthesis of W258

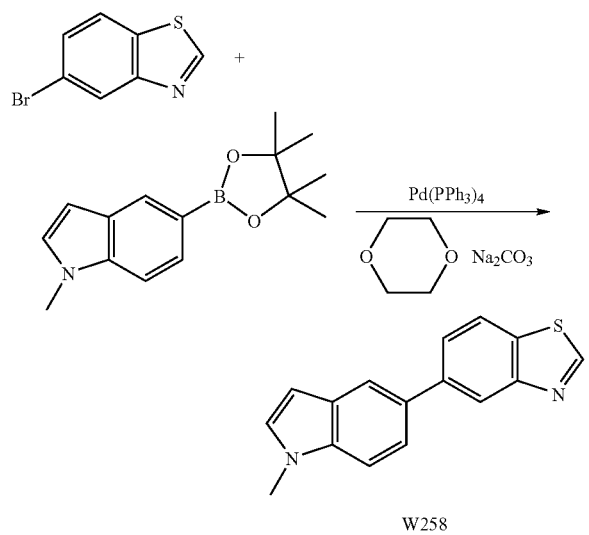

W258

General experimental procedure for Suzuki coupling was followed. Reaction was performed on a 54 mg scale. Product eluted out in 25% EtOAc:Hexanes mixture in a gradient elution on a Combiflash purification system. Isolated 56 mg (85%) of W258 as a white solid. $^1$H NMR (CDCl$_3$, 400 MHz), δ: 9.02 (s, 1H), 8.40-8.41 (d, J=1.6 Hz, 1H), 8.00-8.02 (d, J=8.4 Hz, 1H), 7.93-7.94 (d, J=1.6 Hz, 1H), 7.76-7.79 (dd, J=2.0 Hz, J=8.4 Hz, 1H), 7.56-7.59 (dd, J=2.0 Hz, J=8.4 Hz, 1H), 7.42-7.44 (d, J=8.4 Hz, 1H), 7.11 (d, J=3.2 Hz, 1H), 6.57-6.58 (d, J=3.2 Hz, 1H), 3.85 (s, 3H). MS: 265.0 (M+H$^+$).

Synthesis of W259

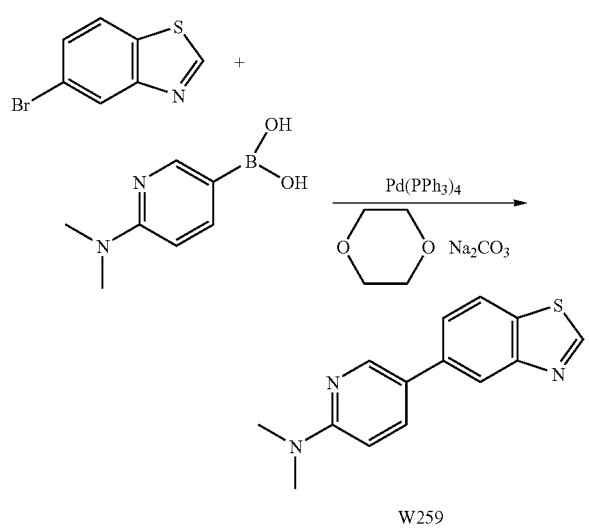

W259

General experimental procedure for Suzuki coupling was followed. Reaction was performed on a 54 mg scale. Product eluted out in 30% EtOAc:Hexanes mixture in a gradient elution on a Combiflash purification system. Isolated 46 mg (72%) of W259 as a light yellow solid. $^1$H NMR (CDCl$_3$, 400 MHz), δ: 9.02 (s, 1H), 8.53 (d, J=2.4 Hz, 1H), 8.27-8.28 (d, J=2.0 Hz, 1H), 7.98-8.00 (d, J=8.4 Hz, 1H), 7.78-7.81 (dd, J=2.4 Hz, J=8.8 Hz, 1H), 7.62-7.64 (dd, J=2.0 Hz, J=8.4 Hz, 1H), 6.63-6.65 (d, J=8.8 Hz, 1H), 3.16 (s, 6H). MS: 256.0 (M+H$^+$).

Synthesis of W260

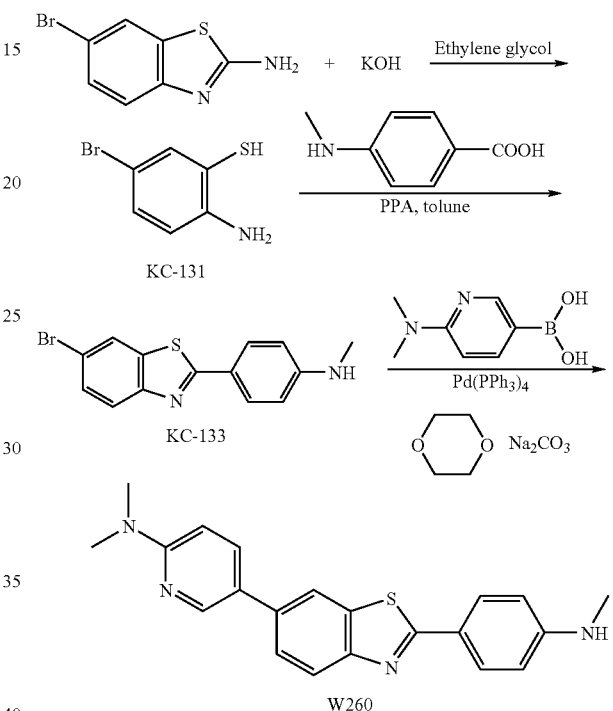

W260

Preparation of KC-131

6-Bromobenzo[d]thiazol-2-amine (1.0 g, 4.36 mmol) was suspended in 50% KOH (4.65 g KOH dissolved in 5 mL water) and ethylene glycol (10 mL). The suspension was heated to reflux for 48 h. Upon cooling to room temperature, toluene (30 mL) was added and the reaction mixture was neutralized with acetic acid. The organic layer was separated, and the aqueous layer was extracted with toluene (2×30 mL). The toluene layers were combined and washed with water and dried over MgSO$_4$. Evaporation of the solvent gave 0.63 g of KC-131 as a light yellow solid (72%). MS: 203.9 (M+H$^+$).

Preparation of KC-133

4-(Methylamino)benzoic acid (151 mg, 1 mmol) and KC-131 (203 mg, 1 mmol) were mixed together with PPA (4 g) and heated to 170° C. under Argon atmosphere for 2 h. The reaction mixture was cooled to room temperature and neutralized with ammonium hydroxide solution to basic condition. The mixture was extracted with EtOAc (3×30 mL), dried over Na$_2$SO$_4$, and concentrated in vacuo. The residue was purified on a silica gel column (EtOAc:Hexanes=2:3) to afford KC-133 as a red brown solid (165 mg, 52% yield). MS: 318.9 (M+H$^+$).

Preparation of W260

General experimental procedure for Suzuki coupling was followed. Reaction was performed on a 20 mg scale. Product eluted out in 30% EtOAc:Hexanes mixture in a gradient elution on a Combiflash purification system. Isolated 11 mg (48%) of W260 as a light yellow solid. $^1$H NMR (CD$_2$Cl$_2$, 400 MHz), δ: 8.46-8.47 (d, J=2.0 Hz, 1H), 7.99-7.80 (d, J=1.6 Hz, 1H), 7.95 (s, 1H), 7.90-7.93 (m, 2H), 7.77-7.80 (dd, J=2.4 Hz, J=8.8 Hz, 1H), 7.59-7.62 (dd, J=2.0 Hz, J=8.4 Hz, 1H), 6.63-6.69 (m, 3H), 4.25 (s, 1H), 3.13 (s, 6H), 2.91 (s, 3H). MS: 361.0 (M+H$^+$).

Synthesis of W269

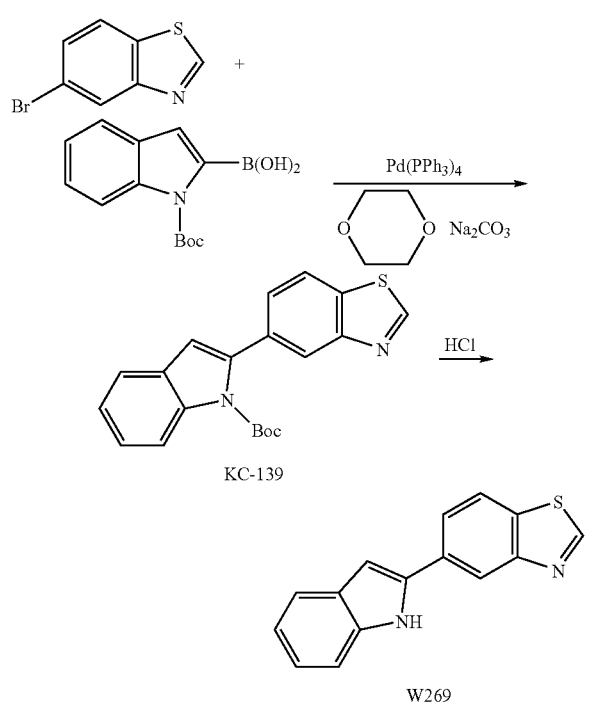

Preparation of KC-139

General experimental procedure for Suzuki coupling was followed. Reaction was performed on a 54 mg scale. Product eluted out in 30% EtOAc:Hexanes mixture in a gradient elution on a Combiflash purification system. Isolated 46 mg (53%) of KC-139 as a white solid. $^1$H NMR (CDCl$_3$, 400 MHz), δ: 9.04 (s, 1H), 8.24 (s, 1H), 8.22 (s, 1H), 7.96-7.98 (d, J=8.4 Hz, 1H), 7.57-7.59 (d, J=8.4 Hz, 1H), 7.50-7.53 (dd, J=1.6 Hz, J=8.4 Hz, 1H), 7.34-7.38 (t, J=8.4 Hz, 1H), 7.25-7.29 (t, J=8.4 Hz, 1H), 6.65 (s, 1H), 1.29 (s, 9H). MS: 351.0 (M+H$^+$).

Preparation of W269

To a round bottom flask equipped with a magnetic stir bar, rubber septum, and argon inlet containing 1,4-dioxane (5 mL) was placed KC-139 (45 mg, 0.129 mmol). To this solution was added HCl in 1,4-dioxane (4M, 4 mL) and the reaction was allowed to stir at room temperature for 5 h. After the reaction was completed, the precipitate was washed with ether (10 mL). The solid was then suspended in EtOAc (10 mL). To the solution was added saturated NaHCO$_3$ solution (5 mL) and stirred for 10 min. The mixture was extracted with EtOAc (2×20 mL), dried over Na$_2$SO$_4$, and concentrated in vacuo to afford W269 as a white solid (28 mg, 87% yield). $^1$H NMR (CD$_3$OD, 400 MHz), δ: 9.27 (s, 1H), 8.46 (d, J=1.6 Hz, 1H), 8.09-8.11 (d, J=8.8 Hz, 1H), 7.95-7.98 (dd, J=1.6 Hz, J=8.4 Hz, 1H), 7.55-7.57 (d, J=8.0 Hz, 1H), 7.41-7.43 (d, J=8.0 Hz, 1H), 7.10-7.12 (t, J=8.0 Hz, 1H), 7.01-7.04 (t, J=8.0 Hz, 1H), 6.93 (s, 1H). MS: 251.0 (M+H$^+$).

Synthesis of W282

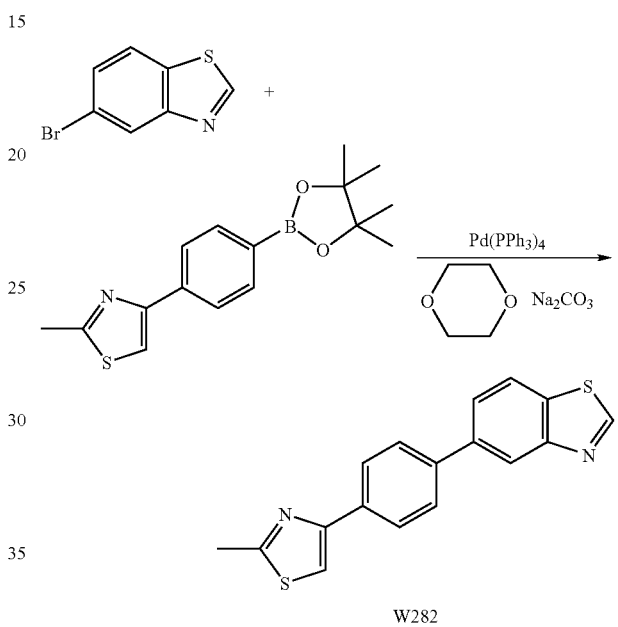

General experimental procedure for Suzuki coupling was followed. Reaction was performed on a 54 mg scale. Product eluted out in 30% EtOAc:Hexanes mixture in a gradient elution on a Combiflash purification system. Isolated 53 mg (69%) of W282 as a white solid. $^1$H NMR (CDCl$_3$, 400 MHz), δ: 9.03 (s, 1H), 8.38-9.39 (d, J=2.0 Hz, 1H), 7.99-8.03 (m, 3H), 7.73-7.75 (m, 3H), 7.38 (s, 1H), 2.82 (s, 3H). MS: 309.0 (M+H$^+$).

Synthesis of W310

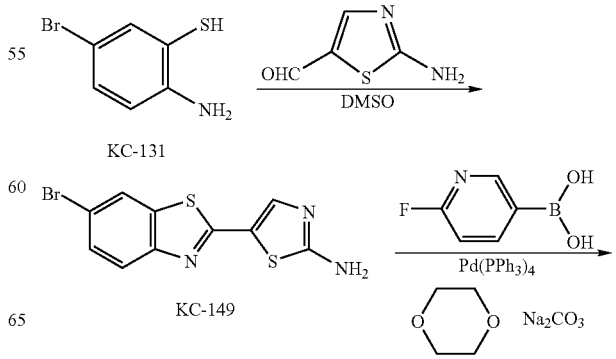

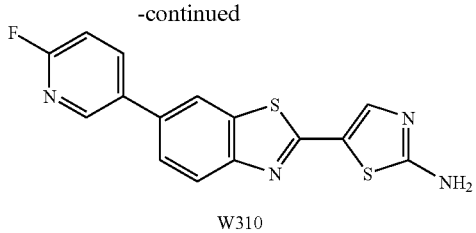

W310

Preparation of KC-149

A mixture of KC-131 (203 mg, 1.0 mmol) and 2-aminothiazole-5-carbaldehyde (128 mg, 1.0 mmol) in DMSO (1 mL) was heated to 170° C. for 30 min. The reaction mixture was cooled to room temperature and poured into water. The organic component was extracted with ethyl acetate (3×10 mL). The combined organic layers were washed with water and dried over MgSO$_4$. Evaporation of the solvent gave a residue that was purified by a silica gel column ((EtOAc:Hexanes=2:3) to give 124 mg of KC-149 as a red brown solid (40%). MS: 311.8 (M+H$^+$).

Preparation of W310

General experimental procedure for Suzuki coupling was followed. Reaction was performed on a 46 mg scale. Product eluted out in 30% EtOAc:Hexanes mixture in a gradient elution on a Combiflash purification system. Isolated 21 mg (44%) of W310 as a brown solid. $^1$H NMR (d$_6$-DMSO, 400 MHz), δ: 8.63-8.64 (d, J=2.8 Hz, 1H), 8.42 (d, J=2.0 Hz, 1H), 8.35-8.40 (dt, J=2.4 Hz, J=8.4 Hz, 1H), 7.94-7.96 (d, J=8.4 Hz, 1H), 7.87 (s, 3H), 7.80-7.82 (dd, J=2.0 Hz, J=8.4 Hz, 1H), 7.31-7.34 (dd, J=2.8 Hz, J=8.8 Hz, 1H). MS: 329.0 (M+H$^+$).

Synthesis of W311

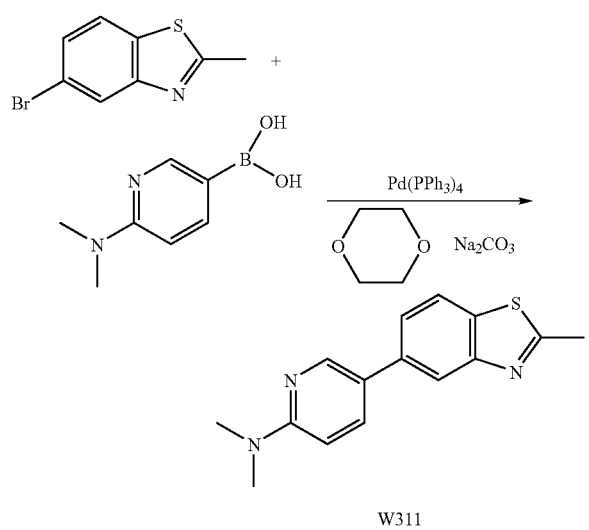

General experimental procedure for Suzuki coupling was followed. Reaction was performed on a 57 mg scale. Product eluted out in 30% EtOAc:Hexanes mixture in a gradient elution on a Combiflash purification system. Isolated 48 mg (72%) of W311 as a light yellow solid. $^1$H NMR (CDCl$_3$, 400 MHz), δ: 8.51 (d, J=2.4 Hz, 1H), 8.08 (d, J=1.6 Hz, 1H), 7.83-7.86 (d, J=8.4 Hz, 1H), 7.75-7.78 (dd, J=2.8 Hz, J=8.8 Hz, 1H), 7.51-7.54 (dd, J=1.6 Hz, J=8.4 Hz, 1H), 6.62-6.64 (d, J=8.8 Hz, 1H), 3.16 (s, 6H), 2.82 (s, 3H). MS: 270.0 (M+H$^+$).

Synthesis of W344, W345, and KC-185

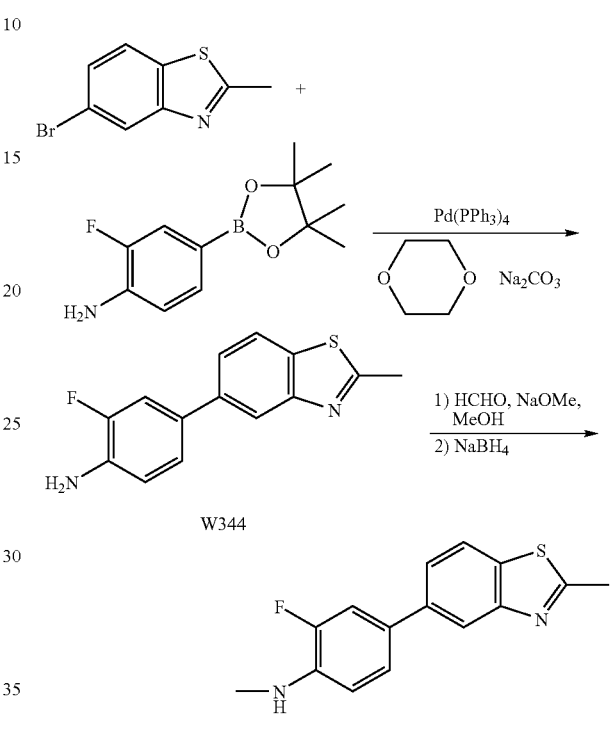

Preparation of W344

General experimental procedure for Suzuki coupling was followed. Reaction was performed on a 114 mg scale. Product eluted out in 30% EtOAc:Hexanes mixture in a gradient elution on a Combiflash purification system. Isolated 88 mg (68%) of W344 as a white solid. $^1$H NMR (CDCl$_3$, 400 MHz), δ: 8.08-8.09 (d, J=1.6 Hz, 1H), 7.82-7.84 (d, J=8.8 Hz, 1H), 7.51-7.54 (dd, J=1.6 Hz, J=8.4 Hz, 1H), 7.30-7.34 (dd, J=2.0 Hz, J=12.4 Hz, 1H), 7.25-7.28 (dd, J=2.0 Hz, J=8.4 Hz, 1H), 6.85-6.89 (q, J=1.2 Hz, J=8.0 Hz, 1H), 2.86 (s, 3H). $^{19}$F NMR (CDCl$_3$, 376 MHz), δ: −135.32. MS: 259.0 (M+H$^+$).

Preparation of W345

To a round bottom flask equipped with a magnetic stir bar, rubber septum, and argon inlet containing CH$_3$OH (5 mL) was placed W344 (54 mg, 0.21 mmol). To this solution was added HCHO (38 mg, 1.26 mmol) and sodium methoxide solution (25% wt. % in methanol, 452 mg). The reaction was allowed to stir at 70° C. for 1 h. To the solution was then added NaBH$_4$ (47 mg, 1.26 mmol). The reaction was allowed stir at 70° C. for 12 h. After the reaction was completed, the solvent was evaporated. The residue was purified on a silica gel column (EtOAc:Hexanes=1:3) to afford W345 as a white solid (55 mg, 96% yield). $^1$H NMR (CDCl$_3$, 400 MHz), δ: 8.08-8.09 (d, J=1.2 Hz, 1H), 7.81-7.84 (d, J=8.4 Hz, 1H), 7.52-7.54 (dd, J=1.6 Hz, J=8.4 Hz, 1H), 7.35-7.38 (dd, J=2.0 Hz, J=8.4 Hz, 1H), 7.29-7.33 (dd, J=2.0 Hz, J=13.2 Hz, 1H), 6.76-6.80 (t, J=8.8 Hz, 1H), 2.94 (s, 3H), 2.86 (s, 3H). $^{19}$F NMR (CDCl$_3$, 376 MHz), δ: −137.20. MS: 273.0 (M+H$^+$).

Synthesis of W346

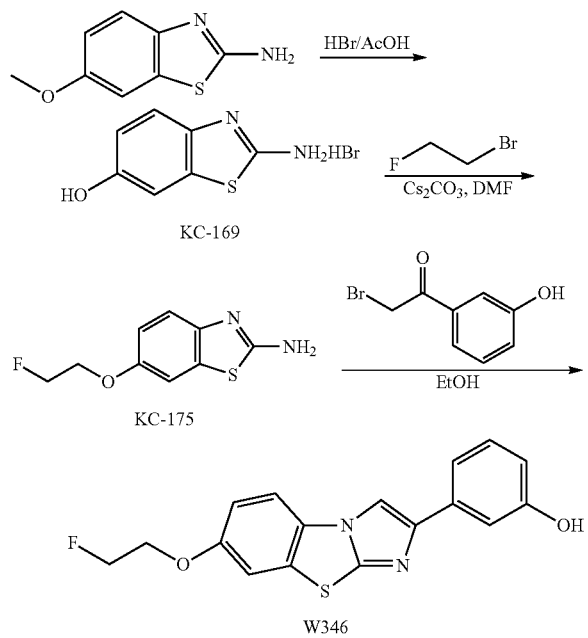

Preparation of KC-169

6-Methoxybenzo[d]thiazol-2-amine (1 g, 5.55 mmol) was dissolved in hydrobromic acid (48%, 1.507 mL, 27.7 mmol) and hydrobromic acid (1.507 mL, 27.7 mmol) in acetic acid. The reaction was heated in a sealed tube at 135° C. for 3 h. After the reaction was completed, the mixture was cooled to room temperature. The precipitate was filtered, washed with water/ether, and dried under vacuum to afford KC-169 as a brown solid (1 g, 73%). MS: 167.0 (M+H$^+$).

Preparation of KC-175

To a round bottom flask equipped with a magnetic stir bar, rubber septum, and argon inlet containing DMF (5 mL) was placed Cs$_2$CO$_3$ (264 mg, 0.809 mmol) and KC-169 (100 mg, 0.405 mmol). To this solution was added 1-bromo-2-fluoroethane (257 mg, 2.02 mmol) and the reaction was allowed to stir at room temperature for 6 h. After the reaction was completed, the solvent was evaporated. To the residue, water (10 mL) was added. The mixture was extracted with EtOAc (3×15 mL), dried over Na$_2$SO$_4$, and concentrated in vacuo. The residue was purified on a silica gel column (EtOAc:Hexanes=2:3) to afford KC-175 as a light brown solid (63 mg, 73% yield). MS: 213.0 (M+H$^+$).

Preparation of W346

To a round bottom flask equipped with a magnetic stir bar, rubber septum, and argon inlet containing EtOH (2 mL) was placed 2-bromo-1-(3-hydroxyphenyl)ethanone (51 mg, 0.236 mmol) and KC-175 (50 mg, 0.236 mmol). The reaction was allowed to stir at 70° C. for 6 h. After the reaction was completed, the reaction was cooled to room temperature. The precipitate was filtered and washed with ether to afford W346 as a white solid (33 mg, 43% yield). $^1$H NMR (d$_6$-DMSO, 400 MHz), δ: 8.71 (s, 1H), 7.95-7.98 (d, J=8.8 Hz, 1H), 7.74-7.75 (d, J=2.4 Hz, 1H), 7.21-7.27 (m, 4H), 6.70-6.72 (dd, J=2.0 Hz, J=7.6 Hz, 1H), 4.84-4.86 (t, J=7.6 Hz, 1H), 4.72-4.74 (t, J=3.6 Hz, 1H), 4.35-4.37 (t, J=3.6 Hz, 1H), 4.28-4.30 (t, J=3.6 Hz, 1H). $^{19}$F NMR (CDCl$_3$, 376 MHz), δ: −222.54. MS: 329.0 (M+H$^+$).

Experimental Section for Fused-Ring Derivatives

General Experimental Procedure for Cyclization

A 50 mL flask was charged with 2-amino-6-methoxy-7-azabenzothiazole (1 equiv), and α-bromoketone (1-2 equiv) in ethanol (20 vol). The suspension was refluxed at 85° C. for 16 h. After cooling to room temperature the solid was filtered, washed with EtOH and ether, dried in vacuo to afford the desired cyclized product as HBr salt. The crude product was stirred in NaHCO$_3$ solution (5%, 5 mL) overnight at room temperature. The solid was filtered and dried to afford the desired free base product.

Synthesis of W373

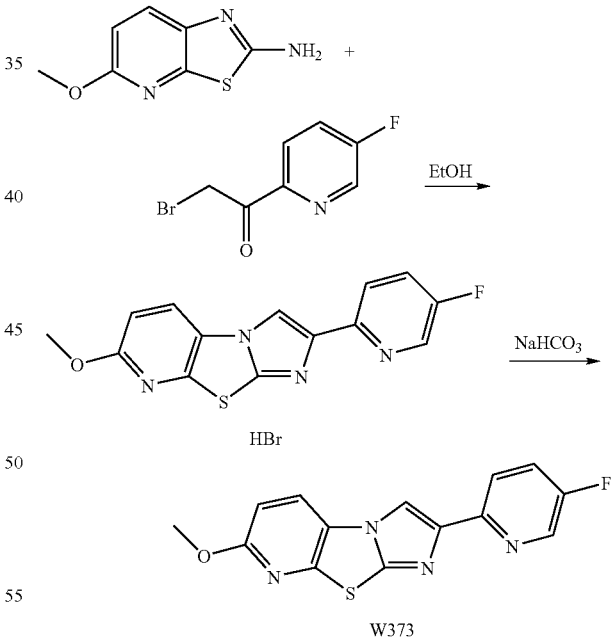

Preparation of W373

General experimental procedure for cyclization reaction was followed. Reaction performed on a 134 mg scale. Isolated 93 mg (42%) of W373 as a grey solid. $^1$H NMR (d$_6$-DMSO, 400 MHz), δ: 8.84 (s, 1H), 8.58-8.59 (d, J=3.2 Hz, 1H), 8.48-8.50 (d, J=8.8 Hz, 1H), 8.01-8.03 (q, J=4.4 Hz, 1H), 7.80-7.83 (dt, J=3.2 Hz, J=8.8 Hz, 1H), 7.07-7.09 (d, J=8.8 Hz, 1H), 3.95 (s, 3H). $^{19}$F NMR (CDCl$_3$, 376 MHz), δ: −129.64. MS: 301.0 (M+H$^+$).

Synthesis of W377

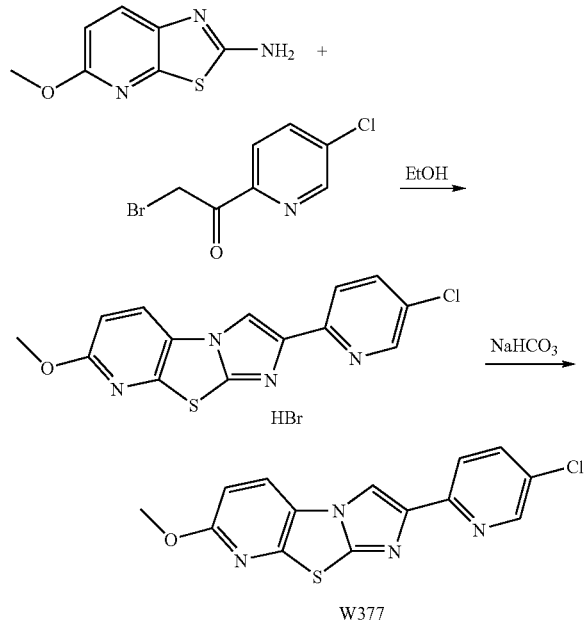

Preparation of W377

General experimental procedure for cyclization reaction was followed. Reaction performed on a 134 mg scale. Isolated 100 mg (43%) of W377 as a white solid. $^1$H NMR (d$_6$-DMSO, 400 MHz), δ: 8.90 (s, 1H), 8.62 (d, J=1.6 Hz, 1H), 8.47-8.49 (d, J=8.8 Hz, 1H), 7.97-7.98 (m, 2H), 7.07-7.09 (d, J=8.8 Hz, 1H), 3.95 (s, 3H). MS: 317.0 (M+H$^+$).

Synthesis of W383

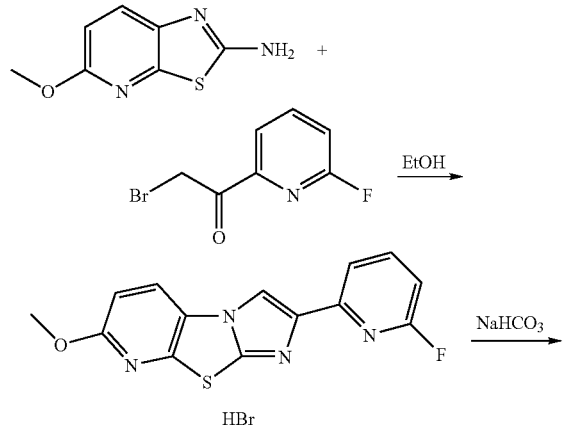

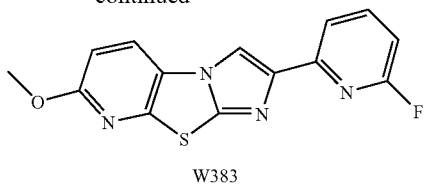

Preparation of W383

General experimental procedure for cyclization reaction was followed. Reaction performed on a 209 mg scale. Isolated 145 mg (42%) of W383 as a brown solid. $^1$H NMR (d$_6$-DMSO, 400 MHz), δ: 8.90 (s, 1H), 8.47-8.49 (d, J=8.8 Hz, 1H), 8.01-8.08 (q, J=8.4 Hz, 1H), 7.85-7.88 (dd, J=2.4 Hz, J=7.6 Hz, 1H), 7.05-7.08 (m, 2H), 3.94 (s, 3H). $^{19}$F NMR (CDCl$_3$, 376 MHz), δ: −68.45. MS: 301.0 (M+H$^+$).

Synthesis of W391

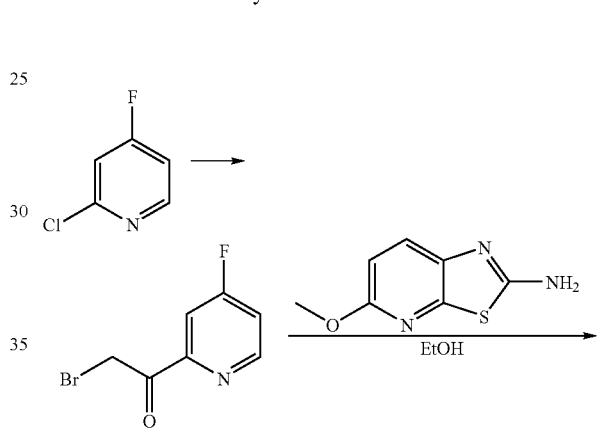

Tetrakis(triphenylphosphine) palladium(0) (0.439 g, 0.380 mmol) was added to a solution containing 2-chloro-4-fluoropyridine (1 g, 7.60 mmol) and tributyl(1-ethoxyvinyl)tin (2.59 ml, 7.60 mmol) in Toluene (15.21 ml). In a capped vial, the reaction was heated to 110° C. for overnight. LC/MS verified that the vinyl enolate intermediate formed. The reaction was cooled to room temperature, filtered thru a plug of Celite and the filtrate concentrated. The resulting residue was diluted with THF (20 mL) and water (2 mL). The reaction mixture was cooled to 0° C. and N-bromosuccinimide (1.624 g, 9.12 mmol) was added. The reaction was stirring for 1 hour and warmed to room temperature. The reaction was diluted with ethyl acetate and washed with water. Separated organics, dried with MgSO$_4$, filtered and concentrated. Purified using Combiflash using 0% to 20% ethyl acetate in hexanes to afford 2-bromo-1-(4-fluoropyridin-2-yl)ethanone (1.4 g, 6.42 mmol, 84% yield) as a light purple oil. $^1$H NMR (CDCl$_3$, 400 MHz), δ: 4.81 (s, 2H), 7.24 (m, 1H), 7.79 (m, 1H), 8.65 (m, 1H).

5-methoxythiazolo[5,4-b]pyridin-2-amine (0.34 g, 1.876 mmol) and 2-bromo-1-(4-fluoropyridin-2-yl)ethanone (0.409 g, 1.876 mmol) were heated to 85° C. in EtOH (9.38 ml) for 3 hours. The reaction was cooled to room temperature and filtered. The solid was washed with ether to remove tin. The HBr salt was diluted with ethyl acetate and washed with saturated sodium bicarbonate. The layers were separated. The organics were dried with MgSO$_4$, filtered, and concentrated to afford W391 (0.1 g, 0.333 mmol, 17.75% yield). $^1$H NMR (DMSO-d$_6$, 400 MHz), δ: 3.91 (s, 3H), 7.05 (m, 1H), 7.21 (m, 1H), 7.67 (m, 1H), 8.46 (m, 1H), 8.58 (m, 1H), 8.90 (s, 1H). MS: 301.0 (M+H$^+$).

Preparation of W273

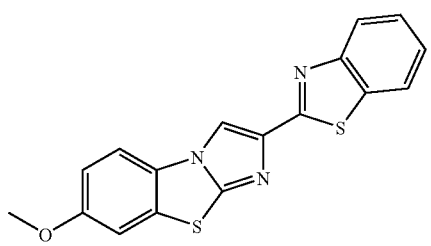 [SMILES: COc1ccc2c(c1)sc1nc(-c3nc4ccccc4s3)cn12]

General experimental procedure for cyclization was followed. Reaction was performed on a 0.05 g scale. Isolated 0.015 g (20%) of W273 as a light yellow solid. $^1$H NMR (CDCl$_3$, 400 MHz) δ: 8.58 (s, 1H), 8.06 (d, J=8.00 Hz, 1H), 7.94 (d, J=7.8 Hz, 1H), 7.60 (d, J=8.8 Hz, 1H), 7.51 (t, J=8.4 Hz, 1H), 7.41 (t, J=8.2 Hz, 1H), 7.24 (d, J=2.4 Hz, 1H), 7.06 (dd, J=8.8 Hz, 2.4 Hz, 1H), 3.73 (q, J=7.1 Hz, 1H), 1.25 (t, J=6.8 Hz, 2H). MS: m/z=338 (M+H$^+$).

Preparation of W272

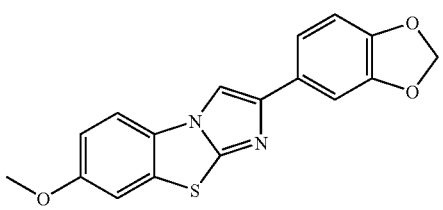 [SMILES: COc1ccc2c(c1)sc1nc(-c3ccc4c(c3)OCO4)cn12]

General experimental procedure for cyclization was followed. Reaction was performed on a 0.05 g scale. Isolated 0.017 g (19%) of W272 as a light yellow solid. $^1$H NMR ((CD$_3$)$_2$SO, 400 MHz) δ: 8.58 (s, 1H), 7.82 (d, J=8.80 Hz, 1H), 7.66 (d, J=2.5 Hz, 1H), 7.33-7.31 (m, 2H), 7.13 (dd, J=8.8 Hz, 2.5 Hz, 1H), 6.95 (d, J=8.4 Hz, 1H), 6.01 (s, 2H), 3.80 (s, 3H). MS: m/z=325 (M+H$^+$).

Preparation of W271

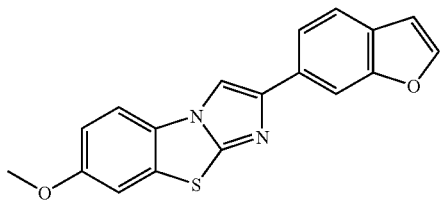 [SMILES: COc1ccc2c(c1)sc1nc(-c3ccc4ccoc4c3)cn12]

General experimental procedure for cyclization was followed. Reaction was performed on a 0.05 g scale. Isolated 0.016 g (19%) of W271 as a light yellow solid. $^1$H NMR (CDCl$_3$, 400 MHz) δ: 8.13 (d, J=1.5 Hz, 1H), 7.91 (s, 1H), 7.80 (dd, J=8.6 Hz, 1.7 Hz, 1H), 7.64 (d, J=2.1 Hz, 1H), 7.53 (d, J=8.6 Hz, 1H), 7.52 (d, J=8.8 Hz, 1H), 7.23 (d, J=2.3 Hz, 1H), 7.02 (dd, J=8.8 Hz, 2.3 Hz, 1H), 6.80 (dd, J=2.1 Hz, 1 Hz, 1H), 3.89 (s, 3H). MS: m/z=321 (M+H$^+$).

Preparation of W296

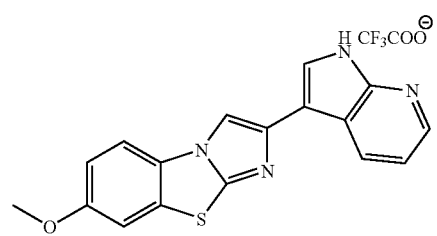

General experimental procedure for cyclization was followed. Reaction was performed on a 0.01 g scale. Isolated 0.004 g (3%) of W296 as a TFA salt after HPLC purification. MS: 321.0 [M+H$^+$-TFA].

$^1$H NMR (CD$_3$OD, 400 MHz) δ: 8.66 (dd, J=1.4 Hz, 8.0 Hz, 1H), 8.54 (s, 1H), 8.37 (dd, J=5.1 Hz, 1.2 Hz, 1H), 7.94 (t, J=4.5 Hz, 2H), 7.56 (d, J=2.6 Hz, 1H), 7.41 (dd, J=8.0 Hz, 5.2 Hz, 1H), 7.20 (dd, J=9.0 Hz, 2.5 Hz, 1H), 3.91 (s, 3H). MS: m/z=321 (M+H$^+$).

Preparation of W297

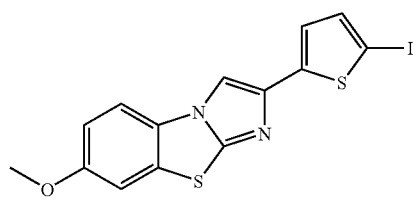 [SMILES: COc1ccc2c(c1)sc1nc(-c3ccc(I)s3)cn12]

General experimental procedure for cyclization was followed. Reaction was performed on a 0.05 g scale. Isolated 0.015 g (24%) of W297 as light brown solid after chromatography on silica gel column. MS: 412.9 (M+H+).

Preparation of W312

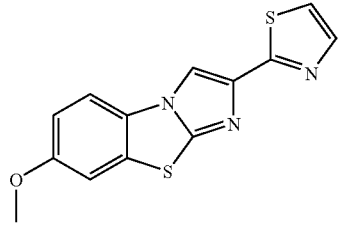 [SMILES: COc1ccc2c(c1)sc1nc(-c3nccs3)cn12]

General experimental procedure for cyclization was followed. Reaction was performed on a 0.05 g scale. Isolated 0.012 g (17%) of W312 as light brown solid. MS: 288 (M+H+).

Preparation of W371

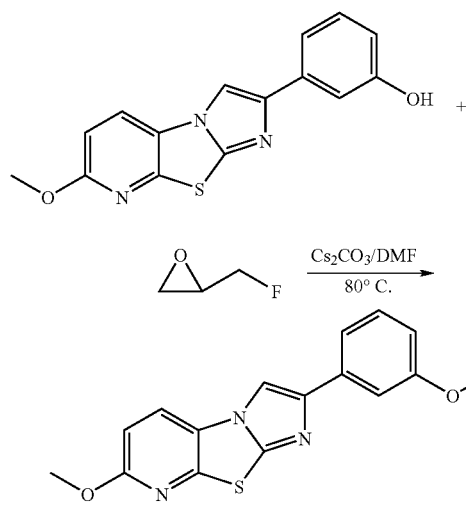

General experimental procedure for cyclization was followed for the synthesis of the phenol. Reaction was performed on 0.1 g scale. Isolated 0.05 g (30%) of the phenol as an off white solid. The phenol (0.05 g, 0.168 mmol) was reacted with epifluorohydrin (0.025 g, 0.337 mmol) in DMF (1 mL) in the presence of Cs$_2$CO$_3$ (0.137 g, 0.421 mmol) at about 80° C. After 4 hrs when LCMS showed no starting material, the reaction was cooled, DMF was removed and chromatographed. After isolation, the product was obtained as off white solid (0.02 g, 32%). MS: 374 (M+H+).

$^1$H NMR ((CD$_3$)$_2$CO, 400 MHz) δ: 8.53 (s, 1H), 8.24 (d, J=8.8 Hz, 2H), 7.55-7.50 (m, 2H), 7.33 (t, J=8.0 Hz, 1H), 6.98 (d, J=8.8 Hz, 1H), 6.88-6.91 (m, 1H), 4.71-4.62 (m, 1H), 4.59 (d, J=5.5 Hz, 1H), 4.59-4.50 (m, 1H), 4.28-4.17 (m, 1H), 4.15-4.12 (m, 2H), 3.99 (s, 3H). MS: m/z=374 (M+H+).

Preparation of W389

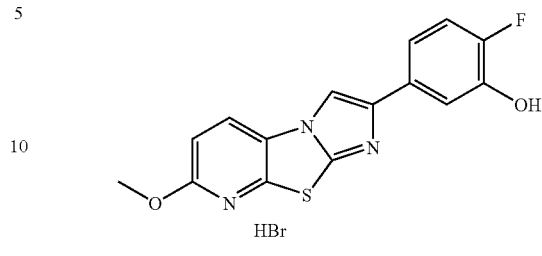

General experimental procedure for cyclization was followed. Reaction was performed on a 0.06 g scale. Isolated 0.012 g (11%) of W389 as light brown solid after filtration. MS: 316.1 (M+H+).

$^1$H NMR ((CD$_3$)$_2$SO, 400 MHz) δ: 9.95 (s, 1H), 8.59 (s, 1H), 8.30 (d, J=8.8 Hz, 1H), 8.42 (dd, J=8.6 Hz, 1.9 Hz, 1H), 7.21-7.12 (m, 2H), 7.03 (d, J=8.8 Hz, 1H), 3.91 (s, 3H). MS: m/z=316.1 (M+H+).

Synthesis of W372 Precursor

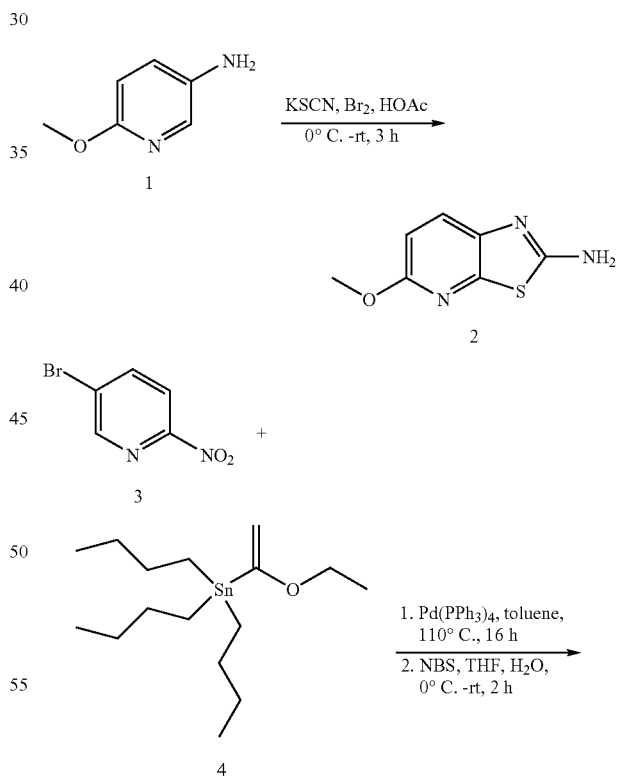

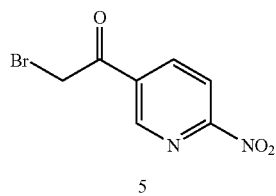

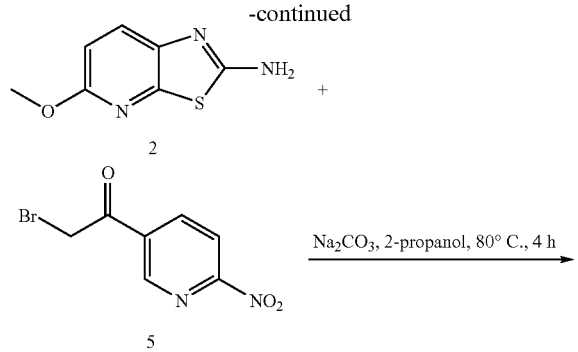

Synthesis of 5-methoxythiazolo[5,4-b]pyridin-2-amine (2)

To a cooled solution of KSCN (20.2 g, 208 mmol, 5 equiv) in HOAc (80 mL) was added dropwise a solution of 3-amino-6-methoxypyridine 1 (5 g, 40.3 mmol, 1.2 equiv) in HOAc (10 mL), followed by a solution of $Br_2$ (2.5 mL, 48.5 mmol) in HOAc (10 mL). The resulting mixture was stirred at 0° C. for 1 h, and then at room temperature for 2 h. It was concentrated in vacuo. The residue was diluted with EtOAc (40 mL), neutralized with sat. $NaHCO_3$ solution. The mixture was filtered. The layers of filtrate were separated. The organic layer was washed with brine (30 mL), dried ($MgSO_4$), filtered and concentrated to give a light red solid (6.8 g, 93%). NMR (400 MHz, DMSO-$d_6$) δ: 7.61 (d, J=8.4 Hz, 1H), 7.43 (s, 1H), 6.69 (d, J=8.4 Hz, 1H), 3.83 (s, 3H). MS: 182 (M+H+).

Synthesis of 2-bromo-1-(6-nitropyridin-3-yl)ethanone (5)

A 100 mL was charged with 2-nitro-5-bromo pyridine 3 (3 g, 14.78 mmol) and tributyl(1-ethoxyvinyl)tin 4 (5.4 mL, 15.89 mmol) in anhydrous toluene (20 mL), tetrakis-(triphenylphosphine)palladium(0) (1.0 g, 0.0865 mmol) was added and the reaction mixture was stirred at 110° C. for 16 h. The reaction mixture was cooled, passed through a Celite® pad and evaporated. The crude residue was re-dissolved in THF-$H_2O$ (50:10) and NBS (2.90 g, 16.29 mmol) was added portion wise at 0° C. over the period of 40 min. The resulting mixture was stirred at RT for 2 h then concentrated to 10 ml. The mixture was extracted with ethyl acetate (2×50 mL) and washed with water (2×50 mL) and brine (1×50 mL) dried over $Na_2SO_4$. The oily residue was purified by on a Combiflash unit. The column was eluted with hexane:DCM (0-80%). The 2-bromo-1-(6-nitropyridin-3-yl)ethanone 5 eluted out with 65-70% of DCM in hexane. After evaporation, a white solid 1.64 g (44%) was isolated. $^1$H NMR (CDCl$_3$) δ: 9.23 (1H, dd, J=2.4 and 0.8 Hz), 8.79 (1H, dd, J=8.4 and 2.4 Hz), 8.45 (1H, dd, J=8.4 and 0.8 Hz), 4.97 (2H, s); MS: 245 (M+H+).

Synthesis of 7-Methoxy-2 (6-nitropyridin-3-yl)imidazo[2,1-b]-8-pyridinothiazole (6) [W372 Precursor]

A 250 mL flask was charged with 5-methoxythiazolo-[5,4-b]pyridine-2-amine 4 (1.025 g, 5.66 mmol), 2-bromo-1-(6-nitropyridin-3-yl)ethanone 3 (1.64 g, 6.69 mmol) and $Na_2CO_3$ (0.599 g, 5.66 mmol) in 2-propanol (20 mL) and was stirred at 80° C. for 4 h. The reaction mixture was cooled and quenched with water and the reddish brown solid was filtered. The solid was sequentially washed with MeOH (10 mL), DCM (10 mL) and Et$_2$O (10 mL) and yellow solid was filtered and air and vacuum dried. $^1$H NMR (DMSO-$d_6$) δ: 9.087 (s, 1H), 9.081 ((s, 1H), 8.53 (dd, J=8.8, 4.0 Hz, 1H), 8.39 (d, J=8.8 Hz, 1H), 8.33 (d, J=8.8 Hz, 1H), 7.08 (d, J=8.8 Hz, 1H), 3.93 (s, 3H); MS: 328 (M+H+).

Preparation of W355 Precursor (W355P)

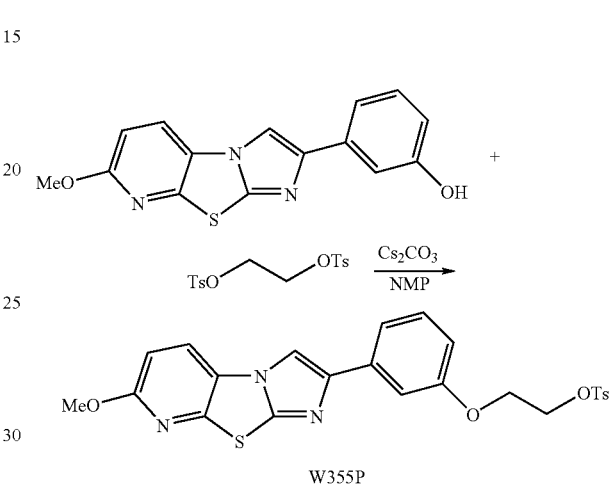

To W354 (38 mg, 0.1 mmol) and ethane-1,2-diyl bis(4-methylbenzenesulfonate) (74 mg, 0.2 mmol) in 1 mL of NMP was added $Cs_2CO_3$ (33 mg, 0.1 mmol). The mixture was stirred at rt for 15 hours and diluted with EtOAc (30 mL). It was washed with water (3×30 mL) and dried over MgSO4. The crude product was purified with silica chromatography (EtOAc in hexane) to afford W355P as a yellow solid (26 mg, 53%). $^1$H NMR (400 MHz, DMSO-d6) δ 8.73 (s, 1H), 8.31 (d, J=8.4 Hz, 1H), 7.82 (d, J=8.4 Hz, 2H), 7.46-7.42 (m, 1H), 7.34-7.30 (m, 1H), 7.08 (d, J=8.8 Hz, 1H), 6.77 (dd, J=7.8, 2.0 Hz, 1H), 4.39-4.37 (m, 2H), 4.23-4.21 (m, 2H), 3.95 (s, 3H); MS (ESI) m/z 496 (M+H+).

W391 Precursor

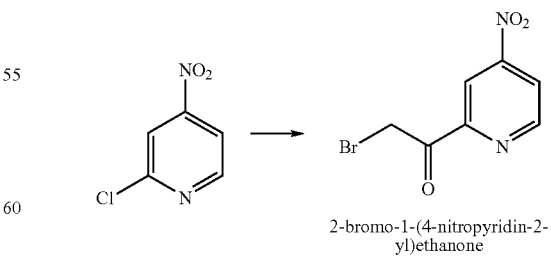

2-bromo-1-(4-nitropyridin-2-yl)ethanone

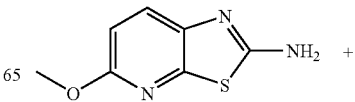

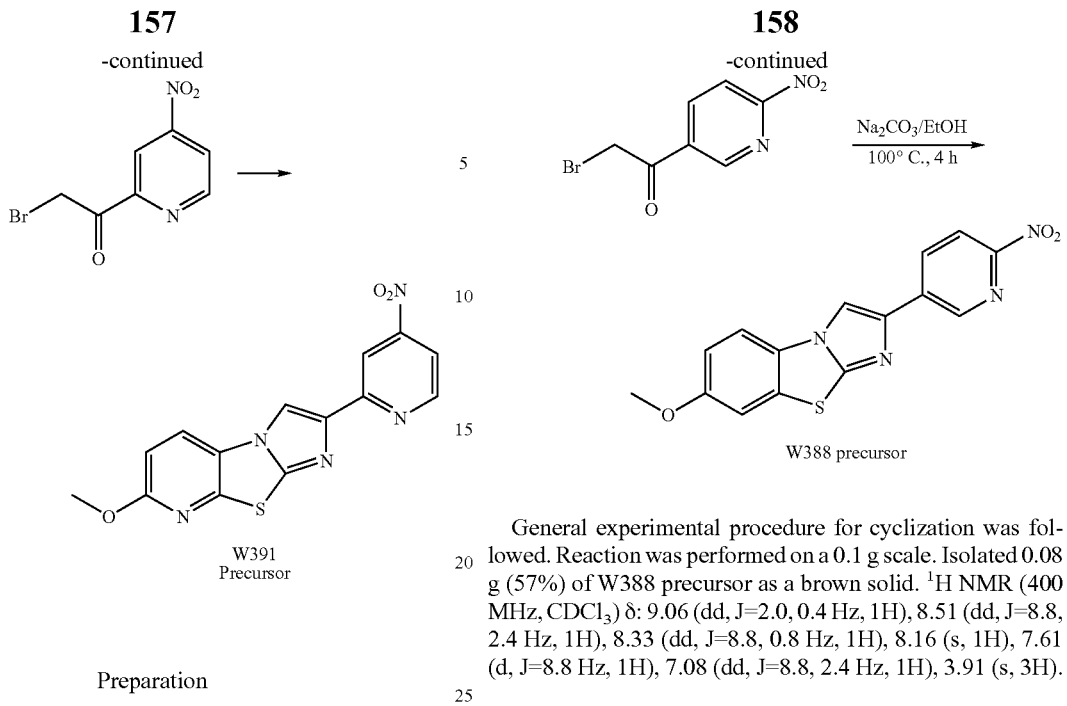

W391 Precursor

Preparation

Tetrakis(triphenylphosphine) palladium(0) (0.364 g, 0.315 mmol) was added to a solution containing 2-chloro-4-nitropyridine (1 g, 6.31 mmol) and Tributyl(1-ethoxyvinyl)tin (2.149 ml, 6.31 mmol) in Toluene (12.61 ml). In a capped vial, the reaction was heated to 110° C. for overnight. LC/MS verified that the vinyl enolate intermediate formed. The reaction was cooled to room temperature, filtered thru a plug of Celite and the filtrate concentrated. The resulting residue was diluted with THF (20 mL) and water (2 mL). The reaction mixture was cooled to 0° C. and N-Bromosuccinimide (1.347 g, 7.57 mmol) was added. The reaction was stirring for 1 hour and warmed to room temperature. The reaction was diluted with ethyl acetate and washed with water. Separated organics, dried with $MgSO_4$, filtered and concentrated. Purified using combiflash using 0% to 20% ethyl acetate in hexanes to afford 2-bromo-1-(4-nitropyridin-2-yl)ethanone (1.1 g, 4.49 mmol, 71.2% yield) as a light purple oil. $^1H$ NMR ($CDCl_3$) δ: 4.81 (s, 2H), 7.24 (m, 1H), 7.80 (m, 1H), 8.66 (m, 1H).

5-methoxythiazolo[5,4-b]pyridin-2-amine (0.740 g, 4.08 mmol) and 2-bromo-1-(4-nitropyridin-2-yl)ethanone (1 g, 4.08 mmol) in Ethanol (20.41 ml) were heated to 85° C. for 3 hours. The reaction was cooled to rt. The solid was filtered and washed with diethyl ether. The solid was diluted with ethyl acetate and washed with saturated $NaHCO_3$. Combined organics, dried with $MgSO_4$, filtered and concentrated to afford W391 Precursor (0.8 g, 2.444 mmol, 59.9% yield) as a yellow solid. $^1H$ NMR (DMSO-$d_6$) δ: 3.92 (s, 3H), 7.06 (m, 1H), 7.97 (m, 1H), 8.45 (m, 1H), 8.47 (m, 1H), 8.90 (m, 1H), 9.00 (s, 1H).

Preparation of W388 Precursor

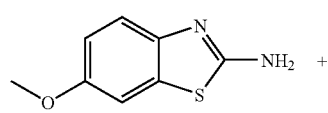

General experimental procedure for cyclization was followed. Reaction was performed on a 0.1 g scale. Isolated 0.08 g (57%) of W388 precursor as a brown solid. $^1H$ NMR (400 MHz, $CDCl_3$) δ: 9.06 (dd, J=2.0, 0.4 Hz, 1H), 8.51 (dd, J=8.8, 2.4 Hz, 1H), 8.33 (dd, J=8.8, 0.8 Hz, 1H), 8.16 (s, 1H), 7.61 (d, J=8.8 Hz, 1H), 7.08 (dd, J=8.8, 2.4 Hz, 1H), 3.91 (s, 3H).

Preparation of W329 Precursor

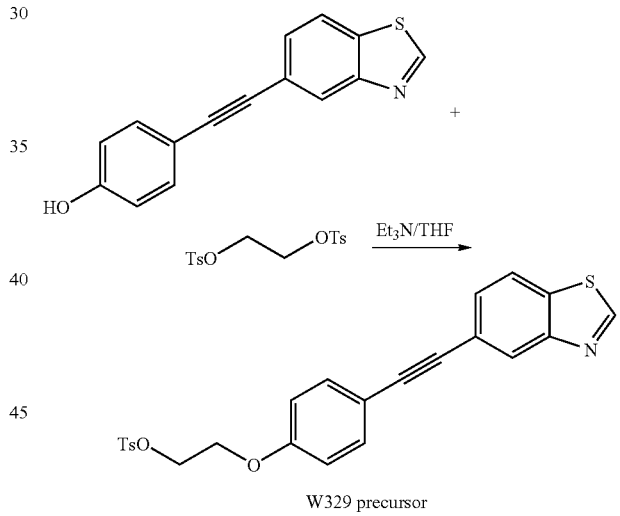

W329 precursor

General experimental procedure for alkylation was followed as described for the preparation of W355 precursor. Reaction was performed on a 0.1 g scale. Isolated 0.066 g (46%) of W329 precursor as a solid. $^1H$ NMR (400 MHz, $CDCl_3$) δ: 9.04 (s, 1H), 8.28 (d, J=1.2 Hz, 1H), 7.93 (d, J=8.0 Hz, 1H), 7.82 (d, J=8.4 Hz, 2H), 7.58 (dd, J=8.4, 1.6 Hz, 1H), 7.48 (d, J=9.2 Hz, 2H), 7.35 (d, J=8.0 Hz, 2H), 6.78 (d, J=8.8 Hz, 2H), 4.39 (t, J=4.4 Hz, 2H), 4.18 (t, J=4.8 Hz, 2H), 2.46 (s, 3H).

Description of Radiolabeling Manufacturing Process and Process Controls

A process flow diagram for the preparation of [F-18]W372 as the example of radio labeling is illustrated in FIG. 1. A general discussion of each step follows the flow chart.

General Process for the Production of [F-18] Fluoride Ion

Fluorine-18 [F-18] is produced by proton bombardment of the stable isotope, oxygen-18 (O-18) in water.

For bombardment, the chemical form of the enriched O-18 is [O-18]$H_2O$. The [F-18]Fluorine produced is aqueous [F-18]fluoride ion. The target water is loaded into an approximately 1-2 mL target and pressurized to approximately 350 psi. The tantalum target body is outfitted with a high strength, durable metal foil. The foil is an alloy referred to as, "Havar®". The major components of Havar® are cobalt, nickel, chromium, and iron. This thin Havar® foil window permits entry of the protons, yet is sufficiently durable to withstand the pressurized water and proton irradiation. The facility utilizes two Siemens RDS-111 Eclipse cyclotron that produces 11 MeV protons with a 40-60 microamp beam current. Either one or two targets may be irradiated to make sufficient [F-18]Fluoride to prepare [F-18]W372 needed for clinical use. The choice to use one target or two targets is determined by the quantity of [F-18]W372 needed for clinical use. Both targets are made of tantalum metal and are used exclusively for the production of F-18.

After proton bombardment, the [O-18]$H_2O$ containing the [F-18]fluoride ion is transferred to a shielded enclosure ("hot cell"). The aqueous [F-18]Fluoride is then separated from the [O-18]$H_2O$.

Extraction of [F-18]Fluoride and Conversion to Anhydrous Form

Aqueous [F-18]Fluoride ion produced in the cyclotron target, as described in the preceding Section, is passed through an anion exchange resin cartridge. The [O-18]$H_2O$ readily passes through the anion exchange resin while [F-18]fluoride is retained. The [F-18]fluoride is eluted from the column using a solution of potassium carbonate (3 mg) in water (0.4 mL) and is collected in a reaction vessel. Kryptofix® 222 (20 mg) dissolved in acetonitrile (1 mL) is added to the aqueous [F-18]fluoride mixture in the reaction vessel. The Kryptofix sequesters the potassium ions preventing the formation of strong $K^+/F$ ion-pairs. This increases the chemical reactivity of the [F-18]fluoride ions.

The mixture is dried by heating between 70-115° C. under a stream of inert gas and/or reduced pressure (250 mbar) and additional aliquots of acetonitrile may added to insure the fluoride mixture is completely dry. This evaporation step removes the water and converts the [F-18] to an anhydrous form, which is much more reactive than aqueous [F-18]fluoride.

Reaction of Anhydrous [F-18]Fluoride with W372 Precursor

A solution of the nitro precursor, (2.0 mg±1.5 mg, 11.7-1.7 µmol) dissolved in anhydrous DMSO (1.0±0.5 mL) is added to the reaction vessel containing the anhydrous [F-18]Fluoride. The vessel is heated to approximately 150±10° C. for 10±5 minutes to induce displacement of the aromatic nitro leaving group by [F-18]fluoride as illustrated in following scheme.

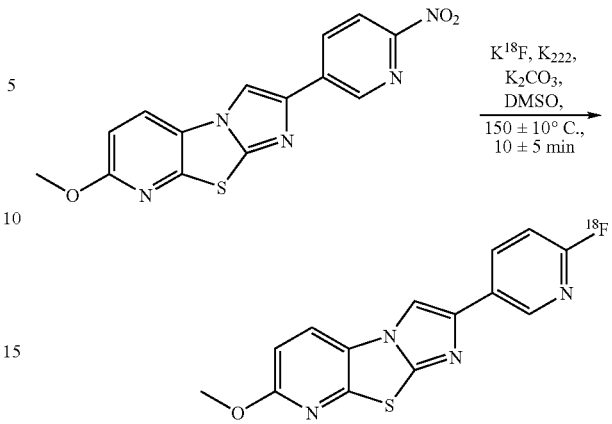

Anhydrous [F-18]Fluoride Displacement Reaction with W372 Precursor

HPLC Purification of [F-18]W372

The reaction mixture containing crude [F-18]W372 is cooled to 37° C. and passed through an $Al_2O_3$ cartridge followed by passing $H_2O$ (3.5±0.5 mL) through the same $Al_2O_3$ cartridge. The solution is then transferred to the HPLC sample loop (4.0 mL) and purified via chromatographic separation using a semi-preparative HPLC column (Either ACE C18 Pyramid, 7µ, 250×10 mm, Phenomenex Luna, C18, 5µ, 10×250 mm or Phenomenex Synergi Hydro-RP C18, 250×10 mm, using an isocratic mobile phase system, 5.0 mL/min, however lower flow rates may be used if there is a high backpressure, or the system may start at a lower flow rate and then increase to the maximum flow rate). The column uses an isocratic solvent system of 40% MeCN: 60% $H_2O$ containing 0.85 mL of 12N HCl per 1000 mL of water. The column effluent is monitored using UV (254 nm) and radiometric detectors connected in series. The purified [F-18]W372 is collected from the column at the retention time window determined for the W372 reference standard which coincides with the time that the radiometric detectors begin showing the main peak. The retention time of the [F-18]W372 in this system is approximately 30±5 minutes.

Formulation, Sterile Filtration and Aseptic Filling of Purified [F-18]W372

The purified [F-18]W372 fraction eluted from the HPLC purification column is diluted with water (50±10 mL) containing 250±25 mg of ascorbic acid and captured onto a C18 SepPak cartridge. The C18 SepPak cartridge is washed with water (10 mL) followed by elution of the product with 0.5-0.9 mL of EtOH. The sample is then diluted with sterile water (9.2-9.5 mL of water) containing 15±5 mg/mL of ascorbic acid to afford a final formulation of [F-18]W372 in a maximum of 10% EtOH:water. The solution is then processed through a 0.22 µm sterile filter into the preloaded collection vial.

The following compounds were also radiolabelled using the general procedures described above starting from 1.0 Ci of [F-18].

TABLE 1

Radiolabeling results of aromatic nitro and chloro compounds

| Cmpd # | Precursor | [F-18] labeled product | Yield (mCi) | Radio-chemical purity | Specific activity* | HPLC condition |
|---|---|---|---|---|---|---|
| W388 | (structure with NO₂) | (structure with ¹⁸F) | 500 | >99% | ND | Gradient: 5% MeCN (+0.05% v/v TFA): 95% water (+0.05% v/v TFA) – 95% MeCN (+0.05% v/v TFA): 5% water (+0.05% v/v TFA) over 40 min |
| W391 | (structure with O₂N) | (structure with ¹⁸F) | 350 | >99% | ND | Gradient: 5% MeCN (+0.05% v/v TFA): 95% water (+0.05% v/v TFA) – 95% MeCN (+0.05% v/v TFA): 5% water (+0.05% v/v TFA) over 40 min |
| W392 | (structure with Cl) | (structure with ¹⁸F) | 291 | >99% | ND | Gradient: 5% MeCN (+0.05% v/v TFA): 95% water (+0.05% v/v TFA) – 95% MeCN (+0.05% v/v TFA): 5% water (+0.05% v/v TFA) over 40 min |

TABLE 1-continued

Radiolabeling results of aromatic nitro and chloro compounds

| Cmpd # | Precursor | [F-18] labeled product | Yield (mCi) | Radio-chemical purity | Specific activity* | HPLC condition |
| --- | --- | --- | --- | --- | --- | --- |
| W332 | (structure with MeO, NO$_2$) | (structure with MeO, $^{18}$F) | 1.05 | >99% | ND | Gradient: 5% MeCN (+0.05% v/v TFA): 95% water (+0.05% v/v TFA) – 95% MeCN (+0.05% v/v TFA): 5% water (+0.05% v/v TFA) over 40 min |

*ND: not determined

Procedures for the Preparation of Other F-18 Radiolabeled Compounds

General Procedure for [18F] Labeling of Aliphatic Tosylate

[18F]Fluoride was prepared using $K_2CO_3$ and Kryptofix-2.2.2 according to the general procedure described above. After cooling, a solution of tosylate precursor (4±1 mg) in anhydrous DMSO (0.5-0.9 mL) was added to the residue of "dry" reactive [$^{18}$F]-fluoride ion in the reaction vessel of the Explora RN synthesis module and the reaction was heated at 115±5° C. for 10 min. The reaction was then cooled to room temperature, and purified by semi-preparative HPLC (column: 10.0 mm×250.0 mm Phenomenex ACE-C18, mobile phase: 5% MeCN (+0.05% v/v TFA): 95% water (+0.05% v/v TFA)-95% MeCN (+0.05% v/v TFA): 5% water (+0.05% v/v TFA) over 40 min.

The following compounds were labeled with the general procedures described above starting from 1.0 Ci of [F-18].

times with 20% ethanol/PBS at room temperature, count the radioactivity, and measure the $K_D$ value.

Figure 2:
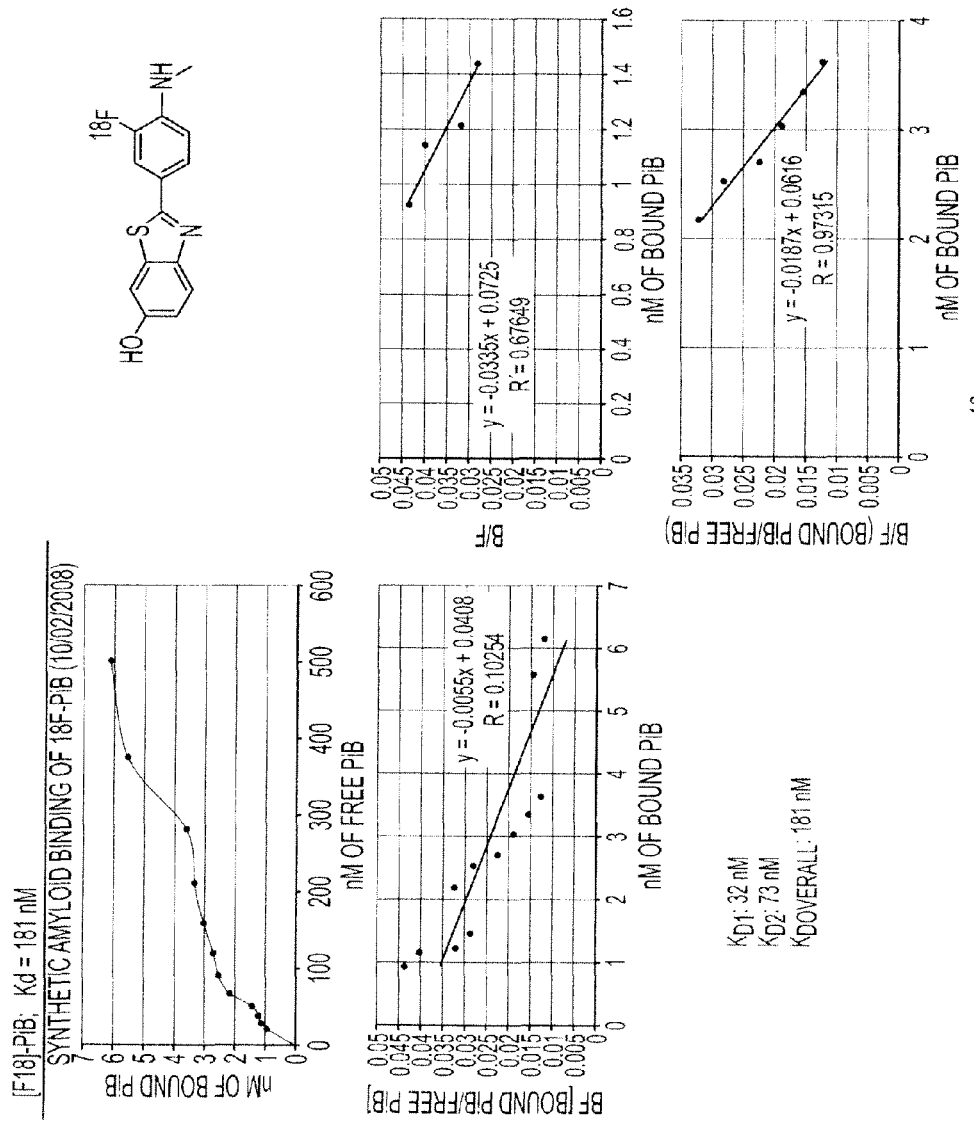
FIG. 2 shows the amyloid fibril binding results for 18F-PiB.
Figure 3:
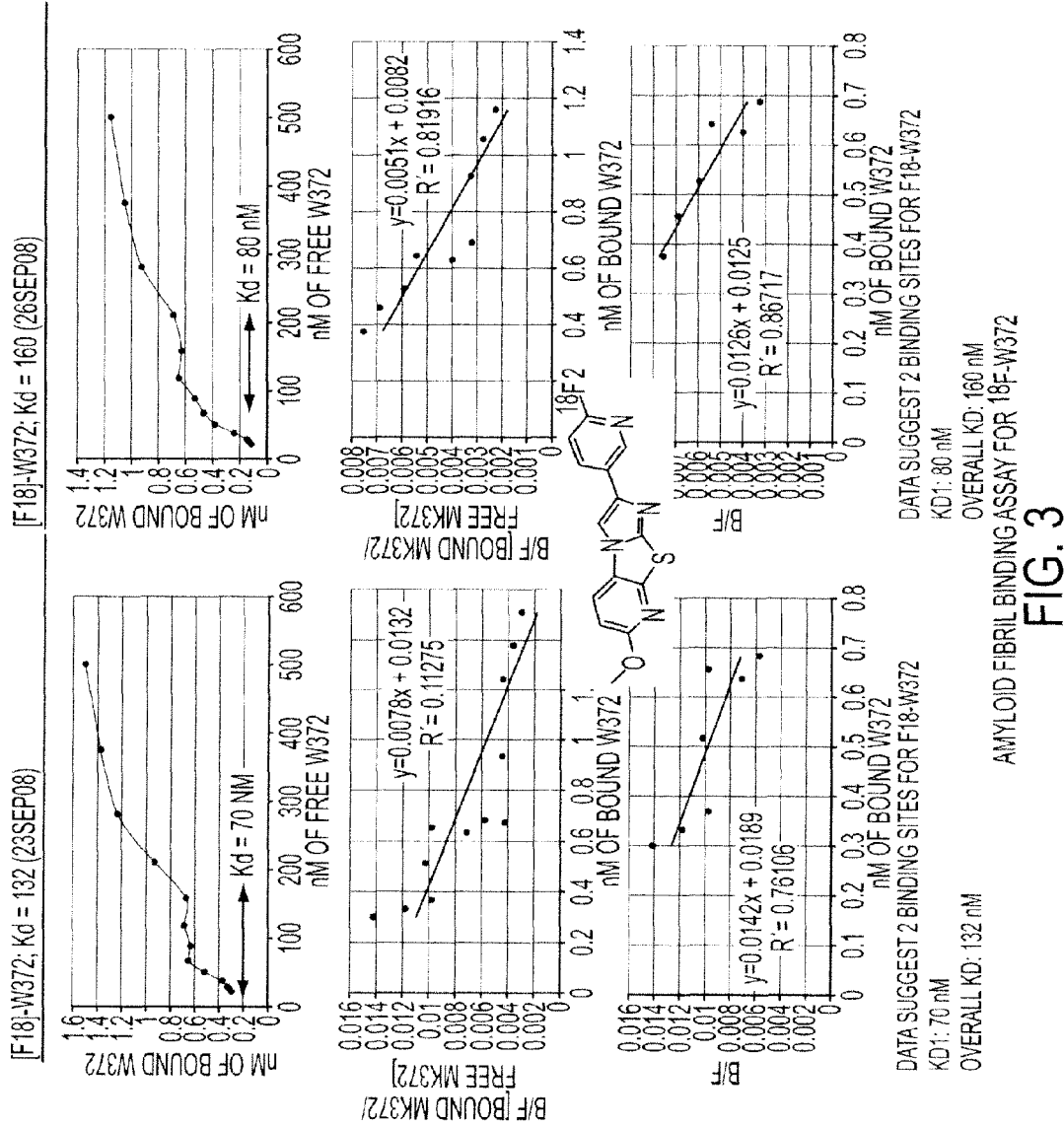
FIG. 3 shows the amyloid fibril binding results for 18F-W372.

Amyloid fibril binding results are shown in FIG. 2 for the known tracer 18F-PiB. Amyloid fibril binding results are shown in FIG. 3 for 18F-W372. The result shows that 18F-W372 has lower $K_D$ value compared with the known compound 18F-PiB, suggesting 18F-W372 has higher binding affinity with synthetic amyloid fibril.

Human Brain Slice Competition Assay Using Autoradiography

Summary of compounds that compete off tracers that bind to AD plaques and fibrils: The following table discloses molecules that successfully compete off a reporter that binds to amyloid plaques and fibrils. Briefly, 5 micron thick human brain slices from regions of the brain bearing high amyloid plaque and fibril burden were incubated with approximately 20 uCi of a radiolabeled tracer in 2.5%:2.5%:95% DMSO:

TABLE 2

Radiolabeling results of aliphatic tosylates

| Cmpd # | Precursor | [F-18] labeled product | Yield (mCi) | Radio-chemical purity | Specific activity* |
| --- | --- | --- | --- | --- | --- |
| W329 | (TsO-ethyl-O-phenyl-alkyne-benzothiazole structure) | ($^{18}$F-ethyl-O-phenyl-alkyne-benzothiazole structure) | 36 | >99% | ND |
| W355 | (MeO-pyridoimidazothiazole-phenyl-O-ethyl-OTs structure) | (MeO-pyridoimidazothiazole-phenyl-O-ethyl-$^{18}$F structure) | 345 | >99% | ND |

*ND: not determined.

Amyloid Fibril (Synthetic A-Beta42) Binding Assay

Incubation of various concentration of [F18]-compound (starting with 200 nM cold compound and 100 µCi of F18-compound) with or without 10 µM of synthetic beta-Amyloid-42 for 90 min Filter through G/F glass fiber, wash filter 2

EtOH:PBS in the presence of blocker (2.5 and 0.25 uM total concentration) or absence of blocker (control). The slices were incubated at rt for 90 min. The slices were then quickly washed in PBS, followed by 70% EtOH:PBS for 2 min, then 30% EtOH:PBS for 2 min and then quickly washed with PBS.

The slices were dried for 30 min and then exposed on autoradiographic film for 20 min. The brain slices were then removed from the slide and the radioactivity counted in a gamma counter. The percent dose remaining, relative to a control with no blocker, at 0.25 uM is represented in the "_max low dose" column. The percent dose remaining, relative to a control with no blocker, at 2.5 uM is represented in the "_max high dose" column. The lower the number, the more effective the compounds displaced the tracer.

TABLE 3

Autoradiography Competition Assay Results.

| Structure | Mol Weight | _max low dose | _max high dose | CMPD ID |
|---|---|---|---|---|
| 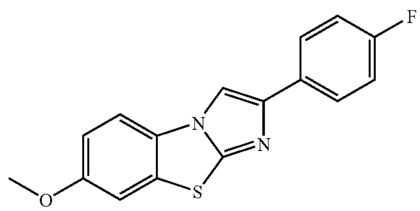 | 298.335 | — | 7.85 | W119 |
| 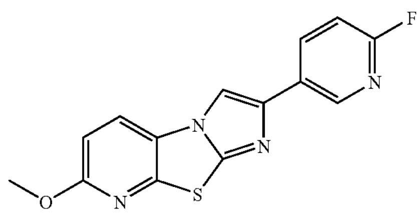 | 300.311 | — | — | W372 |
| 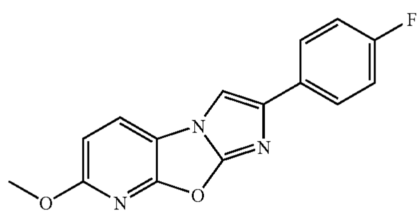 | 283.257 | — | — | W386 |
| 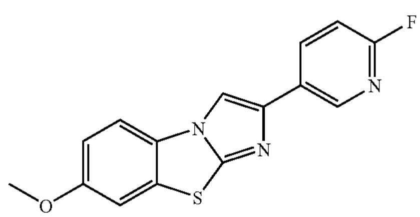 [SMILES: COc1ccc2c(c1)sc1nc(-c3ccc(F)nc3)cn12] | 299.323 | — | — | W388 |
| 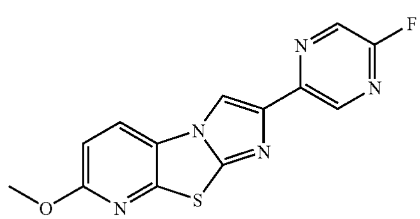 [SMILES: COc1ccc2c(n1)sc1nc(-c3cnc(F)cn3)cn12] | 301.299 | — | — | W392 |
| 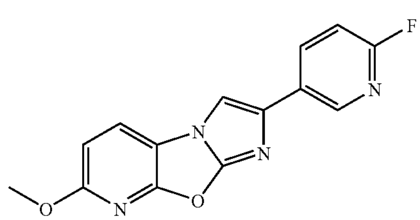 [SMILES: COc1ccc2c(n1)oc1nc(-c3ccc(F)nc3)cn12] | 284.245 | — | — | W393 |

TABLE 3-continued

Autoradiography Competition Assay Results.

| Structure | Mol Weight | _max low dose | _max high dose | CMPD ID |
|---|---|---|---|---|
| 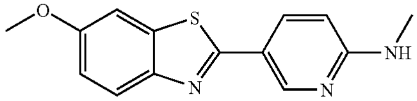 | 271.338 | — | 8.05 | W184 |
| | 240.323 | — | 9.53 | W189 |
| 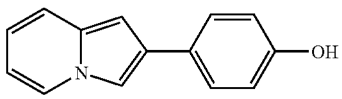 | 209.243 | 35.38 | 3.50 | W103 |
| 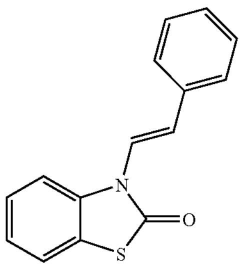 [SMILES: O=c1sc2ccccc2n1/C=C/c1ccccc1] | 253.319 | 29.58 | 7.65 | W88 |
| 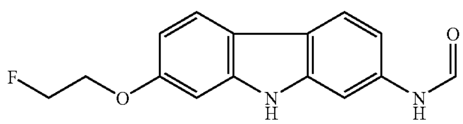 [SMILES: O=CNc1ccc2c(c1)[nH]c1cc(OCCF)ccc12] | 272.274 | 59.97 | 12.29 | CB12 |
| 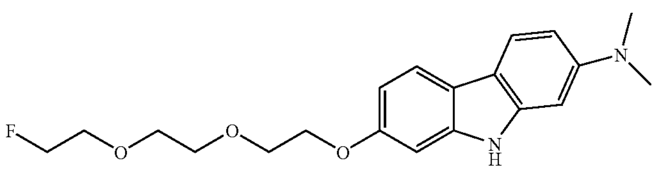 [SMILES: CN(C)c1ccc2c(c1)[nH]c1cc(OCCOCCOCCF)ccc12] | 360.423 | 42.64 | 15.14 | CB7 |
| 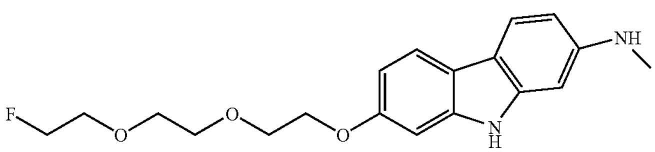 [SMILES: CNc1ccc2c(c1)[nH]c1cc(OCCOCCOCCF)ccc12] | 346.396 | 54.17 | 16.96 | CB4 |
| 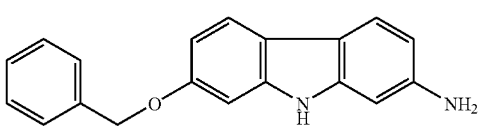 [SMILES: Nc1ccc2c(c1)[nH]c1cc(OCc3ccccc3)ccc12] | 288.343 | 49.95 | 17.60 | W42 |
| | 240.323 | 33.66 | 17.80 | BTA1 |
| 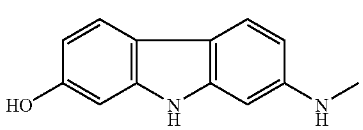 [SMILES: CNc1ccc2c(c1)[nH]c1cc(O)ccc12] | 212.247 | 47.08 | 18.59 | GC3125 |

TABLE 3-continued
Autoradiography Competition Assay Results.
| Structure | Mol Weight | _max low dose | _max high dose | CMPD ID |
|---|---|---|---|---|
| 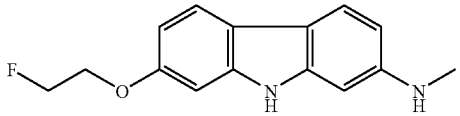 [SMILES: CNc1ccc2c(c1)[nH]c1cc(OCCF)ccc12] | 258.291 | 46.04 | 21.03 | W106 |
| 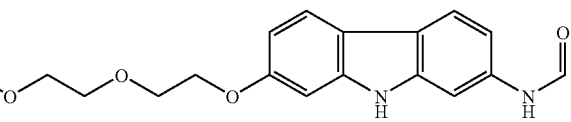 | 360.379 | 69.29 | 21.60 | CB10 |
| 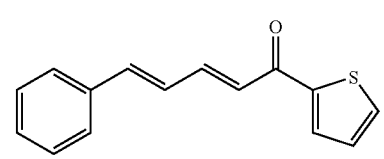 [SMILES: O=C(/C=C/C=C/c1ccccc1)c1cccs1] | 240.32 | 55.16 | 23.51 | W24 |
| 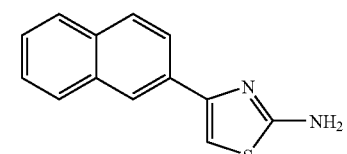 | 226.297 | 69.20 | 27.86 | w18 |
| 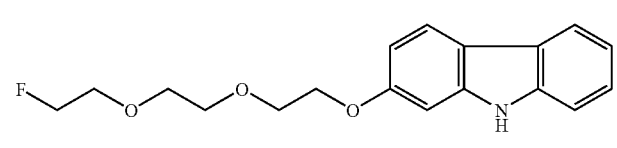 [SMILES: FCCOCCOCCOc1ccc2c(c1)[nH]c1ccccc12] | 317.355 | 69.78 | 29.53 | CB3 |
| 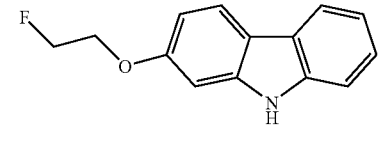 [SMILES: FCCOc1ccc2c(c1)[nH]c1ccccc12] | 229.25 | 74.86 | 30.34 | CB1 |
| 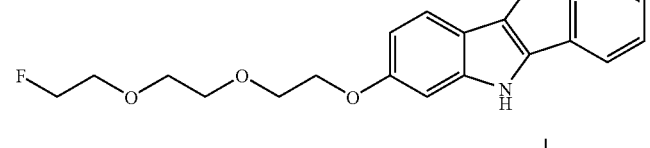 | 373.441 | 81.06 | 30.70 | DHK4-57 |
| 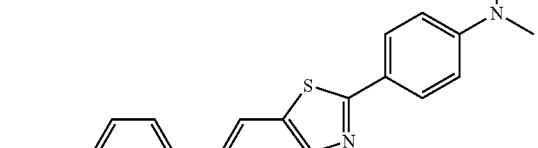 | 322.424 | 69.79 | 31.02 | UG-4-69 |
| 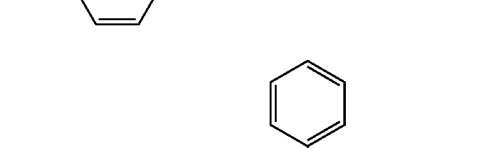 | 254.238 | 68.43 | 34.37 | 73 |

TABLE 3-continued

Autoradiography Competition Assay Results.

| Structure | Mol Weight | _max low dose | _max high dose | CMPD ID |
|---|---|---|---|---|
| 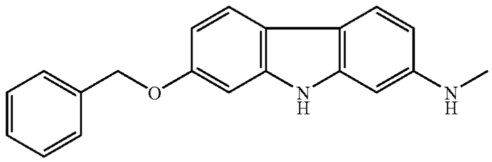 [SMILES: CNc1ccc2c(c1)[nH]c1cc(OCc3ccccc3)ccc12] | 302.37 | 48.35 | 34.77 | W104 |
| 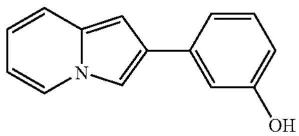 [SMILES: Oc1cccc(-c2cc3ccccn3c2)c1] | 209.243 | 66.38 | 35.16 | W73 |
| 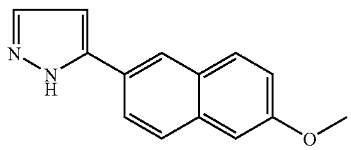 [SMILES: COc1ccc2cc(-c3ccn[nH]3)ccc2c1] | 224.258 | 70.48 | 35.38 | W1 |
| 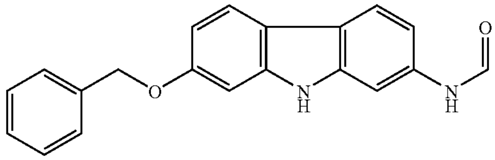 [SMILES: O=CNc1ccc2c(c1)[nH]c1cc(OCc3ccccc3)ccc12] | 316.353 | 42.09 | 36.55 | WZ01169 |
| 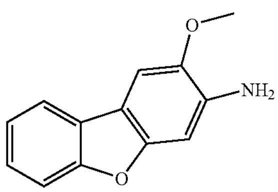 [SMILES: COc1cc2c(cc1N)oc1ccccc12] | 213.232 | 82.52 | 36.72 | W33 |
| 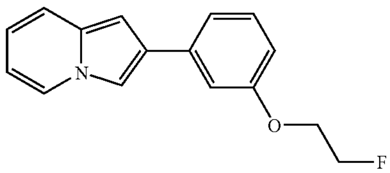 [SMILES: FCCOc1cccc(-c2cc3ccccn3c2)c1] | 255.287 | 97.22 | 40.32 | W84 |
| 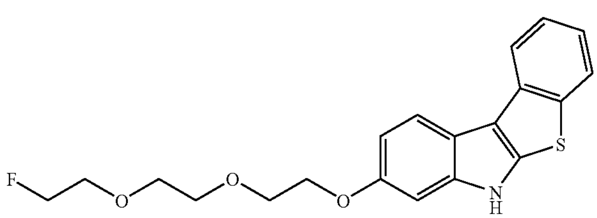 [SMILES: FCCOCCOCCOc1ccc2c(c1)[nH]c1sc3ccccc3c12] | 373.441 | 103.76 | 40.74 | W94 |
| 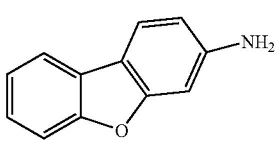 [SMILES: Nc1ccc2c(c1)oc1ccccc12] | 183.206 | 95.11 | 43.52 | W20 |

TABLE 3-continued

Autoradiography Competition Assay Results.

| Structure | Mol Weight | _max low dose | _max high dose | CMPD ID |
|---|---|---|---|---|
| 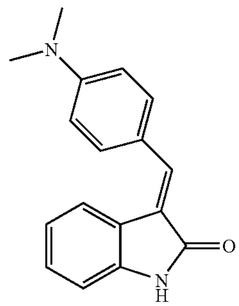 [SMILES: CN(C)c1ccc(/C=C2/C(=O)Nc3ccccc32)cc1] | 264.322 | 105.11 | 45.98 | W12 |
| 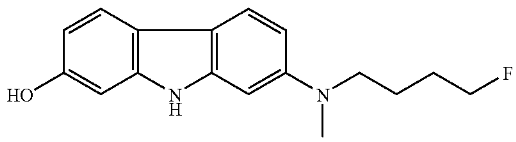 [SMILES: CN(CCCCF)c1ccc2c(c1)[nH]c1cc(O)ccc12] | 286.344 | 114.19 | 49.02 | CB14 |
| 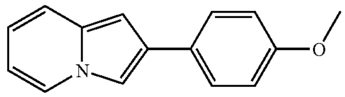 | 223.27 | 81.86 | 51.90 | W82 |
| 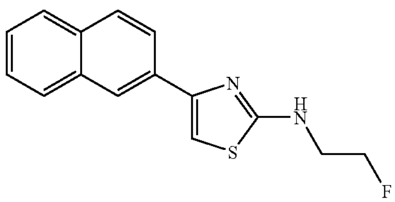 [SMILES: FCCNc1nc(-c2ccc3ccccc3c2)cs1] | 272.341 | 98.06 | 52.00 | TZ001 |
| 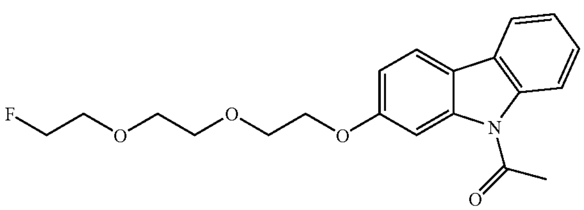 [SMILES: CC(=O)n1c2ccccc2c2ccc(OCCOCCOCCF)cc21] | 359.391 | 91.06 | 62.03 | CB17 |
| 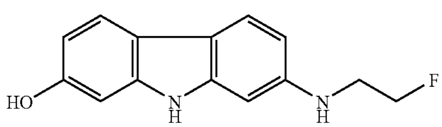 [SMILES: Oc1ccc2c(c1)[nH]c1cc(NCCF)ccc12] | 244.264 | 99.49 | 63.32 | w78 |
| 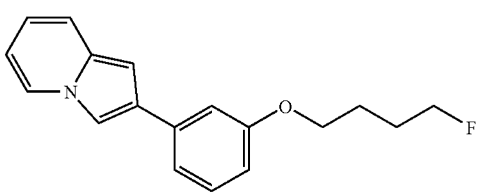 [SMILES: FCCCCOc1cccc(-c2cc3ccccn3c2)c1] | 283.34 | 98.13 | 67.27 | IN3 |
| 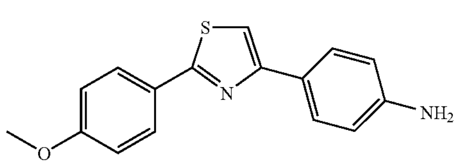 [SMILES: COc1ccc(-c2nc(-c3ccc(N)cc3)cs2)cc1] | 282.36 | 103.16 | 68.37 | 264 |

TABLE 3-continued
Autoradiography Competition Assay Results.
| Structure | Mol Weight | _max low dose | _max high dose | CMPD ID |
|---|---|---|---|---|
| 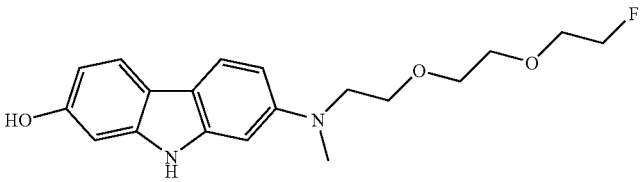 [SMILES: CN(CCOCCOCCF)c1ccc2c(c1)[nH]c1cc(O)ccc12] | 346.396 | 81.33 | 73.62 | W101 |
| 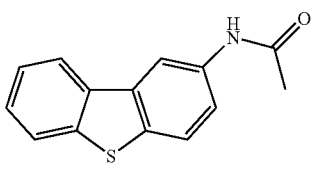 [SMILES: CC(=O)Nc1ccc2sc3ccccc3c2c1] | 241.308 | 84.84 | 73.74 | W34 |
| 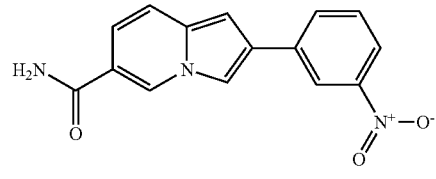 [SMILES: NC(=O)c1ccc2cc(-c3cccc([N+](=O)[O-])c3)cn2c1] | 281.266 | 97.53 | 75.02 | W100 |
| 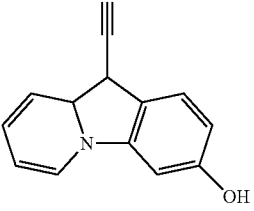 | 210.231 | 87.14 | 76.06 | W99 |
| 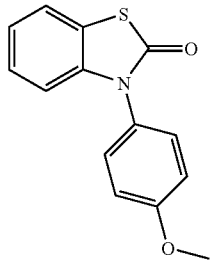 [SMILES: COc1ccc(-n2c(=O)sc3ccccc32)cc1] | 257.308 | 81.29 | 79.87 | UG470 |
| 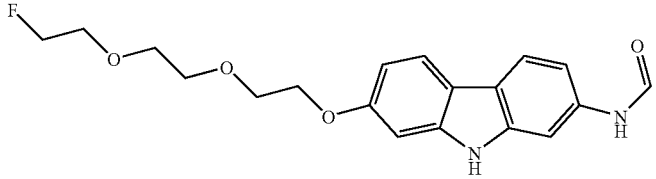 [SMILES: O=CNc1ccc2c(c1)[nH]c1cc(OCCOCCOCCF)ccc12] | 360.379 | 93.92 | 80.06 | CB9 |
| 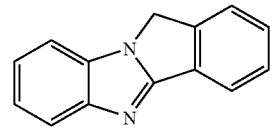 [SMILES: c1ccc2c(c1)Cn1c-2nc2ccccc21] | 206.243 | 96.06 | 81.94 | W81 |

TABLE 3-continued

Autoradiography Competition Assay Results.

| Structure | Mol Weight | _max low dose | _max high dose | CMPD ID |
|---|---|---|---|---|
| 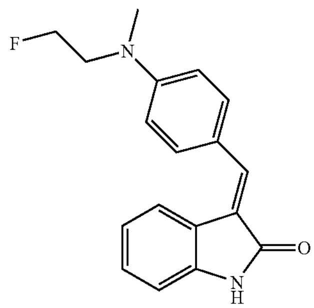 [SMILES: CN(CCF)c1ccc(/C=C2/C(=O)Nc3ccccc32)cc1] | 296.339 | 68.22 | 82.78 | OX-2 |
| 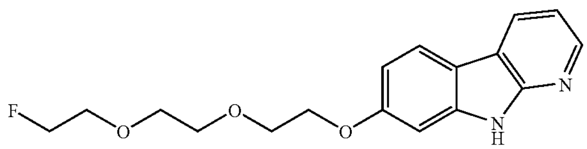 [SMILES: FCCOCCOCCOc1ccc2c(c1)[nH]c1ncccc12] | 318.343 | 88.82 | 85.78 | DHK4-58 |
| 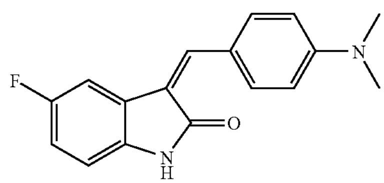 [SMILES: CN(C)c1ccc(/C=C2\C(=O)Nc3ccc(F)cc32)cc1] | 282.312 | 104.61 | 88.00 | W71 |
| 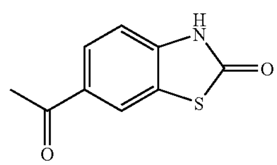 | 193.222 | 112.87 | 88.58 | W92 |
| 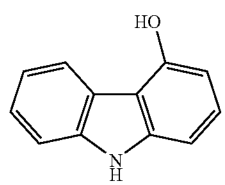 [SMILES: Oc1cccc2[nH]c3ccccc3c12] | 183.206 | 100.46 | 89.32 | W19 |
| 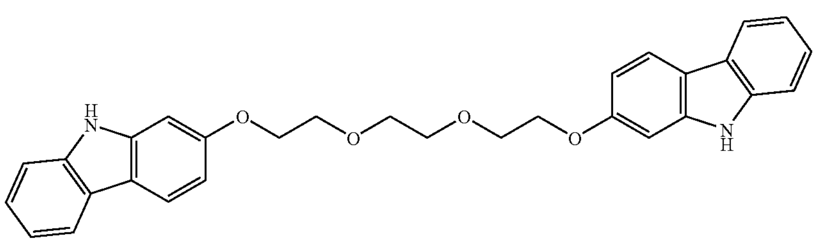 [SMILES: c1ccc2c(c1)[nH]c1cc(OCCOCCOCCOc3ccc4c(c3)[nH]c3ccccc34)ccc12] | 480.554 | 88.20 | 89.53 | W70 |
| 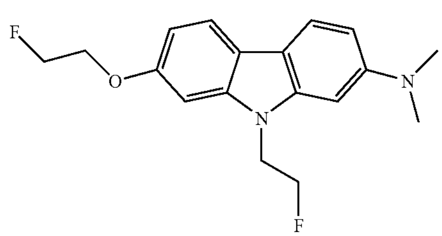 [SMILES: CN(C)c1ccc2c3ccc(OCCF)cc3n(CCF)c2c1] | 318.361 | 91.92 | 92.00 | W102 |

TABLE 3-continued

Autoradiography Competition Assay Results.

| Structure | Mol Weight | _max low dose | _max high dose | CMPD ID |
|---|---|---|---|---|
| 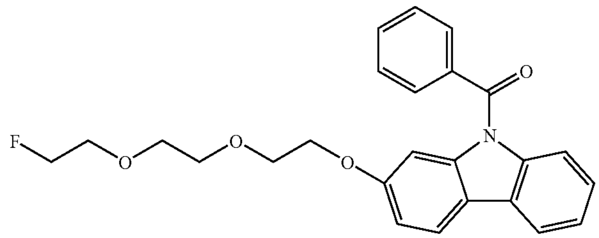 [SMILES: O=C(c1ccccc1)n1c2ccccc2c2ccc(OCCOCCOCCF)cc21] | 421.461 | 104.81 | 94.00 | CB21 |
| 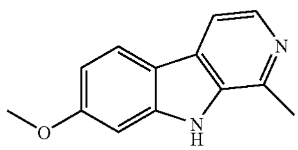 | 212.247 | 105.49 | 94.16 | W65 |
| 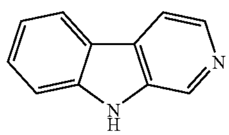 [SMILES: c1ccc2c(c1)[nH]c1cnccc12] | 168.195 | 101.83 | 94.93 | W67 |
| 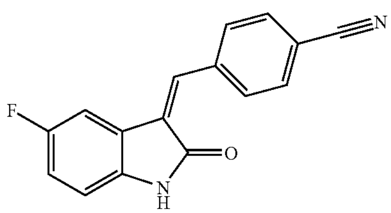 [SMILES: N#Cc1ccc(/C=C2\C(=O)Nc3ccc(F)cc32)cc1] | 264.254 | 92.77 | 96.90 | W79 |
| 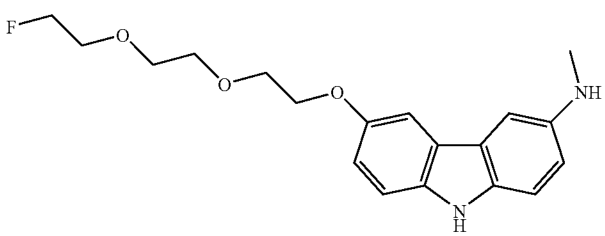 [SMILES: CNc1ccc2[nH]c3ccc(OCCOCCOCCF)cc3c2c1] | 346.396 | 95.89 | 108.49 | CB8 |
| 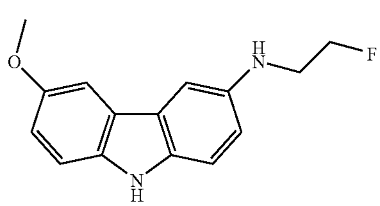 [SMILES: COc1ccc2[nH]c3ccc(NCCF)cc3c2c1] | 258.291 | 108.14 | 110.57 | CB13 |
| 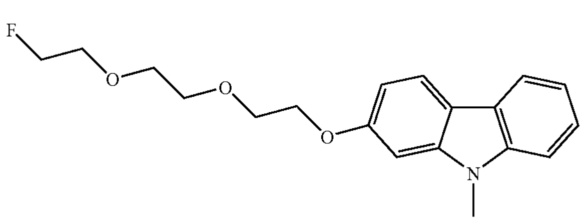 [SMILES: Cn1c2ccccc2c2ccc(OCCOCCOCCF)cc21] | 331.381 | 111.02 | 113.69 | CB6 |

TABLE 3-continued
Autoradiography Competition Assay Results.
| Structure | Mol Weight | _max low dose | _max high dose | CMPD ID |
|---|---|---|---|---|
| 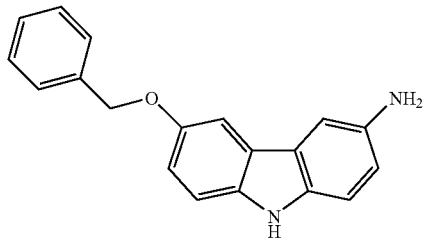 [SMILES: Nc1ccc2[nH]c3ccc(OCc4ccccc4)cc3c2c1] | 288.343 | 105.87 | 115.14 | W60 |
| 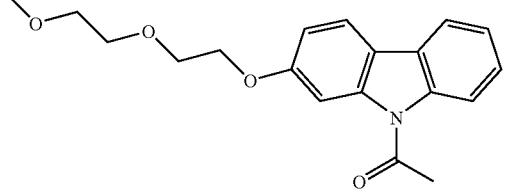 | 359.391 | — | — | CB3 acetamide |
| 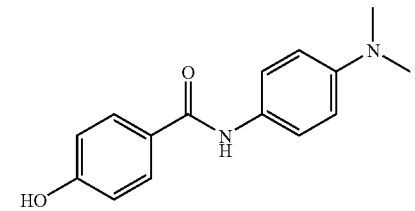 [SMILES: CN(C)c1ccc(NC(=O)c2ccc(O)cc2)cc1] | 256.3 | — | — | W109 |
| 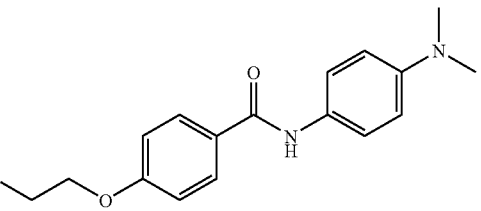 | 302.343 | — | — | W112 |
| 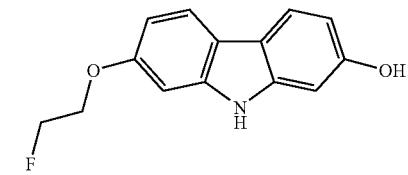 | 245.249 | — | — | W114 |
| 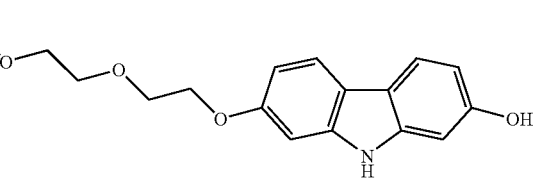 | 333.354 | — | — | W115 |
| 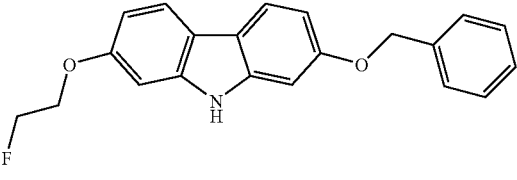 [SMILES: FCCOc1ccc2c(c1)[nH]c1cc(OCc3ccccc3)ccc12] | 335.372 | — | — | W116 |

TABLE 3-continued

Autoradiography Competition Assay Results.

| Structure | Mol Weight | _max low dose | _max high dose | CMPD ID |
|---|---|---|---|---|
| 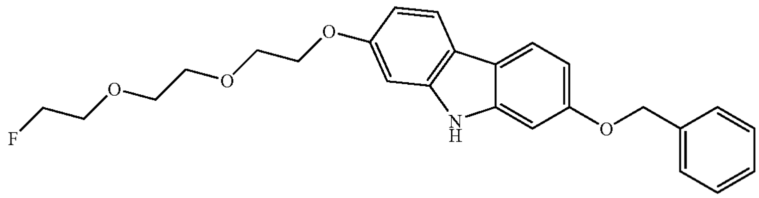 [SMILES: FCCOCCOCCOc1ccc2c(c1)[nH]c1cc(OCc3ccccc3)ccc12] | 423.477 | — | — | W117 |
| 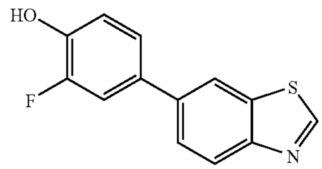 [SMILES: Oc1ccc(-c2ccc3ncsc3c2)cc1F] | 245.272 | — | — | W121 |
| 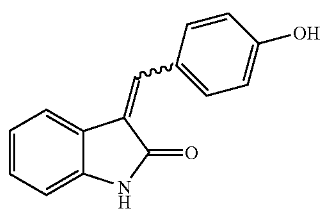 [SMILES: O=C1Nc2ccccc2C1=Cc1ccc(O)cc1] | 237.253 | — | — | W122 |
| 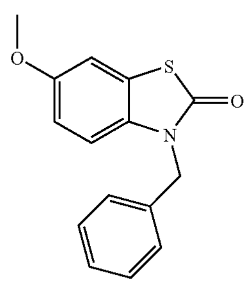 [SMILES: COc1ccc2c(c1)sc(=O)n2Cc1ccccc1] | 271.334 | — | — | W124 |
| 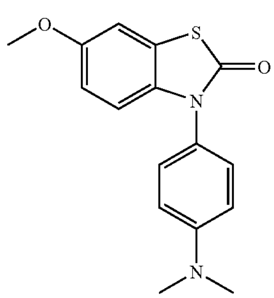 [SMILES: COc1ccc2c(c1)sc(=O)n2-c1ccc(N(C)C)cc1] | 300.375 | — | — | W125 |
| 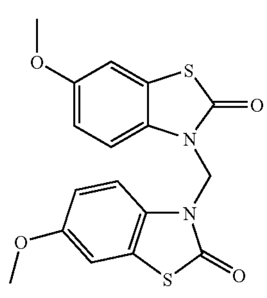 [SMILES: COc1ccc2c(c1)sc(=O)n2Cn1c(=O)sc2cc(OC)ccc21] | 374.434 | — | — | W126 |

TABLE 3-continued

Autoradiography Competition Assay Results.

| Structure | Mol Weight | _max low dose | _max high dose | CMPD ID |
|---|---|---|---|---|
| (structure) | 328.342 | — | — | W129 |
| (structure) | 284.333 | — | — | W136 |
| (structure) | 345.388 | — | — | W137 |

Comparison of Specific Binding of [18F]-W372 with [18F]-PiB

The 5 micron thick human brain slices from regions of the brain bearing high amyloid plaque and fibril burden were incubated with approximately 20 μCi of a known radiolabeled tracer (such as 18F-PiB) in 2.5%:2.5%:95% DMSO:EtOH:PBS in the presence of blocker (concentration from 0.01 μM to 10 μM) or absence of blocker (control). The slices were incubated at room temperature for 90 min. The slices were then quickly washed in PBS, followed by 70% EtOH:PBS for 2 min, then 30% EtOH:PBS for 2 min and then quickly washed with PBS. The slices were dried for 30 min and then exposed on autoradiographic film for 20 min. The brain slices were then removed from the slide and the radioactivity counted in a gamma counter. The percentage of blocking versus the concentrations of blocker was then plotted, and $IC_{50}$ was calculated based on the curve.

Figure 4:
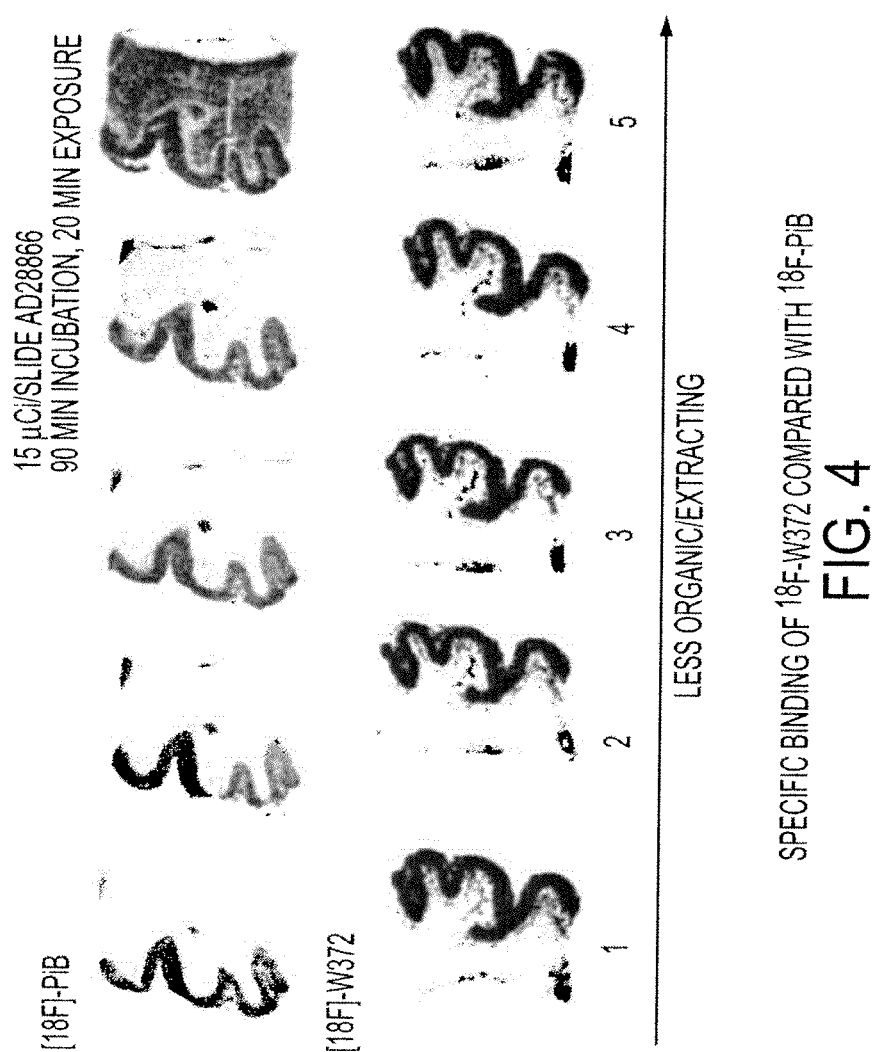
FIG. 4 compares the specific binding of 18F-W372 with 18F-PiB.

FIG. 4 details the specific binding of 18F-W372 compared with the known compound 18F-PiB.

| Washing Conditions | | | | | | | | | |
|---|---|---|---|---|---|---|---|---|---|
| 1) | | 2) | | 3) | | 4) | | 5) | |
| 1X PBS | 1 min | 1X PBS | 1 min | 1X PBS | 1 min | 1X PBS | 1 min | 1X PBS | 1 min |
| 70% EtOH | 2 min | 50% EtOH | 2 min | 50% EtOH | 2 min | 40% EtOH | 2 min | 30% EtOH | 2 min |

-continued

| Washing Conditions | | | | | | | | | |
|---|---|---|---|---|---|---|---|---|---|
| 1) | | 2) | | 3) | | 4) | | 5) | |
| 30% EtOH | 1 min | 50% EtOH | 1 min | 30% EtOH | 1 min | 30% EtOH | 1 min | 20% EtOH | 1 min |
| 1X PBS | 1 min | 1X PBS | 1 min | 1X PBS | 1 min | 1X PBS | 1 min | 1X PBS | 1 min |

A study was conducted to examine the grey to white matter binding ratios for 2 different tracers: 18F-W372 and 18F-PiB. After the human brain slices from AD patients were incubated with a given tracer for 1 hr, the slices were washed with various EtOH:water solutions in an attempt to optimize the grey to white matter ratios. The results were surprising and unexpected in view of previous work performed by other researchers. 18F-W372 displayed excellent grey to white matter binding ratios that are far superior to the result taken from 18F-PiB. More specifically, the white matter binding of 18F-PiB is several shades darker than 18F-W372's white matter binding, indicating low non-specific binding of 18F-W372. The washing data strongly suggests that the 18F-W372 is a viable tracer for imaging AD-related targets due to its unique binding and washout properties. These favorable and unique results also suggest that 18F-W372 would have a more favorable brain washout in living systems, leading to more specific uptake and lowered non-specific binding, leading to a clear advantage over 18F-PiB imaging. In addition, 18F-W372 gives intense, specific stains with excellent white matter wash out, indicating 18F-W372 has lower non-specific binding than 18F-PiB.

Figure 5A:
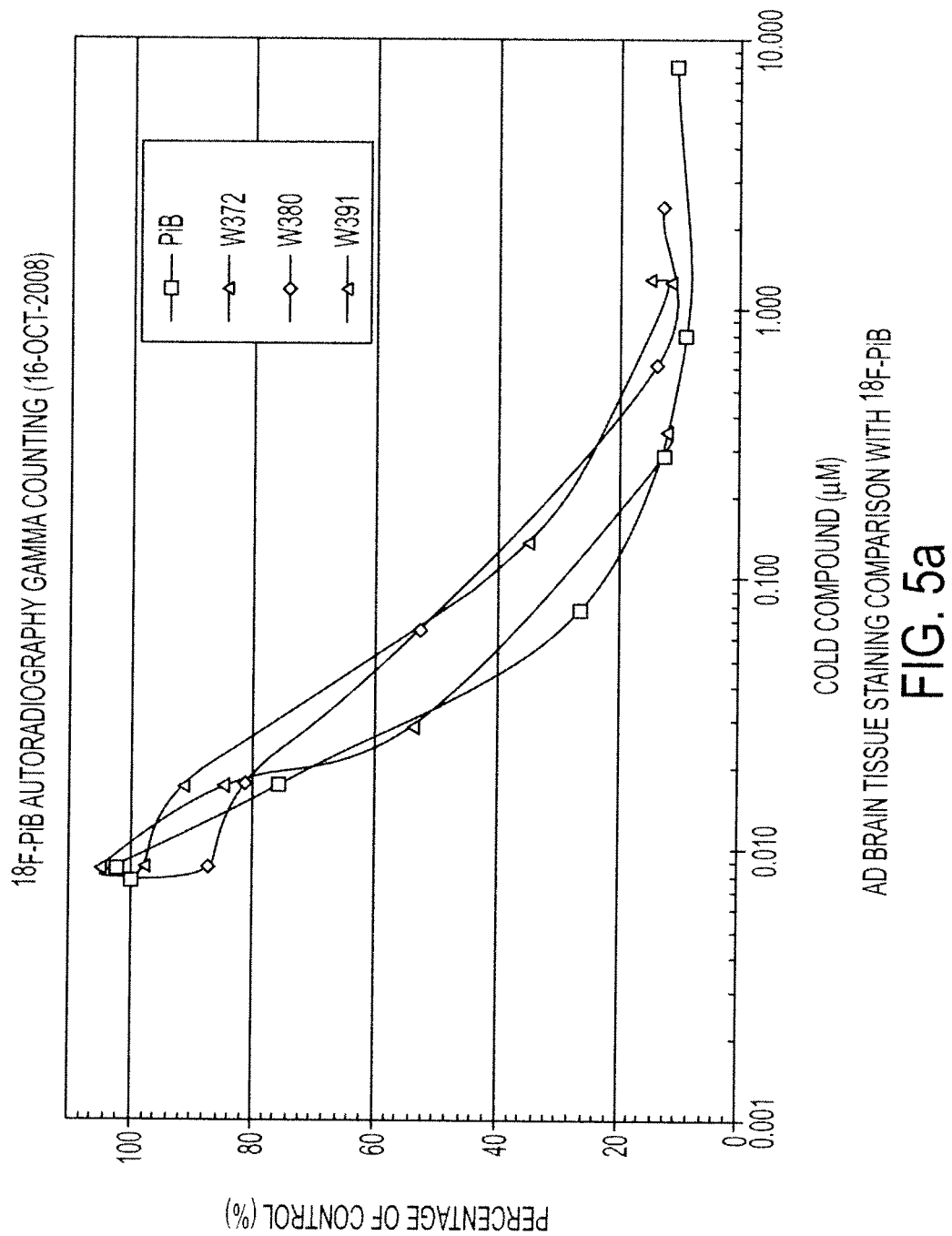
FIGS. 5*a* and 5*b* detail the AD brain tissue staining comparison with 18F-PiB.
Figure 5B:
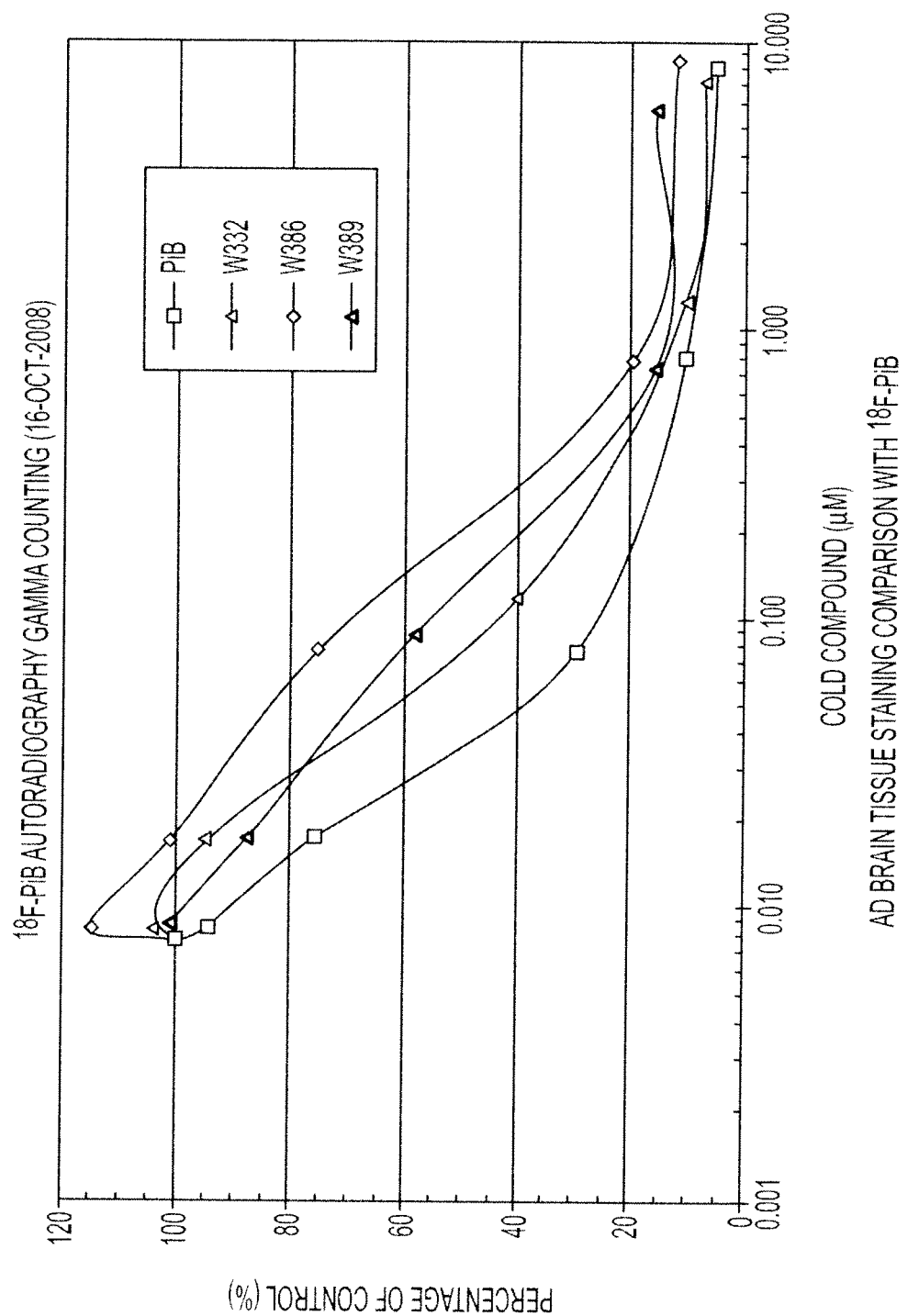

FIGS. 5a and 5b detail the staining comparisons of several compounds compared with 18F-PiB.

| Compound | $IC_{50}$ (18F-PiB)/nM |
|---|---|
| PiB | 38 |
| W372 | 73 |
| W380 | 73 |
| W332 | 79 |
| W389 | 130 |
| W386 | 210 |

Figure 6A:
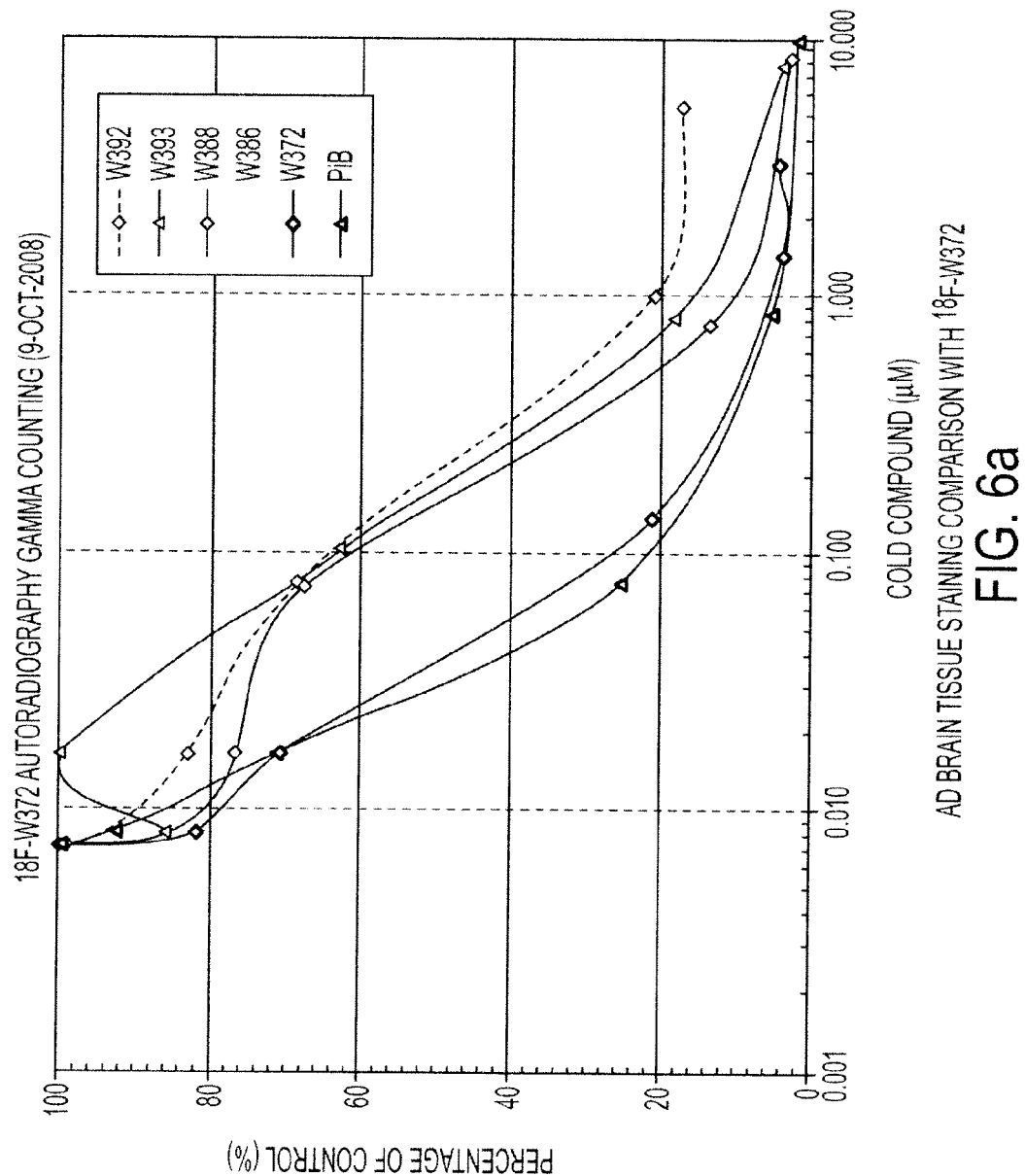
FIGS. 6*a* and 6*b* show AD brain tissue staining with 18F-W372.
Figure 6B:
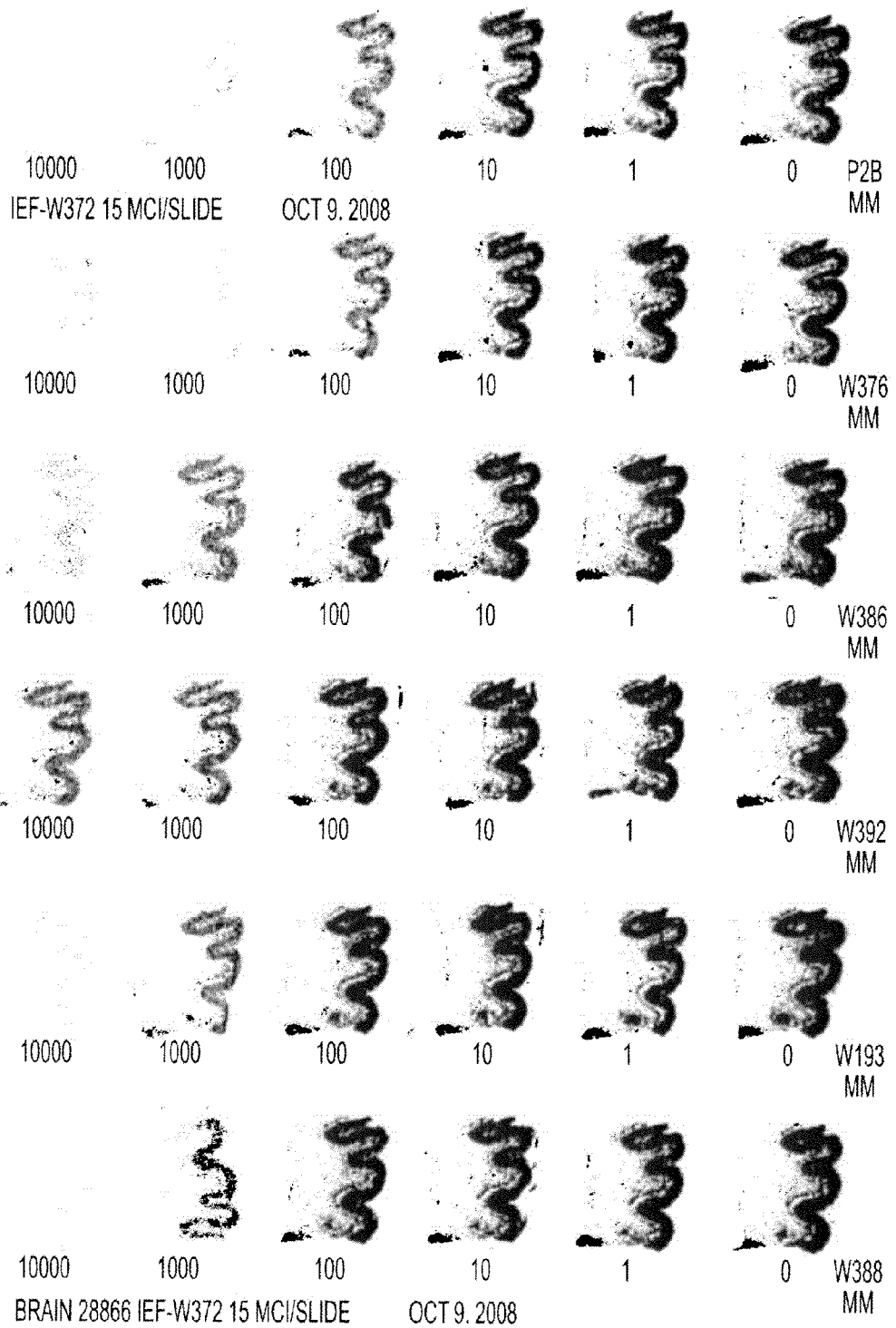
Figure 7A:
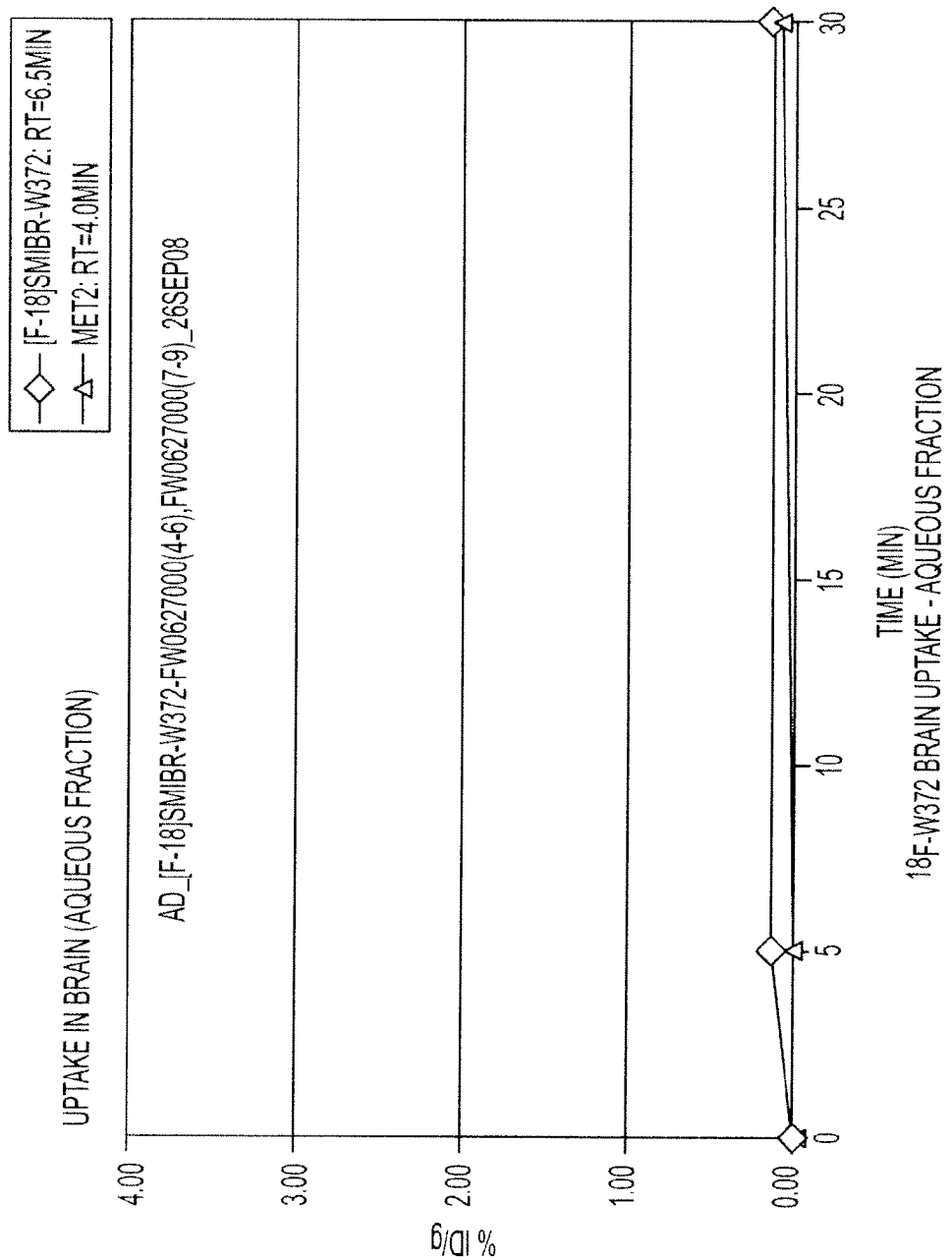
Figure 8B:
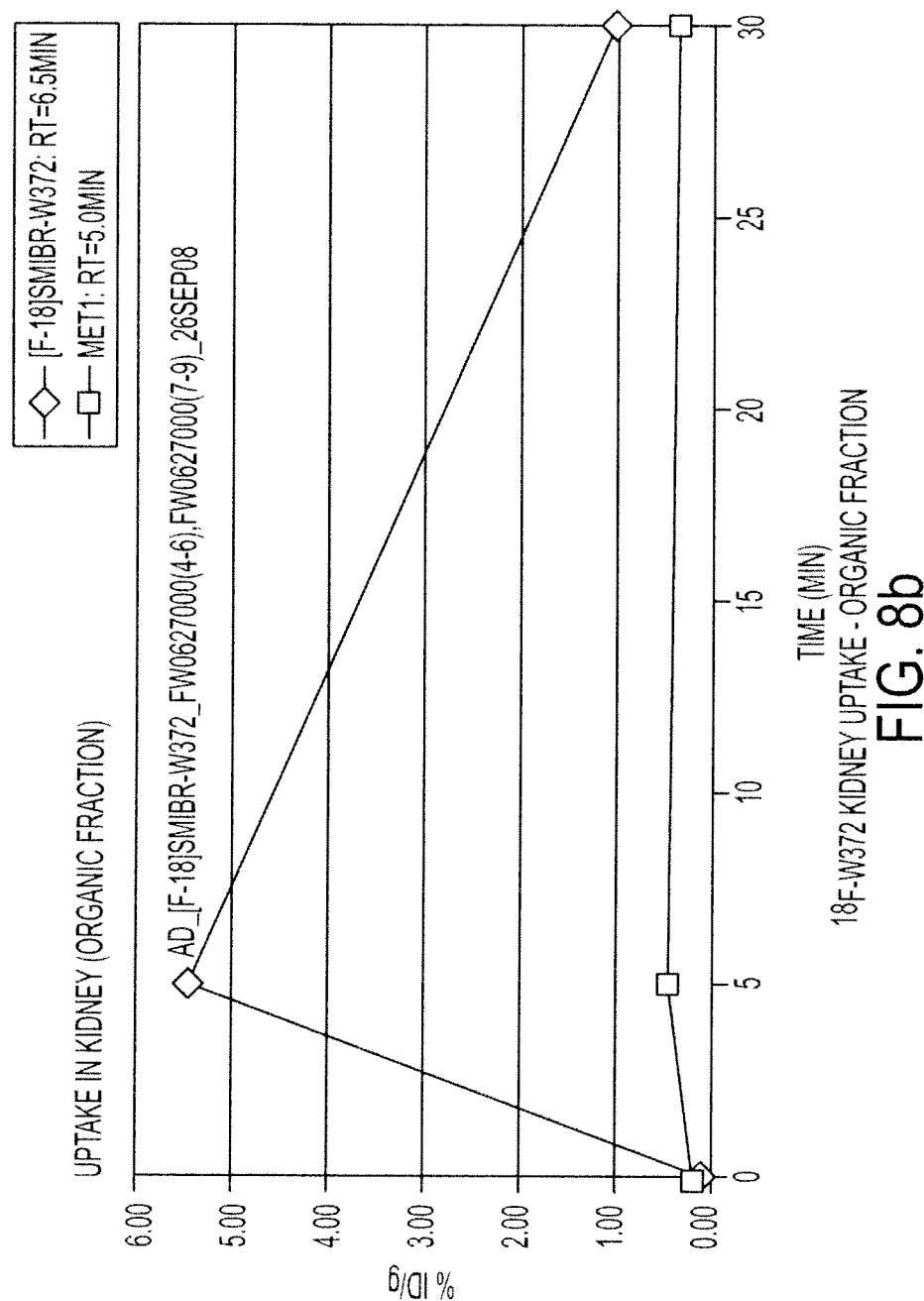
Figure 10B:
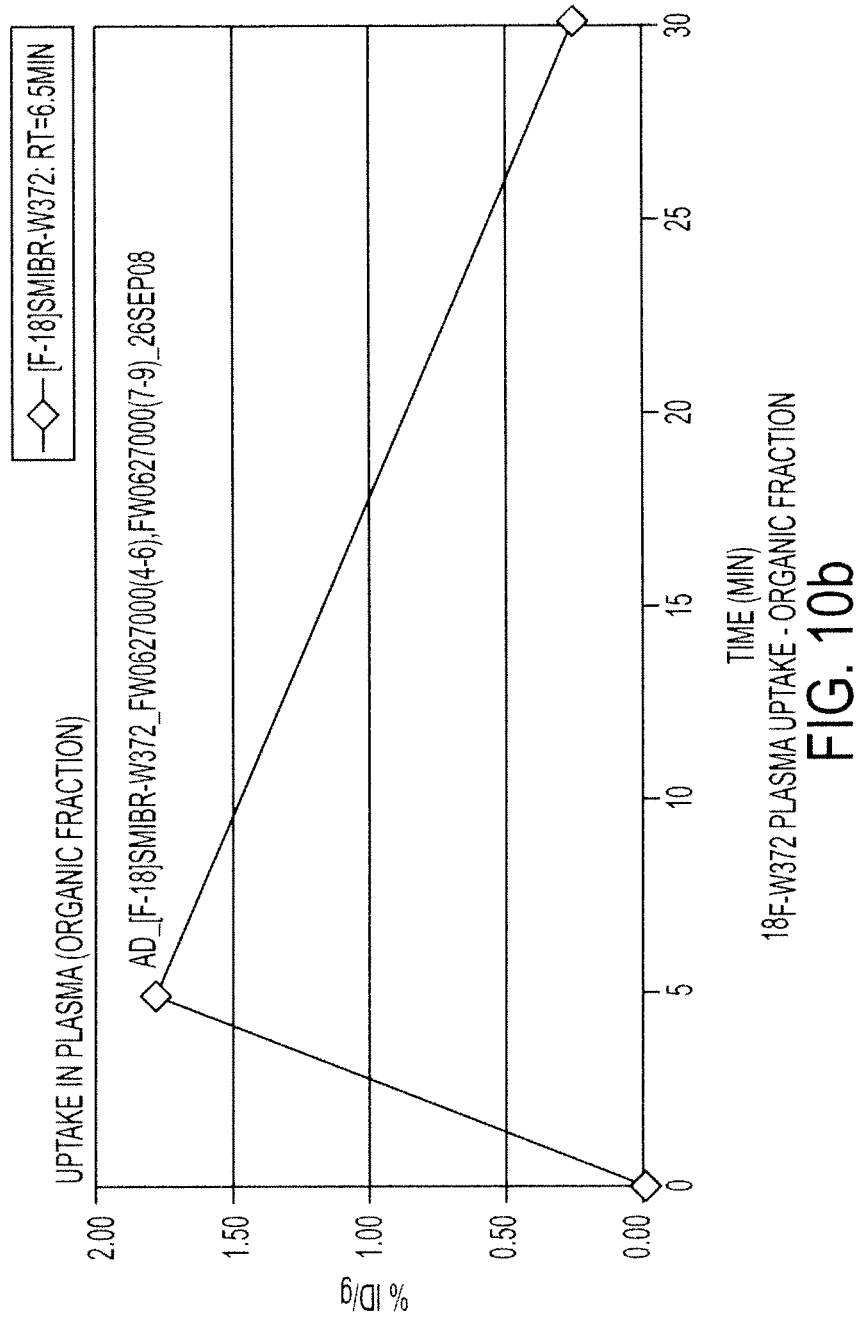

FIGS. 6a and 6b detail the staining comparisons of several compounds compared with 18F-PiB.

| Compound | $IC_{50}$ (18F-W372)/nM |
|---|---|
| PiB | 32 |
| W372 | 37 |
| W386 | 71 |
| W388 | 150 |
| W393 | 170 |
| W392 | 210 |

W372 and its analogs compete directly against 18F-PiB for the same binding sites in human AD brains. This surprising result could not have been predicted given their dissimilar structures and W372's lack of a phenolic OH and terminal NH-Me group, which are deemed essential for binding to AD plaques. Despite W372 lacking both of these functional groups, it still strongly competes with 18F-PiB for binding sites in human AD brains. The results clearly show that W372 and its analogs are as potent as PiB regarding to binding affinity. In addition, 18F-W372 gives nice, strong stains with excellent white matter wash out, indicating 18F-W372 has lower non-specific binding than 18F-PiB.

Mouse Metabolism Studies

Approximately 400 µCi of [F-18]W372 (at a volume of 200 µL) was injected via tail-vein into mice. The animals were sacrificed at 5 minutes (n=3) and 30 minutes (n=3) post-injection. Whole blood was obtained, weighed, and centrifuged at 13,000 RPM (3 minutes) to isolate plasma. The brain, kidneys, and liver were harvested, weighed, and homogenized in lysis buffer. 400 µL of each sample was subsequently removed, mixed with an equal volume of chloroform/methanol (1:1), vigorously vortexed, and placed on dry ice for 3 minutes. After thawing, another centrifugation step at 13,000 RPM (7 minutes) allowed for the separation of lipid ($CHCl_3$) and aqueous ($MeOH/H_2O$) phases. The hydrophobic and hydrophilic fractions were then removed, counted for radioactivity in a PerkinElmer Wizard gamma counter, and finally analyzed by Radio-HPLC (Raytest GmbH/Agilent).

FIGS. 7-10 show the uptake in various organs for 18F-W372. [18]W372 is taken up in the brain (3.8% ID/g) at 5 minutes and washes out to 0.47% ID/g at 30 minutes. [18F]W372 forms two polar metabolites, but very little (0% at 5 min) of the metabolites enter the brain (ratio unchanged: metabolite=2.6:1 at 30 min). The tracer are quickly cleared from the plasma, so that most of the 18F in the plasma is the parent tracer (ratio unchanged:metabolite=1.8:1 at 5 min).

Mouse Brain MicroPET Imaging

Figure 11B:
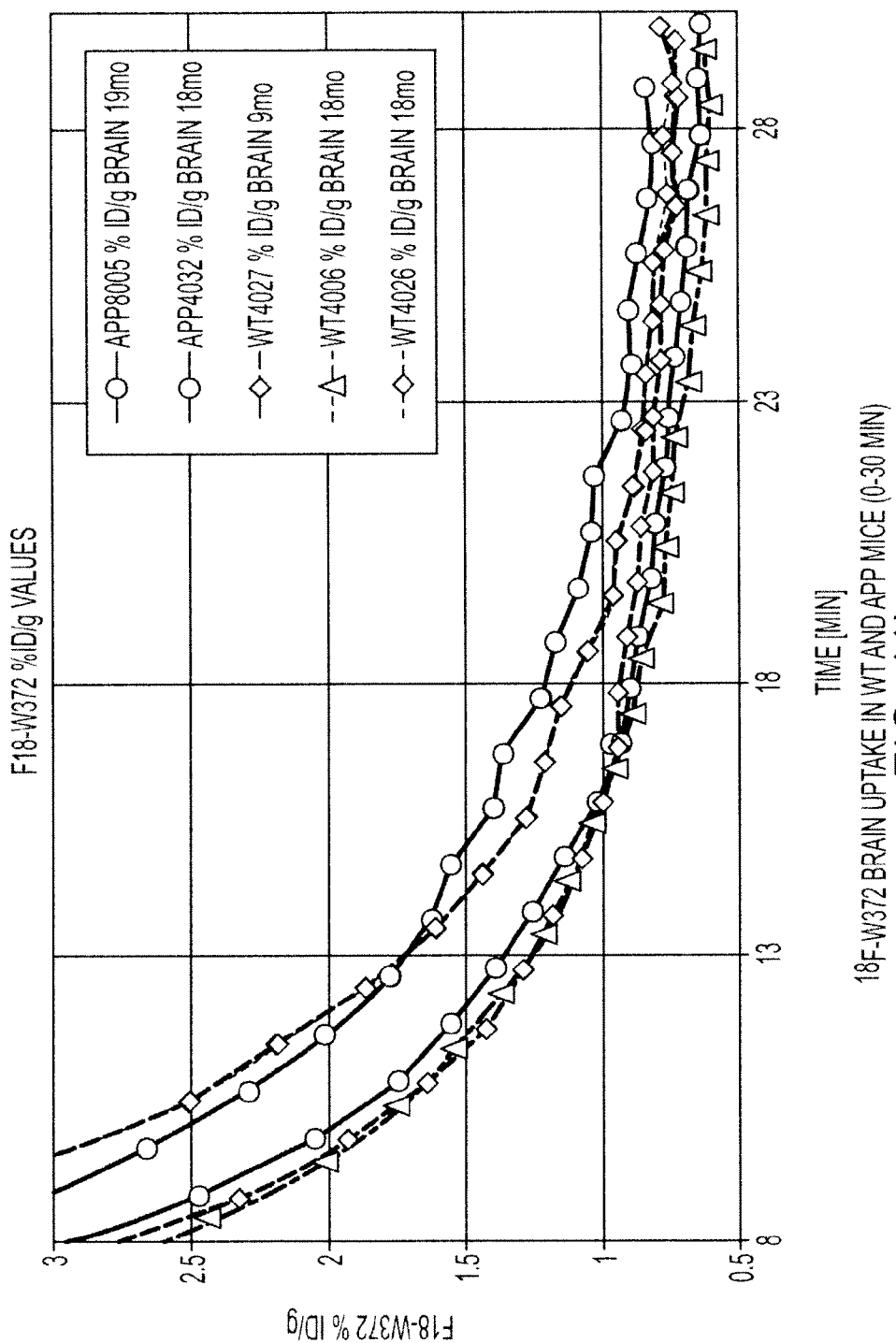
Figure 12A:
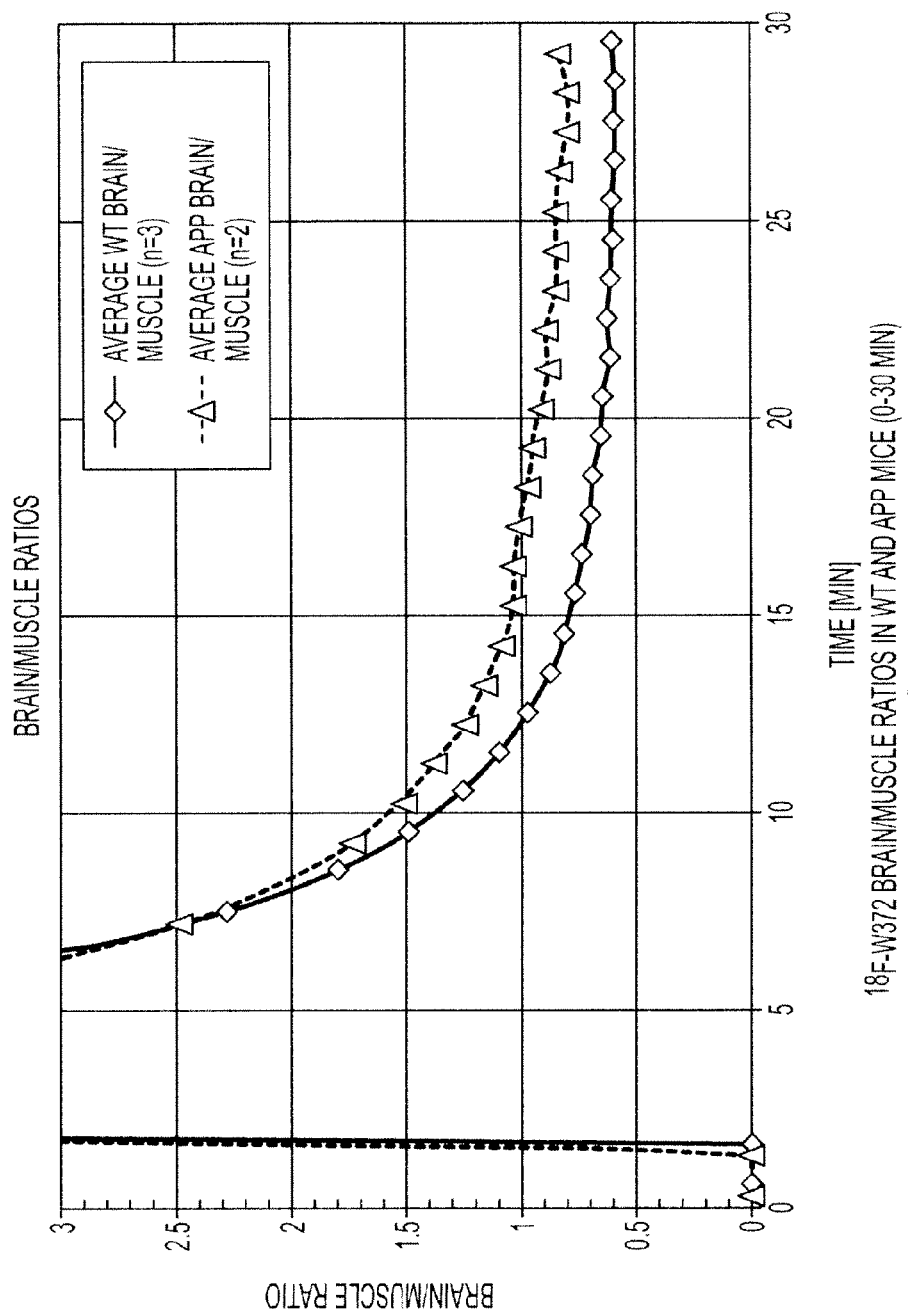
FIGS. 12a and 12b show the 18F-W372 brain/muscle ratios in WT and APP mice.
Figure 12B:
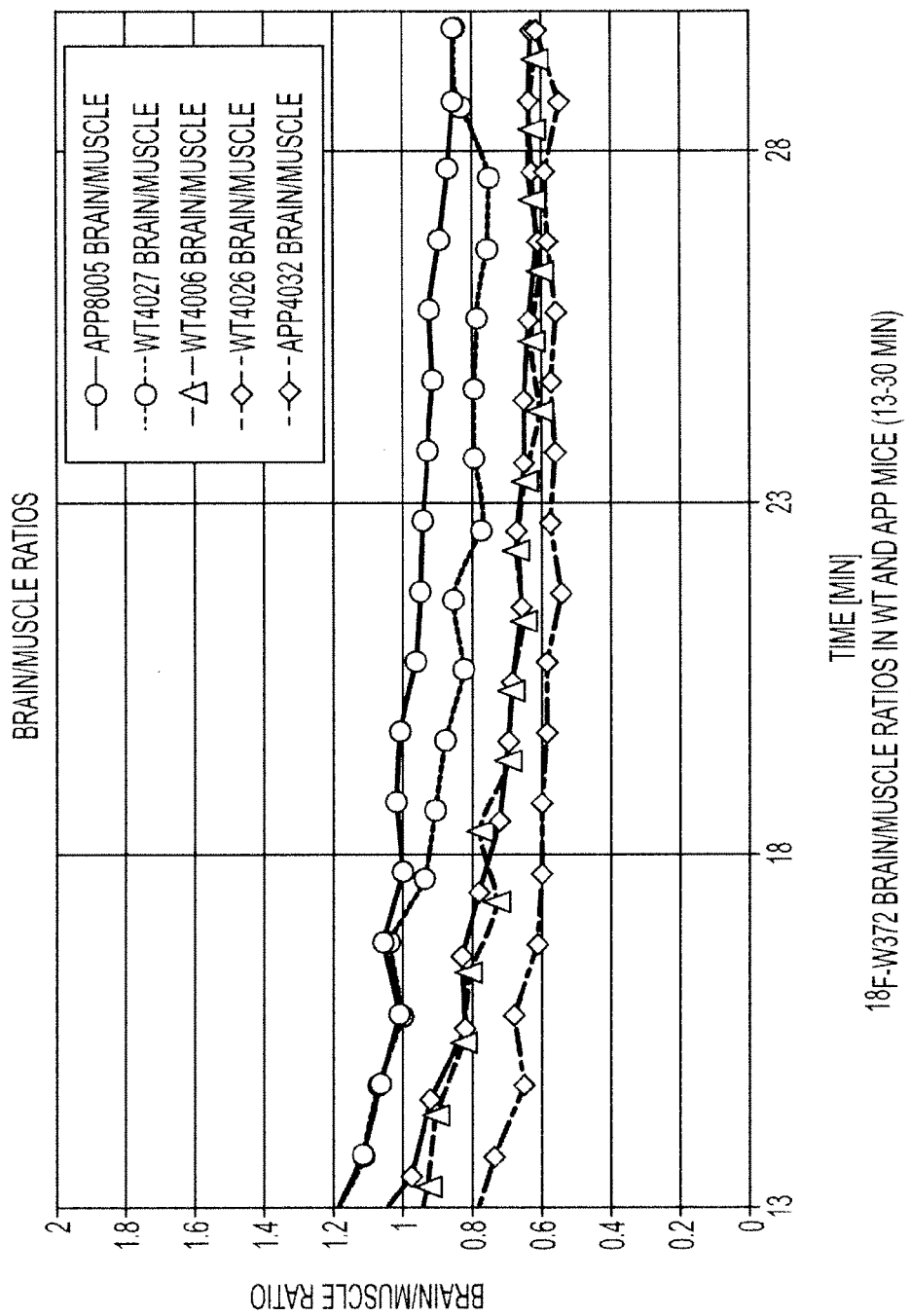

FIGS. 11 and 12 show the results of mouse brain imaging with 18F-W372 in WT and APP mice. [18F]W372 showed very good brain uptake (% ID/g>9%) and wash out. The young WT mouse showed a much higher brain uptake than the old mice. There is not much difference between APP and WT mice, but both App mice do appear to be slightly better retained after 13 min (App:WT=1.5:1).

Brain MicroPET Imaging of [18F]W372 in 19 Months App Mouse

Figure 13:
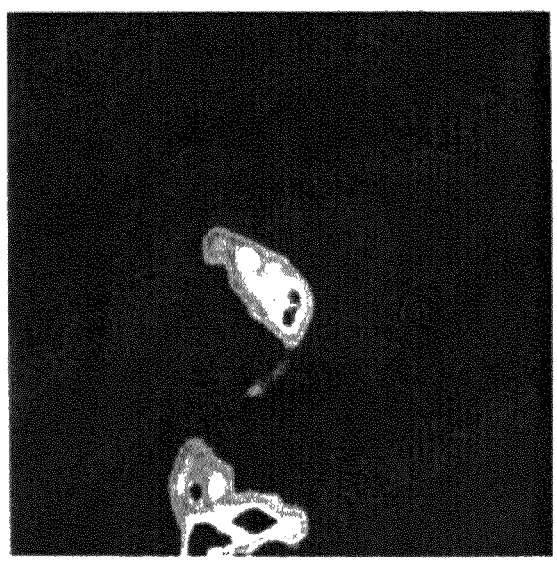
FIG. 13 shows the brain micro-PET imaging of 18F-W372 in APP mice.

FIG. 13 shows the results of mouse brain imaging with 18F-W372 in APP mice.

Comparison of Brain Uptake of [18F]W372 with Known AD Tracer [18F]PiB (30 Minute Dynamic MicroPET Scans in Young/Old, WT/App Mice)

FIGS. 14a and 14b show a comparison of brain uptake between 18F-PiB and 18F-W372 using dynamic microPET scanning in young and old mice. [18F]W372 displays both a surprising high uptake in mice brains (both WT and APP) and sufficiently slow washout such that one can distinguish WT from APP mice. Without being bound by any theory proposed herein, we speculate that the reason behind these results may be that [18F]W372 possesses a faster washout rate than 18F-PiB, which is consistent with the staining data: 18F-PiB requires harsher wash conditions in order to give reasonable grey to white matter ratios. The rapid washout of [18F]W372 is presumably a major factor for its low non-specific binding, yet the washout is slow enough to distinguish WT from APP. This suggests that the W372 displays a unique combination of excellent washout and retention properties in human AD brains that are not obvious from previously reported data.

The invention is further described by the following numbered paragraphs:

1. A radiolabeled amyloid binding compound of any of the formula

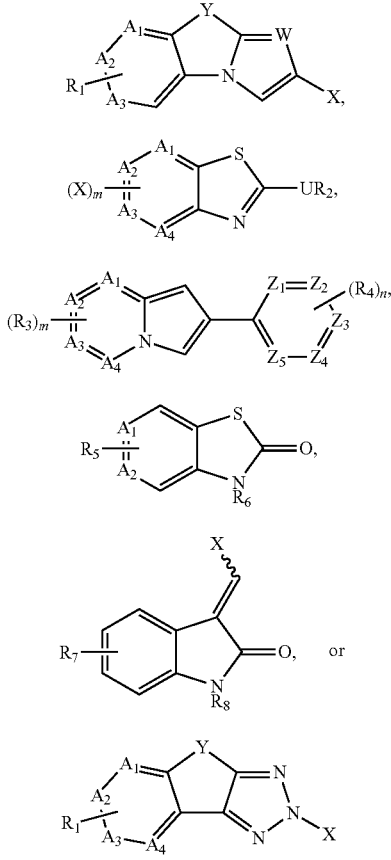

wherein $A_1$-$A_4$ are independently CH or N, provided that no more than two A groups are simultaneously N;

$R_1$ is H, halogen, alkyl, haloalkyl, alkenyl, haloalkenyl, alkynyl, haloalkynyl, cycloalkyl, OH, $OR_8$, $OR_9$, $R_8$—C(O)—, $R_9$—C(O)—, $R_8$—OC(O), $R_9$—OC(O), $R_9$—N($R_{10}$)C(O), $R_9$—N($R_{10}$)C(O), $R_8$—S(O)$_p$—, $R_9$—S(O)$_p$—;

$R_2$ is H, CN, alkyl, haloalkyl, alkenyl, haloalkenyl, alkynyl, haloalkynyl, cycloalkyl, halocycloalkynyl, alkoxy, haloalkoxy, thioalkyl, halothioalkyl, $NH_2$, $NHR_8$, alkoxyalkyl, haloalkoxyalkyl, cycloalkoxyalkyl, aryl, substituted aryl, heteroaryl, substituted heteroaryl;

$R_3$, $R_4$, $R_5$, $R_6$ and $R_7$ are independently H, halogen, OH, CN, $NO_2$, $R_8$, $R_9$, $CH_2R_9$, $CHCHR_9$, $OR_8$, $OR_9$, $NH_2$, $NHR_8$, N($R_8$)$_2$, —C(O)NHR$_8$, —C(O)N($R_8$)$_2$, $R_8$—C(O)—, $R_9$—C(O)—, $R_8$—C(O)O—, $R_9$—C(O)O—, $R_8$—C(O)N—, $R_9$—C(O)N—, $R_8$—OC(O)—, $R_9$—OC(O)—, $R_8$—OC(O)—, $R_9$—OC(O)O—, $R_8$—OC(O)N($R_{10}$)—, $R_9$—OC(O)N($R_{10}$)—, $R_8$—N($R_{10}$)C(O)—, $R_9$—N($R_{10}$)C(O)—, $R_8$—N($R_{10}$)C(O)—, $R_9$—N($R_{10}$)C(O)O—, $R_8$—N($R_{10}$)C(O)N($R_{10}$)—, $R_9$—N($R_{10}$)C(O)N($R_{10}$)—, $R_8$—S(O)$_p$—, $R_9$—S(O)$_p$—, $R_8$—S(O)$_p$N($R_{10}$)—, $R_9$—S(O)$_p$N($R_{10}$)—, $R_8$—N($R_{10}$)S(O)$_p$—, $R_9$—N($R_{10}$)S(O)$_p$—;

$R_8$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, substituted heteroarylalkyl;

$R_9$ is aryl, substituted aryl, heteroaryl, substituted heteroaryl;

$R_{10}$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, arylalkyl, substituted arylalkyl, heteroarylalkyl, substituted heteroarylalkyl;

W=N or CH;

U=Y or a bond;

X=OH, $OR_8$, aryl, substituted aryl, heteroaryl, substituted heteroaryl;

Y=$NR_1$, O, S;

$Z_1$-$Z_5$ are independently CH or N, provided that no more than two Z groups are simultaneously N;

m is 0-4;

n is 0-5; and p is 0-2;

provided that at least one of X, or $R^1$ to $R^{10}$ comprises a radiolabel, as defined herein;

wherein the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;

or a pharmaceutically acceptable salt thereof.

2. A radiolabeled amyloid binding compound of any of the formula

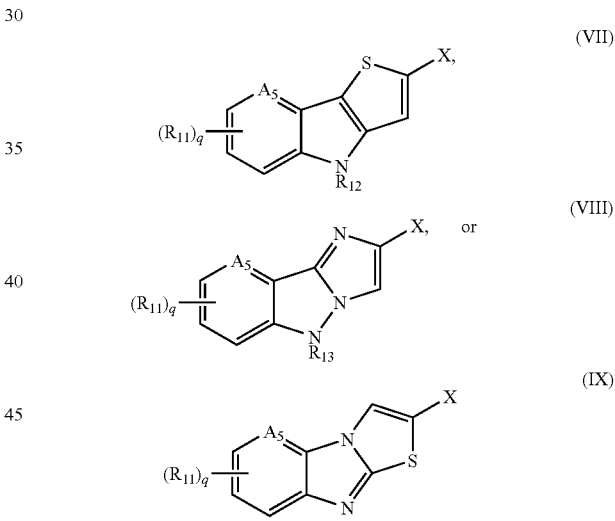

wherein $A_5$ is CH or N;

$R_{11}$ is $R_{10}$, $R_{10}$S—;

$R_{12}$ and $R_{13}$ are independently H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, arylalkyl, substituted arylalkyl, heteroarylalkyl, substituted heteroarylalkyl;

X=aryl, substituted aryl, heteroaryl, substituted heteroaryl; and q is 1 or 2;

provided that at least one of X, or $R^{11}$ to $R^{13}$ comprises a radiolabel, as defined herein;

wherein the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;

or a pharmaceutically acceptable salt thereof.

3. A radiolabeled amyloid binding compound of any of the formula

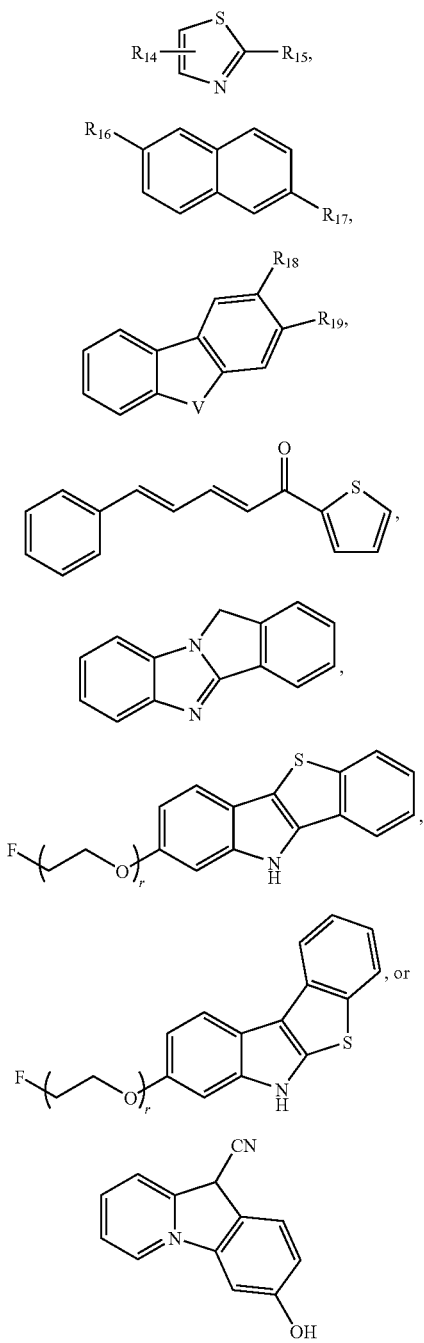

wherein
V is O or S;
$R_{14}$ is aryl, substituted aryl, heteroaryl, substituted heteroaryl, alkenylaryl, alkenyl substituted aryl, alkenylheteroaryl;
$R_{15}$ is $NH_2$, $N(R_{10})_2$, aryl, substituted aryl, heteroaryl, substituted heteroaryl;
$R_{16}$ is heteroaryl or substituted heteroaryl;
$R_{17}$ is $R_{10}O$— or $R_{10}S$—;
$R_{18}$ is H, $R_{10}O$— or $R_8$—C(O)N—;
$R_{19}$ is H or $NH_2$; and
r is 1-3;

provided that at least one of X, or $R^{14}$ to $R^{18}$ comprises a radiolabel, as defined herein;
wherein the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;
or a pharmaceutically acceptable salt thereof.

4. The radiolabeled amyloid binding compound of paragraph 1 wherein,
for formula (I):
$A_1$ and $A_3$ are independently CH or N;
$R_1$ is H, halogen, alkyl, haloalkyl, OH, $OR_8$, $OR_9$;
W=N or CH;
X=aryl, substituted aryl, heteroaryl, substituted heteroaryl;
Y=N-alkyl, N-haloalkyl, O, S;
for formula (II):
$A_2$, $A_3$ and $A_4$ are independently CH or N;
$R_2$ is H, CN, alkyl, haloalkyl, alkenyl, haloalkenyl, alkynyl, haloalkynyl, cycloalkyl, halocycloalkynyl, alkoxy, haloalkoxy, thioalkyl, halothioalkyl, $NH_2$, $NHR_8$, alkoxyalkyl, haloalkoxyalkyl, cycloalkoxyalkyl, aryl, substituted aryl, heteroaryl, substituted heteroaryl;
X=OH, aryl, substituted aryl, heteroaryl, substituted heteroaryl;
m=1-3;
for formula (III):
$A_1$ and $A_2$ are independently CH or N;
$R_3$ is halogen, OH, $OR_8$, $OR_9$, —C(O)$NHR_8$, —C(O)N$(R_8)_2$;
$R_4$ is halogen, OH, CN, $NO_2$, $NH_2$, $OR_8$, $OR_9$, $NHR_8$, $N(R_8)_2$;
m=0-2;
n=1-2;
for formula (IV):
$A_2$ is CH or N;
$R_5$ and $R_6$ are independently H, halogen, OH, $NO_2$, $R_8$, $R_9$, $CH_2R_9$, $CHCHR_9$, $OR_8$, $OR_9$, $R_8$—C(O)—, $R_9$—C(O)—;
for formula (V):
X is H or aryl, wherein the aryl group is optionally substituted with halogen, CN, OH, $OR_8$, —$NHR_8$, or —$N(R_8)_2$;
$R_7$ is H, halogen, CN, —$NO_2$;
$R_8$ is H, alkyl, haloalkyl;
for formula (VI):
$A_1$ and $A_3$ are independently CH or N;
$R_1$ is H, halogen, alkyl, haloalkyl, OH, $OR_8$, $OR_9$;
X=aryl, substituted aryl, heteroaryl, substituted heteroaryl;
or a pharmaceutically acceptable salt thereof.

5. The radiolabeled amyloid binding compound of paragraph 2 wherein, for formula (VII):
$A_5$ is CH or N;
$R_{11}$ is $OR_8$;
$R_{12}$ is H;
X=4-fluorophenyl, 4-cyanophenyl, heteroaryl, substituted heteroaryl; and
q is 1;
for formula (VIII):
$R_{11}$ is $OR_8$;
$R_{13}$ is H; and
q is 1;
for formula (IX):
$R_{11}$ is $OR_8$; and
q is 1;
or a pharmaceutically acceptable salt thereof.

6. The radiolabeled amyloid binding compound of paragraph 3 wherein, for formula (X):
R$_{14}$ is aryl, CHCHaryl;
R$_{15}$ is NH$_2$, N(R$_{10}$)$_2$, aryl, substituted aryl;
for formula (XI):
R$_{16}$ is heteroaryl;
R$_{17}$ is R$_{10}$O—;
for formula (XII):
V is O or S;
R$_{18}$ is H, R$_{10}$O— or R$_8$—C(O)N—;
R$_{19}$ is H or NH$_2$;
for formulas (XV) or (XVI):
r is 1-3;
or a pharmaceutically acceptable salt thereof.

7. The radiolabeled amyloid binding compound of paragraphs 1 or 4 wherein,
for formula (I):
when Y is S,
A$_1$ and A$_3$ are independently CH or N;
R$_1$ is halogen, OH, OR$_B$;
W=N or CH;
X=aryl, substituted aryl, heteroaryl, substituted heteroaryl;
when Y=N-alkyl,
A$_1$-A$_3$ are independently CH;
R$_1$ is H, halogen, alkyl or haloalkyl;
W=N;
X=aryl, substituted aryl;
when Y=O,
A$_1$ is N or CH;
A$_2$-A$_3$ are independently CH;
R$_1$ is halogen, alkyl, haloalkyl or Oalkyl;
W=N;
X=substituted aryl or substituted heteroaryl;
for formula (II):
A$_2$, A$_3$ and A$_4$ are independently CH or N;
R$_2$ is H, CN, alkyl, haloalkyl, alkoxy, haloalkoxy, halothioalkyl, NH$_2$, NHR$_8$, aryl, substituted aryl, heteroaryl, substituted heteroaryl;
U is NH, O, S or a bond;
X=OH, aryl, substituted aryl, heteroaryl, substituted heteroaryl;
m=1;
for formula (III):
A$_1$ and A$_2$ are independently CH or N;
R$_3$ is halogen, OH, Oalkyl, —C(O)NHR$_8$, —C(O)N(R$_8$)$_2$;
R$_4$ is halogen, OH, CN, NO$_2$, NH$_2$, Oalkyl, Ohaloalkyl;
m=1;
n=1;
for formula (IV):
A$_2$ is CH or N;
R$_5$ is H, OH, Oalkyl, Ohaloalkyl, NO$_2$, —C(O)alkyl;
R$_6$ is H, benzyl, aryl, heteroaryl, substituted aryl, CHCHR$_9$;
for formula (V):
X is H or aryl, wherein the aryl group is optionally substituted with halogen, CN, OH, —NH$_2$, —N(alkyl)$_2$, —N(alkyl)(haloalkyl), —Oalkyl;
R$_7$ is H, halogen, CN, —NO$_2$;
R$_8$ is H;
for formula (VI):
A$_1$ and A$_3$ are independently CH or N;
R$_1$ is halogen, OH, OR$_8$;
X=aryl, substituted aryl, heteroaryl, substituted heteroaryl;
or a pharmaceutically acceptable salt thereof.

8. A radiolabeled amyloid binding compound of the formula (Ia)

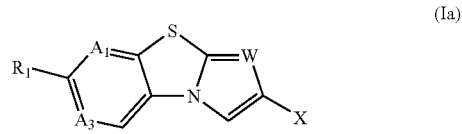

wherein:
A$_1$ and A$_3$ are independently CH or N;
R$_1$ is halogen, OR$_8$, OR$_9$;
R$_8$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, substituted heteroarylalkyl;
R$_9$ is aryl, substituted aryl, heteroaryl, substituted heteroaryl;
W=N or CH; and
X=OH, aryl, substituted aryl, heteroaryl, substituted heteroaryl;
provided that at least one of X and R$_1$ comprises a radiolabel;
wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;
or a pharmaceutically acceptable salt thereof.

9. The radiolabeled amyloid binding compound of paragraph 8, wherein:
A$_1$ is N;
A$_3$ is CH;
R$_1$ is halogen, OR$_8$, OR$_9$;
R$_8$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, substituted heteroarylalkyl;
R$_9$ is aryl, substituted aryl, heteroaryl, substituted heteroaryl;
W=N; and
X=aryl, substituted aryl, heteroaryl, substituted heteroaryl.

10. The radiolabeled amyloid binding compound of paragraphs 8 or 9, wherein:
A$_1$ is N;
A$_3$ is CH;
R$_1$ is OR$_8$;
R$_8$ is H, alkyl, haloalkyl;
W=N; and
X=aryl, substituted aryl, heteroaryl, substituted heteroaryl; and
the radionucleide is $^{18}$F.

11. The radiolabeled amyloid binding compound of any of paragraphs 8-10, wherein:
A$_1$ is N;
A$_3$ is CH;
R$_1$ is OR$_8$;
R$_8$ is alkyl, haloalkyl;
W=N; and
X is selected from the group consisting of phenyl, 3-F phenyl, 3-hydroxyphenyl, 3-alkoxyphenyl, 3-haloalkoxyphenyl, 4-F phenyl, 4-CN phenyl, 4-alkoxyphenyl, 4-haloalkoxyphenyl, 4-aminophenyl, 4-nitrophenyl, 4-alkylaminophenyl, 4-dialkylaminophenyl, 4-pyrrolidinylphenyl, 3-OH,4-F phenyl, 3,4,5-trifluorophenyl, 2-furyl, 2-thienyl, 2-halo-4-thienyl, 4-haloalkyl-2-furyl, 2-thiazolyl, 2-oxazolyl, 2-pyridyl, 4-halo-2-pyridyl, 5-halo-2-pyridyl, 6-halo-2-pyridyl, 2-halo-5-pyridyl, 3-halo-5-pyridyl, 4-halo-5-pyridyl, 2-dialkylamino-5-pyridyl, pyrazinyl, 2-halo-5-pyrazinyl, pyrimidyl, naphthyl, quinolinyl, benzimidazolyl, N-alkylbenzimidazolyl, thiobenzimidazolyl, 5-benzofuranyl, 5-oxindolyl, 2-(2-pyridyl)-5-thienyl; and the radionucleide is $^{18}$F.

12. A radiolabeled amyloid binding compound of the formula (Ib)

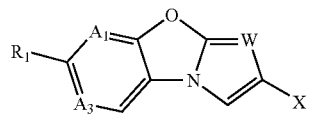

wherein:

$A_1$ and $A_3$ are independently CH or N;

$R_1$ is halogen, $OR_8$, $OR_9$;

$R_8$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, substituted heteroarylalkyl;

$R_9$ is aryl, substituted aryl, heteroaryl, substituted heteroaryl;

W=N or CH; and

X=OH, aryl, substituted aryl, heteroaryl, substituted heteroaryl;

provided that at least one of X and $R_1$ comprises a radiolabel;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;

or a pharmaceutically acceptable salt thereof.

13. The radiolabeled amyloid binding compound of paragraph 12, wherein:

$A_1$ is N;

$A_3$ is CH;

$R_1$ is $OR_8$;

$R_8$ is alkyl, haloalkyl;

W=N; and

X is selected from the group consisting of phenyl, 3-F phenyl, 3-hydroxyphenyl, 3-alkoxyphenyl, 3-haloalkoxyphenyl, 4-F phenyl, 4-CN phenyl, 4-alkoxyphenyl, 4-haloalkoxyphenyl, 4-aminophenyl, 4-nitrophenyl, 4-alkylaminophenyl, 4-dialkylaminophenyl, 4-pyrrolidinylphenyl, 3-OH,4-F phenyl, 3,4,5-trifluorophenyl, 2-furyl, 2-thienyl, 2-halo-4-thienyl, 4-haloalkyl-2-furyl, 2-thiazolyl, 2-oxazolyl, 2-pyridyl, 4-halo-2-pyridyl, 5-halo-2-pyridyl, 6-halo-2-pyridyl, 2-halo-5-pyridyl, 3-halo-5-pyridyl, 4-halo-5-pyridyl, 2-dialkylamino-5-pyridyl, pyrazinyl, 2-halo-5-pyrazinyl, pyrimidyl, naphthyl, quinolinyl, benzimidazolyl, N-alkylbenzimidazolyl, thiobenzimidazolyl, 5-benzofuranyl, 5-oxindolyl, 2-(2-pyridyl)-5-thienyl; and the radionucleide is $^{18}$F.

14. A radiolabeled amyloid binding compound of formula (IIa)

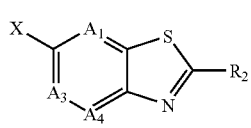

wherein:

$A_1$, $A_3$ and $A_4$ are independently CH or N, provided that no more than two A groups are simultaneously N;

$R_2$ is H, CN, alkyl, haloalkyl, alkoxy, haloalkoxy, $NH_2$, $NHR_8$, alkoxyalkyl, haloalkoxyalkyl, aryl, substituted aryl, heteroaryl, substituted heteroaryl;

$R_8$ is H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, substituted heteroarylalkyl;

X=OH, alkoxy, haloalkoxy, aryl, substituted aryl, heteroaryl, substituted heteroaryl;

provided that at least one of X and $R_1$ comprises a radiolabel; and wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;

or a pharmaceutically acceptable salt thereof.

15. The radiolabeled amyloid binding compound of paragraph 14, wherein:

$A_1$, $A_3$ and $A_4$ are CH;

$R_2$ is H, CN, alkyl, haloalkyl, alkoxy, haloalkoxy, NH-alkyl, NHhaloalkyl, N(alkyl)$_2$, N(alkyl)(haloalkyl), N(haloalkyl)$_2$, 4-aminomethylphenyl, 2-aminomethylphenyl, 2-aminomethyl-5-pyridyl, 4-(NHalkyl)-3-(halophenyl), 2-amino-5-thiazolyl;

X=OH, alkoxy, haloalkoxy, phenyl, 4-alkylphenyl, 4-F phenyl, 4-CN phenyl, 4-alkoxyphenyl, 4-aminophenyl, 4-alkylaminophenyl, 4-dialkylaminophenyl;

provided that at least one of X and $R_2$ comprises a radiolabel; and wherein the radiolabel is $^{18}$F;

or a pharmaceutically acceptable salt thereof.

16. A pharmaceutical composition for in vivo imaging of amyloid deposits, comprising a compound of any one of paragraphs 1 to 15.

17. A method for inhibiting a condition associated with amyloidosis related diseases, the method comprising administering to a patient a therapeutically effective amount of a compound of any of paragraphs 1-15.

18. The method of paragraph 17, wherein the condition is cell degeneration.

19. The method of paragraph 17, wherein the condition is toxicity associated with fibril formation.

20. A method of diagnosing neurodegenerative conditions or a predisposition thereto in a mammal, the method comprising:

a) administering to the mammal a diagnostically effective amount of a radiolabeled compound, wherein the compound passes the blood-brain barrier and preferentially binds to a soluble oligomers, polymers and fibrils in a brain tissue and wherein the compound is selected from the group consisting of compounds of formulae (I)-(XVII);

b) allowing the compound to distribute into the brain tissue; and c) imaging the brain tissue, wherein an increase in binding of the compound to the brain tissue compared to a normal control level of binding indicates that the mammal is suffering from or is at risk of developing neurodegenerative disease.

21. The method of any of paragraphs 17-20, wherein the compound is a compound of any of paragraphs 1 to 15.

22. The method of any of paragraphs 17-21, wherein the neurodegenerative condition is Alzheimer's Disease.

23. A method of diagnosing Alzheimer's Disease (AD) or a predisposition thereto in a mammal, the method comprising:
   a) administering to the mammal a diagnostically effective amount of a radiolabeled compound or composition of any of paragraphs 1-16, wherein the compound passes the blood-brain barrier and preferentially binds to a soluble AD oligomers, polymers and fibrils in a brain tissue;
   b) allowing the compound to distribute into the brain tissue; and
   c) imaging the brain tissue, wherein an increase in binding of the compound to the brain tissue compared to a normal control level of binding indicates that the mammal is suffering from or is at risk of developing Alzheimer's Disease.

24. The method of any of paragraphs 20-23, wherein the radiolabeled compound preferentially binds to fibrils.

25. The method of any of paragraphs 20-24, wherein the increase in binding is at least 10% greater than said normal control value.

26. The method of any of paragraphs 20-25, wherein the compound is administered via intravenous injection.

27. A method for detecting Alzheimer's Disease or a predisposition thereto in the brain of a live mammal, the method comprising:
   a) administering the mammal with a diagnostically effective amount of a radiolabeled compound that passes the blood-brain barrier and preferentially binds to a soluble AD oligomers, polymers and fibrils in the brain, wherein the detectably-labeled compound is a compound of any of paragraphs 1-15;
   b) allowing the compound to distribute into the brain tissue; and
   c) imaging the brain tissue, wherein an increase in binding of the compound to the brain tissue compared to a normal control level of binding indicates that the mammal is suffering from or is at risk of developing Alzheimer's Disease.

28. A method for detecting Alzheimer's Disease or a predisposition thereto in the brain of a live mammal, the method comprising:
   a) administering the mammal with a diagnostically effective amount of a radiolabeled compound of any of paragraphs 1-15, wherein the compound passes the blood-brain barrier and preferentially binds to a soluble AD oligomers, polymers and fibrils in the brain;
   b) allowing the compound to distribute into the brain tissue; and
   c) imaging the brain tissue, wherein an increase in binding of the compound to the brain tissue compared to a normal control level of binding indicates that the mammal is suffering from or is at risk of developing Alzheimer's Disease.

29. The method of paragraph 28, wherein the detection is performed using gamma imaging, magnetic resonance imaging, magnetic resonance spectroscopy or fluorescence spectroscopy.

30. The method of paragraphs 28 or 29, wherein the detection by gamma imaging is PET or SPECT.

31. A method of diagnosing Alzheimer's Disease or a predisposition thereto in a mammal, the method comprising:
   a) administering to the mammal a diagnostically effective amount of a radiolabeled compound, wherein the compound passes the blood-brain barrier and preferentially binds to a soluble or insoluble AD oligomers, polymers, fibrils, hyperphosphorylated tau, neurofibrillary tangles, paired helical filaments and/or neurotoxic soluble oligomers in a brain, and wherein the radiolabeled compound is a compound of any of paragraphs 1-15; and
   (b) employing a nuclear imaging technique selected from the group consisting of positron emission tomography (PET) and single photon emission computed tomography (SPECT) for monitoring or visualizing a distribution of the radiolabeled compound within the brain or within a portion thereof.

32. A method of detecting amyloid deposits in tissue from subject comprising incubating the tissue from the subject with a solution comprising a compound of any of paragraphs 1-15 or a pharmaceutical composition of paragraph 16 and detecting the binding of the probe to at least one amyloid deposit in the tissue.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound of the formula (Ia)

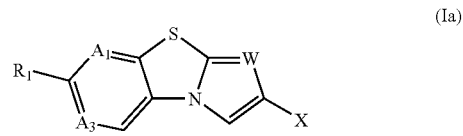

(Ia)

or a pharmaceutically acceptable salt thereof;
wherein:
   $A_1$ is N;
   $A_3$ is CH;
   $R_1$ is halogen, $OR_8$, and $OR_9$;
   $R_8$ is selected from the group consisting of H, alkyl, haloalkyl, alkenyl, haloalkenyl, alkynyl, haloalkynyl, cycloalkyl, halocycloalkyl, alkoxyalkyl, haloalkoxyalkyl, cycloalkoxyalkyl, thioalkoxyalkyl, halothioalkoxyalkyl, cyclothioalkoxyalkyl, aryl, arylalkyl, substituted aryl, substituted arylalkyl, heteroaryl, heteroarylalkyl, substituted heteroaryl, and substituted heteroarylalkyl;
   $R_9$ is selected from the group consisting of aryl, substituted aryl, heteroaryl, and substituted heteroaryl;
   W is N; and
   X is selected from the group consisting of aryl, substituted aryl, heteroaryl, and substituted heteroaryl;
   provided that at least one of X and $R_1$ comprises a halogen or a radiolabel;
   wherein the radiolabel is a radionuclide selected from the group consisting of $^{11}C$, $^{13}N$, $^{15}O$, $^{18}F$, $^{123}I$, $^{124}I$, $^{125}I$, $^{131}I$ and $^{77}Br$.

2. The compound of claim 1, wherein:
   $R_1$ is $OR_8$;
   $R_8$ is selected from the group consisting of H, alkyl, and haloalkyl;
   X is selected from the group consisting of aryl, substituted aryl, heteroaryl, and substituted heteroaryl; and the radionuclide is $^{18}F$.

3. The compound of claim 1, wherein:
   $R_1$ is $OR_8$;
   $R_8$ is selected from the group consisting of and alkyl haloalkyl;

X is selected from the group consisting of phenyl, 3-F phenyl, 3-hydroxyphenyl, 3-alkoxyphenyl, 3-haloalkoxyphenyl, 4-F phenyl, 4-CN phenyl, 4-alkoxyphenyl, 4-haloalkoxyphenyl, 4-aminophenyl, 4-nitrophenyl, 4-alkylaminophenyl, 4-dialkylaminophenyl, 4-pyrrolidinylphenyl, 4-F phenyl, 3,4,5-trifluorophenyl, 2-furyl, 2-thienyl, 2-halo-4-thienyl, 4-haloalkyl-2-furyl, 2-thiazolyl, 2-oxazolyl, 2-pyridyl, 4-halo-2-pyridyl, 5-halo-2-pyridyl, 6-halo-2-pyridyl, 2-halo-5-pyridyl, 3-halo-5-pyridyl, 4-halo-5-pyridyl, 2-dialkylamino-5-pyridyl, pyrazinyl, 2-halo-5-pyrazinyl, pyrimidyl, naphthyl, quinolinyl, benzimidazolyl, N-alkylbenzimidazolyl, thiobenzimidazolyl, 5-benzofuranyl, 5-oxindolyl, and 2-(2-pyridyl)-5-thienyl; and the radionuclide is $^{18}$F.

4. A pharmaceutical composition for in vivo imaging of amyloid deposits, comprising a compound of claim 1.

5. The compound of claim 1, consisting of:

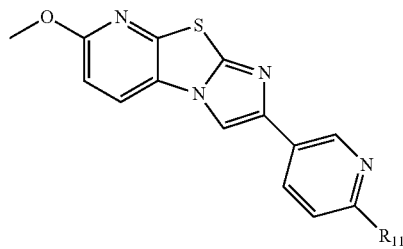

or pharmaceutically acceptable salts thereof,
wherein $R_{11}$ is a halogen or a radionuclide.

6. The compound of claim 5, wherein $R_{11}$ is a radionuclide.

7. The compound of claim 6, wherein $R_{11}$ is $^{18}$F.

8. The compound of claim 1, consisting of:

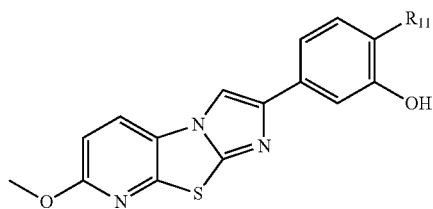

or pharmaceutically acceptable salts thereof,
wherein $R_{11}$ is a halogen or a radionuclide.

9. The compound of claim 8, wherein $R_{11}$ is a radionuclide.

10. The compound of claim 9, wherein $R_{11}$ is $^{18}$F.

11. The compound of claim 1, consisting of:

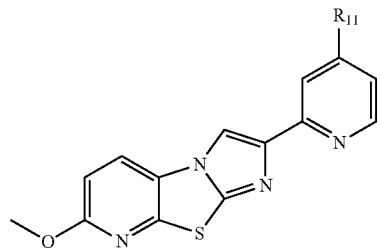

or pharmaceutically acceptable salts thereof;
wherein $R_{11}$ is a halogen or a radionuclide.

12. The compound of claim 11, wherein $R_{11}$ is a radionuclide.

13. The compound of claim 12, wherein $R_{12}$ is $^{18}$F.

14. The compound of claim 1, wherein $R_1$ is $OR_9$.

15. The compound of claim 1, wherein X comprises $^{18}$F.

16. The compound of claim 1, wherein $R_1$ comprises $^{18}$F.

17. The compound of claim 2, wherein $R_8$ is H.

18. The compound of claim 2, wherein $R_8$ is alkyl.

19. The compound of claim 2, wherein $R_8$ is haloalkyl.

20. The compound of claim 14, wherein $R_9$ is aryl.

21. The compound of claim 14, wherein $R_9$ is heteroaryl.

22. The compound of claim 14, wherein $R_9$ is substituted aryl.

23. The compound of claim 14, wherein $R_9$ is substituted heteroaryl.

* * * * *